US007244430B2

(12) United States Patent
Throsby et al.

(10) Patent No.: US 7,244,430 B2
(45) Date of Patent: Jul. 17, 2007

(54) BINDING MOLECULES CAPABLE OF NEUTRALIZING WEST NILE VIRUS AND USES THEREOF

(75) Inventors: Mark Throsby, Utrecht (NL); Cornelis Adriaan De Kruif, De Bilt (NL)

(73) Assignee: Crucell Holland B.V., Leiden (NL)

( * ) Notice: Subject to any disclaimer, the term of this patent is extended or adjusted under 35 U.S.C. 154(b) by 0 days.

(21) Appl. No.: 11/625,613

(22) Filed: Jan. 22, 2007

(65) Prior Publication Data

US 2007/0122801 A1    May 31, 2007

Related U.S. Application Data

(63) Continuation of application No. 11/511,127, filed on Aug. 28, 2006, which is a continuation-in-part of application No. PCT/EP05/56926, filed on Dec. 19, 2005, and a continuation-in-part of application No. PCT/EP05/54002, filed on Aug. 15, 2005, and a continuation-in-part of application No. PCT/EP05/52946, filed on Jun. 23, 2005, and a continuation-in-part of application No. PCT/EP05/52648, filed on Jun. 8, 2005, and a continuation-in-part of application No. PCT/EP05/52160, filed on May 12, 2005, and a continuation-in-part of application No. PCT/EP04/53609, filed on Dec. 12, 2004.

(51) Int. Cl.
*A61K 39/42* (2006.01)
*A61K 39/12* (2006.01)

(52) U.S. Cl. .............................. 424/159.1; 424/137.1; 424/218.1

(58) Field of Classification Search ..................... None
See application file for complete search history.

(56) References Cited

U.S. PATENT DOCUMENTS

| | | | |
|---|---|---|---|
| 6,875,433 | B2 | 4/2005 | Hart et al. |
| 6,946,125 | B2 | 9/2005 | Rahal |
| 7,074,555 | B2 | 7/2006 | Esty et al. |
| 2003/0148261 | A1 | 8/2003 | Fikrig et al. |
| 2004/0009178 | A1 | 1/2004 | Bowdish et al. |
| 2004/0197769 | A1 | 10/2004 | Wong et al. |
| 2004/0258699 | A1 | 12/2004 | Bowdish et al. |
| 2006/0057149 | A1 | 3/2006 | Johnson et al. |
| 2006/0067940 | A1 | 3/2006 | Diamond et al. |
| 2006/0115837 | A1 | 6/2006 | Fremont et al. |
| 2006/0115896 | A1 | 6/2006 | Wong et al. |
| 2006/0269571 | A1 | 11/2006 | Hall et al. |
| 2007/0025992 | A1 | 2/2007 | Takayama et al. |

FOREIGN PATENT DOCUMENTS

| | | |
|---|---|---|
| WO | 02/072036 A2 | 9/2002 |
| WO | 2005/007800 A2 | 1/2005 |
| WO | 2005/106483 A1 | 11/2005 |
| WO | 2005/122741 | 12/2005 |
| WO | 2005/123774 | 12/2005 |
| WO | 2006/031825 | 3/2006 |
| WO | 2006/056006 | 6/2006 |

OTHER PUBLICATIONS

David W. C. Beasley and Alan D. T. Barrett, Identification of Neutralizing Epitopes within Structural Domain III of the West Nile Virus Envelope Protein, Journal of Virology, Dec. 2002, 76(24):13097-13100.*
Goncalvez et al., Chimpanzee Fab Fragments and a Derived Humanized Immunoglobulin G1 Antibody That Efficiently Cross-Neutralize Dengue Type 1 and Type 2 Viruses, Journal of Virology, Dec. 2004, pp. 12910-12918, vol. 78. No. 23.
Chung et al., Antibodies against West Nile Virus Nonstructural Protein NS1 Prevent Lethal Infection through Fc gamma Receptor-Dependent and -Independent Mechanisms, Journal of Virology, Feb. 2006, pp. 1340-1351, vol. 80, No. 3.
Throsby et al., Isolation and Characterization of Human Monoclonal Antibodies from Individuals Infected with West Nile Virus, Journal of Virology, Jul. 2006, pp. 6982-6992, vol. 80, No. 14.
Razumov et al., Neutralizing Monoclonal Antibodies Against Russian Strain of the West Nile Virus, Viral Immunology, 2005, pp. 558-568, vol. 18, No. 3.
Niedrig et al., Monoclonal Antibodies Directed Against Tick-Borne Encephalitis Virus with Neutralizing Activity In Vivo, Acta virologica, 1994, pp. 141-149, vol. 38.
Chen et al., Preparation of monoclonal antibodies against West Nile virus envelope protein domain, Chinese J. Exp. Clin Virol., Sep. 2006, pp. 213-215, vol. 20, No. 3.
Nybakken et al., Structural basis of West Nile virus neutralization by a therapeutic antibody, Nature, Sep. 29, 2005, pp. 764-768, vol. 437.
Blitvich et al., Epitope-Blocking Enzyme-Linked Immunosorbent Assays for the Detection of Serum Antibodies to West Nile Virus in Multiple Avian Species, Journal of Clinical Microbiology, Mar. 2003, pp. 1041-1047, vol. 41, No. 3.
Gould et al., Protective and Therapeutic Capacity of Human Single-Chain Fv-Fc Fusion Proteins against West Nile Virus, Journal of Virology, Dec. 2005, pp. 14606-14613, vol. 79, No. 23.
Roehrig et al., Antibody Prophylaxis and Therapy for Flavivirus Encephalitis Infections, Ann. N. Y. Acad. Sci., Dec. 2001, pp. 286-297, vol. 951.
Oliphant et al., Development of a humanized monoclonal antibody with therapeutic potential against West Nile virus, Nature Medicine, May 2005, pp. 522-530, vol. 11. No. 5.
Sanchez et al., Characterization of neutralizing antibodies to West Nile virus, Virology, 2005, pp. 72-80. vol. 336.
Beasley et al., Identification of Neutralizing Epitopes within Structural Domain III of the West Nile Virus Envelope Protein, Journal of Virology, Dec. 2002, pp. 13097-13100, vol. 76, No. 24.

* cited by examiner

*Primary Examiner*—Stacy B. Chen
(74) *Attorney, Agent, or Firm*—TraskBritt

(57) ABSTRACT

The invention provides human binding molecules specifically binding to West Nile virus and having West Nile virus neutralizing activity, nucleic acid molecules encoding the human binding molecules, compositions comprising the human binding molecules and methods of identifying or producing the human binding molecules. The human binding molecules can be used in the diagnosis, post-exposure prophylaxis and/or treatment of a condition resulting from West Nile virus.

7 Claims, 8 Drawing Sheets

US 7,244,430 B2

BINDING MOLECULES CAPABLE OF NEUTRALIZING WEST NILE VIRUS AND USES THEREOF

CROSS-REFERENCE TO RELATED APPLICATIONS

This application is a continuation of Ser. No. 11/511,127 filed Aug. 28, 2006, which is a continuation in part of the following PCT International Patent Application Nos., each of which designates the United States, PCT/EP2005/052160 filed May 12, 2005, PCT/EP2004/053609 filed Dec. 12, 2004, PCT/EP2005/056926 filed Dec. 19, 2005, PCT/EP2005/054002 filed Aug. 15, 2005, PCT/EP2005/052946 filed Jun. 23, 2005, PCT/EP2005/052648 filed Jun. 8, 2005, the contents of the entirety of each of which are incorporated herein by this reference.

STATEMENT ACCORDING TO 10 C.F.R §152(f)(1) SEQUENCE LISTING FILED IN AN ELECTRONIC MEDIUM

Pursuant to 37 C.F.R § 152(f)(1), and electronic version of the Sequence Listing is submitted concomitan with this application, the contents of which are hereby incorporated by this reference.

TECHNICAL FIELD

The invention relates to biotechnology and medicine. In particular, the invention relates to the diagnosis, prophylaxis and/or treatment of infection by the West Nile virus.

BACKGROUND

West Nile virus ("WNV") is a member of the Flaviviridae family, genus *Flavivirus*. Flaviviruses are small spherical enveloped positive-strand RNA viruses. The *Flavivirus* genus comprises more than 60 highly related viruses including several human pathogens such as inter alia yellow fever virus, Japanese encephalitis virus, St. Louis encephalitis virus, Murray Valley encephalitis virus, tick-borne encephalitis virus, and dengue virus.

WNV was initially isolated in 1937 in the West Nile region of Uganda but has now an almost worldwide distribution including parts of Africa, Asia, Australia, Europe and, most recently, North America. WNV was first diagnosed in the New York area in 1999 and has continued to spread rapidly across North America causing infections in persons in over 40 different states reaching as far as California.

WNV is mainly transmitted to man by mosquitoes but occasionally transmission has been linked to blood transfusion and organ transplantation. WNV infections generally have mild symptoms, which generally last three to six days, varying from a fever of sudden onset, headache, tremors, skin rash to swollen lymph glands. However, in 30% of the cases, particularly in elderly and immunocompromised patients, the disease progresses to a more severe state (e.g., encephalitis or aseptic meningitis), which can lead to death. By 2002, human mortality increased to over 150 cases. Besides infecting humans, WNV is also known to infect horses and several bird species and can cause severe illness and death in those species.

The two main strategies for preventing WNV infections are a) controlling the spread of WNV by spraying large areas with insecticides to kill mosquito vectors and b) reducing the contact between humans and mosquitoes by using personal protection such as anti-insect repellents. Unfortunately, these strategies are however highly inefficacious. Furthermore, there are concerns regarding the toxic effects of insecticides. Moreover, spraying requires repeated applications and is considered to be unreliable, as it does not provide complete coverage of mosquito breeding areas or eradication of mosquitoes.

There is no specific treatment of WNV infection. Treatment has only been supportive, since there are no available anti-viral or other drugs with proven efficacy. The most promising potential treatment options currently available for humans include the anti-viral compounds ribavirin and interferon-alpha2b (Anderson and Rahal, 2002), and human anti-WNV immunoglobulins (Ben Nathan et al., 2003). A disadvantage associated with ribavirin and interferon alpha2b are their significant toxicities. A disadvantage of anti-WNV immunoglobulins is that they are not available in sufficient amounts and are too expensive. In addition, the possibility of contamination by known or unknown pathogens is an additional concern associated with anti-WNV immunoglobulins. Furthermore, in PCT International Application WO 02/072036, the contents of which are incorporated by this reference, it has been suggested that the WNV F protein may be used to prepare murine anti-WNV monoclonal antibodies. However, murine antibodies, in naked or immunoconjugated format, are limited for their use in vivo due to problems associated with administration of murine antibodies to humans, such as short serum half life, an inability to trigger certain human effector functions and elicitation of an unwanted dramatic immune response against the murine antibody in a human. Accordingly, an urgent need exists for a medicament suitable for detection, prevention and/or treatment of WNV infections.

SUMMARY OF THE INVENTION

Described are human binding molecules capable of specifically binding to WNV and capable of neutralizing WNV, Also described are nucleic acid molecules encoding at least the binding region of the human binding molecules Further described is the use of the human binding molecules of the invention in the prophylaxis and/or treatment of a subject having, or at risk of developing, a WNV infection. Besides that, the invention pertains to the use of the human binding molecules of the invention in the diagnosis/detection of WNV.

In one aspect, the invention encompasses binding molecules capable of specifically binding to WNV. Preferably, the binding molecules are human binding molecules. Preferably, the binding molecules of the invention are capable of neutralizing WNV. More preferably, the binding molecules of the invention are capable of binding to and neutralizing both WNV lineage I variants such as inter alia strain 385-99 and WNV lineage II variants such as inter alia strain H-442. In the presently most preferred embodiment, the binding molecules of the invention are capable of neutralizing essentially all WNV variants currently known. In one embodiment, the binding molecules of the invention may even neutralize at least one other flavivirus including, but not limited to, yellow fever virus, Japanese encephalitis virus, St. Louis encephalitis virus, Murray Valley encephalitis virus, tick-borne encephalitis virus, and dengue virus. The binding molecules of the invention may be capable of specifically binding to WNV in activated or inactivated/attenuated form. Methods for inactivating/attenuating viruses are well known in the art and include, but are not limited to, heat inactivation, inactivation by UV irradiation, and inactivation by gamma irradiation.

The binding molecules of the invention may also be capable of specifically binding to one or more fragments of WNV such as inter alia a preparation of one or more proteins and/or (poly)peptides derived from WNV or one or more recombinantly produced WNV proteins and/or polypeptides. Alternatively, the fragments have the form of WNV-like particles. Such particles comprise WNV structural proteins including, but not limited to, the WNV envelope (E) protein and/or the WNV membrane (preM/M) protein. For methods of treatment and/or prevention of WNV the binding molecules are preferably capable of specifically binding to surface accessible proteins of WNV including the E protein and preM/M protein. For diagnostical purposes the binding molecules may also be capable of specifically binding to proteins not present on the surface of WNV including the WNV capsid (C) protein and/or the WNV non-structural (NS) proteins NS1, NS2A, NS2B, NS3, NS4A, NS4B, and NS5. The nucleotide and/or amino acid sequence of proteins of various strains of WNV can be found in the GenBank-database, EMBL-database and/or other databases. The complete or partial genomes of a number of WNV isolates from outbreaks in for instance the United States have been sequenced. The complete sequence of WNV isolated from a dead Chilean flamingo (WN-NY99, strain 382-99) at the Bronx Zoo can be found in the GenBank database under accession number AF196835 (see Lanciotti et al., 1999). The genome of a WNV isolate from human victims of the 1999 New York outbreak (WNV-NY1999) was sequenced and can be found in the GenBank database under accession number AF202541 (see Jia et al., 1999). Partial sequences of isolates from two species of mosquito, a crow and a hawk from Connecticut can be found in the GenBank database under accession numbers AF206517-AF206520, respectively (see Anderson et al., 1999). It is well within the reach of the skilled person to find further sequences of WNV isolates and proteins in databases.

Preferably, the fragment at least comprises an antigenic determinant recognized by the binding molecules of the invention. An "antigenic determinant" as used herein is a moiety, such as a WNV (poly)peptide, protein, glycoprotein, analog or fragment thereof, that is capable of binding to a binding molecule of the invention with sufficiently high affinity to form a detectable antigen-binding molecule complex.

In one embodiment, the binding molecules of the invention are capable of specifically binding to the WNV E protein. The human binding molecules of the invention may be capable of binding to domain I, II and/or III of the E protein. The binding molecules of the invention can be intact immunoglobulin molecules such as polyclonal or monoclonal antibodies or the binding molecules can be antigen-binding fragments including, but not limited to, Fab, F(ab'), F(ab')$_2$, Fv, dAb, Fd, complementarity determining region (CDR) fragments, single-chain antibodies (scFv), bivalent single-chain antibodies, single-chain phage antibodies, diabodies, triabodies, tetrabodies, and (poly)peptides that contain at least a fragment of an immunoglobulin that is sufficient to confer specific antigen binding to the WNV or a fragment thereof. In a preferred embodiment, the human binding molecules having WNV neutralizing activity are administered in IgG1 format.

The binding molecules of the invention can be used in non-isolated or isolated form. Furthermore, the binding molecules of the invention can be used alone or in a mixture comprising at least one binding molecule (or variant or fragment thereof) of the invention. In other words, the binding molecules can be used in combination for example as a pharmaceutical composition comprising two or more binding molecules of the invention, variants or fragments thereof. For example, binding molecules having different, but complementary activities can be combined in a single therapy to achieve a desired prophylactic, therapeutic or diagnostic effect, but alternatively, binding molecules having identical activities can also be combined in a single therapy to achieve a desired prophylactic, therapeutic or diagnostic effect. The mixture may further comprise at least one other therapeutic agent. Preferably, the therapeutic agent is useful in the prophylaxis and/or treatment of a condition resulting from WNV.

Typically, binding molecules according to the invention can bind to their binding partners, i.e., WNV or fragments thereof, with an affinity constant ($K_d$-value) that is lower than $0.2*10^{-4}$ M, $1.0*10^{-5}$ M, $1.0*10^{-6}$ M, $1.0*10^{-7}$ M, preferably lower than $1.0*10^{-8}$ M, more preferably lower than $1.0*10^{-9}$ M, more preferably lower than $1.0*10^{-10}$ M, even more preferably lower than $1.0*10^{-11}$ M, and in particular lower than $1.0*10^{-12}$ M. The affinity constants can vary for antibody isotypes. For example, affinity binding for an IgM isotype refers to a binding affinity of at least about $1.0*10^{-7}$ M. Affinity constants can for instance be measured using surface plasmon resonance, i.e., an optical phenomenon that allows for the analysis of real-time biospecific interactions by detection of alterations in protein concentrations within a biosensor matrix, for example using the BIACORE system (Pharmacia Biosensor AB, Uppsala, Sweden).

The binding molecules according to the invention may bind to WNV or a fragment thereof in soluble form such as for instance in a sample or may bind to WNV or a fragment thereof bound or attached to a carrier or substrate for example microtiter plates, membranes and beads, etc. Carriers or substrates may be made of glass, plastic (e.g., polystyrene), polysaccharides, nylon, nitrocellulose, or Teflon, etc. The surface of such supports may be solid or porous and of any convenient shape. Furthermore, the binding molecules may bind to WNV in purified/isolated or non-purified/non-isolated form.

The binding molecules described herein are capable of neutralizing WNV infectivity. This may be achieved by preventing the attachment of WNV to possible receptors on susceptible host cells or inhibition of the fusion of WNV and cell membranes. Neutralization can, for instance, be measured as described herein. Alternative neutralization assays are described in for instance Collins and Porterfield (1986).

Furthermore, the neutralizing binding molecules of the invention may abolish replication of WNV, be complement fixing human binding molecules capable of assisting in the lysis of WNV, and/or might act as opsonins and augment phagocytosis of WNV either by promoting its uptake via Fc or C3b receptors or by agglutinating WNV to make it more easily phagocytosed.

In a preferred embodiment, the binding molecules described herein comprise at least a CDR3 region, preferably a heavy chain CDR3 region, comprising the amino acid sequence selected from the group consisting of SEQ ID NO:1, SEQ I NO:2, SEQ ID NO:3, SEQ ID NO:4, SEQ ID NO:5, SEQ ID NO:6, SEQ ID NO:7, SEQ ID NO:8. SEQ ID NO:9, and SEQ ID NO:10. Particularly preferred is a binding molecule according to the invention comprising at least a CDR3 region, preferably a heavy chain CDR3 region, comprising the amino acid sequence of SEQ ID NO:10. More preferably, the binding molecule according to the invention comprises at least a heavy chain CDR1 and CDR2 region comprising the amino acid sequence of SEQ ID NOS:30 and 40, respectively. In one embodiment, the binding molecules of the invention may comprise two, three, four, five or even all six CDR regions of the binding molecules of the invention. The heavy chain CDR1 region, heavy chain CDR2 region, light chain CDR1 region, light chain CDR2 region and light chain CDR3 region of each binding molecule of the invention are shown in Table 9. CDR regions are according to Kabat et al. (1991) as described in Sequences of Proteins of Immunological Interest. In a specific embodiment, the binding molecule comprising at least a CDR3 region, preferably a heavy chain CDR3 region, comprising the amino acid sequence of SEQ ID NO:10 comprises a heavy chain CDR1 and heavy chain CDR2 region comprising the amino acid sequence of SEQ ID NOS:30 and 40, respectively, and a light chain CDR1 region comprising the amino acid sequence selected from the group consisting of SEQ ID NOS:236-239, a light chain CDR2 region comprising the amino acid sequence selected from the group consisting of SEQ ID NOS:240-243 and/or a light chain CDR3 region comprising the amino acid sequence selected from the group consisting of SEQ ID NOS:244-247.

In yet another embodiment, the binding molecules according to the invention comprise a heavy chain comprising the variable heavy chain of the amino acid sequence selected from the group consisting of SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, and SEQ ID NO:80. In a further embodiment, the binding molecules according to the invention comprise a light chain comprising the variable light chain of the amino acid sequence selected from the group consisting of SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:229, SEQ ID NO:231, SEQ ID NO:233, and SEQ ID NO:235. Table 8 and 18 specify, next to the heavy chain CDR3 region, the heavy and light chain variable regions of the binding molecule of the invention.

In a further embodiment, the binding molecules of the invention comprise a heavy chain comprising the variable heavy chain of the amino acid sequence selected from the group consisting of SEQ ID NOS:113, 115, 117, 119, 121, 23, 125, 127, 129, and 131. In another embodiment, the binding molecules of the invention comprise a light chain comprising the variable light chain of the amino acid sequence selected from the group consisting of SEQ ID NOS:133, 135, 137, 139, 141, 143, 145, 147, 149, 151, 221, 223, 225, and 227.

In yet a further embodiment, the binding molecules of the invention comprise a heavy chain comprising the amino acid sequence selected from the group consisting of SEQ ID NOS:113, 115, 117, 119,121, 123, 125, 127, 129, and 131, and/or comprise a light chain comprising the amino acid sequence selected from the group consisting of SEQ ID NOS:133, 135, 137, 139, 141, 143, 145, 147, 149, 151, 221, 223, 225, and 227.

In another aspect, the invention includes functional variants of the binding molecules as defined herein. Molecules are considered to be functional variants of a binding molecule according to the invention, if the variants are capable of competing for specifically binding to WNV or a fragment thereof with the parent human binding molecules. In other words, when the functional variants are still capable of binding to WNV or a fragment thereof. Furthermore, molecules are considered to be functional variants of a binding molecule according to the invention, if they have WNV neutralizing activity. Functional variants include, but are not limited to, derivatives that are substantially similar in primary structural sequence, but which contain e.g., in vitro or in vivo modifications, chemical and/or biochemical, that are not found in the parent binding molecule. Such modifications include inter alia acetylation, acylation, covalent attachment of a nucleotide or nucleotide derivative, covalent attachment of a lipid or lipid derivative, cross-linking, disulfide bond formation, glycosylation, hydroxylation, methylation, oxidation, pegylation, proteolytic processing, phosphorylation, and the like.

Alternatively, functional variants can be binding molecules as defined in the invention comprising an amino acid sequence containing substitutions, insertions, deletions or combinations thereof of one or more amino acids compared to the amino acid sequences of the parent binding molecules. Furthermore, functional variants can comprise truncations of the amino acid sequence at either or both the amino or carboxyl termini. Functional variants according to the invention may have the same or different, either higher or lower, binding affinities compared to the parental binding molecule but are still capable of binding to WNV or a fragment thereof. For instance, functional variants according to the invention may have increased or decreased binding affinities for WNV or a fragment thereof compared to the parent binding molecules. Preferably, the amino acid sequences of the variable regions, including, but not limited to, framework regions, hypervariable regions, in particular the CDR3 regions, are modified. Generally, the light chain and the heavy chain variable regions comprise three hypervariable regions, comprising three CDRs, and more conserved regions, the so-called framework regions (FRs). The hypervariable regions comprise amino acid residues from CDRs and amino acid residues from hypervariable loops. Functional variants intended to fall within the scope of the invention have at least about 50% to about 99%, preferably at least about 60% to about 99%, more preferably at least about 70% to about 99%, even more preferably at least about 80% to about 99%, most preferably at least about 90% to about 99%, in particular at least about 95%, to about 99%, and in particular at least about 97% to about 99% amino acid sequence homology with the parent human binding molecules as defined herein. Computer algorithms such as inter alia Gap or Bestfit known to a person skilled in the art can be used to optimally align amino acid sequences to be compared and to define similar or identical amino acid residues. Functional variants can be obtained by altering the parent binding molecules or parts thereof by general molecular biology methods known in the art including, but not limited to, error-prone PCR, oligonucleotide-directed mutagenesis, site-directed mutagenesis and heavy or light chain shuffling. Preferably, the functional variants of the invention have WNV neutralizing activity. This neutralizing activity may either be identical, or be higher or lower compared to the parent binding molecules. Furthermore, the functional variants having neutralizing activity may inhibit or down regulate WNV replication, are complement fixing binding molecules capable of assisting in the lysis of WNV and/or act as opsonins and augment phagocytosis of WNV either by promoting its uptake via Fc or C3b receptors or by agglutinating WNV to make it more easily phagocytosed. Henceforth, when the term (human) binding molecule is used, this also encompasses functional variants of the (human) binding molecule.

In yet a further aspect, the invention includes immunoconjugates, molecules comprising at least one binding molecule as defined herein and further comprising at least one tag, such as, inter alia, a detectable moiety/agent. Also contemplated in the invention are mixtures of immunoconjugates according to the invention or mixtures of at least one immunoconjugates according to the invention and another molecule, such as a therapeutic agent or another binding molecule or immunoconjugate. In a further embodiment, the immunoconjugates of the invention may comprise more than one tag. These tags can be the same or distinct from each other and can be joined/conjugated non-covalently to the binding molecules. The tag(s) can also be joined/conjugated directly to the human binding molecules through covalent bonding. Alternatively, the tag(s) can be joined/conjugated to the binding molecules by means of one or more linking compounds. Techniques for conjugating tags to binding molecules are well known to the skilled artisan.

The tags of the immunoconjugates of the invention may be therapeutic agents, but preferably they are detectable moieties/agents. The tags may also be toxins, such as botulinum toxin or functional parts thereof. Immunoconjugates comprising a detectable agent can be used diagnostically to, for example, assess if a subject has been infected with WNV or monitor the development or progression of a WNV infection as part of a clinical testing procedure tofor example determine the efficacy of a given treatment regimen. However, they may also be used for other detection and/or analytical and/or diagnostic purposes. Detectable moieties/agents include, but are not limited to, enzymes, prosthetic groups, fluorescent materials, luminescent materials, bioluminescent materials, radioactive materials, positron emitting metals, and non-radioactive paramagnetic metal ions. The tags used to label the binding molecules for detection and/or analytical and/or diagnostic purposes depend on the specific detection/analysis/diagnosis techniques and/or methods used such as inter alit immunohistochemical staining of (tissue) samples, flow cytometric detection, scanning laser cytometric detection, fluorescent immunoassays, enzyme-linked immunosorbent assays (ELISAs), radioimmunoassays (RIAs), bioassays (e.g., neutralization assays), Western blotting applications, etc. Suitable labels for the detection/analysis/diagnosis techniques and/or methods known in the art are well within the reach of the skilled artisan.

Furthermore, the human binding molecules or immunoconjugates of the invention can also be attached to solid supports, which are particularly useful for in vitro immunoassays or purification of WNV or a fragment thereof. Such solid supports might be porous or nonporous, planar or non-planar. The binding molecules of the invention can be fused to marker sequences, such as a peptide to facilitate purification. Examples include, but are not limited to, the hexa-histidine tag, the hemagglutinin (HA) tag, the myc tag or the flag tag. Alternatively, an antibody can be conjugated to a second antibody to form an antibody heteroconjugate. In another aspect the binding molecules of the invention may be conjugated/attached to one or more antigens. Preferably, these antigens are antigens which are recognized by the immune system of a subject to which the binding molecule-antigen conjugate is administered. The antigens may be identical, but may also differ from each other. Conjugation methods for attaching the antigens and binding molecules are well known in the art and include, but are not limited to, the use of cross-linking agents. The binding molecules of the invention will bind to WNV and the antigens attached to the binding molecules will initiate a powerful T-cell attack on the conjugate, which will eventually lead to the destruction of the WNV.

Next to producing immunoconjugates chemically by conjugating, directly or indirectly, via for instance a linker, the immunoconjugates can be produced as fusion proteins comprising the binding molecules of the invention and a suitable tag. Fusion proteins can be produced by methods known in the art such asfor example recombinantly by constructing nucleic acid molecules comprising nucleotide sequences encoding the binding molecules in frame with nucleotide sequences encoding the suitable tag(s) and then expressing the nucleic acid molecules.

It is another aspect, the invention provides a nucleic acid molecule encoding at least a binding molecule or immunoconjugate of the invention. Such nucleic acid molecules can be used as intermediates for cloning purposes for example in the process of affinity maturation as described above. In a preferred embodiment, the nucleic acid molecules are isolated or purified.

One of skill in the art appreciate that functional variants of these nucleic acid molecules are also intended to be a part of the invention. Functional variants are nucleic acid sequences that can be directly translated, using the standard genetic code, to provide an amino acid sequence identical to that translated from the parent nucleic acid molecules.

Preferably, the nucleic acid molecules encode binding molecules comprising a CDR3 region, preferably a heavy chain CDR3 region, comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10. In a further embodiment the nucleic acid molecules encode binding molecules comprising two, three, four, five or even all six CDR regions of the binding molecules of the invention.

In another embodiment, the nucleic acid molecules encode binding molecules comprising a heavy chain comprising the variable heavy chain of the amino acid sequence selected from the group consisting of SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, and SEQ ID NO:80. In another embodiment the nucleic acid molecules encode binding molecules comprising a light chain comprising the variable light chain of the amino acid sequence selected from the group consisting of SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:229, SEQ ID NO:231, SEQ ID NO:233, and SEQ ID NO:235.

In a further embodiment, the nucleic acid molecules encode binding molecules comprising a heavy chain comprising the variable heavy chain of the amino acid sequence selected from the group consisting of SEQ ID NOS:113, 115, 117, 119, 121, 123, 125, 127, 129, and 131. In another embodiment, the nucleic acid molecules encode binding molecules comprising a light chain comprising the variable light chain of the amino acid sequence selected from the group consisting of SEQ ID NOS:133, 135, 137, 139, 141, 143, 145, 147, 149, 151, 221, 223, 225, and 227.

In yet a further embodiment, the nucleic acid molecules encode binding molecules comprising a heavy chain comprising the amino acid sequence selected from the group consisting of SEQ ID NOS:113, 115, 117, 119, 121, 123, 125, 127, 129, and 131, and/or comprising a light chain comprising the amino acid sequence selected from the group consisting of SEQ ID NOS:133, 135, 137, 139, 141, 143, 145, 147, 149, 151,221, 223, 225, and 227.

It is another aspect of the invention to provide vectors, i.e., nucleic acid constructs, comprising one or more nucleic acid molecules according to the invention. Vectors can be derived from plasmids such as, inter alia, F, R1, RP1. Col, pBR322, TOL, Ti, etc; cosmids; phages such as lambda, lambdoid, M13, Mu, P1, P22, Qβ, T-even, T-odd, T2, T4, T7, etc; plant viruses. Vectors can be used for cloning and/or for expression of the binding molecules of the invention and might even be used for gene therapy purposes. Vectors comprising one or more nucleic acid molecules according to the invention operably linked to one or more expression-regulating nucleic acid molecules are also covered by the invention. The choice of the vector is dependent on the recombinant procedures followed and the host used. Introduction of vectors in host cells can be effected by inter alia calcium phosphate transfection, virus infection, DEAF-dextran mediated transfection, lipofectamin transfection or electroporation. Vectors may be autonomously replicating or may replicate together with the chromosome into which they have been integrated. Preferably, the vectors contain one or more selection markers. The choice of the markers may depend on the host cells of choice, although this is not critical to the invention as is well known to persons skilled in the art. They include, but are not limited to, kanamycin, neomycin, puromycin, hygromycin, zeocin, thymidine kinase gene from Herpes simplex virus (HSV-TK), dihydrofolate reductase gene from mouse (dhfr). Vectors comprising one or more nucleic acid molecules encoding the human binding molecules as described above operably linked to one or more nucleic acid molecules encoding proteins or peptides that can be used to isolate the human binding molecules are also covered by the invention. These proteins or peptides include, but are not limited to, glutathione-S-transferase, maltose binding protein, metal-binding polyhistidine, green fluorescent protein, luciferase and beta-galactosidase.

Hosts containing one or more copies of the vectors mentioned above are an additional subject of the invention. Preferably, the hosts are host cells. Host cells include, but are not limited to, cells of mammalian, plant, insect, fungal or bacterial origin. Bacterial cells include, but are not limited to, cells from Gram positive bacteria such as several species of the genera *Bacillus, Streptoyces* and *Staphylococcus* or cells of Gram negative bacteria such as several species of the genera *Escherichia*, such as *E. coli*, and *Pseidormonas*. In the group of fungal cells preferably yeast cells are used. Expression in yeast can be achieved by using yeast strains such as inter alia *Pichia pastoris, Saccharomyces cerevisiae* and *Hansenula polymorpha*. Furthermore, insect cells such as cells from *Drosophila* and Sf9 can be used as host cells. Besides that, the host cells can be plant cells such as inter alia cells from crop plants such as forestry plants, or cells from plants providing food and raw materials such as cereal plants, or medicinal plants, or cells from ornamentals, or cells from flower bulb crops. Transformed (transgenic) plants or plant cells are produced by known methods, for example. Agrobacterium-mediated gene transfer, transformation of leaf discs, protoplast transformation by polyethylene glycol-induced DNA transfer, electroporation, sonication, microinjection or bolistic gene transfer. Additionally, a suitable expression system can be a baculovirus system. Expression systems using mammalian cells such as Chinese Hamster Ovary (CHO) cells, COS cells, BHK cells or Bowes melanoma cells are preferred in the invention. Mammalian cells provide expressed proteins with posttranslational modifications that are most similar to natural molecules of mammalian origin. Since the invention deals with molecules that may have to be administered to humans, a completely human expression system would be particularly preferred. Therefore, even more preferably, the host cells are human cells. Examples of human cells are inter alia HeLa, 911, AT1080, A549, 293 and HEK293T cells. In preferred embodiments, the human producer cells comprise at least a functional part of a nucleic acid sequence encoding an adenovirus E1 region in expressible format. In even more preferred embodiments, the host cells are derived from a human retina and immortalized with nucleic acids comprising adenoviral El sequences, such as 911 cells or the cell line deposited at the European Collection of Cell Cultures (ECACC), CAMR, Salisbury, Wiltshire SP4 OJG, Great Britain on 29 Feb. 1996 under number 96022940 and marketed under the trademark PER.C6® (PER.C6 is a registered trademark of Crucell Holland R.V.). For the purposes of this application "PER.C6" refers to cells deposited under number 96022940 or ancestors, passages upstream or downstream as well as descendants from ancestors of deposited cells, as well as derivatives of any of the foregoing. Production of recombinant proteins in host cells can be performed according to methods well known in the art. The use of the cells marketed under the trademark PER.C6® as a production platform for proteins of interest has been described in PCT International Publication WO 00/63403 the disclosure of which is incorporated herein by reference in its entirety.

A method of producing a binding molecule or an immunoconjugate according to the invention is an additional part of the invention. The method comprises the steps of a) culturing a host according to the invention under conditions conducive to the expression of the binding molecule, or immunoconjugate, and b) optionally, recovering the expressed binding molecule or immunoconjugate. The expressed binding molecules or immunoconjugates can be recovered from the cell free extract, but preferably they are recovered from the culture medium. The above method of producing can also be used to make functional variants of the binding molecules and immunoconjugates of the invention. Methods to recover proteins, such as binding molecules, from cell free extracts or culture medium are well known to the man skilled in the art. Binding molecules or immunoconjugates as obtainable by the above-described method are also a part of the invention.

Alternatively, next to the expression in hosts, such as host cells, the binding molecules and immunoconjugates of the invention can be produced synthetically by conventional peptide synthesizers or in cell-free translation systems using RNA nucleic acid derived from DNA molecules according to the invention, Binding molecules and immunoconjugates as obtainable by the above described synthetic production methods or cell-free translation systems are also a part of the invention.

In yet another embodiment, binding molecules of the invention can also be produced in transgenic, non-human, mammals such as idler alia rabbits, goats or cows, and secreted into for instance the milk thereof.

In yet another embodiment, binding molecules according to the invention, preferably human binding molecules specifically binding to WNV or a fragment thereof, may be generated by transgenic non-human mammals, such as for instance transgenic mice or rabbits, that express human immunoglobulin genes. Preferably, the transgenic non-human mammals have a genome comprising a human heavy chain transgene and a human light chain transgene encoding all or a portion of the human binding molecules as described above. The transgenic non-human mammals can be immunized with a purified or enriched preparation of WNV or a fragment thereof. Protocols for immunizing non-human mammals are well established in the art. See *Using Antibodies: A Laboratory Manual*, edited by: E. Harlow, D. Lane (1998). Cold Spring Harbor Laboratory, Cold Spring Harbor, N.Y., and *Current Protocols in Immunology*, edited by. J. E. Coligan, A. M. Kruisbeek, D. H. Margulies, E. M. Shevach, W. Strober (2001), John Wiley & Sons Inc., New York, the disclosures of which are incorporated herein by reference. Immunization protocols often include multiple immunizations, either with or without adjuvants such as Freund's complete adjuvant and Freund's incomplete adjuvant, but may also include naked DNA immunizations. In another embodiment, the human binding molecules are produced by B cells or plasma cells derived from the transgenic animals. In yet another embodiment, the human binding molecules are produced by hybridomas, which are prepared by fusion of B cells obtained from the above-described transgenic non-human mammals to immortalized cells. B cells, plasma cells and hybridomas as obtainable from the above described transgenic nonhuman mammals and human binding molecules as obtainable from the above described transgenic non-human mammals, B cells, plasma cells and hybridomas are also a part of the invention.

In a further aspect, the invention provides a method of identifying binding molecules according to the invention, such as human binding molecules for example monoclonal antibodies or fragments thereof, specifically binding to WNV or nucleic acid molecules encoding such binding molecules and comprises the steps of a) contacting a collection of binding molecules on the surface of replicable genetic packages with WNV or a fragment thereof under conditions conducive to binding, b) selecting at least once for a replicable genetic package binding to the WNV or the fragment thereof, and c) separating and recovering the replicable genetic package binding to the WNV or the fragment thereof from replicable genetic packages that do not bind.

A replicable genetic package as used herein can be prokaryotic or eukaryotic and includes cells, spores, yeasts, bacteria, viruses, (bacterio)phage, ribosomes and polysomes. A preferred replicable genetic package is a phage. The binding molecules, such as for instance single chain Fvs, are displayed on the replicable genetic package, they are attached to a group or molecule located at an exterior surface of the replicable genetic package. The replicable genetic package is a screenable unit comprising a binding molecule to be screened linked to a nucleic acid molecule encoding the binding molecule. The nucleic acid molecule should be replicable either in vivo (e.g., as a vector) or in vitro (e.g., by PCR, transcription and translation). In vivo replication can be autonomous (as for a cell), with the assistance of host factors (as for a virus) or with the assistance of both host and helper virus (as for a phagemid). Replicable genetic packages displaying a collection of binding molecules is formed by introducing nucleic acid molecules encoding exogenous binding molecules to be displayed into the genomes of the replicable genetic packages to form fusion proteins with endogenous proteins that are normally expressed from the outer surface of the replicable genetic packages. Expression of the fusion proteins, transport to the outer surface and assembly results in display of exogenous binding molecules from the outer surface of the replicable genetic packages.

In one embodiment, the selection step in the method according to the invention is performed in the presence of WNV that is inactivated. The inactivation of the WNV may be performed by viral inactivation methods well known to the skilled artisan such as inter alia pasteurization (wet heat), e.g., heat treatment while still in aqueous solution, at 60° C. for ten hours, dry heat treatment, e.g., heat treatment in the lyophilized state, at 80° C. for 72 hours; vapor heat treatment at 60° C. for ten hours and then 80° C. for one hour; treatment with low pH, e.g., ph 4 for six hours to 21 days; treatment with organic solvent/detergent, i.e., addition of organic solvents and detergents (Triton X-100 or Tween-80) to the virus: treatment by means of cold ethanol fractionation; column chromatography; nanofiltration; UV/light irradiation; gamma-irradiation; and addition of iodine. Preferably, the inactivation is performed by gamma- or UV-irradiation. Methods to test if a virus is still infective or partly or completely inactivated are well known to the person skilled in the art. The WNV used in the above method may be non-isolated for example present in serum and/or blood of an infected individual. The WNV used may also be isolated either before or after inactivation. Purification may be performed by means of well-known purification methods suitable for viruses such as for instance centrifugation through a glycerol cushion.

Alternatively, the selection step may be performed in the presence of a fragment of WNV such as recombinant WNV proteins or WNV-like particles expressing one or more WNV proteins such as WNV E and Ni protein. In yet another embodiment, the selection step may be performed in the presence of one or more proteins or (poly)peptides derived from WNV, fusion proteins comprising these proteins or (poly)peptides, and the like. Preferred WNV proteins are WNV proteins present on the surface of WNV such as the E and M protein. Extracellularly exposed parts of these proteins can also be used as selection material. The inactivated WNV or fragment thereof may be immobilized to a suitable material before use. In a specific embodiment the selection can be performed on different materials derived from WNV. For instance, the first selection round can be performed on inactivated WNV, while the second and third selection round can be performed on recombinant WNV E protein and WNV-like particles, respectively. Of course, other combinations are also suitable. Different WNV materials can also be used during one selection/panning step.

In yet a further aspect, the invention provides a method of obtaining a binding molecule specifically binding to WNV or a nucleic acid molecule encoding such a binding molecule specifically binding to a WNV, wherein the method comprises the steps of a) performing the above described method of identifying binding molecules, and b) isolating from the recovered replicable genetic package the binding molecule and/or the nucleic acid molecule encoding the binding molecule. The collection of binding molecules on the surface of replicable genetic packages can be a collection of scFvs or Fabs. Once a new scFv or Fab has been established or identified with the above mentioned method of identifying binding molecules or nucleic acid molecules encoding the binding molecules, the DNA encoding the scFv or Fab cm be isolated from the bacteria or phages and combined with standard molecular biological techniques to make constructs encoding bivalent scFvs or complete human immmunoglobulins of a desired specificity (e.g., IgG, IgA or IgM). These constructs can be transfected into suitable cell lines and complete human monoclonal antibodies can be produced (see Huls et al., 1999; Boel et al., 2000).

As mentioned before, the preferred replicable genetic package is a phage. Phage display methods for identifying and obtaining (human) binding molecules for example monoclonal antibodies, are by now well-established methods known by the person skilled in the art. They are for example described in U.S. Pat. No. 5,696,108; Burton and Barbas, 1994; de Kruif et al., 1995b; and *Phage Display: A Laboratory Manual* 1, edited by C. F. Barbas, D. R. Burton, J. K. Scott and G. J. Silverman (2001), Cold Spring Harbor Laboratory Press, Cold Spring Harbor, N.Y.. All these references are herewith incorporated herein in their entirety. For the construction of phage display libraries, collections of human monoclonal antibody heavy and light chain variable region genes are expressed on the surface of bacteriophage, preferably filamentous bacteriophage, particles, in for example single-chain Fv (seFv) or in Fab format (see de Kruif et al., 1995b). Large libraries of antibody fragment-expressing phages typically contain more than $1.0*10^9$ antibody specificities and may be assembled from the immunoglobulin V regions expressed in the B-lymphocytes of immunized- or non-immunized individuals. In a specific embodiment of the invention the phage library of binding molecules, preferably scFv phage library, is prepared from RNA isolated from cells obtained from a subject that has been vaccinated or exposed to a WNV. RNA can be isolated from inter alia bone marrow or peripheral blood, preferably peripheral blood lymphocytes. The subject can be an animal vaccinated or exposed to WNV, but is preferably a human subject which has been vaccinated or has been exposed to WNV. Preferably, the human subject has recovered from WNV.

Alternatively, phage display libraries may be constructed from immunoglobulin variable regions that have been partially assembled in vitro to introduce additional antibody diversity in the library (semi-synthetic libraries). For example, in vitro assembled variable regions contain stretches of synthetically produced, randomized or partially randomized DNA in those regions of the molecules that are important for antibody specificity for example CDR regions. WNV specific phage antibodies can be selected from the library by for instance immobilizing target antigens such as antigens from WNV on a solid phase and subsequently exposing the target antigens to a phage library to allow binding of phages expressing antibody fragments specific for the solid phase-bound antigen(s). Non-bound phages are removed by washing and bound phages eluted from the solid phase for infection of *E. coli* bacteria and subsequent propagation. Multiple rounds of selection and propagation are usually required to sufficiently enrich for phages binding specifically to the target antigen(s). If desired, before exposing the phage library to target antigens the phage library can first be subtracted by exposing the phage library to non-target antigens bound to a solid phase. Phages may also be selected for binding to complex antigens such as complex mixtures of WNV proteins or (poly)peptides, host cells expressing one or more proteins or (poly)peptides of WNV, WNV-like particles comprising WNV proteins, or whole inactivated WNV. Antigen specific phage antibodies can be selected from the library by incubating a solid phase with bound thereon inactivated WNV with the phage antibody library to let for example the scFv or Fab part of the phage bind to the WNV. After incubation and several washes to remove unbound and loosely attached phages, the phages that have bound with their scFv or Fab part to the WNV are eluted and used to infect *E. coli* to allow amplification of the new specificity. Generally, one or more selection rounds are required to separate the phages of interest from the large excess of non-binding phages. Alternatively, known proteins or (poly)peptides of WNV can be expressed in host cells and these cells can be used for selection of phage antibodies specific for the proteins or (poly)peptides. A phage display method using these host cells can be extended and improved by subtracting non-relevant binders during screening by addition of an excess of host cells comprising no target molecules or non-target molecules that are similar, but not identical, to the target, and thereby strongly enhance the chance of finding relevant binding molecules. Of course, the subtraction may also be performed before or after the screening with WNV or antigens thereof. The process is referred to as the Mabstract® process (Mabstract® is a registered trademark of Crucell Holland B. V., see also U.S. Pat. No. 6,265,150 which is incorporated herein by reference).

In yet another aspect, the invention provides a method of obtaining a binding molecule potentially having neutralizing activity against WNV, wherein the method comprises the steps of a) performing the method of obtaining a binding molecule specifically binding to WNV or a nucleic acid molecule encoding such a binding molecule specifically binding to a WNV as described above, and b) verifying if the binding molecule isolated has neutralizing activity against the WNV. Assays for verifying if a binding molecule has neutralizing activity are well known in the art (see, for instance, Beasley and Barrett, 2002).

In a further aspect, the invention pertains to a binding molecule having neutralizing activity against WNV and being obtainable by the methods as described above, A pharmaceutical composition comprising the binding molecule, the pharmaceutical composition further comprising at least one pharmaceutically acceptable excipient is also an aspect of the invention. Pharmaceutically acceptable excipients are well known to the skilled person. The pharmaceutical composition according to the invention may further comprise at least one other therapeutic agent. Suitable agents are also well known to the skilled artisan.

In yet a further aspect, the invention provides compositions comprising at least one binding molecule, at least one functional variant thereof, at least one immunoconjugate according to the invention or a combination thereof. In addition to that, the compositions may comprise inter alia stabilizing molecules, such as albumin or polyethylene glycol, or salts. Preferably, the salts used are salts that retain the desired biological activity of the binding molecules and do not impart any undesired toxicological effects. If necessary, the human binding molecules of the invention may be coated in or on a material to protect them from the action of acids or other natural or non-natural conditions that may inactivate the binding molecules.

In yet a further aspect, the invention provides compositions comprising at least one nucleic acid molecule as defined in the invention. The compositions may comprise aqueous solutions such as aqueous solutions containing salts (e.g., NaCl or salts as described above), detergents (e.g., SDS) and/or other suitable components.

In another aspect, the invention is concerned with a composition comprising at least two binding molecules, preferably human binding molecules, having WNV neutralizing activity. The binding molecules should be capable of reacting with different, non-competing epitopes of WNV. Preferably, the epitopes are located on the WNV E protein. In one embodiment the first WNV neutralizing binding molecule is capable of reacting with al epitope located in domain II of the WNV E protein and the second WNV neutralizing binding molecule is capable of reacting with an epitope located in domain III of the WNV E protein.

In one embodiment, the compositions comprising two or more binding molecules having WNV neutralizing activity exhibit synergistic WNV neutralizing activity. In other words, the compositions comprise at least two binding molecules having WNV neutralizing activity, characterized in that the binding molecules act synergistically in neutralizing WNV. As used herein, the term "synergistic" means that the combined effect of the binding molecules when used in combination is greater than their additive effects when used individually. In one embodiment none of the binding molecules present in the synergistic WNV neutralizing activity exhibiting compositions may have WNV neutralizing activity when used as an individual binding molecule. Alternatively, one binding molecule of the at least two binding molecules in the compositions exhibiting synergistic WNV neutralizing activity may have WNV neutralizing activity when used individually. In a preferred embodiment both of the at least two binding molecules have WNV neutralizing activity when used individually. In one embodiment, one of the at least two binding molecules in the synergistic WNV neutralizing activity exhibiting compositions may bind to a WNV and the other binding molecule may bind to a cell associated receptor of the WNV. Alternatively, both binding molecules may bind to either the WNV or cell associated receptor. In one embodiment the binding molecules acting synergistically in neutralizing WNV may also be capable of neutralizing other flaviviruses synergistically. The at least two synergistically acting anti-WNV binding molecules may bind to the F protein of WNV. They may bind to different domains such as one binding to domain II and one binding to domain III of the E protein of WNV. Alternatively, the antibodies may bind to the same domain. A way of calculating synergy is by means of the combination index. The concept of the combination index (CI) has been described by Chou and Talalay, 1984. In an alternative embodiment, the compositions comprise two or more binding molecules having different modes of action for example a first binding molecule may have WNV neutralizing activity, while the second binding molecule may be non-neutralizing, and have complement fixing activity.

Furthermore, the invention pertains to pharmaceutical compositions comprising at least one binding molecule (or functional fragment or variant thereof), at least one immunoconjugate according to the invention, at least one composition according to the invention, or combinations thereof. The pharmaceutical composition of the invention further comprises at least one pharmaceutically acceptable excipient.

A pharmaceutical composition according to the invention can further comprise at least one other therapeutic, prophylactic and/or diagnostic agent. Preferably, the pharmaceutical composition comprises at least one other prophylactic and/or therapeutic agent. Preferably, the further therapeutic and/or prophylactic agents are agents capable of preventing and/or treating an infection and/or a condition resulting from WNV. Therapeutic and/or prophylactic agents include, but are not limited to, anti-viral agents. Such agents can be binding molecules, small molecules, organic or inorganic compounds, enzymes, polynucleotide sequences, etc. Other agents that are currently used to treat patients infected with WNV are interferon-alpha and ribavirin. These can be used in combination with the binding molecules of the invention. Agents capable of preventing and/or treating an infection with WNV and/or a condition resulting from WNV that are in the experimental phase might also be used as other therapeutic and/or prophylactic agents useful in the invention.

The binding molecules or pharmaceutical compositions of the invention can be tested in suitable animal model systems prior to use in humans. Such animal model systems include, but are not limited to, a murine model, a hamster model, and geese model system.

Typically, pharmaceutical compositions must be sterile and stable under the conditions of manufacture and storage. The binding molecules, immunoconjugates, nucleic acid molecules or compositions of the invention can be in powder form for reconstitution in the appropriate pharmaceutically acceptable excipient before or at the time of delivery. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Alternatively, the binding molecules, immunoconjugates, nucleic acid molecules or compositions of the invention can be in solution and the appropriate pharmaceutically acceptable excipient can be added and/or mixed before or at the time of delivery to provide a unit dosage injectable form. Preferably, the pharmaceutically acceptable excipient used in the invention is suitable to high drug concentration, can maintain proper fluidity and, if necessary, can delay absorption.

The choice of the optimal route of administration of the pharmaceutical compositions will be influenced by several factors including the physico-chemical properties of the active molecules within the compositions, the urgency of the clinical situation and the relationship of the plasma concentrations of the active molecules to the desired therapeutic effect. For instance, if necessary, the binding molecules of the invention can be prepared with carriers that will protect them against rapid release, such as a controlled release formulation, including implants, transdermal patches, and microencapsulated delivery systems. Biodegradable, biocompatible polymers can inter alia be used, such as ethylene vinyl acetate, polyanhydrides, polyglycolic acid, collagen, polyorthoesters, and polylactic acid. Furthermore, it may be necessary to coat the binding molecules with, or co-administer the binding molecules with, a material or compound that prevents the inactivation of the human binding molecules. For example, the binding molecules may be administered to a subject in an appropriate carrier, for example, liposomes or a diluent.

The routes of administration can be divided into two main categories, oral and parenteral administration. The preferred administration route is intravenous.

Oral dosage forms can be formulated inter alia as tablets, troches, lozenges, aqueous or oily suspensions, dispersable powders or granules, emulsions, hard capsules, soft gelatin capsules, syrups or elixirs, pills, dragees, liquids, gels, or slurries. These formulations can contain pharmaceutically excipients including, but not limited to, inert diluents, granulating and disintegrating agents, binding agents, lubricating agents, preservatives, coloring, flavoring or sweetening agents, vegetable or mineral oils, wetting agents, and thickening agents.

Pharmaceutical compositions of the invention can also be formulated for parenteral administration. Formulations for parenteral administration can be inter alia in the form of aqueous or non-aqueous isotonic sterile non-toxic injection or infusion solutions or suspensions. The solutions or suspensions may comprise agents that are non-toxic to recipients at the dosages and concentrations employed such as 1,3-butanediol, Ringer's solution, Hank's solution, isotonic sodium chloride solution, oils, fatty acids, local anesthetic agents, preservatives, buffers, viscosity or solubility increasing agents, water-soluble antioxidants, oil-soluble antioxidants, and metal chelating agents.

In a further aspect, the binding molecules (functional fragments and variants thereof), immunoconjugates, compositions, or pharmaceutical compositions of the invention can be used as a medicament. So, a method of treatment and/or prevention of a WNV infection using the binding molecules, immunoconjugates, compositions, or pharmaceutical compositions of the invention is another part of the invention. The above-mentioned molecules can inter alia be used in the diagnosis, prophylaxis, treatment, or combination thereof, of one or more conditions resulting from WNV. They are suitable for treatment of yet untreated patients suffering from a condition resulting from WNV and patients who have been or are treated from a condition resulting from WNV. They protect against further infection by WNV for approximately one month and/or will retard the onset or progress of the symptoms associated with WNV. They may also be used in post-exposure prophylaxis, when there is a chance of infection but symptoms are absent. They may also be used as prophylaxis in the transplant of infected organs or in other patient populations at high risk of exposure and progression to disease due to inter alia age or immune status. It is known that WNV causes neuroinvasive disease in humans in <1% of infections with a case-fatality ratio of ±9%. However, ±60% of the survivors have not regained their normal neurological functions after 12 months and many of the 13% of neuroinvasive cases which develop an acute flaccid paralysis (AFP) syndrome do not recover. Persistence of WNV has been described in different vertebrate hosts including in the brain of monkeys. Currently there is no specific therapy for WNV encephalitis.

The above-mentioned molecules or compositions may be employed in conjunction with other molecules useful in diagnosis, prophylaxis and/or treatment. They can be used in vitro, ex vivo or in vivo. For instance, the binding molecules, immunoconjugates or pharmaceutical compositions of the invention can be co-administered with a vaccine against WNV. Alternatively, the vaccine may also be administered before or after administration of the molecules of the invention, instead of a vaccine, interferon-alpha and/or ribavirin can also be employed in conjunction with the binding molecules of the invention.

The molecules are typically formulated in the compositions and pharmaceutical compositions of the invention in a therapeutically or diagnostically effective amount. Alternatively, they may be formulated and administered separately. For instance the other molecules such as interferon-alpha or ribavirin may be applied systemically, while the binding molecules of the invention may be applied intrathecally or intraventricularly.

Dosage regimens can be adjusted to provide the optimum desired response (e.g., a therapeutic response). A suitable dosage range may for instance be 0.1-100 mg/kg body weight, preferably 0.5-15 mg/kg body weight. Furthermore, for example, a single bolus may be administered, several divided doses may be administered over time or the dose may be proportionally reduced or increased as indicated by the exigencies of the therapeutic situation. The molecules and compositions according to the invention are preferably sterile. Methods to render these molecules and compositions sterile are well known in the art. The other molecules useful in diagnosis, prophylaxis and/or treatment can be administered in a similar dosage regimen as proposed for the binding molecules of the invention. If the other molecules are administered separately, they may be administered to a patient prior to (e.g., 2 minutes, 5 minutes, 10 minutes, 15 minutes, 30 minutes, 45 minutes, 60 minutes, 2 hours, 4 hours, 6 hours, 8 hours, 10 hours, 1.2 hours, 14 hours, 16 hours, 18 hours, 20 hours, 22 hours, 24 hours, 2 days, 3 days, 4 days, 5 days, 7 days, 2 weeks, 4 weeks or 6 weeks before), concomitantly with, or subsequent to (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours. 20 hours, 22 hours, 24 hours, 2 days, 3 days, 4 days, 5 days, 7 days, 2 weeks, 4 weeks or 6 weeks after) the administration of one or more of the human binding molecules or pharmaceutical compositions of the invention. The exact dosing regimen is usually sorted out during clinical trials in human patients.

Human binding molecules and pharmaceutical compositions comprising the human binding molecules are particularly useful, and often preferred, when to be administered to human beings as in vivo therapeutic agents, since recipient immune response to the administered antibody will often be substantially less than that occasioned by administration of a monoclonal murine, chimeric or humanized binding molecule.

In another aspect, the invention concerns the use of the (human) binding molecules (functional fragments and variants thereof), immunoconjugates, nucleic acid molecules, compositions or pharmaceutical compositions according to the invention in the preparation of a medicament for the diagnosis, prophylaxis, treatment, or combination thereof, of a condition resulting from WNV.

Next to that, kits comprising at least one binding molecule (functional fragments and variants thereof), at least one immunoconjugate, at least one nucleic acid molecule, at least one composition, at least one pharmaceutical composition, at least one vector, at least one host according to the invention or a combination thereof are also a part of the invention. Optionally, the above-described components of the kits of the invention are packed in suitable containers and labeled for diagnosis, prophylaxis and/or treatment of the indicated conditions. The above-mentioned components may be stored in unit or multi-dose containers as an aqueous, preferably sterile, solution or as a lyophilized, preferably sterile, formulation for reconstitution. The containers may be formed from a variety of materials such as glass or plastic and may have a sterile access port (for example the container may be an intravenous solution bag or a vial having a stopper pierceable by a hypodermic injection needle). The kit may further comprise more containers comprising a pharmaceutically acceptable buffer. It may further include other materials desirable from a commercial and user standpoint, including other buffers, diluents, filters, needles, syringes, culture medium for one or more of the suitable hosts and, possibly, even at least one other therapeutic, prophylactic or diagnostic agent. Associated with the kits can be instructions customarily included in commercial packages of therapeutic, prophylactic or diagnostic products, that contain information about for example the indications, usage, dosage, manufacture, administration, contraindications and/or warnings concerning the use of such therapeutic, prophylactic or diagnostic products.

The invention further pertains to a method of detecting WNV in a sample, wherein the method comprises the steps of a) contacting a sample with a diagnostically effective amount of a binding molecule (functional fragments and variants thereof or an immunoconjugate according to the invention, and b) determining whether the binding molecule or immunoconjugate specifically binds to a molecule of the sample. The sample may be a biological sample including, but not limited to blood, serum, urine, tissue or other biological material from (potentially) infected subjects, or a non-biological sample such as water, drink, etc. The (potentially) infected subjects may be human subjects, but also animals that are suspected as carriers of WNV might be tested for the presence of WNV using the human binding molecules or immunoconjugates of the invention. The sample may first be manipulated to make it more suitable for the method of detection. Manipulation means inter alia treating the sample suspected to contain and/or containing WNV in such a way that the WNV will disintegrate into antigenic components such as proteins, (poly)peptides or other antigenic fragments. Preferably, the human binding molecules or immunoconjugates of the invention are contacted with the sample under conditions which allow the formation of an immunological complex between the human binding molecules and WNV or antigenic components thereof that may be present in the sample. The formation of an immunological complex, if any, indicating the presence of WNV in the sample, is then detected and measured by suitable means. Such methods include, inter alia, homogeneous and heterogeneous binding immunoassays, such as radio-immunoassays (RIA), ELISA, immunofluorescence, immunohistochemistry, FACS, BIACORE and Western blot analyses.

Preferred assay techniques, especially for large-scale clinical screening of patient sera and blood and blood-derived products are ELISA and Western blot techniques. ELISA tests are particularly preferred. For use as reagents in these assays, the binding molecules or immunoconjugates of the invention are conveniently bonded to the inside surface of microtiter wells. The binding molecules or immunoconjugates of the invention may be directly bonded to the microtiter well. However, maximum binding of the binding molecules or immunoconjugates of the invention to the wells might be accomplished by pre-treating the wells with polylysine prior to the addition of the binding molecules or immunoconjugates of the invention. Furthermore, the binding molecules or immunoconjugates of the invention may be covalently attached by known means to the wells. Generally, the binding molecules or immunoconjugates are used between 0.01 to 100 µg/ml for coating, although higher as well as lower amounts may also be used. Samples are then added to the wells coated with the binding molecules or immunoconjugates of the invention.

Furthermore, binding molecules of the invention can be used to identify epitopes of WNV. The epitopes can be linear, but also structural and/or conformational. In one embodiment. binding of binding molecules of the invention to a series of overlapping peptides, such as 15-mer peptides, of a protein from WNV can be analyzed by means of PEPSCAN analysis (see inter alia WO 84/03564, WO 93/09872, Slootstra et al., 1996). The binding of the molecules to each peptide can be tested in a PEPSCAN-based enzyme-linked immunoassay (ELISA). In another embodiment, a random peptide library comprising peptides from WNV can be screened for peptides capable of binding to the binding molecules of the invention. In the above assays the use of neutralizing binding molecules may identify one or more neutralizing epitopes. The peptides/epitopes found can be used as vaccines and for the diagnosis of WNV. In yet a further embodiment, the binding of (neutralizing) binding molecules of the invention to domains of a surface protein of WNV, such as the E or preM/M protein, may be analyzed. Alternatively, the human binding molecules of the invention may identify one or more epitopes of another protein of WNV.

In a further aspect, the invention provides a method of screening a binding molecule (or a functional fragment or variant thereof for specific binding to the same epitope of WNV as the epitope bound by a human binding molecule of the invention, wherein the method comprises the steps of a) contacting a binding molecule to be screened, a binding molecule of the invention and a WNV or fragment thereof, b) measure if the binding molecule to be screened is capable of competing for specifically binding to the WNV or fragment thereof with the binding molecule of the invention. In a further step it may be determined, if the screened binding molecules that are capable of competing for specifically binding to WNV or fragment thereof have neutralizing activity. A binding molecule that is capable of competing for specifically binding to WNV or a fragment thereof with the binding molecule of the invention is another part of the invention. In the above-described screening method, "specifically binding to the same epitope" also contemplates specific binding to substantially or essentially the same epitope as the epitope bound by the a binding molecule of the invention. The capacity to block, or compete with, the binding of the binding molecules of the invention to WNV typically indicates that a binding molecule to be screened binds to an epitope or binding site on WNV that structurally overlaps with the binding site on WNV that is immunospecifically recognized by the binding molecules of the invention. Alternatively, this can indicate that a binding molecule to be screened binds to an epitope or binding site which is sufficiently proximal to the binding site immunospecifically recognized by the binding molecules of the invention to sterically or otherwise inhibit binding of the binding molecules of the invention to WNV.

In general, competitive inhibition is measured by means of an assay, wherein an antigen composition, i.e., a composition comprising WNV or fragments thereof, is admixed with reference binding molecules, i.e., the binding molecules of the invention, and binding molecules to be screened. Usually, the binding molecules to be screened are present in excess. Protocols based upon ELISAs and Western blotting are suitable for use in such simple competition studies. In certain embodiments, one may pre-mix the reference binding molecules with varying amounts of the binding molecules to be screened (e.g., 1:10, 1:20, 1:30, 1:40, 1:50, 1:60, 1:70, 1:80, 1:90 or 1:100) for a period of time prior to applying to the antigen composition. In other embodiments, the reference binding molecules and varying amounts of binding molecules to be screened can simply be admixed during exposure to the antigen composition. In yet another embodiment, the reference binding molecules or binding molecules to be screened are contacted before the binding molecules to be screened or reference binding molecules, respectively, are contacted with the WNV or fragment thereof. In any event, by using species or isotype secondary antibodies one will be able to detect only the bound reference binding molecules, the binding of which will be reduced by the presence of a binding molecule to be screened that recognizes substantially the same epitope. In conducting a binding molecule competition study between a reference binding molecule and any binding molecule to be screened (irrespective of species or isotype), one may first label the reference binding molecule with a detectable label, such asfor example biotin, an enzymatic, a radioactive or other label to enable subsequent identification. In these cases, one would pre-mix or incubate the labeled reference binding molecules with the binding molecules to be screened at various ratios (e.g., 1:10, 1:20, 1:30, 1:40, 1:50, 1:60, 1:70, 1:80, 1:90 or 1:100) and (optionally after a suitable period of time) then assay the reactivity of the labeled reference binding molecules and compare this with a control value in which no potentially competing binding molecule was included in the incubation. The assay may again be any one of a range of immunological assays based upon antibody hybridization, and the reference binding molecules would be detected by means of detecting their label for example using streptavidin in the case of biotinylated reference binding molecules or by using a chromogenic substrate in connection with an enzymatic label (such as 3,3'5,5'-tetramethylbenzidine (TMB) substrate with peroxidase enzyme) or by simply detecting a radioactive label. A binding molecule to be screened that binds to the same epitope as the reference binding molecule will be able to effectively compete for binding and thus will significantly reduce reference binding molecule binding, as evidenced by a reduction in bound label. The reactivity of the (labeled) reference binding molecule in the absence of a completely irrelevant binding molecule would be the control high value. The control low value would be obtained by incubating the labeled reference binding molecule with unlabelled reference binding molecules of exactly the same type, when competition would occur and reduce binding of the labeled reference binding molecule. In a test assay, a significant reduction in labeled reference binding molecule reactivity in the presence of a binding molecule to be screened is indicative of a binding molecule that recognizes the same epitope, i.e., one that "cross-reacts" with the labeled reference binding molecule.

Binding molecules identified by these competition assays ("competitive binding molecules" or "cross-reactive binding molecules") include, but are not limited to, antibodies, antibody fragments and other binding agents that bind to an epitope or binding site bound by the reference binding molecule, i.e., a binding molecule of the invention, as well as antibodies, antibody fragments and other binding agents that bind to an epitope or binding site sufficiently proximal to an epitope bound by the reference binding molecule for competitive binding between the binding molecules to be screened and the reference binding molecule to occur. Preferably, competitive binding molecules of the invention will, when present in excess, inhibit specific binding of a reference binding molecule to a selected target species by at least 10%, preferably by at least 25%, more preferably by at least 50%, and most preferably by at least 75%-90% or even greater. The identification of one or more competitive binding molecules that bind to about, substantially, essentially or at the same epitope as the binding molecules of the invention is a straightforward technical matter. As the identification of competitive binding molecules is determined in comparison to a reference binding molecule, a binding molecule of the invention, it will he understood that actually determining the epitope to which the reference binding molecule and the competitive binding molecule bind is not in any way required in order to identify a competitive binding molecule that binds to the same or substantially the same epitope as the reference binding molecule.

In another aspect, the invention pertains to a method of identifying a binding molecule specifically binding to a virus or a nucleic acid molecule encoding a binding molecule specifically binding to a virus, wherein the method comprises the steps of a) contacting a collection of binding molecules on the surface of replicable genetic packages with a virus-like particle comprising at least one protein of the virus under conditions conducive to binding, b) selecting at least once for a replicable genetic package binding to the virus-like particle, and c) separating and recovering the replicable genetic package binding to the virus-like particle from replicable genetic packages that do not bind.

In another aspect, the invention provides a method of obtaining a binding molecule specifically binding to a virus or a nucleic acid molecule encoding a binding molecule specifically binding to a virus, wherein the method comprise the steps of a) performing the method of identifying a binding molecule specifically binding to a virus or a nucleic acid molecule encoding a binding molecule specifically binding to a virus as described above, and b) isolating from the recovered replicable genetic package the binding molecule and/or the nucleic acid molecule encoding the binding molecule.

In yet another aspect, the invention provides a method of obtaining a binding molecule potentially having neutralizing activity against the virus, wherein the method comprises the steps of performing the method of obtaining a binding molecule specifically binding to a virus or a nucleic acid molecule encoding a binding molecule specifically binding to a virus as described above, and b) verifying if the binding molecule isolated has neutralizing activity against the virus. Further details and specific embodiments of methods of identifying and obtaining binding molecules have been described above.

Preferably, the binding molecule is a human binding molecule as herein defined.

As used herein, "virus-like particle" refers to a virus particle that assembles into intact enveloped viral structures. A virus-like particle does however not contain genetic information sufficient to replicate. Virus-like particles have essentially a similar physical appearance as the wild-type virus, i.e., they are morphologically and antigenically essentially similar to authentic virions. The virus-like particles as used herein may comprise wild-type viral amino acid sequences. The virus-like particles may also include functional copies of certain genes. Furthermore, the virus-like particles may also include foreign nucleic acid. The virus-like particles can be naturally or non-naturally occurring viral particles. They may lack functional copies of certain genes of the wild-type virus, and his may result in the virus-like particle being incapable of some function which is characteristic of the wild-type virus, such as replication and/or cell-cell movement. The missing functional copies of the genes can be provided by the genome of a host cell or on a plasmid present in the host cell, thereby restoring the function of the wild-type virus to the virus-like particle when in the host cell. Preferably, virus-like particles display the same cellular tropism as the wild-type virus. The virus-like particle may be non-infectious, but is preferably infectious. The term "infectious" as used herein means the capacity of the virus-like particle to complete the initial steps of viral cycle that lead to cell entry. In one embodiment, the virus-like particle self assembles. In another embodiment, the above methods are performed using pseudoviruses instead of virus-like particles. Pseudoviruses and their production are well known to the skilled person. Preferably, the pseudoviruses as used herein comprise a heterologous viral envelope protein, such as a WNV E and/or M protein, on their surface.

Virus-like particles can be produced in suitable host cells such as inter alia mammalian cells as described above, They can be produced intracellularly and/or extracellularly and can be harvested, isolated and/or purified as intact virus-like particles by means known to the skilled person such as inter alia affinity chromatography, gel filtration chromatography, ion exchange chromatography, and/or density gradient sedimentation. The protein comprised in and/or on the virus-like particle can be a viral structural protein. Preferably, the protein is a protein present on the surface of the virus such as a viral envelope protein. The protein may be wild-type, modified, chimeric, or a part thereof. A virus-like particle as herein described is also part of the invention. Preferably, the virus-like particle is produced extracellularly when the WNV E and preM/M protein is expressed in host cells, preferably human host cells.

Preferably, the virus is a member of the Flaviviridae family, preferably the genus *Flavivirus* including, but not limited to, Dengue virus, Japanese Encephalitis virus, Kunjin virus, Murray Valley Encephalitis virus. St. Louis Encephalitis virus, Tick-borne Encephalitis virus, Yellow Fever virus and West Nile virus. Other viruses belonging to the genus *Flavivirus* can inter alia be found in Kuno et al. (1998), which is incorporated by reference herein. In a preferred embodiment, the virus is WNV.

In one embodiment, the virus-like particle comprises WNV E protein. In another embodiment, the virus-like particle further comprises WNV M protein. By an "WNV E and M protein" is meant an envelope and membrane protein, respectively, from any WNV strain. Preferably, the WNV E and M protein are derived from a same WNV strain. In one embodiment the WNV E and M protein have the amino acid sequences as herein described.

The replicable genetic package suitable for the above methods of the invention is selected from the group consisting of a phage particle, a bacterium, a yeast, a fungus, a spore of a microorganism and a ribosome.

In one embodiment, the above methods of the invention the collection of binding molecules on the surface of replicable genetic packages is a scFv phage display library.

DETAILED DESCRIPTION OF THE INVENTION

Definitions

Figure 1:
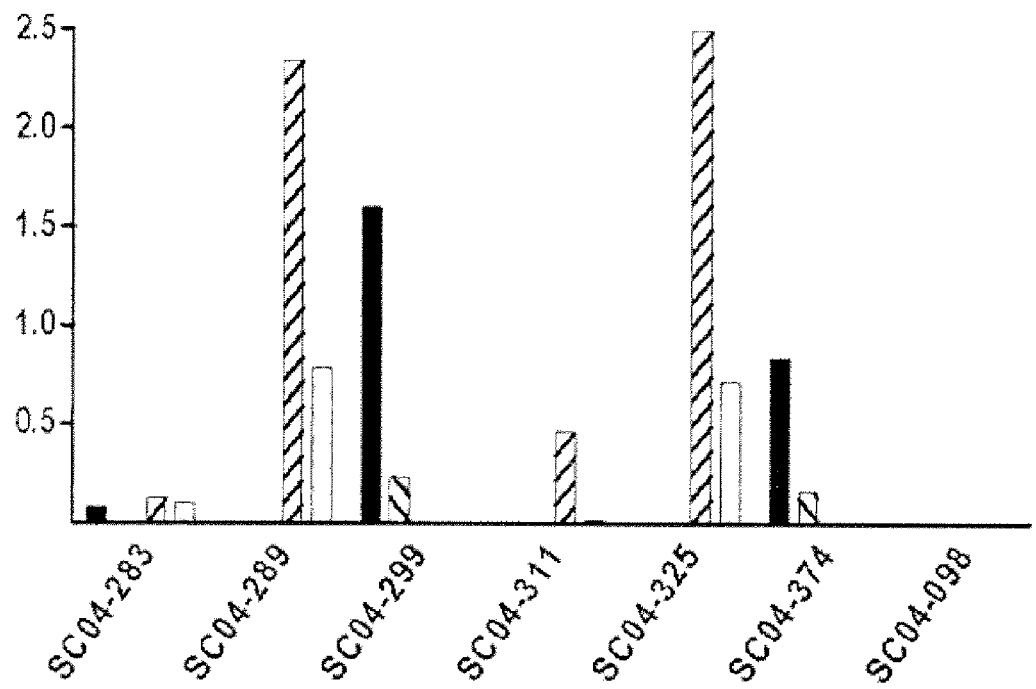
FIG. 1 shows the domain mapping of anti WNV-E protein binding scFvs. On the X-axis the tested scFvs are shown and on the Y-axis the OD 492 nm value is given. The filled bars show competition ELISA of the scFvs with the murine anti-WNV monoclonal antibody 6B6C-1 the striped (upwards from left to right) bars show competition ELISA of the scFvs with the murine anti-WNV monoclonal antibody 7H2, the striped (upwards from right to left) bars show competition ELISA of he scFvs with the anti-WNV monoclonal antibody 4G2, and the open bars show competition ELISA of the scFvs with the anti-WNV monoclonal antibody 3A3.

Amino acid sequence. The term "amino acid sequence" as used herein refers to naturally occurring or synthetic molecules and to a peptide, oligopeptide, polypeptide or protein sequence.

Binding molecule. As used herein the term "binding molecule" refers to an intact immunoglobulin including monoclonal antibodies, such as chimeric, humanized or human monoclonal antibodies, or to an antigen-binding and/or variable domain comprising fragment of an immunoglobulin that competes with the intact immunoglobulin for specific binding to the binding partner of the immunoglobulin for example WNV. Regardless of structure, the antigen-binding fragment binds with the same antigen that is recognized by the intact immunoglobulin. An antigen-binding fragment can comprise a peptide or polypeptide comprising an amino acid sequence of at least two contiguous amino acid residues, at least five contiguous amino acid residues, at least ten contiguous amino acid residues, at least 15 contiguous amino acid residues, at least 20 contiguous amino acid residues, at least 25 contiguous amino acid residues, at least 30 contiguous amino acid residues, at least 35 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least 200 contiguous amino acid residues, or at least contiguous 250 amino acid residues of the amino acid sequence of the binding molecule.

The term "binding molecule," as used herein includes all immunoglobulin classes and subclasses known in the art. Depending on the amino acid sequence of the constant domain of their heavy chains, binding molecules can be divided into the five major classes of intact antibodies: IgA, IgD, IgE, IgG, and IgM, and several of these may be further divided into subclasses (isotypes)for example IgA1, IgA2, IgG1, IgG2, IgG3 and IgG4.

Antigen-binding fragments include, inter alia, Fab, F(ab'). F(ab')2, Fv, dAb, Fd, complementarity determining region (CDR) fragments, single-chain antibodies (scFv), bivalent single-chain antibodies, single-chain phage antibodies, diabodies, triabodies, tetrabodies, (poly)peptides that contain at least a fragment of an immunoglobulin that is sufficient to confer specific antigen binding to the (poly)peptide, etc. The above fragments may be produced synthetically or by enzymatic or chemical cleavage of intact immunoglobulins or they may be genetically engineered by recombinant DNA techniques. The methods of production are well known in the art and are described, for example, in *Antibodies. A Laboratory Manual*, edited by: E. Harlow and D. Lane (1988), Cold Spring Harbor Laboratory, Cold Spring Harbor, N.Y., which is incorporated herein by reference. A binding molecule or antigen-binding fragment thereof may have one or more binding sites. If there is more than one binding site, the binding sites may be identical to one another or they may be different.

The binding molecule can be a naked or unconjugated binding molecule hut can also be part of an immunoconjugate. A naked or unconjugated binding molecule is intended to refer to a binding molecule that is not conjugated, operatively linked or otherwise physically or functionally associated with an effector moiety or tag, such as inter alia a toxic substance, a radioactive substance, a liposome, an enzyme. It will be understood that naked or unconjugated binding molecules do not exclude binding molecules that have been stabilized, multimerized, humanized or in any other way manipulated, other than by the attachment of an effector moiety or tag. Accordingly, all post-translationally modified naked and unconjugated binding molecules are included herewith, including where the modifications are made in the natural binding molecule-producing cell environment, by a recombinant binding molecule-producing cell, and are introduced by the hand of man after initial binding molecule preparation. Of course, the term naked or unconjugated binding molecule does not exclude the ability of the binding molecule to form functional associations with effector cells and/or molecules after administration to the body, as some of such interactions are necessary in order to exert a biological effect. The lack of associated effector group or tag is therefore applied in definition to the naked or unconjugated binding molecule in vitro, not in viva.

Biological sample. As used herein, the term "biological sample" encompasses a variety of sample types, including blood and other liquid samples of biological origin, solid tissue samples such as a biopsy specimen or tissue cultures, or cells derived therefrom and the progeny thereof. The term also includes samples that have been manipulated in any way after their procurement, such as by treatment with reagents, solubilization, or enrichment for certain components, such as proteins or polynucleotides. The term encompasses various kinds of clinical samples obtained from any species, and also includes cells in culture, cell supernatants and cell lysates.

Complementarity, determining regions (CDR). The term "complementarity determining regions" as used herein means sequences within the variable regions of binding molecules, such as immunoglobulins, that usually contribute to a large extent to the antigen binding site which is complementary in shape and charge distribution to the epitope recognized on the antigen. The CD)R regions can be specific for linear epitopes, discontinuous epitopes, or conformational epitopes of proteins or protein fragments, either as present on the protein in its native conformation or, in some cases, as present on the proteins as denatured for example by solubilization in SDS. Epitopes may also consist of posttranslational modifications of proteins.

Deletion. The term "deletion," as used herein, denotes a change in either amino acid or nucleotide sequence in which one or more amino acid or nucleotide residues, respectively, are absent as compared to the parent, often the naturally occurring, molecule.

Expression-regulating nucleic acid sequence. The term "expression-regulating nucleic acid sequence" as used herein refers to polynucleotide sequences necessary for and/or affecting the expression of an operably linked coding sequence in a particular host organism. The expression-regulating, nucleic acid sequences, such as inter alia appropriate transcription initiation, termination, promoter, enhancer sequences; repressor or activator sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion, can be any nucleic acid sequence showing activity in the host organism of choice and can be derived from genes encoding proteins, which are either homologous or heterologous to the host organism. The identification and employment of expression-regulating sequences is routine to the person skilled in the art.

Functional variant. The term "functional variant," as used herein, refers to a binding molecule that comprises a nucleotide and/or amino acid sequence that is altered by one or more nucleotides and/or amino acids compared to the nucleotide and/or amino acid sequences of the parent binding molecule and that is still capable of competing for binding to the binding partner for example WNV, with the parent binding molecule. In other words, the modifications in the amino acid and/or nucleotide sequence of the parent binding molecule do not significantly affect or alter the binding characteristics of the binding molecule encoded by the nucleotide sequence or containing the amino acid sequence, i.e., the binding molecule is still able to recognize and bind its target. The functional variant may have conservative sequence modifications including nucleotide and amino acid substitutions, additions and deletions. These modifications can be introduced by standard techniques known in the art, such as site-directed mutagenesis and random PCR-mediated mutagenesis, and may comprise natural as well as non-natural nucleotides and amino acids.

Conservative amino acid substitutions include the ones in which the amino acid residue is replaced with an amino acid residue having similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cystine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). It will be clear to the skilled artisan that other classifications of amino acid residue families than the one used above can also be employed. Furthermore, a variant may have non-conservative amino acid substitutions for example replacement of an amino acid with an amino acid residue having different structural or chemical properties. Similar minor variations may also include amino acid deletions or insertions, or both. Guidance in determining which amino acid residues may be substituted, inserted, or deleted without abolishing immunological activity may be found using computer programs well known in the art.

A mutation in a nucleotide sequence can be a single alteration made at a locus (a point mutation), such as transition or transversion mutations, or alternatively, multiple nucleotides may be inserted, deleted or changed at a single locus. In addition, one or more alterations may be made at any number of loci within a nucleotide sequence. The mutations may be performed by any suitable method known in the art.

Host. The term "host," as used herein, is intended to refer to an organism or a cell into which a vector such as a cloning vector or an expression vector has been introduced. The organism or cell can be prokaryotic or eukaryotic. It should be understood that this term is intended to refer not only to the particular subject organism or cell, but to the progeny of such an organism or cell as well. Because certain modifications may occur in succeeding generations due to either mutation or environmental influences, such progeny may not, in fact, be identical to the parent organism or cell, but are still included within the scope of the term "host" as used herein.

Human. The term "human," when applied to binding molecules as defined herein, refers to molecules that are either directly derived from a human or based upon a human sequence. When a binding molecule is derived from or based on a human sequence and subsequently modified, it is still to be considered human as used throughout the specification. In other words, the term human, when applied to binding molecules is intended to include binding molecules having variable and constant regions derived from human germline immunoglobulin sequences or based on variable or constant regions occurring in a human or human lymphocyte and modified in some form. Thus, the human binding molecules may include amino acid residues not encoded by human germline immunoglobulin sequences, comprise substitutions and/or deletions (e.g., mutations introduced by for instance random or site-specific mutagenesis in vitro or by somatic mutation in vivo). "Based on" as used herein refers to the situation that a nucleic acid sequence may be exactly copied from a template, or with minor mutations, such as by error-prone PCR methods, or synthetically made matching the template exactly or with minor modifications. Semi-synthetic molecules based on human sequences are also considered to be human as used herein.

Insertion. The term "insertion," also known as the term "addition," denotes a change in an amino acid or nucleotide sequence resulting in the addition of one or more amino acid or nucleotide residues, respectively, as compared to the parent sequence.

Isolated. The term "isolated," when applied to binding molecules as defined herein, refers to binding molecules that are substantially free of other proteins or polypeptides, particularly free of other binding molecules having different antigenic specificities, and are also substantially free of other cellular material and/or chemicals. For example, when the binding molecules are recombinantly produced, they are preferably substantially free of culture medium, and when the binding molecules are produced by chemical synthesis, they are preferably substantially free of chemical precursors or other chemicals, i.e., they are separated from chemical precursors or other chemicals which are involved in the synthesis of the protein. The term "isolated" when applied to nucleic acid molecules encoding binding molecules as defined herein, is intended to refer to nucleic acid molecules in which the nucleotide sequences encoding the binding molecules are free of other nucleotide sequences, particularly nucleotide sequences encoding binding molecules that bind binding partners other than WNV. Furthermore, the term "isolated" refers to nucleic acid molecules that are substantially separated from other cellular components that naturally accompany the native nucleic acid molecule in its natural host for example ribosomes, polymerases, or genomic sequences with which it is naturally associated. Moreover, "isolated" nucleic acid molecules, such as cDNA molecules, can be substantially free of other cellular material, or culture medium when produced by recombinant techniques, or substantially free of chemical precursors or other chemicals when chemically synthesized.

Monoclonal antibody. The term "monoclonal antibody" as used herein refers to a preparation of antibody molecules of single molecular composition. A monoclonal antibody displays a single binding specificity and affinity for a particular epitope. Accordingly, the term "human monoclonal antibody" refers to an antibody displaying a single binding specificity which has variable and constant regions derived from or based on human germline immunoglobulin sequences or derived from completely synthetic sequences. The method of preparing the monoclonal antibody is not relevant.

Naturally occurring. The term "naturally occurring" as used herein as applied to an object refers to the fact that an object can be found in nature. For example, a polypeptide or polynucleotide sequence that is present in an organism that can be isolated from a source in nature and which has not been intentionally modified by man in the laboratory is naturally occurring.

Nucleic acid molecule. The term "nucleic acid molecule" as used in the invention refers to a polymeric form of nucleotides and includes both sense and anti-sense strands of RNA, cDNA, genomic DNA, and synthetic forms and mixed polymers of the above. A nucleotide refers to a ribonucleotide, deoxynucleotide or a modified form of either type of nucleotide. The term also includes single- and double-stranded forms of DNA. In addition, a polynucleotide may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The above term is also intended to include any topological conformation, including single-stranded, double-stranded, partially duplexed, triplex, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. A reference to a nucleic acid sequence encompasses its complement unless otherwise specified. Thus, a reference to a nucleic acid molecule having a particular sequence should be understood to encompass its complementary strand, with its complementary sequence. The complementary strand is also useful for example for anti-sense therapy, hybridization probes and PCR primers.

Operably linked. The term "operably linked" refers to two or more nucleic acid sequence elements that are usually physically linked and are in a functional relationship with each other. For instance, a promoter is operably linked to a coding sequence, if the promoter is able to initiate or regulate the transcription or expression of a coding sequence, in which case the coding sequence should be understood as being "under the control of" the promoter.

Pharmaceutically acceptable excipient. By "pharmaceutically acceptable excipient" is meant any inert substance that is combined with an active molecule such as a drug, agent, or binding molecule for preparing an agreeable or convenient dosage form. The "pharmaceutically acceptable excipient" is an excipient that is non-toxic to recipients at the dosages and concentrations employed, and is compatible with other ingredients of the formulation comprising the drug, agent or binding molecule.

Specifically Binding. The term "specifically binding," as used herein, in reference to the interaction of a binding molecule for example an antibody, and its binding partner for example an antigen, means that the interaction is dependent upon the presence of a particular structure for example an antigenic determinant or epitope, on the binding partner. In other words, the antibody preferentially binds or recognizes the binding partner even when the binding partner is present in a mixture of other molecules or organisms. The binding may be mediated by covalent or non-covalent interactions or a combination of both. In yet other words, the term "specifically binding" means immunospecifically binding to an antigen or a fragment thereof and not immunospecifically binding to other antigens. A binding molecule that immunospecifically binds to an antigen may bind to other peptides or polypeptides with lower affinity as determined by for example radioimmunoassays (RIA), enzyme-linked immunosorbent assays (ELISA), BIACORE, or other assays known in the art. Binding molecules or fragments thereof that immunospecifically bind to an antigen may be cross-reactive with related antigens. Preferably, binding molecules or fragments thereof that immunospecifically bind to an antigen do not cross-react with other antigens.

Substitutions. A "substitution," as used herein, denotes the replacement of one or more amino acids or nucleotides by different amino acids or nucleotides, respectively.

Therapeutically effective amount. The term "therapeutically effective amount" refers to an amount of the binding molecule as defined herein that is effective for preventing, ameliorating and/or treating a condition resulting from infection with WNV.

Treatment. The term "treatment" refers to therapeutic treatment as well as prophylactic or preventative measures to cure or halt or at least retard disease progress. Those in need of treatment include those already inflicted with a condition resulting from infection with WNV as well as those in which infection with WNV is to be prevented. Subjects partially or totally recovered form infection with WNV might also be in need of treatment. Prevention encompasses inhibiting or reducing the spread of WNV or inhibiting or reducing the onset, development or progression of one or more of the symptoms associated with infection with WNV.

Vector. The term "vector" denotes a nucleic acid molecule into which a second nucleic acid molecule can be inserted for introduction into a host where it will be replicated, and in some cases expressed. In other words, a vector is capable of transporting a nucleic acid molecule to which it has been linked. Cloning as well as expression vectors are contemplated by the term "vector," as used herein. Vectors include, but are not limited to, plasmids, cosmids, bacterial artificial chromosomes (BAC) and yeast artificial chromosomes (YAC) and vectors derived from bacteriophages or plant or animal (including human) viruses. Vectors comprise an origin of replication recognized by the proposed host and in case of expression vectors, promoter and other regulatory regions recognized by the host. A vector containing a second nucleic acid molecule is introduced into a cell by transformation, transfection, or by making use of viral entry mechanisms. Certain vectors are capable of autonomous replication in a host into which they are introduced (e.g., vectors having a bacterial origin of replication can replicate in bacteria). Other vectors can be integrated into the genome of a host upon introduction into the host, and thereby are replicated along with the host genome.

EXAMPLES

To illustrate the invention, the following examples are provided. The examples are not intended to limit the scope of the invention in any way.

Example 1

Construction of scFv Phage Display Library Using RNA Extracted from Peripheral Blood of WNV Convalescent Donors.

From three convalescent WNV patients samples of blood were taken one, two and three months after infection. Peripheral blood leukocytes were isolated by centrifugation and the blood serum was saved and frozen at −80° C. All donors at all time points had high titers of neutralizing antibodies to WNV as determined using a virus neutralization assay. Total RNA was prepared from the cells using organic phase separation and subsequent ethanol precipitation. The obtained RNA was dissolved in RNAse free water and the concentration was determined by OD 260 nm measurement. Thereafter, the RNA was diluted to a concentration of 100 ng/μl. Next, 1 μg of RNA was converted into cDNA as follows: To 10 μl total RNA, 13 μl DEPC-treated ultrapure water and 1 μl random hexamers (500 ng/μl) were added and the obtained mixture was heated at 65° C. for five minutes and quickly cooled on wet-ice. Then, 8 μl 5× First-Strand buffer, 2 μl dNTP (10 mM each), 2 μl DTT (0.1 M), 2 μl Rnase-inhibitor (40 U/μl) and 2 μl Superscript™III MMLV reverse transcriptase (200 U/μl) were added to the mixture, incubated at room temperature for five minutes and incubated for one hour at 50° C. The reaction was terminated by heat inactivation, i.e., by incubating the mixture for 15 minutes at 75° C.

The obtained cDNA products were diluted to a final volume of 200 μl with DEPC-treated ultrapure water. The OD 260 nm of a 50 times diluted solution (in 10 mM Tris buffer) of the dilution of the obtained cDNA products gave a value of 0.1.

For each donor, 5 to 10 μl of the diluted cDNA products were used as template for PCR amplification of the immunoglobulin gamma heavy chain family and kappa or lambda light chain sequences using specific oligonucleotide primers (see Tables 1-6). PCR reaction mixtures contained, besides the diluted cDNA products, 25 pmol sense primer and 25 pmol anti-sense primer in a final volume of 50 µl of 20 mM Tris-HCl (pH 8.4), 50 mM KCl, 2.5 mM MgCl$_2$, 250 µM dNTPs and 1.25 units Taq polymerase. In a heated-lid thermal cycler having a temperature of 96° C., the mixtures obtained were quickly melted for two minutes, followed by 30 cycles of: 30 seconds at 96° C., 30 seconds at 60° C. and 60 seconds at 72° C.

In a first round amplification, each of seventeen light chain variable region sense primers (eleven for the lambda light chain (see Table 1) and six for the kappa light chain (see Table 2) were combined with an anti-sense primer recognizing the C-kappa called HuCk 5'-ACACTCTC-CCCTGTTGAAGCT CTT-3' (see SEQ ID NO:81) or C-lambda constant region HuCλ2 5'-TGAACATTCTG-TAGGGGCCACTG-3' (see SEQ ID NO:82) and HuCλ7 5' -AGACCATTCTGCAGGGGCCACTG-3' (see SEQ ID NO:83) (the HuCλ2 and HuCλ7 anti-sense primers were mixed to equimolarity before use), yielding four times 17 products of about 600 base pairs. These products were purified on a 2% agarose gel and isolated from the gel using Qiagen gel-extraction columns. ¹/₁₀ of each of the isolated products was used in an identical PCR reaction as described above using the same seventeen sense primers, whereby each lambda light chain sense primer was combined with one of the three Jlambda-region specific anti-sense primers and each kappa light chain sense primer was combined with one of the five Jkappa-region specific anti-sense primers. The primers used in the second amplification were extended with restriction sites (see Table 3) to enable directed cloning in the phage display vector PDV-C06 (see SEQ ID NO:84). This resulted in four times 63 products of approximately 350 base pairs that were pooled to a total of ten fractions. This number of fractions was chosen to maintain the natural distribution of the different light chain families within the library and not to over or under represent certain families. The number of alleles within a family was used to determine the percentage of representation within a library (see Table 4). In the next step, 2.5 µg of pooled fraction and 100 µg PDV-C06 vector were digested with SalI and NotI and purified from gel. Thereafter, a ligation was performed overnight at 16° C. as follows. To 500 ng PDV-C06 vector 70 ng pooled fraction was added in a total volume of 50 µl ligation mix containing 50 mM Tris-HCl (pH 7.5), 10 mM MgCl$_2$, 10 mM DTT, 1 mM ATP, 25 µg/ml BSA and 2.5 µl T4 DNA Ligase (400 U/µl). This procedure was followed for each pooled fraction. The ligation mixes were purified by phenol/chloroform, followed by a chloroform extraction and ethanol precipitation, methods well known to the skilled artisan. The DNA obtained was dissolved in 50 µl ultrapure water and per ligation mix two times 2.5 µl aliquots were electroporated into 40 µl of TG1 competent E. coli bacteria according to the manufacturer's protocol (Stratagene). Transformants were grown overnight at 37° C. in a total of 30 dishes (three dishes per pooled fraction- dimension of dish. 240 mm×40 mm) containing 2TY agar supplemented with 50 µg/ml ampicillin and 4.5% glucose. A (sub)library of variable light chain regions was obtained by scraping the transformants from the agar plates. This (sub)library was directly used for plasmid DNA preparation using a Qiagen™ QIAFilter MAXI prep kit.

For each donor the heavy chain immunoglobulin sequences were amplified from the same cDNA preparations in a similar two round PCR procedure and identical reaction parameters as described above for the light chain regions with the proviso that the primers depicted in Tables 5 and 6 were used. The first amplification was performed using a set of nine sense directed primers (see Table 5: covering all families of heavy chain variable regions) each combined with an IgG specific constant region anti-sense primer called HuCIgG 5'-GTC CAC CTT GGT GTT OCT GGG CTT-3' (SEQ ID NO:85) yielding four times nine products of about 650 base pairs. These products were purified on a 2% agarose gel and isolated from the gel using Qiagen gel-extraction columns. ¹/₁₀ of each of the isolated products was used in an identical PCR reaction as described above using the same nine sense primers, whereby each heavy chain sense primer was combined with one of the four JH-region specific anti-sense primers. The primers used in the second round were extended with restriction sites (see Table 6) to enable directed cloning in the light chain (sub)library vector. This resulted per donor in 36 products of approximately 350 base pairs. These products were pooled for each donor per used (VH) sense primer into nine fractions. The products obtained were purified using Qiagen PCR purification columns. Next, the fractions were digested with SfiI and XhoI and ligated in the light chain (sub)library vector, which was cut with the same restriction enzymes, using the same ligation procedure and volumes as described above for the light chain (sub)library. Alternatively, the fractions were digested with VcoI and XhoI and ligated in the light chain vector, which was cut with the same restriction enzymes, using the same ligation procedure and volumes as described above for the light chain (sub)library. Ligation purification and subsequent transformation of the resulting definitive library was also performed as described above for the light chain (sub)library and at this point the ligation mixes of each donor were combined per VH pool. The transformants were grown in 27 dishes (three dishes per pooled fraction; dimension of dish: 240 mm×240 mm) containing 2TY agar supplemented with 50 µg/ml ampicillin and 4.5% glutose. All bacteria were harvested in 2TY culture medium containing 50 µg/ml ampicillin and 4.5% glucose, mixed with glycerol to 15% (v/v) and frozen in 1.5 ml aliquots at 80° C. Rescue and selection of each library were performed as described below.

Example 2

Selection of Phages Carrying Single Chain Fv Fragments Specifically Recognizing WNV Envelope (E) Protein Antibody fragments were selected using antibody phage display libraries, general phage display technology and MAbstract® technology, essentially as described in U.S. Pat. No. 6,265,150 and in WO 98/15833 (both of which are incorporated by reference herein). The antibody phage libraries used were two different semi-synthetic scFv phage libraries (JK1994 and WT2000) and the immune library prepared as described in Example 1. The first semi-synthetic scFv phage library (JK1994) has been described in de Kruif et al., 1995b, the second one (WT2000) was build essentially as described in de Kruif et al., 1995b. Briefly, the library has a semi-synthetic format whereby variation was incorporated in the heavy and light chain V genes using degenerated oligonucleotides that incorporate variation within CDR regions. Only VH3 heavy chain genes were used, in combination with kappa and lambda light chain genes. CDR1 and CDR3 of the heavy chain and CDR3 of the light chain were recreated synthetically in a PCR-based approach similar as described in de Kruif et al., 1995b. The thus created V region genes were cloned sequentially in scFv format in a phagemid vector and amplified to generate a phage library as described before. Furthermore, the methods and helper phages as described in PCT International publication WO 02/103012 (incorporated by reference herein) were used in the invention. For identifying phage antibodies recognizing WNV E protein, phage selection experiments were performed using whole WNV (called strain USA99b or strain 385-99) inactivated by gamma irradiation (50 Gy for one hour), recombinantly expressed WNV E protein (strain 382-99), and/or WNV-like particles expressing WNV E protein (strain 382-99) on their surface.

The recombinantly expressed E protein was produced as follows. The nucleotide sequence coding for the preM/M protein and the full length E protein of WNV strain 382-99 (see SEQ ID NO:86 for the amino acid sequence of a fusion protein comprising both WNV polypeptides) was synthesized. Amino acids 1-93 of SEQ ID NO:86 constitute the WNV preM protein, amino acids 94-168 of SEQ ID NO:86 constitute the WNV M protein, amino acids 169-669 of SEQ ID NO:86 constitute the WNV E protein (the soluble WNV E protein (ectodomain) constitutes amino acids 169-574 of SEQ ID NO:86, while the WNV E protein stein and transmembrane region constitutes amino acids 575-669 of SEQ ID NO:86) The synthesized nucleotide sequence was cloned into the plasmid pAdapt and the plasmid obtained was called pAdapt.WNV.prM-E (FL).

To produce a soluble secreted form of the E protein a construct was made lacking the transmembrane spanning regions present in the final 95 amino acids at the carboxyl terminal of the full length E protein (truncated form). For that purpose the full length construct pAdapt.WNV.prM-E (FL) was PCR amplified with the primers CMV-Spe (SEQ ID NO:87) and WNV-E-95 REV (SEQ ID NO:88) and the fragment obtained was cloned into the plasmid pAdapt.myc.his to create the plasmid called pAdapt.WNV –95. Next, the region coding for the preM protein, the truncated E protein, the Myc tag and His tag were PCR amplified with the primers clefsmaquwnv (SEQ ID NO:89) and reverse WNVmychis (SEQ ID NO:90) and cloned into the vector pSyn-C03 containing the HAVT20 leader peptide using the restriction sites EcoRI and SpeI. The expression construct obtained, pSyn-C03-WNV-E –95, was transfected into 90% confluent HEK293T cells using lipofectamine according to the manufacturers instructions. The cells were cultured for five days in serum-free ultra CHO medium, hen the medium was harvested and purified by passage over HisTrap chelating columns (Amersham Bioscience) pre-charged with nickel ions. The truncated E protein was eluted with 5 ml of 250 mM imidazole and further purified by passage over a G-75 gel filtration column equilibrated with phosphate buffered saline (PBS). Fractions obtained were analyzed by SDS-PAGE analysis and Western blotting using the WNV-E protein specific murine antibody 7H2 (Biorelience, see Beasley and Barrett 2002). Three 5 ml fractions containing a single band of ~45 kDa that was immunoreactive with antibody 7H2 were aliquoted and stored at –20° C. until further use. The protein concentration was determined by OD 280 nm.

WNV-like particles were produced as follows. The construct pSyn-C03-WNV-E-95 described above and pcDNA3.1 (Invitrogen) were digested with the restriction endonucleases MunI and XbaI and the construct pAdapt.WNV.prM-E (FL) described above was digested with the restriction endonucleases ClaI and XbaI. The resulting fragments were combined in a tree-point ligation to produce the construct pSyn-H-preM/E FL. This construct contained the full length E protein and expressed the two structural WNV proteins, protein M and E, required for assembly of an enveloped virion. The construct was transfected into 70% confluent HEK293T cells using lipofectamine according to the manufacturer's instructions. The cells were cultured for three days in serum-free ultra CHO medium, then the medium was harvested, layered on to a 30% glycerol solution at a 2:1 ratio and pelleted by centrifugation for two hours at 120,000*g at 4° C. The WNV-like particles were resuspended in PBS, aliquoted ad stored at –80° C. Aliquots were analyzed by SDS-PAGE analysis and Western blotting using the WNV-E protein specific murine antibody 7H2 (Biorelience).

Before inactivation, whole WNV was purified by pelleting through a 30% glycerol solution as described above for WNV-like particles. The purified WNV was resuspended in 10 mM Tris/HCl pH 7.4 containing 10 mM EDTA and 200 mM NaCl, the obtained preparation was kept on dry ice during inactivation, tested for infectivity and stored at –80° C. in small aliquots. Aliquots were analyzed by SDS-PAGE analysis and Western blotting using the WNV-E protein specific murine antibody 7H2 (Biorelience).

Whole inactivated WNV, WNV-like particles or recombinantly expressed soluble E protein were diluted in PBS. 2-3 ml of the preparation was added to MaxiSorp™ Nunc-Immuno Tubes (Nunc) and incubated overnight at 4° C. on a rotating wheel. An aliquot of a phage library (500 µl, approximately $10^{13}$ cfu, amplified using CT helper phage (see WO 02/103012)) was blocked in blocking buffer (2% Protifar in PBS) for one to two hours at room temperature. The blocked phage library was added to the immunotubes, incubated for two hours at room temperature, and washed with wash buffer (0.1% v/v Tween-20 in PBS) to remove unbound phages. Bound phages were eluted from the anti-en by incubation with 1 ml of 50 mM Glycine-HCl pH 2.2 for 10 minutes at room temperature. Subsequently, the eluted phages were mixed with 0.5 ml of 1 M Tris-HCl pH 7.5 to neutralize the pH. This mixture was used to infect 5 ml of an XL1-Blue E. Coli culture that had been grown at 37° C. to an OD 600 nm of approximately 0.3. The phages were allowed to infect the XL1-Blue bacteria for 30 minutes at 37° C. Then, the mixture was centrifuged for ten minutes at 3200*g at room temperature and the bacterial pellet was resuspended in 0.5 ml 2-trypton yeast extract (2TY) medium. The obtained bacterial suspension was divided over two 2TY agar plates supplemented with tetracycline ampicillin and glucose. After overnight incubation of the plates at 37° C., the colonies were scraped from the plates and used to prepare an enriched phage library, essentially as described by De Kruif et al. (1995a) and WO 02/103012. Briefly, scraped bacteria were used to inoculate 2TY medium containing ampicillin, tetracycline and glucose and grown at a temperature of 37° C. to an OD 600 nm of ~0.3. CT helper phages were added and allowed to infect the bacteria after which the medium was changed to 2TY containing ampicillin, tetracycline and kanamycin. Incubation was continued overnight at 30° C. The next day, the bacteria were removed from the 2TY medium by centrifugation after which the phages in the medium were precipitated using polyethylene glycol (PEG) 6000/NaCl. Finally, the phages were dissolved in 2 ml of PBS with 1% bovine serum albumin (BSA), filter-sterilized and used for the next round of selection.

Typically, two rounds of selections were performed before isolation of individual phage antibodies. After the second round of selection, individual E. coli colonies were used to prepare monoclonal phage antibodies. Essentially, individual colonies were grown to log-phase in 96 well plate format and infected with CT helper phages after which phage antibody production was allowed to proceed overnight. The produced phage antibodies were PEG/NaCl-precipitated and filter-sterilized and tested in ELISA for binding to WNV-like particles purified as described supra.

Example 3

Validation of the WNV Specific Single-chain Phage Antibodies

Selected single-chain phage antibodies that were obtained in the screens described above were validated in ELISA for specificity, i.e., binding to WNV E protein, whole inactivated WNV and WNV-like particles, all purified as described supra. Additionally, the single-chain phage antibodies were also tested for binding to 5% FBS. For this purpose, whole inactivated WNV, the WNV E protein, WNV-like particles or 5% FBS preparation was coated to Maxisorp™ ELISA plates. In addition, whole inactivated rabies virus was coated onto the plates as a control. After coating, the plates were blocked in PBS containing 1% Protifar for one hour at room temperature. The selected single-chain phage antibodies were incubated for 15 minutes in an equal volume of PBS containing 1% Protifar to obtain blocked phage antibodies. The plates were emptied, and the blocked single-chain phage antibodies were added to the wells. Incubation was allowed to proceed for one hour, the plates were washed in PBS containing 0.1% v/v Tween-20 and bound phage antibodies were detected (using OD 492 nm measurement) using an anti-M13 antibody conjugated to peroxidase. As a control, the procedure was performed simultaneously without single-chain phage antibody, with a negative control single-chain phage antibody directed against rabies virus glycoprotein (antibody called SC02-447), with a negative control single-chain phage antibody directed against SARS-CoV (antibody called SC03-014) and a positive control single-chain phage antibody directed against rabies virus. As shown in Table 7, the selected phage antibodies called SC04-271, SC04-274, SC04-283, SC04-289, SC04-299, SC04-311, SC04-325, SC04-353, SC04-361 and SC04-374 displayed significant binding to immobilized whole inactivated WNV (see Table 7) and WNV-like particles (data not shown). In addition, for SC04-325, SC04-353, SC04-361 and SC04-374 no binding to rabies virus was observed. When the ELISA was performed with recombinantly expressed purified soluble WNV E protein prepared as described supra all single-chain phage antibodies bound with the exception of SC04-283, SC04-299, SC04-353 and SC04-361, suggesting they either bind to a region not present in the truncated soluble E protein, bind to an unrelated protein on the virion surface, do not bind to the monomeric form of the E protein or do not bind because of the phage antibody format.

Example 4

Characterization of the WNV Specific scFvs

From the selected specific single-chain phage antibody (scFv) clones plasmid DNA was obtained and nucleotide sequences were determined according to standard techniques. The nucleotide sequences of the scFvs (including restriction sites for cloning) called SC04-271, SC04-274, SC04-283, SC04-289, SC04-299, SC04-311, SC04-325, SC04-353, SC04-361 and SC04-374 are shown in SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, and SEQ D NO:79, respectively. The amino acid sequences of the scFvs called SC04-271, SC04-274, SC04-283, SC04-289, SC04-299, SC04-311, SC04-325, SC04-353, SC04-361 and SC04-374 are shown in SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, and SEQ ID NO:80, respectively.

The VH and VL gene identity (see I. M. Tomlinson, S. C. Williams, O. Ignatovitch, S. J. Corbett, G. Winter, *V-BASE Sequence Directory*, Cambridge United Kingdom: MRC Centre for Protein Engineering (1997)) and heavy chain CDR3 sequences of the scFvs specifically binding WNV are depicted in Table 8. Table 9 shows the other CDR regions of the WNV specific scFvs.

Example 5

Construction of Fully Human Immunoglobulin Molecules (Human Monoclonal Anti-WNV Antibodies) from the Selected Anti-WNV Single Chain Fvs Heavy and light chain variable regions of the scFvs called SC04-271, SC04-274, SC04-283, SC04-299, SC04-311, SC04-325, and SC04-374 were PCR-amplified using oligonucleotides to append restriction sites and/or sequences for expression in the IgG expression vectors pSyn-C18-HCγ1 (see SEQ ID NO:91) pSyn-C05-Cκ(see SEQ ID NO:92) and pSyn-C04-Cλ (see SEQ ID NO:93). The heavy chain variable regions of the scFvs called SC04-271, SC04-274, SC04-283, SC04-299, SC04-311, SC04-325, and SC04-374 were cloned into the vector pSyn-C18-HCγ1; the light chain variable regions of the scFv called SC04-274, SC04-283 and SC04-325 were cloned into the vector pSyn-C05-Cκ; the light chain variable regions of the scFvs called SC04-271, SC04-299, SC04-311, and SC04-374 were cloned into the vector pSyn-C04-Cλ. The VL kappa genes were first amplified using the following oligonucleotide sets; SC04-274, 5K-G (SEQ ID NO:94) and sy3K-F (SEQ ID NO:95); SC04-283, 5K-B (SEQ ID NO:96) and sy3K-F (SEQ ID NO:95); SC04-325, 5K-J (SEQ ID NO:97) and sy3K-F (SEQ ID NO:95) and the PCR products cloned into vector pSyn-C05-Cκ. The VL lambda genes were first amplified using the following oligonucleotides sets; SC04-271, 5L-B (SEQ ID NO:98) and sy3L-E (SEQ ID NO:99); SC04-299, 5L-G (SEQ ID NO:100) and sy3L-Cmod (SEQ ID NO:101); SC04-311, 5L-C (SEQ ID NO:102) and sy3L-Cmod (SEQ ID NO:101); SC04-374, 5L-C (SEQ ID NO 102) and sy3L-Cmod (SEQ ID NO:101) and the PCR products cloned into vector pSyn-CO4-Cλ. Nucleotide sequences for all constructs were verified according to standard techniques known to the skilled artisan. VH genes were first amplified using the following oligonucleotide sets: SC04-271, 5H-H (SEQ ID NO:103) and sy3H-A (SEQ ID NO:104); SC04-274, 5H-H (SEQ ID NO:103) and sy3H-C (SEQ ID NO:105); SC04-283, 5H-H (SEQ ID NO:103) and sy3H-A (SEQ ID NO:104); SC04-299, 5H-C (SEQ ID NO: 106) and sy3H-C (SEQ ID NO:105); SC04-311, 5H-C (SEQ ID NO:106) and sy3H-A (SEQ ID NO:104): SC04-325, 5H-A (SEQ ID NO107) and sy3H-A (SEQ ID NO:104); SC04-374; First 5H-N (SEQ ID NO:108) and sy3H-D (SEQ ID NO:109). Thereafter, the PCR products were cloned into vector pSyn-C18-HCγ1 and nucleotide sequences were verified according to standard techniques known to the skilled person in the art.

Heavy and light chain variable regions of the scFvs called SC04-289, SC04-353, and SC04-361 were cloned directly by restriction digest for expression in the IgG expression vectors pIg-C911-HCgamma1 (see SEQ ID NO:110) and pIg-C909-Ckappa (see SEQ ID NO:111. The heavy chain variable regions of the scFvs called SC04-289, SC04-353, and SC04-361 were cloned into the vector pIg-C911-HC-gamma1 by restriction digest using the enzymes SfiI and XhoI and the light chain variable region of the scFv called SC04-289, SC04-353, and SC04-361 were cloned into the vector pIg-C909-Ckappa by restriction digest using the enzymes SalI and NotI. Thereafter, the nucleotide sequences were verified according to standard techniques known to the person skilled in the at .

The resulting expression constructs pgG104-271C18, pgG104-274C18, pgG104-283C18, pgG104-289C911, pgG104-299C18, pgG104-311C18, pgG104-325C18, pgG104-353C911, pgG104-361C911, and pgG104-374C18 encoding the anti-WNV human IgG1 heavy chains and pgG104-271C04, pgG104-274C05, pgG104-283C05, pgG104-289C909, pgG104-299C04, pgG 104-311C04, pgG104-325C05, pgG104-353C909, pgG104-361C909, and pgG104-374C04 encoding the anti-WNV human IgG1 light chains were transiently expressed in combination in 293T cells and supernatants containing human IgG1 antibodies were obtained. The nucleotide sequences of the heavy chains of the antibodies called CR4271, CR4274, CR4283, CR4289, CR4299, CR4311, CR4325, CR4353, CR4361, and CR4374 are shown in SEQ ID NOS:112, 114, 116, 118, 120, 122, 124, 126, 128, and 130, respectively. The amino acid sequences of the heavy chains of the antibodies called CR4271, CR4274, CR4283, CR4289, CR4299, CR4311, CR4325, CR4353, CR4361, and CR4374 are shown in SEQ ID NOS:113, 115, 117, 119, 121, 123, 125, 127, 129, and 131, respectively.

The nucleotide sequences of the light chain of antibodies CR4271, CR4274, CR4283, CR4289, CR4299, CR4311, CR4325, CR4353, CR4361, and CR4374 are shown in SEQ ID NOS:132, 134, 136, 138, 140, 142, 144, 146, 148, and 150, respectively. The amino acid sequences of the light chain of antibodies CR4271, CR4274, CR4283, CR4289, CR4299, CR4311, CR4325, CR4353, CR4361, and CR4374 are shown in SEQ ID NOS:133. 135, 137, 139, 141, 143, 145, 147, 149, and 151, respectively. A person skilled in the art can determine the variable regions of the heavy and light chains of the above antibodies by following Kabat et al. (1991), as described in Sequences of Proteins of Immunological Interest. The human anti-WNV IgG1 antibodies were validated for their ability to bind to irradiated WNV in ELISA essentially as described for scFvs (see Table 10), Three dilutions of the respective antibodies in blocking buffer were tested. The positive control was the murine anti-WNV antibody 7H2 and the negative control was an anti-rabies virus antibody.

Alternatively, batches of greater than 1 mg of each antibody were produced and purified using standard procedures. The antibodies were then titrated on a fixed concentration of irradiated West Nile virus and tested in ELISA as described above. The results are shown in Table 11. As a negative control an anti-rabies virus antibody was used. All antibodies showed binding to the virus in a dose dependent manner.

Figure 5:
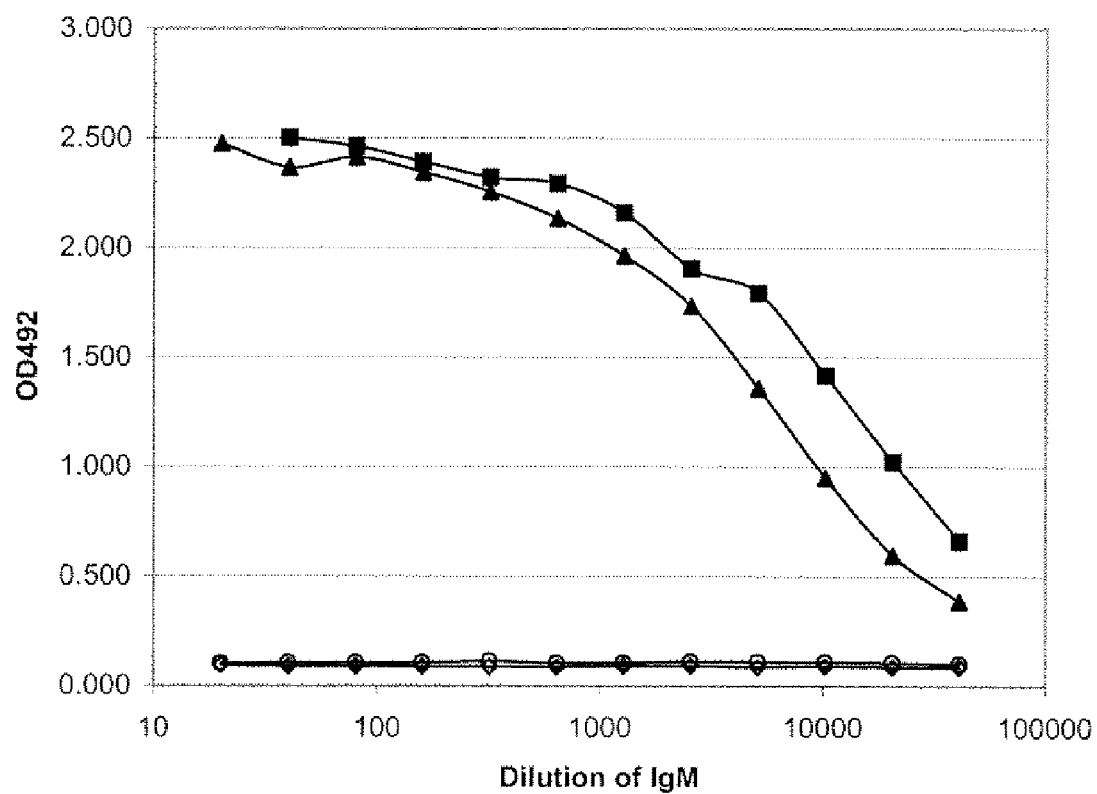
FIG. 5. Binding curve of IgM form of CR4374 (CRM4374) to virus-like particles (VLPs). Two different purification runs are shown ▲ and ■, IgM; and ○ and ◇, control).

Furthermore, CR4374 was converted into a fully human IgM format by removing the gamma Fc region from construct pgG104-374C18 by restriction digestion with the endonucleases NheI and XbaI. The vector pCR-IgM (SEQ ID NO:216) containing a mu Fc region was digested with the same restriction enzymes and the obtained mu Fc region was ligated into vector pgG104-374C18 and fused in frame with the variable heavy chain gene derived from SC04-374 to make vector pgM104-374C899. This construct was transiently expressed in combination together with the light chain construct pgG104-374C04 (see above) in 293T cells and supernatants containing human IgM antibodies were obtained. The nucleotide sequence of vector pgM104-374C899 is shown in SEQ ID NO:217. The amino acid sequence of the heavy chain the antibody called CRM4374 is shown in SEQ ID NO:218. The IgM antibody was purified from the supernatant by adding ammonium sulphate to a final concentration of 2.4 M and incubating the mixture overnight on ice, while stirring. The precipitated IgM was recovered by centrifugation at 10,395×g for 30 minutes. The pellet was resuspended in PBS and further purified by gel filtration. A HiLoad 26/60 Superdex 200 prep grade column (GE Healthcare) equilibrated with PBS was loaded with the resuspended IgM and fractions were collected from the column, while being flushed under a constant flow rate with PBS. The first major elution peak, which contained the purified IgM, was collected. Binding activity of the antibody was confirmed by titration on West Nile virus-like particles (VLPs) (see FIG. 5).

Example 6

In Vitro Neutralization of WNV by WNV Specific scFvs and IgGs (Virus Neutralization Assay)

In order to determine whether the selected scFvs are capable of blocking WNV infection, in vitro virus neutralization assays (VNA) are performed. The VNA are performed on Vero cells (ATCC CCL 81). The WNV strain 385-99 which is used in the assay is diluted to a titer of $4 \times 10^3$ TCID$_{50}$/ml (50% tissue culture infective dose per ml), with the titer calculated according to the method of Spearman and Kaerber. The scFv preparations are serially two-fold-diluted in PBS starting from 1:2 (1:2-1:1024). 25 µl of the respective scFv dilution is mixed with 25 µl of virus suspension (100 TCID$_{50}$25 µl) and incubated for one hour at 37° C. The suspension is then pipetted twice in triplicate into 96-well plates, Next, 50 µl of a freshly trypsinized and homogenous suspension of Vero cells (1:3 split of the confluent cell monolayer of a T75-flask) resuspended in DMEM with 10% v/v fetal calf serum and antibiotics is added. The inoculated cells are cultured for three to four days at 37° C. and observed daily for the development of cytopathic effect (CPE). CPE is compared to the positive control (WNV inoculated cells) and negative controls (mock-inoculated cells or cells incubated with scFV only). The complete absence of CPE in an individual cell culture is defined as protection (=100% titer reduction). The serum dilution giving protection in 50% percent of wells (i.e., three out of six wells) is defined as the 50% neutralizing antibody titer. The murine neutralizing antibody 7H2 (Biorelience) is used as a positive control in the assay. A 50% neutralization titer of $\leq 1:4$ (meaning the antibody is diluted 4 times or more) is regarded as specific evidence of neutralizing activity of the scFv against WNV.

Alternatively, in vitro virus neutralization assays (VNA) were performed in order to determine whether the anti-WNV IgGs were capable of blocking WNV infection. The VNA were performed essentially as described for scFvs, with the proviso that the serum dilution giving protection in 66% percent of wells (i.e., two out of three wells) was defined as the 66% neutralizing antibody titer and a 66% neutralization titer of $\leq 1:2$ was regarded as specific evidence of neutralizing activity of the IgG against WNV.

Supernatants containing the human anti-WNV antibodies called CR4271, CR4274, CR4283, CR4289, CR4299, CR4311. CR4325, CR4353, CR4361, and CR374 were expressed as described in Example 5 and subjected to the above-described VNA. All antibodies had a neutralizing titer ≦1:2. The potency of the antibodies (in µg/ml) is given in Table 12. The neutralizing antibodies recognized WNV E protein by Western Blot analysis or immunoprecipitation of an inactivated WNV preparation (data not shown).

Example 7

WNV E Protein Competition ELISA with scFvs

To identify antibodies that bind to non-overlapping, non-competing epitopes, a WNV E protein competition ELISA is performed. Nunc-Immuno™ Maxisorp F96 plates (Nunc) are coated overnight at 4° C. with a 1:100 dilution of purified WNV E protein (100 µl) in PBS (50 µl). Uncoated protein is washed away before the wells are blocked with 100 µl PBS containing 1% Protifar for one hour at room temperature. Subsequently, the blocking solution is discarded and 50 µl of the non-purified anti-WNV scFvs in PBS containing 1% Protifar (2× diluted) is added. Wells are washed five times with 100 µl of PBS containing 0.05% Tween-20. Then, 50 µl biotinylated anti-WNV competitor murine monoclonal IgGs, 7H2 or 6B6C-1, is added to each well, incubated for five minutes at room temperature, and the wells washed five times with 100 µl of PBS containing 0.05% Tween-20. To detect the binding of 7H2 or 6B6C-1, 50 µl of a 1:2000 dilution of streptavidin-HRP antibody (Becton Dickinson) is added to the wells and incubated for one hour at room temperature. Wells are washed again as above and the ELISA is further developed by addition of 100 µl of OPD reagent (Sigma). The reaction is stopped by adding 50 µl 1 M $H_2SO_4$ before measuring the OD at 492 nm.

Alternatively, to investigate if antibodies are capable of binding to non-overlapping, non-competing epitopes, the following competition ELISA was performed. Nunc-Immuno™ Maxisorp P96 plates (Nunc) were coated overnight at 4° C. with a 1:1000 dilution with either of the murine anti-WNV monoclonal IgGs 7H2 (see Beasley and Barrett 2002) or 6B6C-1 (see Roehrig et al. 1983. Blitvich et al. 2003, and Roehrig et al. 2001). Uncoated antibody was washed away before the wells were blocked with 100 µl PBS containing 1% Protifar for one hour at room temperature. Subsequently, the blocking solution was discarded and 100 µl of purified recombinant WNV-E protein in PBS containing 1% Protifar (2× diluted) was added and incubated for one hour at room temperature. Wells were washed three times with 100 µl of PBS containing 0.05% Tween-20. Then, 100 µl of anti-WNV scFvs were added to the wells and incubated for one hour at room temperature. The wells were then washed five times with 100 µl of PBS containing 0.05% Tween-20. To detect the binding of scFV, 100 µl of a 1:4000 dilution of anti-VSV-HRP antibody (Boehringer Mannheim) was added to the wells and incubated for one hour at room temperature. Wells were washed again as above and the ELISA was further developed by addition of 100 µl of OPD reagent (Sigma). The reaction was stopped by adding 50 Ill µl M $H_2SO_4$ before measuring the OD at 492 nm. The results of the assay are shown in FIG. 1 for the scFv SC04-283, SC04-289, SC04-299, SC04-311, SC04-325, and SC04-374. When recombinant WNV-E protein was captured with the antibody 7H2, whose binding epitope has been mapped to domain III, the scFv SC04-299 and SC04-374 were blocked from binding, whereas SC04-289, SC04-311, and SC04-325 were able to bind. In contrast, when the antibody 6B6C-1, whose binding epitope has been mapped to domain II, was used for capture, SC04-299 and SC04-374 were able to bind recombinant WNV-E protein, but SC04-289, SC04-311, and SC04-325 were blocked from binding. These data indicate that both SC04-299 and SC04-374 bind to an epitope in domain III of the WNV-E protein and SC04-289, SC04-311, and SC04-325 bind to an epitope in domain II of the WNV-E protein. SC04-283 was not blocked by either antibody, suggesting that it might recognize an epitope away from the binding regions of 7H2 and 6B6C-1. Similar results as above were observed for the monoclonal antibodies called 4G2 and 3A3 which recognize an epitope on domain II and III, respectively. It has been suggested that domain III is the putative receptor binding site responsible for cellular attachment, while it has been suggested that domain II of the WNV-E protein contains the fusion peptide necessary for viral entry into the cytoplasm of the infected cell. The scFvs SC04-271 and SC04-274 did not bind to recombinant WNV-E protein either directly coated or coated by means of any of the two murine antibodies (data not shown). The negative control SC04-098 also did not bind to recombinant WNV-E protein coated by means of any of the two murine antibodies.

Example 8

In vivo Protection by Anti-WNV Monoclonal Antibodies from Lethal WNV Infection in a Murine Challenge Model A murine challenge model was adapted from the literature (see Ben-Nathan et al. 2003; Beasley et al. 2002; Wang et a. 2001). In Ben-Nathan et al. (2003) four-week old BALB/c mice were used and the animals were inoculated intraperitoneally (i.p.) with 20-times the viral dose resulting in 50% survival ($LD_{50}$) of WNV strain ISR52 ($LD_{50}$ was equivalent to 5 pfu). Under this dosing mice succumbed to infection six to seven days after inoculation and reached 100% mortality after eleven days. In another study, the WNV strain USA99 (used in the experiments described here) was shown to have an $LD_{50}$ of 0.5 pfu. This is ten-fold lower than the $LD_{50}$ of ISR52, which may indicate a higher degree of neuroinvasiveness for this viral strain or differences associated with the mouse strain used (see Beasley et al. 2002).

To determine the i.p., $LD_{50}$ of USA99 in four-week BALB/c mice, animals (five per group) were injected with USA99 at $TCID_{50}$ (tissue culture infectious dose) of 100, 30, 10, 3, 1, 0.3, 0.1, 0.03 the 50% in two separate experiments. The $LD_{50}$ calculated from the first experiment was 5.75 $TCID_{50}$ and from the second experiment 13.25 $TCID_{50}$. For the calculation of the viral dose in further experiments the average of the two experiments, i.e., 9.5 $TCID_{50}$, was calculated by probit regression analysis.

The protective capacity of the in vitro neutralizing antibodies CR4271, CR4274, CR4283, CR4289, CR4299, CR4311, CR4325, CR4353, CR4361, and CR4374 was tested in the in vivo model. Purified antibodies were injected i.p. into four-week BALB/c mice (five animals per group) at a concentration of 15 mg/kg. After 24 hours, the WNV strain USA99 was injected i.p. at a dose of 20-times the $LD_{50}$) calculated. The animals were observed for signs of disease over 21 days and sacrificed when symptoms of encephalitis were evident. In the model unprotected animals generally succumbed to infection between day 8 and day 10.

Table 13 shows that one antibodies, CR4374, is 100% protective in vitro and an additional antibody CR4353 is 75% protective at the dose of 15 mg/kg. The positive control antibody 7H2 (an anti-WNV murine monoclonal) was fully protective and the negative control antibody (binding an irrelevant antigen) showed no protection in the experiment.

To establish a dose protection relationship, the protective antibodies CR4353 and CR4374 were titrated in the mouse model using doses of 10, 3, 1, 0.3, 0.1, 0.03, 0.01, 0.003 and 0.001 mg/kg. A negative control antibody binding an irrelevant antigen was included as a control at a dose 10 mg/kg.

Figure 2:
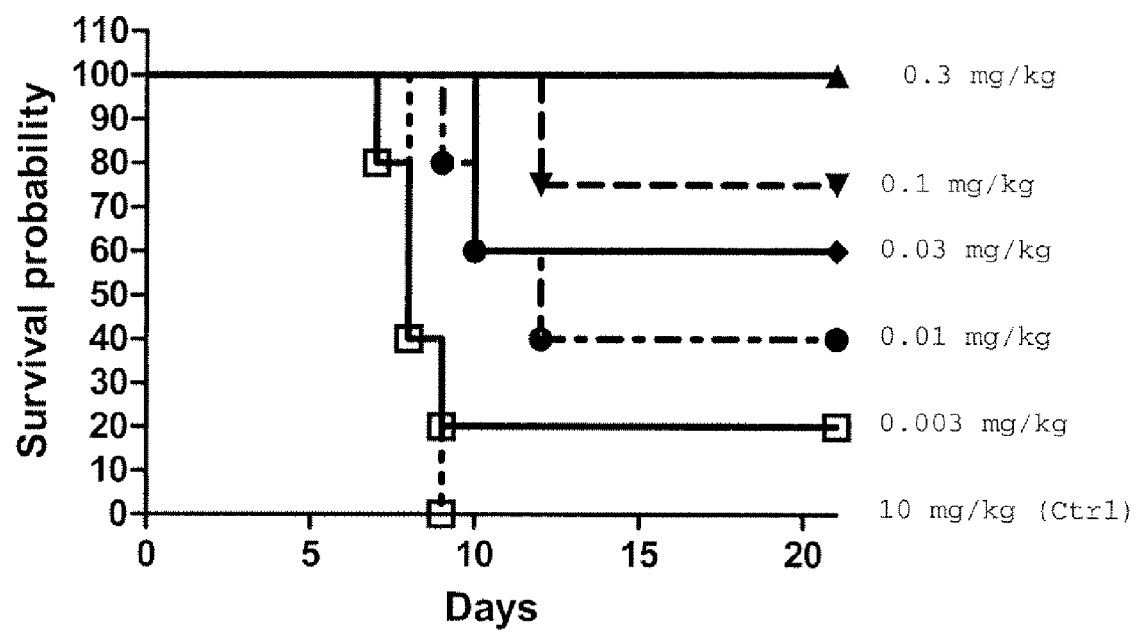
FIG. 2 shows the titration of anti-WNV monoclonal antibody CR4374 in a murine WNV challenge model. From top to bottom titration of anti-WNV monoclonal antibody CR4374 using doses of 0.3, 0.1, 0.03, 0.01, and 0.003 mg/kg and titration with a control antibody at a concentration of 10 mg/g are shown. On the X-axis days are shown and on the Y-axis the survival probability (%) is represented.

As shown in FIG. 2, the antibody CR4374 is 100% protective at a dose of 0.3 mg/kg. The doses 10, 3 and 1 mg/kg were also 100% protective (data not shown). FIG. 2 also shows that there is a direct correlation between dose and protective capacity. The 50% protective dose calculated by probit regression analysis is 0.013 mg/kg.

Figure 3:
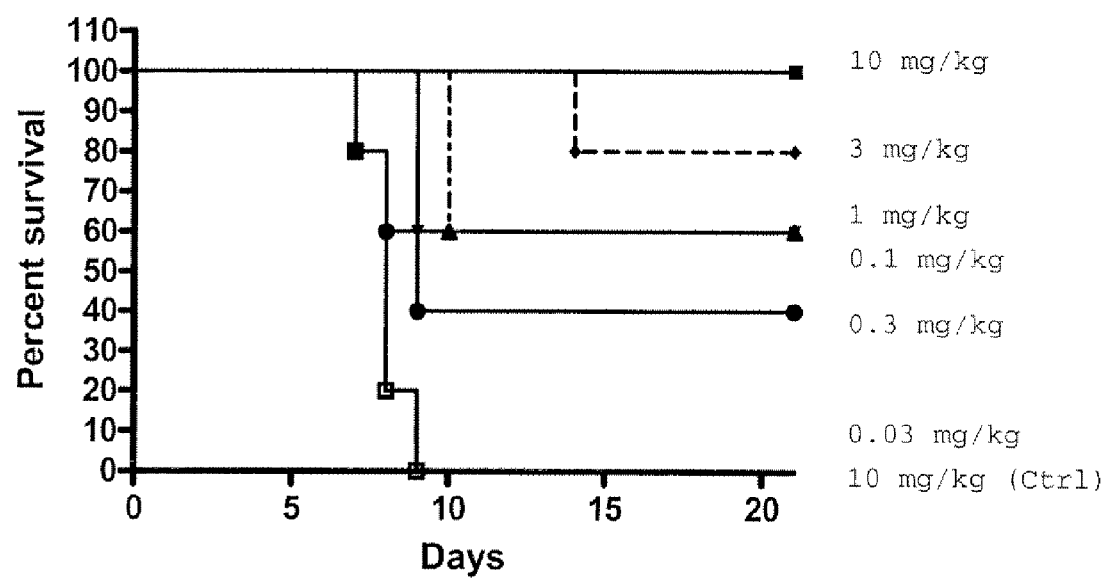
FIG. 3 shows the titration of anti-WNV monoclonal antibody CR4353 in a murine WNV challenge model. From top to bottom titration of anti-WNV monoclonal antibody CR4353 using doses of 10, 3, 1, 0.1, 0.3, and 0.03 mg/kg and titration with a control antibody at a concentration of 10 mg/kg are shown. On the X-axis days are shown and on the Y-axis the survival probability is represented.
Figure 4:
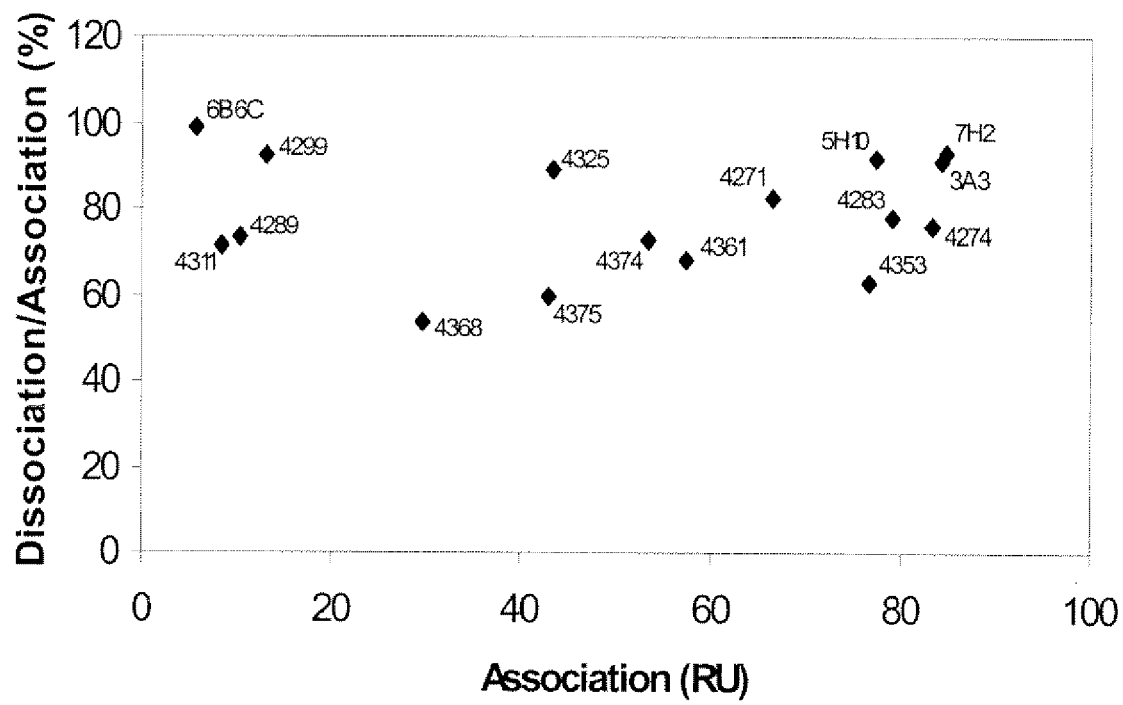
FIG. 4. Affinity ranking of antibodies using surface plasmon resonance. Antibodies with a relatively high affinity for West Nile Virus are located in the upper right corner of this plot, indicating good association and slow dissociation. The average of two measurements is shown for each antibody.

FIG. 3 shows that the antibody CR4353 is 100% protective at a dose of 10 mg/kg. Moreover, FIG. 3 shows that there is a direct correlation between dose and protective capacity. The 50% protective dose calculated by probit regression analysis is 0.357 mg/kg The titration data of the antibodies were compared by probit regression analysis. Values for he Pearson Goodness-of-Fit test (Chi Square=10.38, DF=30, p=1.00) demonstrated that the model was valid and the results of the Parallelism Test (Chi Square=3.47, DF=3, p=0.324) meant that the curves could be reliably compared. The values for the 50% protective dose and 95% protective dose are summarized in Table 14.

Example 9

Affinity Analysis Using Biacore

Affinity studies were performed using surface plasmon resonance analysis with a BIAcore3000™ analytical system at 25° C., using HBS-EP (Biacore AB, Sweden) as running buffer at a flow rate of 30 µl/minute. IgG CR4283 was immobilized on a research grade CM5 four-flow channel (Fc) sensor chip (Biacore AB, Sweden) using amine coupling. A constant amount of inactivated and purified West Nile Virus was then captured on the chip via the immobilized CR4283, followed by injection of a varying amount of the antibody of interest to analyze the binding interaction between this antibody and the captured virus. Regeneration using 15. 20, 30 or 40 mM NaOH was performed at the end of each measurement to remove bound antibody as well as captured virus, while leaving the immobilized CR4283 on the chip.

For affinity ranking studies, 60 µl purified West Nile virus was injected, followed by injection of 40 µl 1000 nM antibody. Then, running buffer was applied for 770 seconds, followed by regeneration of the CM5 chip with 5 µl 30 or 40 mM NaOH. The resonance signals expressed as resonance units (RU) were recorded as a function of time for each antibody. The response after the association phase was determined, as well as the response after 370 seconds of dissociation. The dissociation response expressed as percentage of the association response was then plotted against the association response (see FIG. 4). Antibodies CR4368 and CR4375 have the same heavy chain CDR3 as CR4374, but differ in other parts of the sequences. Mouse monoclonal antibodies 7H2, 3A3, 5H10 (all from BioReliance) and 6B6C-1 (Chemicon) were included for comparison. Antibodies with a relatively high affinity are located in the upper right corner of the plot, indicating good association combined with slow dissociation.

Affinity constants were determined for CR4283, CR4353, CR4374 and mouse antibody 7H2. After capture of 22, 23 or 60 µl West Nile virus, 40 µl of antibody was injected, followed by a dissociation phase of 770 seconds, and regeneration using 5 µl 15, 20 or 30 mM NaOH. Twelve concentrations in two-fold dilutions from 1000 nM down to 0.39 nM were measured for each antibody. The resulting data were fitted using a bivalent analyte model and the dissociation constant KD was calculated. Average KD values from duplicate experiments were 0.8±0.6 nM for CR4283, 6.5±0.4 nM for CR4353, 56±4 nM for CR4374 and 0.32±0.06 nM for 7H2.

Example 10

In vitro Neutralization Potency by Plaque Reduction Neutralization Test (PRNT)

To further investigate the neutralizing activity of the anti-WNV antibodies of the invention a PRNT was developed. Briefly, Vero-E6 cells were trypsinized and counted. $2.5\times10^5$ cells were added to each well of a twelve-well plate and incubated overnight at 37° C. in a humidified $CO_2$ incubator. Serial dilutions (ten-fold) of a titrated stock of West Nile virus USA99b were made in complete medium. Equal volume (250 µl) mixtures of virus (100 pfu) and serial dilutions of purified IgG1 antibodies were incubated in duplicate at 37° C. for one hour. Dilutions of both virus and antibodies were done in DMEM medium. The mixture was then added (400 µl) to the twelve-well plates containing Vero cell monolayers after careful aspiration of the overnight medium. After the plates had been incubated at 37° C. for one hour, an 1.5 ml overlay of CMC carboxymethyl-cellulose medium with 10% FBS (v/v) (CMC:complete medium) was added per well and the plates placed in a humidified CO incubator for three days at 37° C. One day before staining the CMC:complete medium was removed from the wells and replaced with a mixture of CMC:PBS (1:1: v/v) containing 8.25 mg/ml of neutral red (2 ml neutral red at 3.3 g/l in 80 ml CMC:PBS). Plates were incubated one day further at 37° C. in a humidified $CO_2$ incubator, after which the number of visible plaques was quantified.

To analyze the antibody potency data from the PRNT a binary regression model known as probit analysis was used. Probit analysis is valid, if it can be assumed that the probability of neutralizing WNV in vitro follows a normal distribution with regard to the amount of antibodies used. The assumption of normality most likely holds on a logarithmic scale, hence the neutralization of virus was modeled as a function of the logarithm of the amount of antibodies administered. Antibodies were compared directly in the regression model, with significance level alpha set at 0.05. Antibody concentrations yielding 50% and 90% neutralization were estimated from the model, together with 95% confidence intervals. A summary of the final analysis of the panel is given in Table 15. Taking the PRNT50 and PRNT90 values into account, CR4374 is the most potent neutralizing antibody. CR4353 has a lower PRNT50 value, but its PRNT90 value is high due to the fact that it retains neutralizing activity at very low concentrations, but is not able to completely neutralize the virus even at very high concentrations. The above may be related to differences in the mechanisms of action of both antibodies. As shown above however, CR4374 is more protective than CR4353 in the murine challenge model. For CR4271, CR4274 and CR4283 no value could be given for PRNT50, because of low potency and for CR4368 and CR4361 no value could be given for PRNT90, because of the high degree of uncertainty again due to low potency. By converting CR4374 into IgM format (CRM4374) the in vitro potency was increased dramatically (see Tables 15 and 18).

Example 11

Measurement of the Breadth of Neutralizing Activity Against Different West Nile Virus and *Flavivirus* Strains by Plaque Reduction Neutralization Test (PRNT)

Using the assay described above, the anti-WNV IgG1 antibody CR4374, that was protective in the murine challenge model, was tested for its neutralizing potency against different strains of West Nile virus (see Table 16 for the description of the WNV strains tested) and other flaviviruses including yellow fever virus, Japanese encephalitis virus, St. Louis encephalitis virus and dengue virus 2 and 4. CR4374 had no significant neutralizing activity against any of the other flaviviruses (data not shown). CR4374 neutralized however all of the lineage I and lineage II WNV strains tested with equal potency with the exception of TUN97 which was even neutralized significantly better than USA99b, the original strain used for selection (see Table 17).

Example 12

Figure 6:
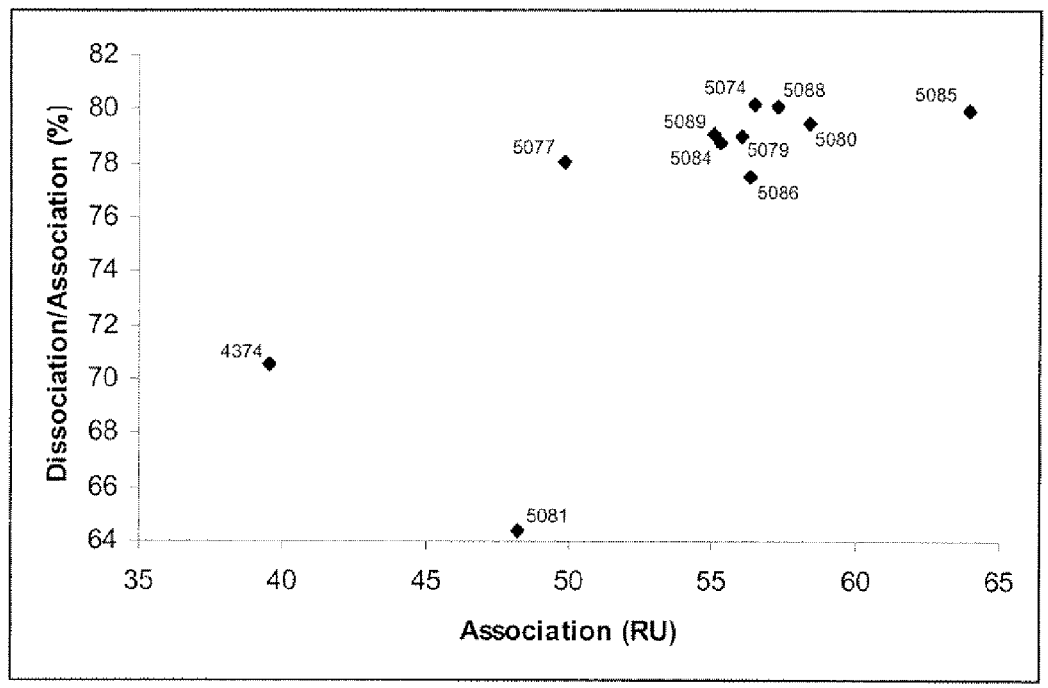
FIG. 6. Affinity ranking of affinity matured CR4374 variants using surface plasmon resonance. Antibodies with a relatively high affinity for West Nile Virus are located in the upper right corner of this plot, indicating good association and slow dissociation. The average of two measurements is shown for each antibody.

Affinity Maturation of CR4374 and Affinity and Neutralizing Potency Analysis Using Biacore and Plaque Reduction Neutralization Test, Respectively Affinity maturation of CR4374 was performed as follows. The variable heavy chain region of SC04-374 was cloned into the (sub)library of variable light chain regions according to the same method as described in Example 1 for cloning of the heavy chain repertoire into the (sub)library. Phage display selections using the constructed library were performed essentially as described in Example 2, followed by screening and analysis of selected clones essentially as described in Examples 3 and 4. The nucleotide and amino acid sequences of the selected scFvs SC05-074, SC05-080s, SC05-085 and SC05-088 as well as the amino acid sequences of their CDR regions are shown in Tables 18 and 19, respectively. Fully human immunoglobulin molecules of isolated clones were generated essentially as described in Example 5, using vector pIg-C910-Clambda (SEQ ID NO:219) instead of pIg-C909-Ckappa for cloning of the light chains. The nucleotide sequences of the light chains of the affinity matured immunoglobulins called CR5074, CR5080, CR5085 and CR5088 are shown in SEQ ID NO:220, SEQ ID NO:222, SEQ ID NO:224, and SEQ ID NO:226. The amino acid sequences of the light chains of the affinity matured immunoglobulins called CR5074, CR5080, CR5085 and CR5088 are shown in SEQ ID NO:221, SEQ ID NO:223, SEQ ID NO:225, and SEQ ID NO:227. A person skilled in the art can determine the variable region of the light chains of the above antibodies by following Kabat et al. (1991) as described in *Sequences of Proteins of Immunological Interest*. Affinity ranking studies with these affinity matured immunoglobulins were performed using surface plasmon resonance analysis essentially as described in Example 9. The dissociation response expressed as percentage of the association response was plotted against the association response (see FIG. 6). As shown in FIG. 6, the affinity of all but one mutated antibody (CR5081) had clearly improved. Affinity constants for the mutated immunoglobulins CR5074, CR5080, CR5085 and CR5088 were also determined essentially as described in Example 9. Average KD values from duplicate experiments were 3.9±0.5 nM for CR5074, 2.7±0.1 nM for CR5080, 3.7±0.7 nM for CR5085, and 1.7±0.1 nM for CR5088. These KD values are all an order of magnitude higher compared to CR4374.

In addition to the affinity, the neutralizing potency of the mutated immunoglobulins against West Nile virus strain USA99b was measured by PRNT. From Table 20 can be deducted that the PRNT50 and PRNT90 values of all affinity matured immunoglobulins are an order of magnitude higher compared to CR4374. This is in agreement with the affinity data.

Example 13

Systemic and Intrathecal/Intraventricular Therapy of WNV Encephalitis in a Hamster Model with Anti-WNV Monoclonal Antibodies or Combinations thereof With or Without Interferon-alpha It is investigated by means of a hamster model of WNV encephalitis, if the administration of the anti-WNV monoclonal antibodies of the invention in combination with interferon-alpha has a beneficial effect on the course of established human WNV encephalitis through reduction of viral load in the cerebrospinal fluid and brain, reduction of neuronal death, reduction of mortality, reduction of neurological signs and symptoms and/or prevention of persistent infection. To model the intrathecal administration of the antibodies, which is the preferred route used in humans, the antibodies of the invention are installed intraventricularily in the animals, because it is technically easier to perform. It has been shown that hamsters can be infected with WNV and that this species is well suited to evaluate the effects of therapeutic strategies because of the balanced mortality after WNV infection (Morrey et al., 2004a). The animals develop an encephalitis with neurological symptoms and approximately 50% do not survive the infection, if left untreated. Outbread Syrian golden hamsters (female, seven to eleven weeks) are used for the experiments and challenged s.c. with $10^4$ TCID$_{50}$ of the NY99 strain of WNV. For establishment of the model and evaluation of the efficacy of peripheral vs. intraventricular administration of the human monoclonal antibodies of the invention and interferon-alpha, animals are given the antibodies with or without interferon-alpha (Infergen™, Intermune, Inc., Brisbane, Calif., USA). (a) prophylactically intraperitoneally (i.p.) 24 hours pre-challenge, (b) as post-exposure prophylaxis/early systemical therapy i.p. at day 1, 2, 3, etc., post infection until first encephalitic symptoms appear (usually at day 6), and (c) as early intraventricular (i.v.) therapy at onset of encephalitic symptoms. The experimental details of the above treatments are:

(a) prophylactic passive immunization: antibodies are administered at a dose range of 30, 100, 300, 1000, and 3000 µg/kg 24 hours pre-challenge. The endpoint is mortality. Preferably, the mortality is reduced by at least 90%.

(b) post-exposure prophylaxis (PEP)/early therapy of infection: antibodies are administered at a dose range of 1×, 10×, and 100× the minimal prophylactic dose leading to a 90% reduction of mortality at day 1 post infection, day 2 post infection, day 3 post infection, etc., until the first day of encephalitic symptoms. The endpoint is mortality. Preferably, the mortality is reduced by at least 50%.

(c) Early therapy of established encephalitis: antibodies are administered systemically at a dose of 10× the minimal systemical therapeutic dose for 50% mortality reduction at the latest time point of early therapy of infection. Furthermore, antibodies are administered intraventricularly at a dose of 1× and 10× the minimal systemical therapeutic dose for 50% mortality reduction at the latest time point of early therapy of infection. The antibodies are administered the first day of severe neurological symptoms (normally day 6). The endpoints are (a) mortality, (b) viral load in cerebrospinal fluid (CSF), (c) neurological symptoms and behavioral changes, and (d) persistent infection, as measured by immunostaining and RT/PCR. Preferably, the mortality is reduced by at least 50%, the viral load in the CSF is reduced by at least 99, the neurological and behavioral sequelae in treated animals is significantly reduced and no persistent infection does occur. The above treatments are performed without interferon-alpha and with interferon-alpha at concentrations of 0.5 and 5 µg/kg. For the intraventricular administration of the antibodies a procedure for stereotactically guided injections into the brain ventricles using a Hamilton syringe is developed. Recently, a stereotactic atlas has been published that helps to identify the appropriate coordinates (Morin & Wood, 2001). Furthermore, a technique is developed that allows to take samples of cerebrospinal fluid via a guiding cantula that has been implanted into the lateral ventricle.

Neuropathological changes due to the infection are evaluated in surviving and non-surviving animals of the treatment and control group at different time points. Viral antigen will be detected in different regions of the brain known to be preferentially infected by WNV (e.g., cerebellum, brain stem, deep gray nuclei), using immunohistochemistry and quantitative RT/PCR. Because the virus targets Purkinje cells in the cerebellum which leads to neurological deficits, a range of neurological tests are established for assessing the behavioral effects of WNV infection. A strong predictor of mortality in hamster is the ramp-climbing test (see Morrey et al. 2004b), Other tests are used to follow the dynamics of these behavioral disturbances, and to assess the long-term effects of treatments. These techniques have been established for studying the effects of the occlusion of the middle cerebral artery (MCA-O; e.g., van der Staay et al., 1996a,b), and to assess the behavioral effects of hemorrhage (subdural hematoma) in rodents (e.g., Eijkenboom et al., 2000). One of the tests expected to be sensitive to virus-induced infections is the analysis of walking patterns (see Leyssen et al., 2003). Because hippocampal and cortical areas may be affected through apoptotic processes, the long term cognitive performance of untreated survivors, treated animals and uninfected control animals is also investigated. Furthermore, the cone-field spatial discrimination task, in which an animal must learn to collect food from four out of 16 alternative locations, is used for testing spatial cognition. Sample size considerations for endpoint mortality based on $\chi 2$ testing are shown in Table 21.

Sample size considerations for other tests are shown in Tables 22 and 23. Differences among treatment groups in weight, ramp climbing and viral titers in cerebrospinal fluid are analyzed using the t-test. Survival data are analyzed using the Wilcoxon test.

Example 14

In vivo Protection by Affinity Maturated Anti-WNV Monoclonal Antibody CR5080 from Lethal WNV Infection in a Murine Challenge Model The murine challenge model was essentially as described above (see Example 8) except animals were inoculated intraperitoneally (i.p.) with 100-times the viral dose resulting in 50% survival ($LD_{50}$) of WNV strain USA99. To establish the dose protection relationship of CR5080 it was titrated along with the parent antibody CR4374 in the mouse model using doses of 1, 0.3, 0.1, 0.03, 0.01, 0.003 and 0.001 mg/kg. A negative control antibody binding an irrelevant antigen was included as a control at a dose 1 mg/kg.

Figure 7:
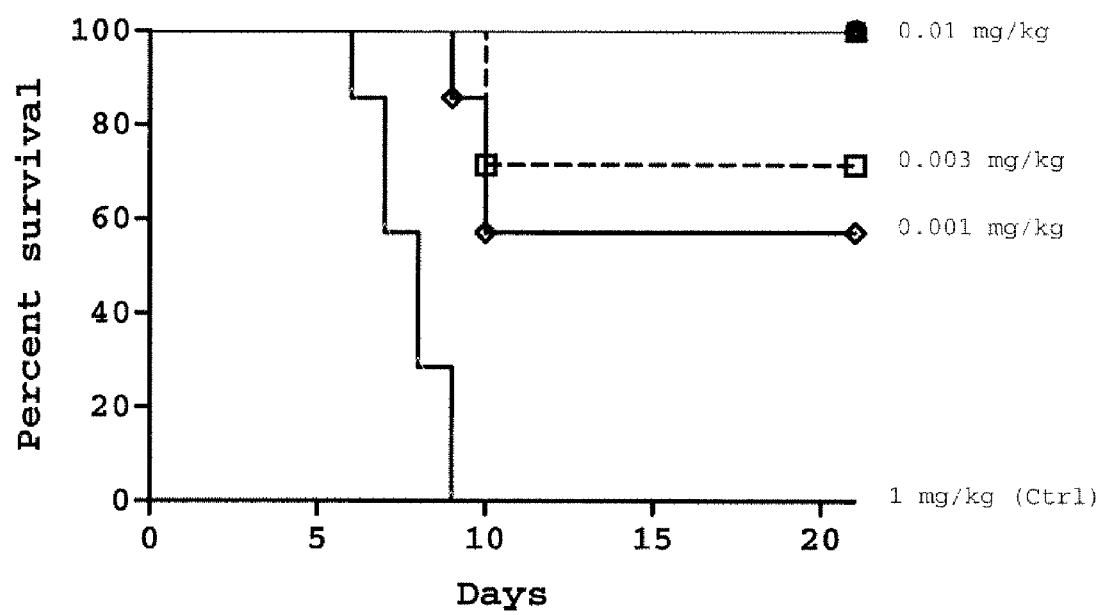
FIG. 7 shows the titration of anti-WNV monoclonal antibody CR5080 in a murine WNV challenge model. From top to bottom titration of anti-WNV monoclonal antibody CR5080 using doses of 0.01, 0.003, and 0.001 mg/kg and titration with a control antibody at a concentration of 1 mg/kg are shown. On the X-axis days are shown and on the Y-axis the survival probability (%) is represented.

As shown in FIG. 7, the antibody CR5080 is 100% protective at a dose of 0.01 mg/kg. The doses 1, 0.3, 0.1 and 0.03 mg/kg were also 100% protective (data not shown). FIG. 7 also shows that there is a direct correlation between dose and protective capacity. The parental antibody CR4374 that was included in this study was found to be fully protective at a dose of 0.1 mg/kg (data not shown). The 50% protective dose calculated by probit regression analysis for CR5080 is 0.00075 mg/kg compared to 0.011 mg/kg for CR4374. Thus, in both the in vitro neutralization assay and in vivo protection model the affinity maturated variant CR5080 is an order of magnitude more potent than its parent antibody CR4374. The consistency of the model is demonstrated by the fact that the 50% protective dose for CR4374 in this experiment (0.011 mg/kg) is similar to that calculated in Example 8 (0.013 mg/kg).

Example 15

Epitope Fine Mapping of the Antibodies CR4374 and CR5080

To map the location of the binding epitope of CR4374 and CR5080 more precisely within domain III of the WNV E protein, neutralization escape variants were generated. WNV strain USA99 (100 PFU) in MM (maintenance medium; DMEM, 5% FCS with antibiotic) was mixed one to one with CR4374 to a final concentration equal to the PRNT95 (1 µg/ml) and incubated for one hour at 37° C. The mixture was added to Vero-E6 cells grown to sub-confluency in GM (growth medium; 10% ECS in DMEM with 1% penicillin/streptomycin) in six-well flat bottom plates at 37° C./10% $CO_2$ in a humidified chamber. After a further hour of incubation the inoculum was aspirated and replaced with GM containing the antibody CR4374 at the selecting concentration of PRNT95 (1 µg/ml). Three days post infection potential escape variants were passaged. Supernatant (50 µl) was removed from each well and incubated with 1 ml of MM containing 1 µg/ml of CR4374 for one hour at 37° C./10% $CO_2$. The mixture was then inoculated onto cells (six-well plate) for one hour, removed and replaced with fresh GM containing 1 µg/ml of CR4374 and incubated further. The virus preparation was passaged a total of three times. To generate plaques for purification, supernatant (50 µl) was mixed with 1 ml of MM, placed on Vero-E6 cells and kept at 37° C./10% $CO_2$ for one hour. The inoculum was replaced with 3 ml of 1.8% agarose/2× growth medium and incubated for 2 days at 37° C./10% $CO_2$. Then an overlay of 1% agarose/neutral red 0.025% was added for visualization of the plaques. The above attempt failed to generate any escape mutants and therefore the procedure was repeated, but this time with a lower concentration of CR4374 (0.75 µg/ml). However, this attempt also failed. The third experiment was done with 0.5 µg/ml of CR4374 and resulted in a small number of plaques that could be picked. Six of these were individually mixed with 1 ml MM each and used to infect fresh Vero-E6 cells on a six-well plate. After three days, supernatant was harvested from each well and checked for infection by indirect immunofluorescence. Each virus was further amplified in 75 cm² flasks containing confluent Vero-E6 cells for three to four days. After harvest, the supernatant was aliquoted and kept at −70° C. until further use. The escape viruses were titrated and the neutralizing potency of CR4374 at PRNT95 (i.e., 1 μg/ml) against 100 PFU of each virus was determined as described in Example 10. The experiment was done in duplicate and as shown in Table 24, five out of six of the escape viruses met the predefined cut off of less than or equal to 20% neutralization by CR4374, although none of them were completely resistant to neutralization. This was consistent with the difficulty in generating the escape viruses and may indicate that mutation of the binding epitope of CR4374 is inherently difficult for the virus. Next, viral RNA was extracted using organic phase separation and subsequent ethanol precipitation. The obtained RNA was dissolved in RNAse free water and the concentration was determined by OD260 nm measurement, cDNA was prepared as described in Example 1 and amplified with the sense primer WN-313F (SEQ ID NO:248) and the antisense primers WN-2588R (SEQ ID NO:249) and WN1617R (SEQ ID NO:250). The products were cloned into a standard vector and the nucleotide sequences of the prM and envelope protein were determined according to standard techniques known to the skilled person in the art using the overlapping primer set WN-1242F (SEQ ID NO:251), WN-708F (SEQ ID NO:252), WN-1026F (SEQ ID NO:253) WN-1449F (SEQ ID NO:254), WN-1991F (SEQ ID NO.255), WN-315F (SEQ ID NO:256), WN-2585R (SEQ ID NO:257), WN-2086R (SEQ ID NO:258), WN-1560R (SEQ ID NO:259), WN-1049R (SEQ ID NO:260), WN-741R (SEQ D NO:261). Comparison of the escape viruses' sequences compared to USA99 revealed that the five escape viruses each contained a non-silent substitution of cytosine to uracil at position 1601 of the prM/E nucleotide sequence. This resulted in a substitution at position E365 of alanine to valine in the amino acid sequence. This residue is exposed as part of a peptide loop on the lateral face of domain III and would therefore be accessible for antibody binding. Moreover, this loop is one of four exposed peptide loops on domain III that make up a region predicted to harbor the cell attachment site of the virus. Thus, antibody binding in this region may neutralize the virus by blocking virus attachment to the cell surface.

Figure 8:
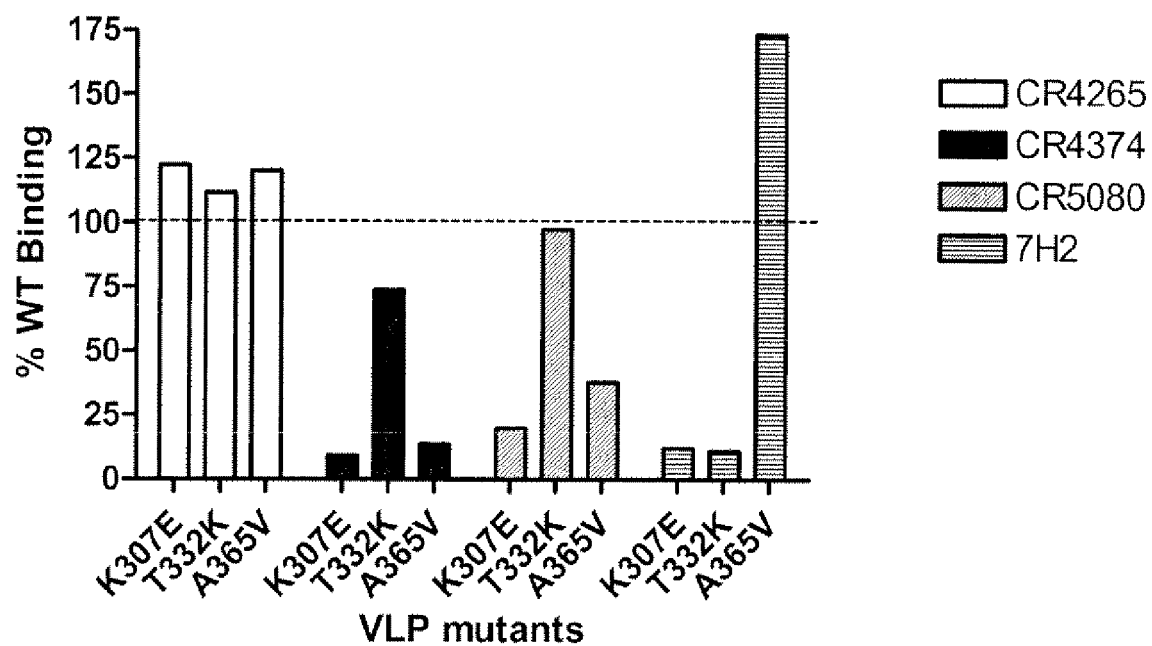
FIG. 8 shows four antibodies, CR4265 (white bars, bars 1-3 counting from the left side), CR4374 (black bars, bars 4-6 counting from the left side), CR5080 (bars having diagonal lines, bars 7-9 counting from the left side) and 7H2 (bars having horizontal lines, bars 10-12 counting from the left side) that were titrated for binding to wild-type and mutant VLPs by ELISA. Binding activity was normalized to wild-type binding levels (% WT binding).

To confirm that CR5080 as well as CR4374 binds in this region of the envelope protein and to determine the contribution of adjacent peptide loops of domain III in the binding epitope, various VLP mutants were constructed and produced. More specifically a VLP with the mutation identified in the CR4374 escape viruses (A365V) was generated along with two other mutants with the substitutions K307E and T332K. Both of these residues appear on adjacent solvent exposed peptide loops of domain III and their mutation has been reported to abrogate the neutralizing activity of potent domain III binding monoclonal antibodies (see Beasly et al. (2002); Oliphant, et al. (2005)). Mutations were introduced into the VLP construct (described in Example 2) using a QuickChange II kit (Stratagene) in combination with the primers K307E forward (SEQ ID NO:262), K307E reverse (SEQ ID NO:263), T332K forward (SEQ ID NO:264), T332K reverse (SEQ ID NO:265), A365V forward (SEQ ID NO:266) and A365V reverse (SEQ ID NO:267) according to the manufacturer's instructions. After PCR the resulting fragment was cloned back into the original expression vector using the restriction sites BamHI and PmeI. The constructs were verified by sequencing and the mutant and wildtype VLPs were produced and purified as described in Example 2. Four antibodies were titrated for binding to the wild-type and mutant VLP by ELISA as described in Example 3 and binding activity normalized to wild-type (WT) binding levels. As shown in FIG. 8, antibody CR4265, included as a positive control as its binding site is outside domain III, bound equally well to all mutants. As expected from the escape viruses' data binding of CR4374 to the mutant A365V was reduced dramatically compared to wild-type. The mutation K307E also blocked CR4374 binding, but about 75% binding was still retained with mutation T332K. The same pattern of binding was observed with CR5080, however, the relative intensity of binding was higher probably due to its higher binding affinity. Binding to A365V was about 37%, of binding to wild-type, suggesting that it might retain significant neutralizing activity against viruses with this mutation. The potent murine monoclonal 7H2, like CR4374 and CR5080, did not bind to the mutant K307E but remarkably bound almost two-fold better to mutant A365V than to wild-type. The reason for this difference is unknown. Most significantly, however was the lack of binding of 7H2 to the mutant T332K, which confirms previous reports (see Beasly et al. (2002)). In comparison, CR5080 bound this mutant equally well as wild-type and CR4374 still bound about 75% compared to wild-type. Thus, based on this data CR4374 (and also CR5080) and 71H2 are likely to bind overlapping but different epitopes. Consequently. CR4374 and CR5080 can be used to neutralize virus strains (e.g., lineage II WNV strain H-442) that are not neutralized by 7H2, as they comprise the mutation T332K (see Beasly et al. (2002)). In a prophylactic setting the combination of 7H2 or a similar antibody and CR4374 (or CR5080) might dramatically increase the odds of a virus escaping neutralization, thus making the combination safer than either antibody alone.

TABLE 1

Human lambda chain variable region primers (sense).

| Primer name | Primer nucleotide sequence | SEQ ID NO: |
|---|---|---|
| HuVλ1A | 5'-CAGTCTGTGCTGACT CAGCCACC-3' | SEQ ID NO: 152 |
| HuVλ1B | 5'-CAGTCTGTGYTGACG CAGCCGCC-3' | SEQ ID NO: 153 |
| HuVλ1C | 5'-CAGTCTGTCGTGACG CAGCCGCC-3' | SEQ ID NO: 154 |
| HuVλ2 | 5'-CARTCTGCCCTGACT CAGCCT-3' | SEQ ID NO: 155 |
| HuVλ3A | 5'-TCCTATGWGCTGACT CAGCCACC-3' | SEQ ID NO: 156 |
| HuVλ3B | 5'-TCTTCTGAGCTGACT CAGGACCC-3' | SEQ ID NO: 157 |
| HuVλ4 | 5'-CACGTTATACTGACT CAACCGCC-3' | SEQ ID NO: 158 |
| HuVλ5 | 5'-CAGGCTGTGCTGACT CAGCCGTC-3' | SEQ ID NO: 159 |
| HuVλ6 | 5'-AATTTTATGCTGACT CAGCCCCA-3' | SEQ ID NO: 160 |
| HuVλ7/8 | 5'-CAGRCTGTGGTGACY CAGGAGCC-3' | SEQ ID NO: 161 |
| HuVλ9 | 5'-CWGCCTGTGCTGACT CAGCCMCC-3' | SEQ ID NO: 162 |

TABLE 2

Human kappa chain variable region primers (sense).

| Primer name | Primer nucleotide sequence | SEQ ID NO: |
|---|---|---|
| HuVκ1B | 5'-GACATCCAGWTGACCC AGTCTCC-3' | SEQ ID NO: 163 |
| HuVκ2 | 5'-GATGTTGTGATGACT CAGTCTCC-3' | SEQ ID NO: 164 |
| HuVκ3 | 5'-GAAATTGTGWTGACR CAGTCTCC-3' | SEQ ID NO: 165 |

TABLE 2-continued

Human kappa chain variable region primers (sense).

| Primer name | Primer nucleotide sequence | SEQ ID NO: |
|---|---|---|
| HuVκ4 | 5'-GATATTGTGATGACC CACACTCC-3' | SEQ ID NO: 166 |
| HuVκ5 | 5'-GAAACGACACTCACG CAGTCTCC-3' | SEQ ID NO: 167 |
| HuVκ6 | 5'-GAAATTGTGCTGACTC AGTCTCC-3' | SEQ ID NO: 168 |

TABLE 3

Human kappa chain variable region primers extended with SalI restriction sites (sense), human kappa chain J-region primers extended with NotI restriction sites (anti-sense), human lambda chain variable region primers extended with SalI restriction sites (sense) and human lambda chain J-region primers extended with NotI restriction sites (anti-sense).

| Primer name | Primer nucleotide sequence | SEQ ID NO: |
|---|---|---|
| HuVκ1B-SalI | 5'-TGAGCACACAGGTCG ACGGACATCCAGWTGACC CAGTCTCC-3' | SEQ ID NO: 169 |
| HuVκ2-SalI | 5'-TGAGCACACAGGTCG ACGGATGTTGTGATGACT CAGTCTCC-3' | SEQ ID NO: 170 |
| HuVκ3B-SalI | 5'-TGAGCACACAGGTCG ACGGAAATTGTGWTGACR CAGTCTCC-3' | SEQ ID NO: 171 |
| HuVκ4B-SalI | 5'-TGAGCACACAGGTCG ACGGATATTGTGATGACC CACACTCC-3' | SEQ ID NO: 172 |
| HuVκ5-SalI | 5'-TGAGCACACAGGTCGACG GAAACGACACTCACGCAGTCT CC-3' | SEQ ID NO: 173 |
| HuVκ6-SalI | 5'-TGAGCACACAGGTCG ACGGAAATTGTGCTGACT CAGTCTCC-3' | SEQ ID NO: 174 |
| HuJκ1-NotI | 5'-GAGTCATTCTCGACTTGC GGCCGCACGTTTGATTTCCAC CTTGGTCCC-3' | SEQ ID NO: 175 |
| HuJκ2-NotI | 5'-GAGTCATTCTCGACT TGCGGCCGCACGTTTGAT CTCCAGCTTGGTCCC-3' | SEQ ID NO: 176 |
| HuJκ3-NotI | 5'-GAGTCATTCTCGACTTGC GGCCGCACGTTTGATATCCAC TTTGGTCCC-3' | SEQ ID NO: 177 |
| HuJκ4-NotI | 5'-GAGTCATTCTCGACT TGCGGCCGCACGTTTGAT CTCCACCTTGGTCCC-3' | SEQ ID NO: 178 |
| HuJκ5-NotI | 5'-GAGTCATTCTCGACTTGC GGCCGCACGTTTAATCTCCAG TCGTGTCCC-3' | SEQ ID NO: 179 |
| HuVλ1A-SalI | 5'-TGAGCACACAGGTCGACG CAGTCTGTGCTGACTCAGCCA CC-3' | SEQ ID NO: 180 |
| HuVλ1B-SalI | 5'-TGAGCACACAGGTCGACG CAGTCTGTGYTGACGCAGCCG CC-3' | SEQ ID NO: 181 |
| HuVλ1C-SalI | 5'-TGAGCACACAGGTCGACG CAGTCTGTCGTGACGCAGCCG CC-3' | SEQ ID NO: 182 |
| HuVλ2-SalI | 5'-TGAGCACACAGGTCGACG CARTCTGCCCTGACTCAGC CT-3' | SEQ ID NO: 183 |
| HuVλ3A-SalI | 5'-TGAGCACACAGGTCGACG TCCTATGWGCTGACTCAGCCA CC-3' | SEQ ID NO: 184 |
| HuVλ3B-SalI | 5'-TGAGCACACAGGTCGACG TCTTCTGAGCTGACTCAGGAC CC-3' | SEQ ID NO: 185 |
| HuVλ4-SalI | 5'-TGAGCACACAGGTCGACG CACGTTATACTGACTCAACCG CC-3' | SEQ ID NO: 186 |

TABLE 3-continued

Human kappa chain variable region primers extended with SalI restriction sites (sense), human kappa chain J-region primers extended with NotI restriction sites (anti-sense), human lambda chain variable region primers extended with SalI restriction sites (sense) and human lambda chain J-region primers extended with NotI restriction sites (anti-sense).

| Primer name | Primer nucleotide sequence | SEQ ID NO: |
|---|---|---|
| HuVλ5-SalI | 5'-TGAGCACACAGGTCGACG CAGGCTGTGCTGACTCAGCCG TC-3' | SEQ ID NO: 187 |
| HuVλ6-SalI | 5'-TGAGCACACAGGTCGACG AATTTTATGCTGACTCAGCCC CA-3' | SEQ ID NO: 188 |
| HuVλ7/8-SalI | 5'-TGAGCACACAGGTCGACG CAGRCTGTGGTGACYCAGGAG CC-3' | SEQ ID NO: 189 |
| HuVλ9-SalI | 5'-TGAGCACACAGGTCGACG CWGCCTGTGCTGACTCAGCCM CC-3' | SEQ ID NO: 190 |
| HuJλ1-NotI | 5'-GAGTCATTCTCGACTTGC GGCCGCACCTAGGACGGTGAC CTTGGTCCC-3' | SEQ ID NO: 191 |
| HuJλ2/3-NotI | 5'-GAGTCATTCTCGACTTGC GGCCGCACCTAGGACGGTCAG CTTGGTCCC-3' | SEQ ID NO: 192 |
| HuJλ4/5-NotI | 5'-GAGTCATTCTCGACTTGC GGCCGCACYTAAAACGGTGAG CTGGGTCCC-3' | SEQ ID NO: 193 |

TABLE 4

Distribution of the different light chain products over the ten fractions.

| Light chain products | Number of alleles | Fraction number | alleles/fration |
|---|---|---|---|
| Vk1B/Jk1-5 | 19 | 1 and 2 | 9.5 |
| Vk2/Jk1-5 | 9 | 3 | 9 |
| Vk3B/Jk1-5 | 7 | 4 | 7 |
| Vk4B/Jk1-5 | 1 | 5 | 5 |
| Vk5/Jk1-5 | 1 | | |
| Vk6/Jk1-5 | 3 | | |
| Vλ1A/Jl1-3 | 5 | 6 | 5 |
| Vλ1B/Jl1-3 | | | |
| Vλ1C/Jl1-3 | | | |
| Vλ2/Jl1-3 | 5 | 7 | 5 |
| Vλ3A/Jl1-3 | 9 | 8 | 9 |
| Vλ3B/Jl1-3 | | | |
| Vλ4/Jl1-3 | 3 | 9 | 5 |
| Vλ5/Jl1-3 | 1 | | |
| Vλ6/Jl1-3 | 1 | | |
| Vλ7/8/Jl1-3 | 3 | 10 | 6 |
| Vλ9/Jl1-3 | 3 | | |

TABLE 5

Human IgG heavy chain variable region primers (sense).

| Primer name | Primer nucleotide sequence | SEQ ID NO: |
|---|---|---|
| HuVH1B/7A | 5'-CAGRTGCAGCTGGTG CARTCTGG-3' | SEQ ID NO: 194 |
| HuVH1C | 5'-SAGGTCCAGCTGGTR CAGTCTGG-3' | SEQ ID NO: 195 |
| HuVH2B | 5'-SAGGTGCAGCTGGTG GAGTCTGG-3' | SEQ ID NO: 196 |
| HuVH3B | 5'-SAGGTGCAGCTGGTG GAGTCTGG-3' | SEQ ID NO: 197 |
| HuVH3C | 5'-GAGGTGCAGCTGGTG GAGWCYGG-3' | SEQ ID NO: 198 |
| HuVH4B | 5'-CAGGTGCAGCTACAG CAGTGGGG-3' | SEQ ID NO: 199 |

TABLE 5-continued

Human IgG heavy chain variable region primers (sense).

| Primer name | Primer nucleotide sequence | SEQ ID NO: |
|---|---|---|
| HuVH4C | 5'-CAGSTGCAGCTGCAG GAGTCSGG-3' | SEQ ID NO: 200 |
| HuVH5B | 5'-GARGTGCAGCTGGTG CAGTCTGG-3' | SEQ ID NO: 201 |
| HuVH6A | 5'-CAGGTACAGCTGCAG CAGTCAGG-3' | SEQ ID NO: 202 |

TABLE 6

Human IgG heavy chain variable region primers extended with SfiI/NcoI restriction sites (sense) and human IgG heavy chain J-region primers extended with XhoI/BstEII restriction sites (anti-sense).

| Primer name | Primer nucleotide sequence | SEQ ID NO: |
|---|---|---|
| HuVH1B/7A-SfiI | 5'-GTCCTCGCAACTGCG GCCCAGCCGGCCATGGCC CAGRTGCAGCTGGTGCAR TCTGG-3' | SEQ ID NO: 203 |
| HuVH1C-SfiI | 5'-GTCCTCGCAACTGCG GCCCAGCCGGCCATGGCC SAGGTCCAGCTGGTRCAG TCTGG-3' | SEQ ID NO: 204 |
| HuVH2B-SfiI | 5'-GTCCTCGCAACTGCG GCCCAGCCGGCCATGGCC CAGRTCACCTTGAAGGAG TCTGG-3' | SEQ ID NO: 205 |
| HuVH3B-SfiI | 5'-GTCCTCGCAACTGCGGCC CAGCCGGCCATGGCCSAGGTG CAGCTGGTGGAGTCTGG-3' | SEQ ID NO: 206 |
| HuVH3C-SfiI | 5'-GTCCTCGCAACTGCG GCCCAGCCGGCCATGGCC GAGGTGCAGCTGGTGGAG WCYGG-3' | SEQ ID NO: 207 |
| HuVH4B-SfiI | 5'-GTCCTCGCAACTGCG GCCCAGCCGGCCATGGCC CAGGTGCAGCTACAGCAG TGGGG-3' | SEQ ID NO: 208 |
| HuVH4C-SfiI | 5'-GTCCTCGCAACTGCGGCC CAGCCGGCCATGGCCCAGSTG CAGCTGCAGGAGTCSGG-3' | SEQ ID NO: 209 |
| HuVH5B-SfiI | 5'-GTCCTCGCAACTGCG GCCCAGCCGGCCATGGCC GARGTGCAGCTGGTGCAG TCTGG-3' | SEQ ID NO: 210 |
| HuVH6A-SfiI | 5'-GTCCTCGCAACTGCG GCCCAGCCGGCCATGGCC CAGGTACAGCTGCAGCAG TCAGG-3' | SEQ ID NO: 211 |

TABLE 6-continued

Human IgG heavy chain variable region primers extended with SfiI/NcoI restriction sites (sense) and human IgG heavy chain J-region primers extended with XhoI/BstEII restriction sites (anti-sense).

| Primer name | Primer nucleotide sequence | SEQ ID NO: |
|---|---|---|
| HuJH1/2-XhoI | 5'-GAGTCATTCTCGACTCGA GACGGTGACCAGGGTGCC-3' | SEQ ID NO: 212 |
| HuJH3-XhoI | 5'-GAGTCATTCTCGACT CGAGACGGTGACCATTGT CCC-3' | SEQ ID NQ: 213 |
| HuJH4/5-XhoI | 5'-GAGTCATTCTCGACT CGAGACGGTGACCAGGGT TCC-3' | SEQ ID NO: 214 |
| HuJH6-XhoI | 5'-GAGTCATTCTCGACTCGA GACGGTGACCGTGGTCCC-3' | SEQ ID NO: 215 |

TABLE 7

Binding of single-chain (scFv) phage antibodies to West Nile virus (WNV), recombinant WNV E protein, FBS, and rabies virus as measured by ELISA at 492 nm).

| Name phage antibody | WN virus | WNV E protein | FBS (5%) | Rabies virus |
|---|---|---|---|---|
| SC04-271 | 0.984 | 0.608 | ND | ND |
| SC04-274 | 0.961 | 0.496 | ND | ND |
| SC04-283 | 1.205 | 0.074 | ND | ND |
| SC04-289 | 0.759 | 1.389 | ND | ND |
| SC04-299 | 1.075 | 0.072 | ND | ND |
| SC04-311 | 1.036 | 1.538 | ND | ND |
| SC04-325 | 1.183 | 1.397 | ND | 0.053 |
| SC04-353 | 1.002 | 0.099 | ND | 0.057 |
| SC04-361 | 0.660 | 0.076 | ND | 0.059 |
| SC04-374 | 0.975 | 1.360 | ND | 0.056 |
| SC02-447 | 0.094 | 0.057 | 0.041 | ND |
| SC03-014 | 0.061 | 0.060 | ND | 0.062 |
| Pos. control | 0.067 | 0.056 | ND | 0.991 |

ND means not determined

TABLE 8

Data of the WNV specific single-chain Fvs.

| Name scFv | SEQ ID NO of nucl. sequence | SEQ ID NO of amino acid sequence* | HCDR3 (SEQ ID NO:) | VH-locus | VL-locus |
|---|---|---|---|---|---|
| SC04-271 | 61 | 62 (Vh 1-122; Vl 139-248) | RPGYDYGFYYFD Y (SEQ ID NO: 1) | 5-51 (DP-73) | Vl 2 (2a2 - V1-04) |
| SC04-274 | 63 | 64 (Vh 1-130; Vl 147-259) | LRGPYYDFWNGY RETHDAFNV (SEQ ID NO: 2) | 5-51 (DP-73) | Vk IV (B3 - DPK24) |
| SC04-283 | 65 | 66 (Vh 1-130; Vl 147-253) | LTFRRGYSGSDSF LPPGDFDY (SEQ ID NO: 3) | 5-51 (DP-73) | Vk I (L12) |
| SC04-289 | 67 | 68 (Vh 1-125; Vl 142-250) | DVVGVGASDYYY YMDV (SEQ ID NO: 4) | 5-51 (DP-73) | Vk III (L2 - DPK21) |

TABLE 8-continued

Data of the WNV specific single-chain Fvs.

| Name scFv | SEQ ID NO of nucl. sequence | SEQ ID NO of amino acid sequence* | HCDR3 (SEQ ID NO:) | VH-locus | VL-locus |
|---|---|---|---|---|---|
| SC04-299 | 69 | 70 (Vh 1-124; Vl 141-250) | ESGGPIWYKYYG VDV (SEQ ID NO: 5) | 3-30 (DP-49) | Vl 1 (1a - V1-11) |
| SC04-311 | 71 | 72 (Vh 1-119; Vl 136-245) | GYNSGHYFDY (SEQ ID NO: 6) | 3-30 (DP-49) | Vl 1 (1b - V1-19) |
| SC04-325 | 73 | 74 (Vh 1-117; Vl 134-246) | GGMATTPGLDY (SEQ ID NO: 7) | 1-69 (DP-10) | Vk IV (B3 - DPK24) |
| SC04-353 | 75 | 76 (Vh 1-127; Vl 144-250) | DFWSGYSMVDSY YYYMDV (SEQ ID NO: 8) | 3-30 (DP-49) | Vk III (A27 - DPK22) |
| SC04-361 | 77 | 78 (Vh 1-130; Vl 147-259) | LRGPYYDFWNGY RETHDAFNV (SEQ ID NO: 9) | 5-51 (DP-73) | Vk IV (B3 - DPK24) |
| SC04-374 | 79 | 80 (Vh 1-130; Vl 147-257) | HRYYDISGYYRLF SDAFDI (SEQ ID NO: 10) | 2-05 | Vl 1 (1e - V1-13) |

*between brackets the amino acids making up the heavy chain variable region (VH) and the light chain variable region (VL) is shown

TABLE 9

Data of the CDR regions of the WNV specific single-chain Fvs.

| Name scFv | HCDR1 (SEQ ID NO:) | HCDR2 (SEQ ID NO:) | LCDR1 (SEQ ID NO:) | LCDR2 (SEQ ID NO:) | LCDR3 (SEQ ID NO:) |
|---|---|---|---|---|---|
| SC04-271 | 21 | 31 | 41 | 51 | 11 |
| SC04-274 | 22 | 32 | 42 | 52 | 12 |
| SC04-283 | 23 | 33 | 43 | 53 | 13 |
| SC04-289 | 24 | 34 | 44 | 54 | 14 |
| SC04-299 | 25 | 35 | 45 | 55 | 15 |
| SC04-311 | 26 | 36 | 46 | 56 | 16 |
| SC04-325 | 27 | 37 | 47 | 57 | 17 |
| SC04-353 | 28 | 38 | 48 | 58 | 18 |
| SC04-361 | 29 | 39 | 49 | 59 | 19 |
| SC04-374 | 30 | 40 | 50 | 60 | 20 |

TABLE 10

Binding of IgG1 antibodies to WNV as measured by ELISA (OD 492 nm).

| | WN virus (dilution) | | |
|---|---|---|---|
| Antibody | 1:5* | 1:25 | 1:125 |
| CR4271 | 1.785 | 1.853 | 1.818 |
| CR4274 | 2.308 | 2.351 | 2.164 |
| CR4299 | 1.477 | 1.337 | 0.929 |
| CR4311 | 1.047 | 0.817 | 0.754 |
| CR4374 | 2.321 | 2.272 | 2.121 |
| pos ctrl | 2.092 | 2.122 | 2.135 |
| neg ctrl | 0.062 | 0.056 | 0.046 |

*dilution of the antibody

TABLE 11

Binding of IgG1 antibodies to WNV as measured by ELISA (OD 492 nm).

| Ab | 20.000 | 10.000 | 5.000 | 2.500 | 1.250 | 0.630 | 0.310 | 0.160 | 0.078 | 0.039 | 0.000 |
|---|---|---|---|---|---|---|---|---|---|---|---|
| CR4271 | 1.554 | 1.632 | 1.585 | 1.488 | 1.560 | 1.580 | 1.449 | 1.414 | 1.199 | 0.761 | 0.003 |
| CR4274 | 1.698 | 1.645 | 1.538 | 1.492 | 1.519 | 1.378 | 1.146 | 0.841 | 0.448 | 0.003 | |
| CR4283 | 1.678 | 1.645 | 1.761 | 1.621 | 1.633 | 1.618 | 1.542 | 1.564 | 1.351 | 1.019 | 0.003 |
| CR4289 | ND | 0.752 | 0.586 | 0.492 | 0.415 | 0.351 | 0.313 | 0.250 | 0.209 | 0.147 | 0.003 |
| CR4299 | 1.193 | 1.125 | 1.073 | 1.031 | 0.977 | 0.891 | 0.756 | 0.610 | 0.446 | 0.227 | 0.003 |
| CR4311 | 0.852 | 0.773 | 0.627 | 0.527 | 0.444 | 0.352 | 0.236 | 0.174 | 0.105 | 0.044 | 0.003 |
| CR4325 | 1.545 | 1.656 | 1.444 | 1.245 | 1.048 | 0.845 | 0.597 | 0.421 | 0.269 | 0.132 | 0.003 |
| CR4353 | ND | 1.567 | 1.554 | 1.432 | 1.418 | 1.330 | 1.169 | 1.069 | 0.734 | 0.595 | 0.003 |
| CR4374 | 1.687 | 1.723 | 1.645 | 1.577 | 1.499 | 1.451 | 1.242 | 0.997 | 0.729 | 0.458 | 0.003 |
| Neg. control | 0.051 | ND | ND | ND | ND | ND | ND | ND | ND | ND | |

TABLE 12

Potency of the anti-WNV antibodies in the 66% neutralizing antibody titer assay.

| Antibody name | µg/ml |
|---|---|
| CR4271 | 13.50 |
| CR4274 | 11.00 |
| CR4283 | 23.44 |
| CR4289 | 10.13 |
| CR4299 | 3.00 |
| CR4311 | 20.00 |
| CR4325 | 5.25 |
| CR4353 | 2.11 |
| CR4361 | 2.50 |
| CR4374 | 0.34 |

TABLE 13

Protection from lethal WNV challenge in mice by anti-WNV monoclonal antibodies.

| Antibody (15 mg/kg) | Surviving animals |
|---|---|
| CR4271 | 3/5 |
| CR4274 | 0/5 |
| CR4283 | 1/5 |
| CR4289 | 1/5 |
| CR4299 | 0/5 |
| CR4311 | 1/5 |
| CR4325 | 1/5 |
| CR4353 | 3/4* |
| CR4361 | 1/5 |
| CR4374 | 5/5 |
| 7H2 | 5/5 |
| Negative Control IgG1 | 0/5 |

*Four instead of five mice tested due to injection error as measured by IgG1 levels in serum of mouse taken 24 hours after antibody injection.

TABLE 14

Probit analysis of the protective activity of human anti-WNV IgG1 in a murine lethal challenge model

| Antibody | 50% protection (µg/kg) | 95% protection (µg/kg) |
|---|---|---|
| CR4374 | 12.9 | 270 |
| CR4353 | 357 | 7475 |

TABLE 15

Neutralizing potency against West Nile virus strain USA99b as measured by PRNT.

| Antibody | PRNT50 (95% CI) (µg/ml) | PRNT90 (95% CI) (µg/ml) |
|---|---|---|
| CR4271 | >100 | NA |
| CR4274 | >100 | NA |
| CR4283 | >100 | NA |
| CR4289 | 2.62 (1.16-6.10) | 37.4 (13.7-241) |
| CR4299 | 0.78 (0.28-1.82) | 10.3 (3.92-67.7) |
| CR4311 | 2.91 (2.26-3.74) | 39.6 (27.3-62.3) |
| CR4325 | 1.45 (0.66-3.05) | 15.8 (6.58-75.6) |
| CR4353 | 0.026 (0.012-0.045) | 36.4 (19.1-82.6) |
| CR4361 | 2.03 (0.90-4.34) | >100 |
| CR4368 | 2.05 (1.07-3.76) | >100 |
| CR4374 | 0.18 (0.17-0.20) | 0.95 (0.82-1.12) |
| CRM4374 | <0.1 | <0.1 |
| CR4375 | 0.17 (0.12-0.23) | 2.29 (1.59-3.67) |
| 7H2 | 0.0030 (0.0020-0.0040) | 0.026 (0.020-0.037) |
| 6B6C-1 | 0.70 (0.37-1.55) | 6.32 (2.42-106) |
| 5H10 | 0.016 (0.009-0.024) | 0.096 (0.074-0.140) |
| 3A3 | 0.0062 (0.0044-0.0079) | 0.042 (0.031-0.067) |

TABLE 16

Description of WNV strains used.

| Name | Strain | Origin | Year | Source | Lineage | CHOb* |
|---|---|---|---|---|---|---|
| USA99b | 385-99 | United States | 1999 | Bird | I | + |
| FRA00 | PaAn001 | France | 2000 | Horse | I | + |
| TUN97 | PaH001 | Tunisia | 1997 | Human | I | + |
| SEN90 | ArD-76104 | Senegal | 1990 | Mosquito | II | − |
| CAR82 | ArB3573/82 | Central African Republic | 1982 | Tick | II | + |
| MAD78 | DakAnMg798 | Madagascar | 1978 | Bird | II | − |

*CHOb means glycosylation

TABLE 17

Neutralizing potency of CR4374 against lineage I and II strains of WNV.

| Virus | PRNT50 (95% CI) | PRNT90 (95% CI) |
|---|---|---|
| USA99b | 0.17 (0.11-0.25) | 0.82 (0.50-1.77) |
| TUN97 | 0.03 (0.02-0.04) | 0.22 (0.15-0.39) |
| FRA00 | 0.11 (0.08-0.15) | 1.36 (0.09-2.33) |
| SEN90 | 0.29 (0.11-0.67) | 3.92 (1.49-25.37) |
| MAD78 | 0.12 (0.09-0.16) | 4.12 (2.78-6.68) |
| CAR82 | 0.14 (0.08-0.22) | 2.90 (1.52-7.49) |

TABLE 18

Data of the affinity matured immunoglobulins.

| Name scFv | SEQ ID NO of nucl. sequence | SEQ ID NO of amino acid sequence* | VH-locus | VL-locus |
|---|---|---|---|---|
| SC05-074 | 228 | 229 (Vh 1-130; Vl 147-257) | 2-05 | Vl 1 (1e—V1-13) |
| SC05-080 | 230 | 231 (Vh 1-130; Vl 147-257) | 2-05 | Vl 1 (1e—V1-13) |
| SC05-085 | 232 | 233 (Vh 1-130; Vl 147-257) | 2-05 | Vl 1 (1e—V1-13) |

TABLE 18-continued

Data of the affinity matured immunoglobulins.

| Name scFv | SEQ ID NO of nucl. sequence | SEQ ID NO of amino acid sequence* | VH-locus | VL-locus |
|---|---|---|---|---|
| SC05-088 | 234 | 235 (Vh 1-130; Vl 147-257) | 2-05 | Vl 1 (1e—V1-13) |

*between brackets the amino acids making up the heavy chain variable region (VH) and the light chain variable region (VL) is shown

TABLE 19

Data of the CDR regions of the affinity matured immunoglobulins.

| Name scFv | HCDR1 (SEQ ID NO:) | HCDR2 (SEQ ID NO:) | HCDR3 (SEQ ID NO:) | LCDR1 (SEQ ID NO:) | LCDR2 (SEQ ID NO:) | LCDR3 (SEQ ID NO:) |
|---|---|---|---|---|---|---|
| SC05-074 | 30 | 40 | 10 | 236 | 240 | 244 |
| SC05-080 | 30 | 40 | 10 | 237 | 241 | 245 |
| SC05-085 | 30 | 40 | 10 | 238 | 242 | 246 |
| SC05-088 | 30 | 40 | 10 | 239 | 243 | 247 |

TABLE 20

Neutralizing potency of affinity matured and IgM variants of CR4374 against WNV USA99b.

| Virus | PRNT50 (95% CI) (µg/ml) | PRNT90 (95% CI) (µg/ml) |
|---|---|---|
| CR5074 | 0.013 (0.009-0.020) | 0.067 (0.044-0.106) |
| CR5080 | 0.016 (0.010-0.023) | 0.080 (0.052-0.128) |
| CR5085 | 0.015 (0.010-0.023) | 0.077 (0.050-0.121) |
| CR5088 | 0.017 (0.011-0.026) | 0.087 (0.057-0.139) |
| CRM4374 | 0.011 (0.007-0.017) | 0.057 (0.037-0.091) |

TABLE 21

Number of animals that are required in each group to demonstrate the indicated difference in survival.

| Mortality in experimental group | Mortality in control group | |
|---|---|---|
| | 50% | 90% |
| 0% | 15 | 6 |
| 5% | 19 | 7 |
| 10% | 25 | 8 |
| 15% | 33 | 9 |
| 20% | — | 10 |

TABLE 22

Sample size considerations for the distance hamsters climbed in ten seconds.

| Number of animals | Difference in mean climbing distance between control and experimental groups |
|---|---|
| 6 | 72 cm |
| 10 | 53 cm |
| 15 | 42 cm |
| 19 | 37 cm |

Calculation based on SD of 40 cm

TABLE 23

Sample size considerations for Difference in mean weight change.

| Number of animals | Difference in mean weight change between control and experimental groups |
|---|---|
| 6 | 5.4% |
| 10 | 4.0% |
| 15 | 3.2% |
| 19 | 2.8% |

Calculation based on SD of 3%

TABLE 24

Percentage neutralization of escape viruses by CR374 (1 µg/ml)

| | Virus 1 | Virus 2 | Virus 3 | Virus 4 | Virus 5 | Virus 6 |
|---|---|---|---|---|---|---|
| Exp. 1 | 29.1 | 22.7 | 12.0 | 16.6 | 25.4 | 20.0 |
| Exp. 2 | 22.3 | 8.2 | 16.7 | 18.5 | 15.4 | 12.2 |
| Average | 26 | 15 | 14 | 18 | 20 | 16 |

REFERENCES

Anderson J. F., T. G. Andreadis, C. R. Vossbrinck, S. Tirrell, E. M. Wakem, R. A. French, A. E. Garmendia and U. J. Van Kruiningen (1999), Isolation of West Nile virus from mosquitoes, crows, and a Cooper's hawk in Connecticut. *Science* 286:2331-2333.

Anderson J. F. and J. J. Rahal (2002). Efficacy of interferon alpha-2b and ribavirin against WNV in vitro. *Emerg. Infect. Dis.* 8107-108.

Beasley D. W. and A. D. Barrett (2002), Identification of neutralizing epitopes within structural domain III of the West Nile virus envelope protein. *J. Virol.* 76:13097-13100.

Beasley D. W., L. Li, M. T. Suderman and A. D. Barrett (2002), Mouse neuroinvasive phenotype of West Nile virus strains varies depending upon virus genotype. *Virology* 296:17-23.

Ben-Nathan D., S. Lustig, G. Tam, S. Robinzon, S. Segal and B. Rager-Zisman (2003), Prophylactic and therapeutic efficacy of human intravenous immunoglobulin in treating WNV infection in mice. *J. Infect. Dis.* 188:5-12.

Blitvich B. J., N. L. Marlence, R. A. Hall, C. H. Calisher, R. A. Bowen, J. T. Roehrig, N. Komar, S. A. Langevin and B. J. Beaty (2003), Epitope-blocking enzyme-linked immunosorbent assays for the detection of serum antibodies to West Nile virus in multiple avian species. *J. Clin. Microbiol.* 41:1041-1047.

Boel E., S. Verlaan, M. J. Poppelier, N. A. Westerdaal, J. A. Van Strijp and T. Logtenberg (2000), Functional human monoclonal antibodies of all isotypes constructed from phage display library-derived single-chain Fv antibody fragments. *J. Immunol. Methods* 239:153-166.

Burton D. R. and C. F. Barbas (1994), Human antibodies from combinatorial libraries. *Adv. Immunol.* 57:191-280.

Chou T. C. and P. Talalay (1984), Quantitative analysis of dose-effect relationships: the combined effects of multiple drugs or enzyme inhibitors. *Adv. Enzyme Regul.* 22:27-55.

De Kruif J., L. Terstappen, E. Boel and T. Logtenberg (1995a), Rapid selection of cell subpopulation-specific human monoclonal antibodies from a synthetic phage antibody library. *Proc. Natl. Acad. Sci. USA* 92:3938.

De Kruif J., E. Boel and T. Logtenberg (1995b), Selection and application of human single-chain Fv antibody fragments from a semi-synthetic phage antibody display library with designed CDR3 regions., *J. Mol. Biol.* 248: 97-105.

Eijkenboom M., I. Gerlach, R. Jork, D. Lowe and F. J. van der Staay (2000), Effects of subdural haematoma on sensorimotor functioning and spatial learning, in rats. *Neuropharmacology* 39:817-834.

Gollins S. W. and J. S. Porterfield (.1986), A new mechanism for the neutralization of enveloped viruses by antiviral antibody. *Nature* 321:244-246.

Huls G., I. J. Heijnen, E. Cuomo, J. van der Linden, E. Boel, J. van de Winkel and T. Logtenberg (1999), Antitumor immune effector mechanisms recruited by phage display-derived fully human IgG1 and IgA1 monoclonal antibodies. *Cancer Res.* 59:5778-5784.

Jia X. Y., T. Briese, I. Jordan, A. Rambaut, H. C. Chi, J. S. Mackenzie, R. A. Hall, J. Scherret and W. I. Lipkin (1999), Genetic analysis of West Nile New York 1999 encephalitis virus. *The Lancet* 354:1971-1972.

Kuno G., G. J. Chang, K. R. Tsuchiya, N. Karabatsos and C. B. Cropp (1998), Phylogeny of the genus Flavivirus. *J. Virol.* 72:73-83.

Lanciotti R. S., J. T. Roehrig, V. Deubel, J. Smith, M. Parker, K. Steele, B. Crise, K. E. Volpe, M. B. Crabtree, J. H. Scherret, R. A. Hall, J. S. MacKenzie, C. B. Cropp, B. Panigrahy, E. Ostlund, B. Schmitt, M. Malkinson, C. Banet, J. Weissman, N. Komar, H. M. Savage, W. Stone, T. McNamara and D. J. Gubler (1999), Origin of the West Nile virus responsible for an outbreak of encephalitis in the northeastern United States. *Science* 286:2333-2337.

Leyssen P., R. Croes, P. Rau, S. Heiland, E. Verbeken, R. Sciot, J. Paeshuyse, N. Charlier, E. De Clercq, U. Meyding-Lamadé and J. Neyts (2003), Acute encephalitis, a polyomyelitis-like syndrome and neurological sequelae in a hamster model for flavivirus infections. *Brain Pathology* 13:279-290.

Morin L. P. and R. I. Wood (2001), A Stereotaxic Atlas of the Golden Hamster Brain. New York, Elsevier.

Morrey J. D., W. D. Craig, J. G. Julander, L. M. Blatt, D. F. Smee and R. W. Sidwell (2004a), Effect of interferon-alpha and interferon-inducers on West Nile virus in mouse and hamster animal models. *Aniviral Chemistry and Chemotherapy* 15:101-109.

Morrey J. D., C. W. Day, J. G. Julander, A. L. Olsen, R. W. Sidewell, C. D. Cheney and L. M. Blatt (2004b), Modeling hamsters for evaluating West Nile virus therapies. *Antiviral Research* 63:41-50.

Oliphant T., M. Engle, G. E. Nybakken, C. Doane, S. Johnson, L. Huang, S. Gorlatov. E. Mehlhop, A. Marri, K. M. Chung, G. D. Ebel, L. D. Kramer, D. H. Fremont and M. S. Diamond (2005), Development of a humanized monoclonal antibody with therapeutic potential against West Nile virus. *Nat. Med.* 11:522-530.

Roehrig J. T., J. H. Mathews and D. W. Trent (1983), identification of epitopes on the E glycoprotein of Saint Louis encephalitis virus using monoclonal antibodies. *J. Virol.* 128:118-126.

Roehrig J. T, T. A. Staudinger, A. R. Hunt, J. H. Mathews and C. D. Blair (2001), Antibody prophylaxis and therapy for flavivirus encephalitis infections. *Ann. NY Acad. Sci.* 951:286-297.

Slootstra J. W., W. C. Puijk, G. J. Ligtvoet, J. P. Langeveld, R. H. Meloen (1996), Structural aspects of antibody-antigen interaction revealed through small random peptide libraries. *Mol. Divers.* 1:87-96.

van der Staay F. J., K.-H. Augstein and E. Horváth (.1996a), Sensorimotor impairments in rats with cerebral infarction, induced by unilateral occlusion of the left middle cerebral artery: strain differences and effects of the occlusion site. *Brain Research* 735:271-284.

van der Staay F. J., K.-H. Augstein and E. Horváth (1996b), Sensorimotor impairments in Wistar Kyoto rats with cerebral infarction, induced by unilateral occlusion of the middle cerebral artery: recovery of function. *Brain Research* 715:1.80-188.

Wang T., J. F. Anderson, L. A. Magnarelli, S. J. Wong, R. A. Koski and E. Fikrig (2001), Immunization of mice against West Nile virus with recombinant envelope protein. *J. Immunol.* 167:5273-5277.

What is claimed is:

1. An isolated human antibody capable of specifically binding to domain III of an E protein of a lineage I West Nile virus ("WNV") and having WNV neutralizing activity, wherein the antibody comprises a heavy chain comprising SEQ ID NO: 131.

2. An antigen-binding fragment of the antibody of claim 1, wherein the antigen-binding fragment binds to domain III of an E protein of a lineage I West Nile virus ("WNV").

3. The antibody of claim 1, wherein the antibody is produced by a phage display library.

4. The antibody of claim 1 further comprising a variable light chain comprising SEQ ID NO: 151.

5. A composition comprising the antibody of claim 1 and a pharmaceutical carrier.

6. A composition comprising the antigen-binding fragment of claim 2 and a pharmaceutical carrier.

7. A composition comprising the antibody of claim 4 and a pharmaceutical carrier.

* * * * *

SEQUENCE LISTING

<160> NUMBER OF SEQ ID NOS: 267

<210> SEQ ID NO 1
<211> LENGTH: 13
<212> TYPE: PRT
<213> ORGANISM: Artificial sequence

```
<220> FEATURE:
<223> OTHER INFORMATION: HCDR3

<400> SEQUENCE: 1

Arg Pro Gly Tyr Asp Tyr Gly Phe Tyr Tyr Phe Asp Tyr
1               5                   10

<210> SEQ ID NO 2
<211> LENGTH: 21
<212> TYPE: PRT
<213> ORGANISM: Artificial sequence
<220> FEATURE:
<223> OTHER INFORMATION: HCDR3

<400> SEQUENCE: 2

Leu Arg Gly Pro Tyr Tyr Asp Phe Trp Asn Gly Tyr Arg Glu Thr His
1               5                   10                  15

Asp Ala Phe Asn Val
            20

<210> SEQ ID NO 3
<211> LENGTH: 21
<212> TYPE: PRT
<213> ORGANISM: Artificial sequence
<220> FEATURE:
<223> OTHER INFORMATION: HCDR3

<400> SEQUENCE: 3

Leu Thr Phe Arg Arg Gly Tyr Ser Gly Ser Asp Ser Phe Leu Pro Pro
1               5                   10                  15

Gly Asp Phe Asp Tyr
            20

<210> SEQ ID NO 4
<211> LENGTH: 16
<212> TYPE: PRT
<213> ORGANISM: Artificial sequence
<220> FEATURE:
<223> OTHER INFORMATION: HCDR3

<400> SEQUENCE: 4

Asp Val Val Gly Val Gly Ala Ser Asp Tyr Tyr Tyr Tyr Met Asp Val
1               5                   10                  15

<210> SEQ ID NO 5
<211> LENGTH: 15
<212> TYPE: PRT
<213> ORGANISM: Artificial sequence
<220> FEATURE:
<223> OTHER INFORMATION: HCDR3

<400> SEQUENCE: 5

Glu Ser Gly Gly Pro Ile Trp Tyr Lys Tyr Tyr Gly Val Asp Val
1               5                   10                  15

<210> SEQ ID NO 6
<211> LENGTH: 10
<212> TYPE: PRT
<213> ORGANISM: Artificial sequence
<220> FEATURE:
<223> OTHER INFORMATION: HCDR3

<400> SEQUENCE: 6

Gly Tyr Asn Ser Gly His Tyr Phe Asp Tyr
1               5                   10
```

```
<210> SEQ ID NO 7
<211> LENGTH: 11
<212> TYPE: PRT
<213> ORGANISM: Artificial sequence
<220> FEATURE:
<223> OTHER INFORMATION: HCDR3

<400> SEQUENCE: 7

Gly Gly Met Ala Thr Thr Pro Gly Leu Asp Tyr
1               5                   10

<210> SEQ ID NO 8
<211> LENGTH: 18
<212> TYPE: PRT
<213> ORGANISM: Artificial sequence
<220> FEATURE:
<223> OTHER INFORMATION: HCDR3

<400> SEQUENCE: 8

Asp Phe Trp Ser Gly Tyr Ser Met Val Asp Ser Tyr Tyr Tyr Tyr Met
1               5                   10                  15

Asp Val

<210> SEQ ID NO 9
<211> LENGTH: 21
<212> TYPE: PRT
<213> ORGANISM: Artificial sequence
<220> FEATURE:
<223> OTHER INFORMATION: HCDR3

<400> SEQUENCE: 9

Leu Arg Gly Pro Tyr Tyr Asp Phe Trp Asn Gly Tyr Arg Glu Thr His
1               5                   10                  15

Asp Ala Phe Asn Val
            20

<210> SEQ ID NO 10
<211> LENGTH: 19
<212> TYPE: PRT
<213> ORGANISM: Artificial sequence
<220> FEATURE:
<223> OTHER INFORMATION: HCDR3

<400> SEQUENCE: 10

His Arg Tyr Tyr Asp Ile Ser Gly Tyr Tyr Arg Leu Phe Ser Asp Ala
1               5                   10                  15

Phe Asp Ile

<210> SEQ ID NO 11
<211> LENGTH: 10
<212> TYPE: PRT
<213> ORGANISM: Artificial sequence
<220> FEATURE:
<223> OTHER INFORMATION: LCDR3

<400> SEQUENCE: 11

Ser Ser Tyr Thr Ser Ser Ser Thr Tyr Val
1               5                   10

<210> SEQ ID NO 12
<211> LENGTH: 9
<212> TYPE: PRT
<213> ORGANISM: Artificial sequence
<220> FEATURE:
<223> OTHER INFORMATION: LCDR3
```

```
<400> SEQUENCE: 12

Gln Gln Tyr Tyr Ser Thr Pro Pro Thr
1               5

<210> SEQ ID NO 13
<211> LENGTH: 9
<212> TYPE: PRT
<213> ORGANISM: Artificial sequence
<220> FEATURE:
<223> OTHER INFORMATION: LCDR3

<400> SEQUENCE: 13

Gln Gln Tyr Asn Thr Tyr Pro Leu Thr
1               5

<210> SEQ ID NO 14
<211> LENGTH: 10
<212> TYPE: PRT
<213> ORGANISM: Artificial sequence
<220> FEATURE:
<223> OTHER INFORMATION: LCDR3

<400> SEQUENCE: 14

Gln Gln Tyr Asn Asn Trp Pro Pro Ile Thr
1               5                   10

<210> SEQ ID NO 15
<211> LENGTH: 11
<212> TYPE: PRT
<213> ORGANISM: Artificial sequence
<220> FEATURE:
<223> OTHER INFORMATION: LCDR3

<400> SEQUENCE: 15

Ala Ala Trp Asp Asp Thr Leu Ser Ala Trp Val
1               5                   10

<210> SEQ ID NO 16
<211> LENGTH: 11
<212> TYPE: PRT
<213> ORGANISM: Artificial sequence
<220> FEATURE:
<223> OTHER INFORMATION: LCDR3

<400> SEQUENCE: 16

Gly Thr Trp Asp Ser Ser Leu Thr Ala Val Val
1               5                   10

<210> SEQ ID NO 17
<211> LENGTH: 9
<212> TYPE: PRT
<213> ORGANISM: Artificial sequence
<220> FEATURE:
<223> OTHER INFORMATION: LCDR3

<400> SEQUENCE: 17

Gln Gln Tyr Tyr Ser Thr Pro Leu Thr
1               5

<210> SEQ ID NO 18
<211> LENGTH: 8
<212> TYPE: PRT
<213> ORGANISM: Artificial sequence
<220> FEATURE:
<223> OTHER INFORMATION: LCDR3
```

```
<400> SEQUENCE: 18

Gln Gln Tyr Gly Ser Ser Leu Thr
1               5

<210> SEQ ID NO 19
<211> LENGTH: 9
<212> TYPE: PRT
<213> ORGANISM: Artificial sequence
<220> FEATURE:
<223> OTHER INFORMATION: LCDR3

<400> SEQUENCE: 19

Gln Gln Tyr Tyr Asn Thr Pro Ile Thr
1               5

<210> SEQ ID NO 20
<211> LENGTH: 11
<212> TYPE: PRT
<213> ORGANISM: Artificial sequence
<220> FEATURE:
<223> OTHER INFORMATION: LCDR3

<400> SEQUENCE: 20

Gln Ser Tyr Asp Ser Ser Leu Ser Gly Ser Val
1               5                   10

<210> SEQ ID NO 21
<211> LENGTH: 5
<212> TYPE: PRT
<213> ORGANISM: Artificial sequence
<220> FEATURE:
<223> OTHER INFORMATION: HCDR1

<400> SEQUENCE: 21

Asn Tyr Trp Ile Gly
1               5

<210> SEQ ID NO 22
<211> LENGTH: 5
<212> TYPE: PRT
<213> ORGANISM: Artificial sequence
<220> FEATURE:
<223> OTHER INFORMATION: HCDR1

<400> SEQUENCE: 22

Ser Tyr Trp Ile Gly
1               5

<210> SEQ ID NO 23
<211> LENGTH: 5
<212> TYPE: PRT
<213> ORGANISM: Artificial sequence
<220> FEATURE:
<223> OTHER INFORMATION: HCDR1

<400> SEQUENCE: 23

Thr Tyr Trp Ile Gly
1               5

<210> SEQ ID NO 24
<211> LENGTH: 5
<212> TYPE: PRT
<213> ORGANISM: Artificial sequence
<220> FEATURE:
<223> OTHER INFORMATION: HCDR1

<400> SEQUENCE: 24
```

Ser Asn Trp Ile Thr
1               5

<210> SEQ ID NO 25
<211> LENGTH: 5
<212> TYPE: PRT
<213> ORGANISM: Artificial sequence
<220> FEATURE:
<223> OTHER INFORMATION: HCDR1

<400> SEQUENCE: 25

Gly Tyr Ala Met His
1               5

<210> SEQ ID NO 26
<211> LENGTH: 5
<212> TYPE: PRT
<213> ORGANISM: Artificial sequence
<220> FEATURE:
<223> OTHER INFORMATION: HCDR1

<400> SEQUENCE: 26

Lys Asp Ala Met His
1               5

<210> SEQ ID NO 27
<211> LENGTH: 5
<212> TYPE: PRT
<213> ORGANISM: Artificial sequence
<220> FEATURE:
<223> OTHER INFORMATION: HCDR1

<400> SEQUENCE: 27

Ser Tyr Ala Ile Ser
1               5

<210> SEQ ID NO 28
<211> LENGTH: 5
<212> TYPE: PRT
<213> ORGANISM: Artificial sequence
<220> FEATURE:
<223> OTHER INFORMATION: HCDR1

<400> SEQUENCE: 28

Asn Tyr Ala Met His
1               5

<210> SEQ ID NO 29
<211> LENGTH: 5
<212> TYPE: PRT
<213> ORGANISM: Artificial sequence
<220> FEATURE:
<223> OTHER INFORMATION: HCDR1

<400> SEQUENCE: 29

Thr Tyr Trp Ile Gly
1               5

<210> SEQ ID NO 30
<211> LENGTH: 7
<212> TYPE: PRT
<213> ORGANISM: Artificial sequence
<220> FEATURE:
<223> OTHER INFORMATION: HCDR1

<400> SEQUENCE: 30

```
Thr Ser Gly Val Gly Val Gly
1               5
```

```
<210> SEQ ID NO 31
<211> LENGTH: 17
<212> TYPE: PRT
<213> ORGANISM: Artificial sequence
<220> FEATURE:
<223> OTHER INFORMATION: HCDR2

<400> SEQUENCE: 31

Ile Ile Tyr Pro Gly Asp Ser Asp Thr Arg Tyr Ser Pro Ser Val Gln
1               5                   10                  15
Gly
```

```
<210> SEQ ID NO 32
<211> LENGTH: 17
<212> TYPE: PRT
<213> ORGANISM: Artificial sequence
<220> FEATURE:
<223> OTHER INFORMATION: HCDR2

<400> SEQUENCE: 32

Ile Ile Tyr Pro Gly Asp Ser Asp Thr Arg Tyr Ser Pro Ser Phe Gln
1               5                   10                  15
Gly
```

```
<210> SEQ ID NO 33
<211> LENGTH: 17
<212> TYPE: PRT
<213> ORGANISM: Artificial sequence
<220> FEATURE:
<223> OTHER INFORMATION: HCDR2

<400> SEQUENCE: 33

Ile Ile Tyr Pro Gly Asp Ser Asp Thr Ile Tyr Ser Pro Ser Phe Gln
1               5                   10                  15
Gly
```

```
<210> SEQ ID NO 34
<211> LENGTH: 17
<212> TYPE: PRT
<213> ORGANISM: Artificial sequence
<220> FEATURE:
<223> OTHER INFORMATION: HCDR2

<400> SEQUENCE: 34

Arg Ile Asp Pro Ser Asp Ser Tyr Thr Asn Tyr Ser Pro Ser Phe Gln
1               5                   10                  15
Gly
```

```
<210> SEQ ID NO 35
<211> LENGTH: 17
<212> TYPE: PRT
<213> ORGANISM: Artificial sequence
<220> FEATURE:
<223> OTHER INFORMATION: HCDR2

<400> SEQUENCE: 35

Val Ile Ser Tyr Asp Gly Ser Glu Lys Tyr Ser Ala Asp Ser Val Lys
1               5                   10                  15
Gly
```

```
<210> SEQ ID NO 36
<211> LENGTH: 17
<212> TYPE: PRT
<213> ORGANISM: Artificial sequence
<220> FEATURE:
<223> OTHER INFORMATION: HCDR2

<400> SEQUENCE: 36

Val Ile Ser Tyr Asp Gly Ser Asp Lys His Tyr Ala Asp Ser Val Lys
1               5                   10                  15
Gly

<210> SEQ ID NO 37
<211> LENGTH: 14
<212> TYPE: PRT
<213> ORGANISM: Artificial sequence
<220> FEATURE:
<223> OTHER INFORMATION: HCDR2

<400> SEQUENCE: 37

Gly Ile Phe Gly Thr Ala Ser Tyr Ala Gln Lys Phe Gln Gly
1               5                   10

<210> SEQ ID NO 38
<211> LENGTH: 17
<212> TYPE: PRT
<213> ORGANISM: Artificial sequence
<220> FEATURE:
<223> OTHER INFORMATION: HCDR2

<400> SEQUENCE: 38

Val Ile Ser Tyr Asp Gly Gly Asn Lys Tyr Tyr Ala Asp Ser Val Lys
1               5                   10                  15
Gly

<210> SEQ ID NO 39
<211> LENGTH: 17
<212> TYPE: PRT
<213> ORGANISM: Artificial sequence
<220> FEATURE:
<223> OTHER INFORMATION: HCDR2

<400> SEQUENCE: 39

Ile Ile Tyr Pro Ala Asp Ser Asp Thr Arg Tyr Ser Pro Ser Phe Gln
1               5                   10                  15
Gly

<210> SEQ ID NO 40
<211> LENGTH: 16
<212> TYPE: PRT
<213> ORGANISM: Artificial sequence
<220> FEATURE:
<223> OTHER INFORMATION: HCDR2

<400> SEQUENCE: 40

Val Ile Tyr Trp Asn Asp Asp Lys Leu Tyr Arg Pro Ser Leu Lys Ser
1               5                   10                  15

<210> SEQ ID NO 41
<211> LENGTH: 14
<212> TYPE: PRT
<213> ORGANISM: Artificial sequence
<220> FEATURE:
<223> OTHER INFORMATION: LCDR1

<400> SEQUENCE: 41
```

```
Thr Gly Thr Ser Ser Asp Val Gly Gly Tyr Asn Tyr Val Ser
1               5                   10
```

<210> SEQ ID NO 42
<211> LENGTH: 17
<212> TYPE: PRT
<213> ORGANISM: Artificial sequence
<220> FEATURE:
<223> OTHER INFORMATION: LCDR1

<400> SEQUENCE: 42

```
Lys Ser Ser Gln Ser Val Leu Tyr Ser Ser Asn Asn Lys Asn Tyr Leu
1               5                   10                  15
Ala
```

<210> SEQ ID NO 43
<211> LENGTH: 11
<212> TYPE: PRT
<213> ORGANISM: Artificial sequence
<220> FEATURE:
<223> OTHER INFORMATION: LCDR1

<400> SEQUENCE: 43

```
Arg Ala Ser Gln Ser Ile Ser Ser Trp Leu Ala
1               5                   10
```

<210> SEQ ID NO 44
<211> LENGTH: 12
<212> TYPE: PRT
<213> ORGANISM: Artificial sequence
<220> FEATURE:
<223> OTHER INFORMATION: LCDR1

<400> SEQUENCE: 44

```
Arg Thr Ser Gln Ser Val Ser Ser Ser Tyr Leu Gly
1               5                   10
```

<210> SEQ ID NO 45
<211> LENGTH: 13
<212> TYPE: PRT
<213> ORGANISM: Artificial sequence
<220> FEATURE:
<223> OTHER INFORMATION: LCDR1

<400> SEQUENCE: 45

```
Ser Gly Ser Ser Ser Asn Ile Gly Asn Tyr Gly Val Asn
1               5                   10
```

<210> SEQ ID NO 46
<211> LENGTH: 13
<212> TYPE: PRT
<213> ORGANISM: Artificial sequence
<220> FEATURE:
<223> OTHER INFORMATION: LCDR1

<400> SEQUENCE: 46

```
Ser Gly Thr Ser Ser Asn Ile Gly Asp Asn Tyr Val Ser
1               5                   10
```

<210> SEQ ID NO 47
<211> LENGTH: 17
<212> TYPE: PRT
<213> ORGANISM: Artificial sequence
<220> FEATURE:
<223> OTHER INFORMATION: LCDR1

```
<400> SEQUENCE: 47

Lys Ser Ser Gln Ser Val Leu Tyr Ser Ser Asn Asn Lys Asn Tyr Leu
1               5                   10                  15

Ala

<210> SEQ ID NO 48
<211> LENGTH: 12
<212> TYPE: PRT
<213> ORGANISM: Artificial sequence
<220> FEATURE:
<223> OTHER INFORMATION: LCDR1

<400> SEQUENCE: 48

Arg Ala Ser Gln Ser Val Ser Asn Thr Phe Leu Ala
1               5                   10

<210> SEQ ID NO 49
<211> LENGTH: 17
<212> TYPE: PRT
<213> ORGANISM: Artificial sequence
<220> FEATURE:
<223> OTHER INFORMATION: LCDR1

<400> SEQUENCE: 49

Lys Ser Ser Gln Asn Ile Leu Asp Asn Ser Asp Asn Lys Asn Phe Leu
1               5                   10                  15

Ala

<210> SEQ ID NO 50
<211> LENGTH: 14
<212> TYPE: PRT
<213> ORGANISM: Artificial sequence
<220> FEATURE:
<223> OTHER INFORMATION: LCDR1

<400> SEQUENCE: 50

Thr Gly Ser Ser Ser Asn Ile Gly Ala Gly Tyr Asp Val His
1               5                   10

<210> SEQ ID NO 51
<211> LENGTH: 7
<212> TYPE: PRT
<213> ORGANISM: Artificial sequence
<220> FEATURE:
<223> OTHER INFORMATION: LCDR2

<400> SEQUENCE: 51

Asp Val Ser Asn Arg Pro Leu
1               5

<210> SEQ ID NO 52
<211> LENGTH: 7
<212> TYPE: PRT
<213> ORGANISM: Artificial sequence
<220> FEATURE:
<223> OTHER INFORMATION: LCDR2

<400> SEQUENCE: 52

Trp Ala Ser Thr Arg Glu Ser
1               5

<210> SEQ ID NO 53
<211> LENGTH: 7
<212> TYPE: PRT
<213> ORGANISM: Artificial sequence
```

```
<220> FEATURE:
<223> OTHER INFORMATION: LCDR2

<400> SEQUENCE: 53

Ala Ala Ser Ser Leu Gln Ser
1               5

<210> SEQ ID NO 54
<211> LENGTH: 7
<212> TYPE: PRT
<213> ORGANISM: Artificial sequence
<220> FEATURE:
<223> OTHER INFORMATION: LCDR2

<400> SEQUENCE: 54

Gly Ala Ser Ile Arg Ala Thr
1               5

<210> SEQ ID NO 55
<211> LENGTH: 7
<212> TYPE: PRT
<213> ORGANISM: Artificial sequence
<220> FEATURE:
<223> OTHER INFORMATION: LCDR2

<400> SEQUENCE: 55

Tyr Asp Asp Leu Leu Pro Ser
1               5

<210> SEQ ID NO 56
<211> LENGTH: 7
<212> TYPE: PRT
<213> ORGANISM: Artificial sequence
<220> FEATURE:
<223> OTHER INFORMATION: LCDR2

<400> SEQUENCE: 56

Asp Asn Asn Lys Arg Pro Ser
1               5

<210> SEQ ID NO 57
<211> LENGTH: 7
<212> TYPE: PRT
<213> ORGANISM: Artificial sequence
<220> FEATURE:
<223> OTHER INFORMATION: LCDR2

<400> SEQUENCE: 57

Trp Ala Ser Thr Arg Glu Ser
1               5

<210> SEQ ID NO 58
<211> LENGTH: 7
<212> TYPE: PRT
<213> ORGANISM: Artificial sequence
<220> FEATURE:
<223> OTHER INFORMATION: LCDR2

<400> SEQUENCE: 58

Gly Ala Ser Ser Arg Ala Thr
1               5

<210> SEQ ID NO 59
<211> LENGTH: 7
<212> TYPE: PRT
<213> ORGANISM: Artificial sequence
<220> FEATURE:
```

<223> OTHER INFORMATION: LCDR2

<400> SEQUENCE: 59

Trp Ala Ser Ala Arg Glu Ser
1               5

<210> SEQ ID NO 60
<211> LENGTH: 7
<212> TYPE: PRT
<213> ORGANISM: Artificial sequence
<220> FEATURE:
<223> OTHER INFORMATION: LCDR2

<400> SEQUENCE: 60

Gly Asn Ser Asn Arg Pro Ser
1               5

<210> SEQ ID NO 61
<211> LENGTH: 747
<212> TYPE: DNA
<213> ORGANISM: Artificial sequence
<220> FEATURE:
<223> OTHER INFORMATION: SC04-271
<220> FEATURE:
<221> NAME/KEY: CDS
<222> LOCATION: (1)..(747)

<400> SEQUENCE: 61

| gag gtg cag ctg gtg gag act gga gca gag gtg aaa aag ccc ggg gag | 48 |
| Glu Val Gln Leu Val Glu Thr Gly Ala Glu Val Lys Lys Pro Gly Glu | |
| 1               5                   10                  15 | |
| tct ctg agg att tcc tgt aag ggt tct gga tac acc ttt aac aat tat | 96 |
| Ser Leu Arg Ile Ser Cys Lys Gly Ser Gly Tyr Thr Phe Asn Asn Tyr | |
|             20                  25                  30 | |
| tgg atc ggc tgg gtg cgc cag atg ccc ggg aaa ggc ctg gag tgg atg | 144 |
| Trp Ile Gly Trp Val Arg Gln Met Pro Gly Lys Gly Leu Glu Trp Met | |
|         35                  40                  45 | |
| ggg atc atc tat cct ggt gac tct gat acc aga tac agc ccg tcc gtc | 192 |
| Gly Ile Ile Tyr Pro Gly Asp Ser Asp Thr Arg Tyr Ser Pro Ser Val | |
|     50                  55                  60 | |
| caa ggc cac gtc acc atc tca gcc gac aag tcc atc aac acc gcc tac | 240 |
| Gln Gly His Val Thr Ile Ser Ala Asp Lys Ser Ile Asn Thr Ala Tyr | |
| 65                  70                  75                  80 | |
| ctg cag tgg agc agc ctg aag gcc tcg gac acc gcc gtg tat tac tgt | 288 |
| Leu Gln Trp Ser Ser Leu Lys Ala Ser Asp Thr Ala Val Tyr Tyr Cys | |
|                 85                  90                  95 | |
| gcg aga cgg cct gga tac gac tat gga ttt tac tac ttt gac tac tgg | 336 |
| Ala Arg Arg Pro Gly Tyr Asp Tyr Gly Phe Tyr Tyr Phe Asp Tyr Trp | |
|             100                 105                 110 | |
| ggc cag gga acc ctg gtc acc gtc tcg agc ggt acg ggc ggt tca ggc | 384 |
| Gly Gln Gly Thr Leu Val Thr Val Ser Ser Gly Thr Gly Gly Ser Gly | |
|         115                 120                 125 | |
| gga acc ggc agc ggc act ggc ggg tcg acg cag tct gcc ctg act cag | 432 |
| Gly Thr Gly Ser Gly Thr Gly Gly Ser Thr Gln Ser Ala Leu Thr Gln | |
|     130                 135                 140 | |
| cct cgc tca gtg tcc ggg tct cct gga cag tca gtc acc atc tcc tgc | 480 |
| Pro Arg Ser Val Ser Gly Ser Pro Gly Gln Ser Val Thr Ile Ser Cys | |
| 145                 150                 155                 160 | |
| act gga acc agc agt gat gtt ggt ggt tat aac tat gtc tcc tgg tac | 528 |
| Thr Gly Thr Ser Ser Asp Val Gly Gly Tyr Asn Tyr Val Ser Trp Tyr | |
|                 165                 170                 175 | |
| caa cat cac cca ggc aaa gcc ccc aaa ctc atg att tat gat gtc agt | 576 |
| Gln His His Pro Gly Lys Ala Pro Lys Leu Met Ile Tyr Asp Val Ser | |

```
                    180                 185                 190
aat cgg ccc tta ggg gtt tct aat cgc ttc tct ggc tcc aag tct ggc      624
Asn Arg Pro Leu Gly Val Ser Asn Arg Phe Ser Gly Ser Lys Ser Gly
        195                 200                 205 aac acg gcc tcc ctg acc atc tct ggg ctc cag gct gag gac gag gct      672
Asn Thr Ala Ser Leu Thr Ile Ser Gly Leu Gln Ala Glu Asp Glu Ala
    210                 215                 220 gat tat tac tgc agc tca tat aca agc agc agc act tat gtc ttc gga      720
Asp Tyr Tyr Cys Ser Ser Tyr Thr Ser Ser Ser Thr Tyr Val Phe Gly
225                 230                 235                 240 act ggg acc cat ctc acc gtt tta agt                                  747
Thr Gly Thr His Leu Thr Val Leu Ser
                245

<210> SEQ ID NO 62
<211> LENGTH: 249
<212> TYPE: PRT
<213> ORGANISM: Artificial sequence
<220> FEATURE:
<223> OTHER INFORMATION: SC04-271

<400> SEQUENCE: 62

Glu Val Gln Leu Val Glu Thr Gly Ala Glu Val Lys Lys Pro Gly Glu
1               5                   10                  15

Ser Leu Arg Ile Ser Cys Lys Gly Ser Gly Tyr Thr Phe Asn Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Val
    50                  55                  60

Gln Gly His Val Thr Ile Ser Ala Asp Lys Ser Ile Asn Thr Ala Tyr
65                  70                  75                  80

Leu Gln Trp Ser Ser Leu Lys Ala Ser Asp Thr Ala Val Tyr Tyr Cys
                85                  90                  95

Ala Arg Arg Pro Gly Tyr Asp Tyr Gly Phe Tyr Tyr Phe Asp Tyr Trp
            100                 105                 110

Gly Gln Gly Thr Leu Val Thr Val Ser Ser Gly Thr Gly Gly Ser Gly
        115                 120                 125

Gly Thr Gly Ser Gly Thr Gly Gly Ser Thr Gln Ser Ala Leu Thr Gln
    130                 135                 140

Pro Arg Ser Val Ser Gly Ser Pro Gly Gln Ser Val Thr Ile Ser Cys
145                 150                 155                 160

Thr Gly Thr Ser Ser Asp Val Gly Gly Tyr Asn Tyr Val Ser Trp Tyr
                165                 170                 175

Gln His His Pro Gly Lys Ala Pro Lys Leu Met Ile Tyr Asp Val Ser
            180                 185                 190

Asn Arg Pro Leu Gly Val Ser Asn Arg Phe Ser Gly Ser Lys Ser Gly
        195                 200                 205

Asn Thr Ala Ser Leu Thr Ile Ser Gly Leu Gln Ala Glu Asp Glu Ala
    210                 215                 220

Asp Tyr Tyr Cys Ser Ser Tyr Thr Ser Ser Ser Thr Tyr Val Phe Gly
225                 230                 235                 240

Thr Gly Thr His Leu Thr Val Leu Ser
                245

<210> SEQ ID NO 63
<211> LENGTH: 780
```

```
<212> TYPE: DNA
<213> ORGANISM: Artificial sequence
<220> FEATURE:
<223> OTHER INFORMATION: SC04-274
<220> FEATURE:
<221> NAME/KEY: CDS
<222> LOCATION: (1)..(780)

<400> SEQUENCE: 63 cag gtc cag ctg gtg cag tct gga gca gag gtg aaa aag ccc ggg gag     48
Gln Val Gln Leu Val Gln Ser Gly Ala Glu Val Lys Lys Pro Gly Glu
1               5                   10                  15 tct ctg aag atc tcc tgt aag ggt tct gga tac agc ttt acc agc tac     96
Ser Leu Lys Ile Ser Cys Lys Gly Ser Gly Tyr Ser Phe Thr Ser Tyr
            20                  25                  30 tgg atc ggc tgg gtg cgc cag atg ccc ggg aaa ggc ctg gag tgg atg    144
Trp Ile Gly Trp Val Arg Gln Met Pro Gly Lys Gly Leu Glu Trp Met
        35                  40                  45 ggc atc atc tat cct ggt gac tct gat acc aga tac agc ccg tcc ttc    192
Gly Ile Ile Tyr Pro Gly Asp Ser Asp Thr Arg Tyr Ser Pro Ser Phe
    50                  55                  60 caa ggc cag gtc acc atc tca gcc gac agg tcc atc agc acc gcc tac    240
Gln Gly Gln Val Thr Ile Ser Ala Asp Arg Ser Ile Ser Thr Ala Tyr
65                  70                  75                  80 ctg cag tgg agc agc ctg aag gcc tcg gac acc gcc atg tat tac tgt    288
Leu Gln Trp Ser Ser Leu Lys Ala Ser Asp Thr Ala Met Tyr Tyr Cys
                85                  90                  95 gcg aga ctc cga ggc ccc tat tac gat ttt tgg aat ggc tat cgg gag    336
Ala Arg Leu Arg Gly Pro Tyr Tyr Asp Phe Trp Asn Gly Tyr Arg Glu
            100                 105                 110 aca cat gat gct ttt aat gtg tgg ggc caa ggg acc acg gtc acc gtc    384
Thr His Asp Ala Phe Asn Val Trp Gly Gln Gly Thr Thr Val Thr Val
        115                 120                 125 tcg agc ggt acg ggc ggt tca ggc gga acc ggc agc ggc act ggc ggg    432
Ser Ser Gly Thr Gly Gly Ser Gly Gly Thr Gly Ser Gly Thr Gly Gly
    130                 135                 140 tcg acg gac atc cag atg acc cag tct cca gac tcc ctg gct gtg tct    480
Ser Thr Asp Ile Gln Met Thr Gln Ser Pro Asp Ser Leu Ala Val Ser
145                 150                 155                 160 ctg ggc gag agg gcc acc atc aac tgc aag tcc agc cag agt gtt tta    528
Leu Gly Glu Arg Ala Thr Ile Asn Cys Lys Ser Ser Gln Ser Val Leu
                165                 170                 175 tac agc tcc aac aat aag aac tac tta gct tgg tac cag cag aaa cca    576
Tyr Ser Ser Asn Asn Lys Asn Tyr Leu Ala Trp Tyr Gln Gln Lys Pro
            180                 185                 190 gga cag cct cct aag ctg ctc att tac tgg gca tct acc cgg gaa tcc    624
Gly Gln Pro Pro Lys Leu Leu Ile Tyr Trp Ala Ser Thr Arg Glu Ser
        195                 200                 205 ggg gtc cct gac cga ttc agt ggc agc ggg tct ggg aca gat ttc act    672
Gly Val Pro Asp Arg Phe Ser Gly Ser Gly Ser Gly Thr Asp Phe Thr
    210                 215                 220 ctc acc atc agc agc ctg cag gct gaa gat gtg gca gtt tat tat tgt    720
Leu Thr Ile Ser Ser Leu Gln Ala Glu Asp Val Ala Val Tyr Tyr Cys
225                 230                 235                 240 cag caa tat tat agt act cct ccg act ttc ggc gga ggg acc aag gtg    768
Gln Gln Tyr Tyr Ser Thr Pro Pro Thr Phe Gly Gly Gly Thr Lys Val
                245                 250                 255 gag atc aaa cgt                                                     780
Glu Ile Lys Arg
            260
```

<210> SEQ ID NO 64
<211> LENGTH: 260
<212> TYPE: PRT
<213> ORGANISM: Artificial sequence
<220> FEATURE:
<223> OTHER INFORMATION: SC04-274

<400> SEQUENCE: 64

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Arg Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Arg Gly Pro Tyr Tyr Asp Phe Trp Asn Gly Tyr Arg Glu
            100                 105                 110

Thr His Asp Ala Phe Asn Val Trp Gly Gln Gly Thr Thr Val Thr Val
        115                 120                 125

Ser Ser Gly Thr Gly Gly Ser Gly Gly Thr Gly Ser Gly Thr Gly Gly
    130                 135                 140

Ser Thr Asp Ile Gln Met Thr Gln Ser Pro Asp Ser Leu Ala Val Ser
145                 150                 155                 160

Leu Gly Glu Arg Ala Thr Ile Asn Cys Lys Ser Ser Gln Ser Val Leu
                165                 170                 175

Tyr Ser Ser Asn Asn Lys Asn Tyr Leu Ala Trp Tyr Gln Gln Lys Pro
            180                 185                 190

Gly Gln Pro Pro Lys Leu Leu Ile Tyr Trp Ala Ser Thr Arg Glu Ser
        195                 200                 205

Gly Val Pro Asp Arg Phe Ser Gly Ser Gly Ser Gly Thr Asp Phe Thr
    210                 215                 220

Leu Thr Ile Ser Ser Leu Gln Ala Glu Asp Val Ala Val Tyr Tyr Cys
225                 230                 235                 240

Gln Gln Tyr Tyr Ser Thr Pro Pro Thr Phe Gly Gly Gly Thr Lys Val
                245                 250                 255

Glu Ile Lys Arg
            260
```

<210> SEQ ID NO 65
<211> LENGTH: 762
<212> TYPE: DNA
<213> ORGANISM: Artificial sequence
<220> FEATURE:
<223> OTHER INFORMATION: SC04-283
<220> FEATURE:
<221> NAME/KEY: CDS
<222> LOCATION: (1)..(762)

<400> SEQUENCE: 65

```
gaa gtg cag ctg gtg cag tct gga gca gag gtg aaa aag tcc ggg gag      48
Glu Val Gln Leu Val Gln Ser Gly Ala Glu Val Lys Lys Ser Gly Glu
1               5                   10                  15 tct ctg aag atc tcc tgt aag ggt tct gga tac acc ttt aat acc tac      96
Ser Leu Lys Ile Ser Cys Lys Gly Ser Gly Tyr Thr Phe Asn Thr Tyr
```

```
                 20                  25                  30
tgg atc ggc tgg gtg cgc cag atg ccc ggg aaa ggc ctg gag tgg atg      144
Trp Ile Gly Trp Val Arg Gln Met Pro Gly Lys Gly Leu Glu Trp Met
         35                  40                  45 ggg atc att tat cct ggt gac tct gat acc ata tac agc ccg tcc ttc      192
Gly Ile Ile Tyr Pro Gly Asp Ser Asp Thr Ile Tyr Ser Pro Ser Phe
 50                  55                  60 caa ggc cag gtc acc atc tca gcc gac aag tcc atc agc acc gcc tac      240
Gln Gly Gln Val Thr Ile Ser Ala Asp Lys Ser Ile Ser Thr Ala Tyr
65                  70                  75                  80 ctg cag tgg agc agc ctg aag gcc tcg gac agc gcc atg tat tac tgt      288
Leu Gln Trp Ser Ser Leu Lys Ala Ser Asp Ser Ala Met Tyr Tyr Cys
                 85                  90                  95 gcg aga ctt acc ttt cga cgt gga tat agt ggc tcc gat tcg ttt ctc      336
Ala Arg Leu Thr Phe Arg Arg Gly Tyr Ser Gly Ser Asp Ser Phe Leu
            100                 105                 110 cct ccg ggg gac ttt gac tac tgg ggc cag gga acc ctg gtc acc gtc      384
Pro Pro Gly Asp Phe Asp Tyr Trp Gly Gln Gly Thr Leu Val Thr Val
        115                 120                 125 tcg agc ggt acg ggc ggt tca ggc gga acc ggc agc ggc act ggc ggg      432
Ser Ser Gly Thr Gly Gly Ser Gly Gly Thr Gly Ser Gly Thr Gly Gly
    130                 135                 140 tcg acg gac atc cag atg acc cag tct cct tcc acc ctg tct gca tct      480
Ser Thr Asp Ile Gln Met Thr Gln Ser Pro Ser Thr Leu Ser Ala Ser
145                 150                 155                 160 gta gga gac aga gtc acc atc act tgc cgg gcc agt cag agt att agt      528
Val Gly Asp Arg Val Thr Ile Thr Cys Arg Ala Ser Gln Ser Ile Ser
                165                 170                 175 agc tgg ttg gcc tgg tat cag cag aaa cca ggg aaa gcc cct aat ctc      576
Ser Trp Leu Ala Trp Tyr Gln Gln Lys Pro Gly Lys Ala Pro Asn Leu
            180                 185                 190 ctg atc tat gct gca tcc agt ttg caa agt ggg gtc cca tca agg ttc      624
Leu Ile Tyr Ala Ala Ser Ser Leu Gln Ser Gly Val Pro Ser Arg Phe
        195                 200                 205 agc ggc agt gga tct ggg aca gat ttc act ctc acc atc agc agc ctg      672
Ser Gly Ser Gly Ser Gly Thr Asp Phe Thr Leu Thr Ile Ser Ser Leu
    210                 215                 220 cag cct gat gac tct gca act tat tac tgc caa cag tat aat act tat      720
Gln Pro Asp Asp Ser Ala Thr Tyr Tyr Cys Gln Gln Tyr Asn Thr Tyr
225                 230                 235                 240 ccc ctc act ttc ggc gga ggg acc aag gtg gaa atc aaa cgt              762
Pro Leu Thr Phe Gly Gly Gly Thr Lys Val Glu Ile Lys Arg
                245                 250

<210> SEQ ID NO 66
<211> LENGTH: 254
<212> TYPE: PRT
<213> ORGANISM: Artificial sequence
<220> FEATURE:
<223> OTHER INFORMATION: SC04-283

<400> SEQUENCE: 66

Glu Val Gln Leu Val Gln Ser Gly Ala Glu Val Lys Lys Ser Gly Glu
1               5                   10                  15

Ser Leu Lys Ile Ser Cys Lys Gly Ser Gly Tyr Thr Phe Asn Thr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Ile Tyr Ser Pro Ser Phe
    50                  55                  60
```

```
Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Ser Ala Met Tyr Tyr Cys
                 85                  90                  95

Ala Arg Leu Thr Phe Arg Arg Gly Tyr Ser Gly Ser Asp Ser Phe Leu
            100                 105                 110

Pro Pro Gly Asp Phe Asp Tyr Trp Gly Gln Gly Thr Leu Val Thr Val
            115                 120                 125

Ser Ser Gly Thr Gly Gly Ser Gly Gly Thr Gly Ser Gly Thr Gly Gly
    130                 135                 140

Ser Thr Asp Ile Gln Met Thr Gln Ser Pro Ser Thr Leu Ser Ala Ser
145                 150                 155                 160

Val Gly Asp Arg Val Thr Ile Thr Cys Arg Ala Ser Gln Ser Ile Ser
                165                 170                 175

Ser Trp Leu Ala Trp Tyr Gln Gln Lys Pro Gly Lys Ala Pro Asn Leu
            180                 185                 190

Leu Ile Tyr Ala Ala Ser Ser Leu Gln Ser Gly Val Pro Ser Arg Phe
        195                 200                 205

Ser Gly Ser Gly Ser Gly Thr Asp Phe Thr Leu Thr Ile Ser Ser Leu
    210                 215                 220

Gln Pro Asp Asp Ser Ala Thr Tyr Tyr Cys Gln Gln Tyr Asn Thr Tyr
225                 230                 235                 240

Pro Leu Thr Phe Gly Gly Gly Thr Lys Val Glu Ile Lys Arg
                245                 250

<210> SEQ ID NO 67
<211> LENGTH: 753
<212> TYPE: DNA
<213> ORGANISM: Artificial sequence
<220> FEATURE:
<223> OTHER INFORMATION: SC04-289
<220> FEATURE:
<221> NAME/KEY: CDS
<222> LOCATION: (1)..(753)

<400> SEQUENCE: 67 cag atg cag ctg gtg caa tct gga gca gag gtg aaa aag ccc ggg gag      48
Gln Met Gln Leu Val Gln Ser Gly Ala Glu Val Lys Lys Pro Gly Glu
1               5                   10                  15 tct ctg agg atc tcc tgt aag ggt tct gga tac agc ttt acc agt aac      96
Ser Leu Arg Ile Ser Cys Lys Gly Ser Gly Tyr Ser Phe Thr Ser Asn
            20                  25                  30 tgg atc acc tgg gtg cgc cag atg ccc ggg aaa ggc ctg gag tgg atg     144
Trp Ile Thr Trp Val Arg Gln Met Pro Gly Lys Gly Leu Glu Trp Met
        35                  40                  45 ggg agg att gat cct agt gac tct tat acc aac tac agc ccg tcc ttc     192
Gly Arg Ile Asp Pro Ser Asp Ser Tyr Thr Asn Tyr Ser Pro Ser Phe
    50                  55                  60 caa ggc cac gtc acc atc tca gct gac aag tcc atc agc act gcc tac     240
Gln Gly His Val Thr Ile Ser Ala Asp Lys Ser Ile Ser Thr Ala Tyr
65                  70                  75                  80 ctg cag tgg agc agc ctg aag gcc tcg gac acc gcc atg tat tac tgt     288
Leu Gln Trp Ser Ser Leu Lys Ala Ser Asp Thr Ala Met Tyr Tyr Cys
                85                  90                  95 gcg aga gac gta gtt ggg gtg gga gct tcc gac tac tat tac atg         336
Ala Arg Asp Val Val Gly Val Gly Ala Ser Asp Tyr Tyr Tyr Met
            100                 105                 110 gac gtc tgg ggc aaa ggg acc acg gtc acc gtc tcg agc ggt acg ggc     384
Asp Val Trp Gly Lys Gly Thr Thr Val Thr Val Ser Ser Gly Thr Gly
```

```
Asp Val Trp Gly Lys Gly Thr Thr Val Thr Val Ser Ser Gly Thr Gly
        115                 120                 125 ggt tca ggc gga acc ggc agc ggc act ggc ggg tcg acg gaa att gtg    432
Gly Ser Gly Gly Thr Gly Ser Gly Thr Gly Gly Ser Thr Glu Ile Val
        130                 135                 140 ttg acg cag tct cca ggc acc ctg tct ttg tct cca ggg gaa aca gcc    480
Leu Thr Gln Ser Pro Gly Thr Leu Ser Leu Ser Pro Gly Glu Thr Ala
145                 150                 155                 160 acc ctc tcc tgc agg acc agt cag agt gtt agt agc agc tac tta ggc    528
Thr Leu Ser Cys Arg Thr Ser Gln Ser Val Ser Ser Ser Tyr Leu Gly
                165                 170                 175 tgg tac cag cag aaa cct ggc cag gct ccc agg ctc ctc atc tat ggt    576
Trp Tyr Gln Gln Lys Pro Gly Gln Ala Pro Arg Leu Leu Ile Tyr Gly
            180                 185                 190 gca tcc atc agg gcc act ggc atc cca gcc agg ttc agt ggc agt ggg    624
Ala Ser Ile Arg Ala Thr Gly Ile Pro Ala Arg Phe Ser Gly Ser Gly
        195                 200                 205 tct ggg aca gag ttc act ctc acc atc gac agc cta cag tct gaa gat    672
Ser Gly Thr Glu Phe Thr Leu Thr Ile Asp Ser Leu Gln Ser Glu Asp
    210                 215                 220 ttt gca gtt tat tac tgt cag cag tat aat aac tgg cct ccg atc acc    720
Phe Ala Val Tyr Tyr Cys Gln Gln Tyr Asn Asn Trp Pro Pro Ile Thr
225                 230                 235                 240 ttc ggc caa ggg aca cga ctg gag att aaa cgt                        753
Phe Gly Gln Gly Thr Arg Leu Glu Ile Lys Arg
                245                 250

<210> SEQ ID NO 68
<211> LENGTH: 251
<212> TYPE: PRT
<213> ORGANISM: Artificial sequence
<220> FEATURE:
<223> OTHER INFORMATION: SC04-289

<400> SEQUENCE: 68

Gln Met Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Asn
                20                  25                  30

Trp Ile Thr Trp Val Arg Gln Met Pro Gly Lys Gly Leu Glu Trp Met
            35                  40                  45

Gly Arg Ile Asp Pro Ser Asp Ser Tyr Thr Asn Tyr Ser Pro Ser Phe
        50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Val Val Gly Val Gly Ala Ser Asp Tyr Tyr Tyr Met
                100                 105                 110

Asp Val Trp Gly Lys Gly Thr Thr Val Thr Val Ser Ser Gly Thr Gly
        115                 120                 125

Gly Ser Gly Gly Thr Gly Ser Gly Thr Gly Gly Ser Thr Glu Ile Val
        130                 135                 140

Leu Thr Gln Ser Pro Gly Thr Leu Ser Leu Ser Pro Gly Glu Thr Ala
145                 150                 155                 160

Thr Leu Ser Cys Arg Thr Ser Gln Ser Val Ser Ser Ser Tyr Leu Gly
                165                 170                 175

Trp Tyr Gln Gln Lys Pro Gly Gln Ala Pro Arg Leu Leu Ile Tyr Gly
```

|  |  | 180 |  |  |  | 185 |  |  |  | 190 |  |
|---|---|---|---|---|---|---|---|---|---|---|---|
| Ala | Ser | Ile | Arg | Ala | Thr | Gly | Ile | Pro | Ala | Arg | Phe | Ser | Gly | Ser | Gly |
|  |  | 195 |  |  |  | 200 |  |  |  | 205 |  |

Ser Gly Thr Glu Phe Thr Leu Thr Ile Asp Ser Leu Gln Ser Glu Asp
            210                     215                     220

Phe Ala Val Tyr Tyr Cys Gln Gln Tyr Asn Asn Trp Pro Pro Ile Thr
225                     230                     235                     240

Phe Gly Gln Gly Thr Arg Leu Glu Ile Lys Arg
                245                     250

<210> SEQ ID NO 69
<211> LENGTH: 753
<212> TYPE: DNA
<213> ORGANISM: Artificial sequence
<220> FEATURE:
<223> OTHER INFORMATION: SC04-299
<220> FEATURE:
<221> NAME/KEY: CDS
<222> LOCATION: (1)..(753)

<400> SEQUENCE: 69

```
gag gtg cag ctg gtg gag act ggg gga ggc gtg gtc cag cct ggg agg      48
Glu Val Gln Leu Val Glu Thr Gly Gly Gly Val Val Gln Pro Gly Arg
1               5                   10                  15 tcc ctg aga ctc tcc tgt gca gcc tct gga ttc acc ttc agt ggc tat      96
Ser Leu Arg Leu Ser Cys Ala Ala Ser Gly Phe Thr Phe Ser Gly Tyr
            20                  25                  30 gct atg cac tgg gtc cgc cag gct cca ggc aag ggg cta gac tgg gtg     144
Ala Met His Trp Val Arg Gln Ala Pro Gly Lys Gly Leu Asp Trp Val
        35                  40                  45 gca gtt ata tca tat gat gga agt gaa aaa tat tcc gcc gac tct gtg     192
Ala Val Ile Ser Tyr Asp Gly Ser Glu Lys Tyr Ser Ala Asp Ser Val
    50                  55                  60 aag ggc cgg ttc acc atc tcc aga gac aat tcc aag aac acg ctc tat     240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tat tgt     288
Leu Gln Met Asn Ser Leu Arg Ala Glu Asp Thr Ala Val Tyr Tyr Cys
                85                  90                  95 gcg aaa gag tcc ggg gga cct ata tgg tac aag tac tac ggc gtg gac     336
Ala Lys Glu Ser Gly Gly Pro Ile Trp Tyr Lys Tyr Tyr Gly Val Asp
            100                 105                 110 gtc tgg ggc caa ggg acc acg gtc acc gtc tcg agc ggt acg ggc ggt     384
Val Trp Gly Gln Gly Thr Thr Val Thr Val Ser Ser Gly Thr Gly Gly
        115                 120                 125 tca ggc gga acc ggc agc ggc act ggg tcg acg tcc tat gtg ctg         432
Ser Gly Gly Thr Gly Ser Gly Thr Gly Gly Ser Thr Ser Tyr Val Leu
    130                 135                 140 act cag cca ccc tcg ctg tct gca gcc ccc agg cag agg gtc acc atc     480
Thr Gln Pro Pro Ser Leu Ser Ala Ala Pro Arg Gln Arg Val Thr Ile
145                 150                 155                 160 tcc tgt tct gga agc agc tcc aat atc gga aat tat ggt gtg aac tgg     528
Ser Cys Ser Gly Ser Ser Ser Asn Ile Gly Asn Tyr Gly Val Asn Trp
                165                 170                 175 tac cag cag ctc cca gga aag gct ccc aaa ctc ctc atc tat tat gat     576
Tyr Gln Gln Leu Pro Gly Lys Ala Pro Lys Leu Leu Ile Tyr Tyr Asp
            180                 185                 190 gat ctg ctg ccc tca ggg gtc tct gac cga ttc tct ggc tcc aag tct     624
Asp Leu Leu Pro Ser Gly Val Ser Asp Arg Phe Ser Gly Ser Lys Ser
        195                 200                 205
```

-continued

```
ggc acc tca gcc tcc ctg gcc atc agt ggg ctc cag tct gag gat gaa    672
Gly Thr Ser Ala Ser Leu Ala Ile Ser Gly Leu Gln Ser Glu Asp Glu
        210                 215                 220 ggt gat tat tac tgt gca gcg tgg gat gac acc cta agt gct tgg gtg    720
Gly Asp Tyr Tyr Cys Ala Ala Trp Asp Asp Thr Leu Ser Ala Trp Val
225                 230                 235                 240 ttc ggc gga ggg acc aag ctg acc gtc cta ggt                        753
Phe Gly Gly Gly Thr Lys Leu Thr Val Leu Gly
                245                 250
```

<210> SEQ ID NO 70
<211> LENGTH: 251
<212> TYPE: PRT
<213> ORGANISM: Artificial sequence
<220> FEATURE:
<223> OTHER INFORMATION: SC04-299

<400> SEQUENCE: 70

```
Glu Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Ala Met His Trp Val Arg Gln Ala Pro Gly Lys Gly Leu Asp Trp Val
        35                  40                  45

Ala Val Ile Ser Tyr Asp Gly Ser Glu Lys Tyr Ser Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Ser Gly Gly Pro Ile Trp Tyr Lys Tyr Tyr Gly Val Asp
            100                 105                 110

Val Trp Gly Gln Gly Thr Thr Val Thr Val Ser Ser Gly Thr Gly Gly
        115                 120                 125

Ser Gly Gly Thr Gly Ser Gly Thr Gly Ser Thr Ser Tyr Val Leu
    130                 135                 140

Thr Gln Pro Pro Ser Leu Ser Ala Ala Pro Arg Gln Arg Val Thr Ile
145                 150                 155                 160

Ser Cys Ser Gly Ser Ser Asn Ile Gly Asn Tyr Gly Val Asn Trp
                165                 170                 175

Tyr Gln Gln Leu Pro Gly Lys Ala Pro Lys Leu Leu Ile Tyr Tyr Asp
            180                 185                 190

Asp Leu Leu Pro Ser Gly Val Ser Asp Arg Phe Ser Gly Ser Lys Ser
        195                 200                 205

Gly Thr Ser Ala Ser Leu Ala Ile Ser Gly Leu Gln Ser Glu Asp Glu
    210                 215                 220

Gly Asp Tyr Tyr Cys Ala Ala Trp Asp Asp Thr Leu Ser Ala Trp Val
225                 230                 235                 240

Phe Gly Gly Gly Thr Lys Leu Thr Val Leu Gly
                245                 250
```

<210> SEQ ID NO 71
<211> LENGTH: 738
<212> TYPE: DNA
<213> ORGANISM: Artificial sequence
<220> FEATURE:
<223> OTHER INFORMATION: SC04-311
<220> FEATURE:
<221> NAME/KEY: CDS

<222> LOCATION: (1)..(738)

<400> SEQUENCE: 71

| | | | | | | | | | | | | | | | | |
|---|---|---|---|---|---|---|---|---|---|---|---|---|---|---|---|---|
| gaa | gtg | cag | ctg | gtg | cag | tct | ggg | gga | ggc | gtg | gtc | cag | cct | ggc | agg | 48 |
| Glu | Val | Gln | Leu | Val | Gln | Ser | Gly | Gly | Gly | Val | Val | Gln | Pro | Gly | Arg | |
| 1 | | | | 5 | | | | | 10 | | | | | 15 | | |
| tcc | ctg | aga | ctc | tcc | tgt | gta | gcc | tct | gga | ttc | acc | ttc | agt | aag | gac | 96 |
| Ser | Leu | Arg | Leu | Ser | Cys | Val | Ala | Ser | Gly | Phe | Thr | Phe | Ser | Lys | Asp | |
| | | | 20 | | | | | 25 | | | | | 30 | | | |
| gct | atg | cac | tgg | gtc | cgc | cag | gct | cca | ggc | aag | ggg | cta | gag | tgg | gtg | 144 |
| Ala | Met | His | Trp | Val | Arg | Gln | Ala | Pro | Gly | Lys | Gly | Leu | Glu | Trp | Val | |
| | | 35 | | | | | 40 | | | | | 45 | | | | |
| gca | gtt | ata | tca | tat | gat | gga | agt | gat | aaa | cac | tac | gca | gac | tcc | gtg | 192 |
| Ala | Val | Ile | Ser | Tyr | Asp | Gly | Ser | Asp | Lys | His | Tyr | Ala | Asp | Ser | Val | |
| 50 | | | | | 55 | | | | | 60 | | | | | | |
| aag | ggc | cga | gtc | acc | atc | tcc | aga | gac | aat | tcc | agg | aaa | acg | ctg | tat | 240 |
| Lys | Gly | Arg | Val | Thr | Ile | Ser | Arg | Asp | Asn | Ser | Arg | Lys | Thr | Leu | Tyr | |
| 65 | | | | 70 | | | | | 75 | | | | | 80 | | |
| ctg | cga | atg | gac | agc | ctg | aga | gct | gag | gac | acg | gct | cta | tat | tac | tgt | 288 |
| Leu | Arg | Met | Asp | Ser | Leu | Arg | Ala | Glu | Asp | Thr | Ala | Leu | Tyr | Tyr | Cys | |
| | | | | 85 | | | | | 90 | | | | | 95 | | |
| gcg | aga | gga | tac | aac | tct | ggt | cat | tac | ttt | gac | tac | tgg | ggc | cag | gga | 336 |
| Ala | Arg | Gly | Tyr | Asn | Ser | Gly | His | Tyr | Phe | Asp | Tyr | Trp | Gly | Gln | Gly | |
| | | | 100 | | | | | 105 | | | | | 110 | | | |
| acc | ctg | atc | acc | gtc | tcg | agc | ggt | acg | ggc | ggt | tca | ggc | gga | acc | ggc | 384 |
| Thr | Leu | Ile | Thr | Val | Ser | Ser | Gly | Thr | Gly | Gly | Ser | Gly | Gly | Thr | Gly | |
| | | 115 | | | | | 120 | | | | | 125 | | | | |
| agc | ggc | act | ggc | ggg | tcg | acg | cag | tct | gtg | ctg | acg | cag | ccg | ccc | tca | 432 |
| Ser | Gly | Thr | Gly | Gly | Ser | Thr | Gln | Ser | Val | Leu | Thr | Gln | Pro | Pro | Ser | |
| 130 | | | | | 135 | | | | | 140 | | | | | | |
| gtg | tct | gcg | gcc | cca | gga | cag | aag | gtc | acc | atc | tcc | tgc | tct | gga | acc | 480 |
| Val | Ser | Ala | Ala | Pro | Gly | Gln | Lys | Val | Thr | Ile | Ser | Cys | Ser | Gly | Thr | |
| 145 | | | | | 150 | | | | | 155 | | | | | 160 | |
| agc | tcc | aat | att | ggg | gat | aat | tat | gta | tcc | tgg | tac | cag | cac | ctc | cca | 528 |
| Ser | Ser | Asn | Ile | Gly | Asp | Asn | Tyr | Val | Ser | Trp | Tyr | Gln | His | Leu | Pro | |
| | | | | 165 | | | | | 170 | | | | | 175 | | |
| gga | aca | gcc | ccc | aaa | ctc | ctc | att | tat | gac | aat | aat | aag | cga | ccc | tca | 576 |
| Gly | Thr | Ala | Pro | Lys | Leu | Leu | Ile | Tyr | Asp | Asn | Asn | Lys | Arg | Pro | Ser | |
| | | | 180 | | | | | 185 | | | | | 190 | | | |
| ggg | att | cct | gac | cga | ttc | tct | ggc | tcc | aag | tct | ggc | acg | tca | gcc | acc | 624 |
| Gly | Ile | Pro | Asp | Arg | Phe | Ser | Gly | Ser | Lys | Ser | Gly | Thr | Ser | Ala | Thr | |
| | | 195 | | | | | 200 | | | | | 205 | | | | |
| ctg | ggc | gtc | acc | gga | ctc | cag | act | ggg | gac | gag | gcc | gat | tat | tac | tgc | 672 |
| Leu | Gly | Val | Thr | Gly | Leu | Gln | Thr | Gly | Asp | Glu | Ala | Asp | Tyr | Tyr | Cys | |
| 210 | | | | | 215 | | | | | 220 | | | | | | |
| gga | aca | tgg | gat | agc | agc | ctg | act | gct | gtg | gtc | ttc | ggc | gga | ggg | acc | 720 |
| Gly | Thr | Trp | Asp | Ser | Ser | Leu | Thr | Ala | Val | Val | Phe | Gly | Gly | Gly | Thr | |
| 225 | | | | | 230 | | | | | 235 | | | | | 240 | |
| aag | ctg | acc | gtc | cta | ggt | | | | | | | | | | | 738 |
| Lys | Leu | Thr | Val | Leu | Gly | | | | | | | | | | | |
| | | | | 245 | | | | | | | | | | | | |

<210> SEQ ID NO 72
<211> LENGTH: 246
<212> TYPE: PRT
<213> ORGANISM: Artificial sequence
<220> FEATURE:
<223> OTHER INFORMATION: SC04-311

<400> SEQUENCE: 72

Glu Val Gln Leu Val Gln Ser Gly Gly Gly Val Val Gln Pro Gly Arg

```
                1               5                      10                      15
          Ser Leu Arg Leu Ser Cys Val Ala Ser Gly Phe Thr Phe Ser Lys Asp
                          20                      25                      30

Ala Met His Trp Val Arg Gln Ala Pro Gly Lys Gly Leu Glu Trp Val
                      35                      40                      45

Ala Val Ile Ser Tyr Asp Gly Ser Asp Lys His Tyr Ala Asp Ser Val
                  50                      55                      60

Lys Gly Arg Val Thr Ile Ser Arg Asp Asn Ser Arg Lys Thr Leu Tyr
          65                      70                      75                      80

Leu Arg Met Asp Ser Leu Arg Ala Glu Asp Thr Ala Leu Tyr Tyr Cys
                          85                      90                      95

Ala Arg Gly Tyr Asn Ser Gly His Tyr Phe Asp Tyr Trp Gly Gln Gly
                          100                     105                     110

Thr Leu Ile Thr Val Ser Ser Gly Thr Gly Ser Gly Gly Thr Gly
                      115                     120                     125

Ser Gly Thr Gly Gly Ser Thr Gln Ser Val Leu Thr Gln Pro Pro Ser
                      130                     135                     140

Val Ser Ala Ala Pro Gly Gln Lys Val Thr Ile Ser Cys Ser Gly Thr
          145                     150                     155                     160

Ser Ser Asn Ile Gly Asp Asn Tyr Val Ser Trp Tyr Gln His Leu Pro
                          165                     170                     175

Gly Thr Ala Pro Lys Leu Leu Ile Tyr Asp Asn Asn Lys Arg Pro Ser
                          180                     185                     190

Gly Ile Pro Asp Arg Phe Ser Gly Ser Lys Ser Gly Thr Ser Ala Thr
                          195                     200                     205

Leu Gly Val Thr Gly Leu Gln Thr Gly Asp Glu Ala Asp Tyr Tyr Cys
                      210                     215                     220

Gly Thr Trp Asp Ser Ser Leu Thr Ala Val Val Phe Gly Gly Gly Thr
          225                     230                     235                     240

Lys Leu Thr Val Leu Gly
                          245
```

<210> SEQ ID NO 73
<211> LENGTH: 741
<212> TYPE: DNA
<213> ORGANISM: Artificial sequence
<220> FEATURE:
<223> OTHER INFORMATION: SC04-325
<220> FEATURE:
<221> NAME/KEY: CDS
<222> LOCATION: (1)..(741)

<400> SEQUENCE: 73

```
cag atg cag ctg gtg cag tct ggg gct gag gtg aag aag cct ggg tcc         48
Gln Met Gln Leu Val Gln Ser Gly Ala Glu Val Lys Lys Pro Gly Ser
1               5                   10                  15 tcg gtg aag gtc tcc tgc aag gct tct gga gac acc ttc agc agt tat         96
Ser Val Lys Val Ser Cys Lys Ala Ser Gly Asp Thr Phe Ser Ser Tyr
                20                  25                  30 gct atc agc tgg gtg cga cag gcc cct gga caa ggg ctt gag tgg atg        144
Ala Ile Ser Trp Val Arg Gln Ala Pro Gly Gln Gly Leu Glu Trp Met
            35                  40                  45 gga ggg atc ttt ggt aca gca agc tac gca cag aag ttc cag ggc aga        192
Gly Gly Ile Phe Gly Thr Ala Ser Tyr Ala Gln Lys Phe Gln Gly Arg
        50                  55                  60 gtc acg att acc gcg gac gaa tcc acg agc aca gcc tac atg gag ctg        240
Val Thr Ile Thr Ala Asp Glu Ser Thr Ser Thr Ala Tyr Met Glu Leu
65                  70                  75                  80
```

```
agc agc ctg aga tct gag gac acg gcc gtg tat tac tgt gcg aga gga      288
Ser Ser Leu Arg Ser Glu Asp Thr Ala Val Tyr Tyr Cys Ala Arg Gly
                85                  90                  95 ggg atg gct aca aca ccg gga ctt gac tac tgg ggc cag gga acc ctg      336
Gly Met Ala Thr Thr Pro Gly Leu Asp Tyr Trp Gly Gln Gly Thr Leu
            100                 105                 110 gtc acc gtc tcg agc ggt acg ggc ggt tca ggc gga acc ggc agc ggc      384
Val Thr Val Ser Ser Gly Thr Gly Gly Ser Gly Gly Thr Gly Ser Gly
        115                 120                 125 act ggg tcg acg gac atc cag ttg acc cag tct cca gac tcc ctg          432
Thr Gly Ser Thr Asp Ile Gln Leu Thr Gln Ser Pro Asp Ser Leu
    130                 135                 140 gct gtg tct ctg ggc gag agg gcc acc atc aac tgc aag tcc agc cag      480
Ala Val Ser Leu Gly Glu Arg Ala Thr Ile Asn Cys Lys Ser Ser Gln
145                 150                 155                 160 agt gtt tta tac agc tcc aac aat aag aac tac tta gct tgg tac cag      528
Ser Val Leu Tyr Ser Ser Asn Asn Lys Asn Tyr Leu Ala Trp Tyr Gln
                165                 170                 175 cag aaa cca gga cag cct cct aag ctg ctc att tac tgg gca tct acc      576
Gln Lys Pro Gly Gln Pro Pro Lys Leu Leu Ile Tyr Trp Ala Ser Thr
            180                 185                 190 cgg gaa tcc ggg gtc cct gac cga ttc agt ggc agc ggg tct ggg aca      624
Arg Glu Ser Gly Val Pro Asp Arg Phe Ser Gly Ser Gly Ser Gly Thr
        195                 200                 205 gat ttc act ctc acc atc agc agc ctg cag gct gaa gat gtg gca gtt      672
Asp Phe Thr Leu Thr Ile Ser Ser Leu Gln Ala Glu Asp Val Ala Val
    210                 215                 220 tat tac tgt cag caa tat tat agt acc ccg ttg acg ttc ggc caa ggg      720
Tyr Tyr Cys Gln Gln Tyr Tyr Ser Thr Pro Leu Thr Phe Gly Gln Gly
225                 230                 235                 240 acc aag gtg gag atc aaa cgt                                          741
Thr Lys Val Glu Ile Lys Arg
                245

<210> SEQ ID NO 74
<211> LENGTH: 247
<212> TYPE: PRT
<213> ORGANISM: Artificial sequence
<220> FEATURE:
<223> OTHER INFORMATION: SC04-325

<400> SEQUENCE: 74

Gln Met Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Phe Gly Thr Ala Ser Tyr Ala Gln Lys Phe Gln Gly Arg
    50                  55                  60

Val Thr Ile Thr Ala Asp Glu Ser Thr Ser Thr Ala Tyr Met Glu Leu
65                  70                  75                  80

Ser Ser Leu Arg Ser Glu Asp Thr Ala Val Tyr Tyr Cys Ala Arg Gly
                85                  90                  95

Gly Met Ala Thr Thr Pro Gly Leu Asp Tyr Trp Gly Gln Gly Thr Leu
            100                 105                 110

Val Thr Val Ser Ser Gly Thr Gly Gly Ser Gly Gly Thr Gly Ser Gly
        115                 120                 125
```

-continued

```
Thr Gly Gly Ser Thr Asp Ile Gln Leu Thr Gln Ser Pro Asp Ser Leu
        130                 135                 140

Ala Val Ser Leu Gly Glu Arg Ala Thr Ile Asn Cys Lys Ser Ser Gln
145                 150                 155                 160

Ser Val Leu Tyr Ser Ser Asn Asn Lys Asn Tyr Leu Ala Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Gln Gln Tyr Tyr Ser Thr Pro Leu Thr Phe Gly Gln Gly
225                 230                 235                 240

Thr Lys Val Glu Ile Lys Arg
                245
```

<210> SEQ ID NO 75
<211> LENGTH: 753
<212> TYPE: DNA
<213> ORGANISM: Artificial sequence
<220> FEATURE:
<223> OTHER INFORMATION: SC04-353
<220> FEATURE:
<221> NAME/KEY: CDS
<222> LOCATION: (1)..(753)

<400> SEQUENCE: 75

```
gaa gtg cag ctg gtg cag tct ggg gga ggc gtg gtc cag cct ggg agg    48
Glu Val Gln Leu Val Gln Ser Gly Gly Gly Val Val Gln Pro Gly Arg
1               5                   10                  15 tcc ctg aga ctc tcc tgt gca gcc tct gga ttc acc ttc agt aat tat    96
Ser Leu Arg Leu Ser Cys Ala Ala Ser Gly Phe Thr Phe Ser Asn Tyr
            20                  25                  30 gct atg cac tgg gtc cgc cag gct cca ggc aag ggg cta gag tgg gtg   144
Ala Met His Trp Val Arg Gln Ala Pro Gly Lys Gly Leu Glu Trp Val
        35                  40                  45 gca gtt ata tca tat gat gga ggt aat aaa tac tac gca gac tcc gtg   192
Ala Val Ile Ser Tyr Asp Gly Gly Asn Lys Tyr Tyr Ala Asp Ser Val
    50                  55                  60 aag ggc cga ttc acc atg tcc aga gac aat tcc aag aac acg ctg tat   240
Lys Gly Arg Phe Thr Met Ser Arg Asp Asn Ser Lys Asn Thr Leu Tyr
65                  70                  75                  80 ctg caa atg aac agc ctg aga gct gag gac acg gct gtg tat tat tgt   288
Leu Gln Met Asn Ser Leu Arg Ala Glu Asp Thr Ala Val Tyr Tyr Cys
                85                  90                  95 gcg aga gat ttt tgg agt ggt tac tca atg gta gac tcc tac tac tac   336
Ala Arg Asp Phe Trp Ser Gly Tyr Ser Met Val Asp Ser Tyr Tyr Tyr
            100                 105                 110 tac atg gac gtg tgg ggc aag ggg acc acg gtc acc gtc tcg agc ggt   384
Tyr Met Asp Val Trp Gly Lys Gly Thr Thr Val Thr Val Ser Ser Gly
        115                 120                 125 acg ggc ggt tca ggc gga acc ggc agc ggc act ggc ggg tcg acg gaa   432
Thr Gly Gly Ser Gly Gly Thr Gly Ser Gly Thr Gly Gly Ser Thr Glu
    130                 135                 140 acg aca ctc acg cag tcc cca ggc acc ctg tct ttg tct ccc ggg gaa   480
Thr Thr Leu Thr Gln Ser Pro Gly Thr Leu Ser Leu Ser Pro Gly Glu
145                 150                 155                 160 aga gcc acc ctc tcc tgc aga gcc agt cag agt gtt agc aac acc ttc   528
Arg Ala Thr Leu Ser Cys Arg Ala Ser Gln Ser Val Ser Asn Thr Phe
```

```
                        165                 170                 175
tta gcc tgg tac cag cag aaa cct ggc cag gct ccc agg ctc ctc atc         576
Leu Ala Trp Tyr Gln Gln Lys Pro Gly Gln Ala Pro Arg Leu Leu Ile
            180                 185                 190 tat ggt gca tcc agc agg gcc act ggc atc cca gac agg ttc agt ggc         624
Tyr Gly Ala Ser Ser Arg Ala Thr Gly Ile Pro Asp Arg Phe Ser Gly
            195                 200                 205 agt ggg tct ggg aca gac ttc act ctc acc atc agc aga ctg gag cct         672
Ser Gly Ser Gly Thr Asp Phe Thr Leu Thr Ile Ser Arg Leu Glu Pro
        210                 215                 220 gaa gat ttt gca gcg tat tac tgt cag cag tat ggt agc tcg ctc act         720
Glu Asp Phe Ala Ala Tyr Tyr Cys Gln Gln Tyr Gly Ser Ser Leu Thr
225                 230                 235                 240 ttc ggc cct ggg acc aaa gtg gat atc aaa cgt                             753
Phe Gly Pro Gly Thr Lys Val Asp Ile Lys Arg
                    245                 250

<210> SEQ ID NO 76
<211> LENGTH: 251
<212> TYPE: PRT
<213> ORGANISM: Artificial sequence
<220> FEATURE:
<223> OTHER INFORMATION: SC04-353

<400> SEQUENCE: 76

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Asn Lys Tyr Tyr Ala Asp Ser Val
    50                  55                  60

Lys Gly Arg Phe Thr Met Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Trp Ser Gly Tyr Ser Met Val Asp Ser Tyr Tyr Tyr
            100                 105                 110

Tyr Met Asp Val Trp Gly Lys Gly Thr Thr Val Thr Val Ser Ser Gly
        115                 120                 125

Thr Gly Gly Ser Gly Gly Thr Gly Ser Gly Thr Gly Gly Ser Thr Glu
    130                 135                 140

Thr Thr Leu Thr Gln Ser Pro Gly Thr Leu Ser Leu Ser Pro Gly Glu
145                 150                 155                 160

Arg Ala Thr Leu Ser Cys Arg Ala Ser Gln Ser Val Ser Asn Thr Phe
                165                 170                 175

Leu Ala Trp Tyr Gln Gln Lys Pro Gly Gln Ala Pro Arg Leu Leu Ile
            180                 185                 190

Tyr Gly Ala Ser Ser Arg Ala Thr Gly Ile Pro Asp Arg Phe Ser Gly
        195                 200                 205

Ser Gly Ser Gly Thr Asp Phe Thr Leu Thr Ile Ser Arg Leu Glu Pro
    210                 215                 220

Glu Asp Phe Ala Ala Tyr Tyr Cys Gln Gln Tyr Gly Ser Ser Leu Thr
225                 230                 235                 240

Phe Gly Pro Gly Thr Lys Val Asp Ile Lys Arg
                    245                 250
```

<210> SEQ ID NO 77
<211> LENGTH: 780
<212> TYPE: DNA
<213> ORGANISM: Artificial sequence
<220> FEATURE:
<223> OTHER INFORMATION: SC04-361
<220> FEATURE:
<221> NAME/KEY: CDS
<222> LOCATION: (1)..(780)

<400> SEQUENCE: 77

| | | | | | | | | | | | | | | | | |
|---|---|---|---|---|---|---|---|---|---|---|---|---|---|---|---|---|
| gag | gtc | cag | ctg | gta | cag | tct | gga | gca | gaa | gtg | aaa | aag | ccc | ggg | gag | 48 |
| Glu | Val | Gln | Leu | Val | Gln | Ser | Gly | Ala | Glu | Val | Lys | Lys | Pro | Gly | Glu | |
| 1 | | | | 5 | | | | | 10 | | | | | 15 | | |
| tct | ctg | aag | atc | tcc | tgt | aag | gcc | tct | gga | ttc | agc | ttt | agc | acc | tat | 96 |
| Ser | Leu | Lys | Ile | Ser | Cys | Lys | Ala | Ser | Gly | Phe | Ser | Phe | Ser | Thr | Tyr | |
| | | | 20 | | | | | 25 | | | | | 30 | | | |
| tgg | atc | ggc | tgg | gta | cgc | cag | atg | ccc | ggg | aaa | ggc | ctg | gag | tgg | atg | 144 |
| Trp | Ile | Gly | Trp | Val | Arg | Gln | Met | Pro | Gly | Lys | Gly | Leu | Glu | Trp | Met | |
| | | 35 | | | | | 40 | | | | | 45 | | | | |
| ggg | atc | atc | tat | cct | gct | gac | tct | gat | acc | aga | tac | agc | ccg | tcc | ttc | 192 |
| Gly | Ile | Ile | Tyr | Pro | Ala | Asp | Ser | Asp | Thr | Arg | Tyr | Ser | Pro | Ser | Phe | |
| 50 | | | | | 55 | | | | | 60 | | | | | | |
| caa | ggc | cag | gtc | acc | atc | tca | gcc | gac | aag | tcc | atc | agc | acc | gcc | tac | 240 |
| Gln | Gly | Gln | Val | Thr | Ile | Ser | Ala | Asp | Lys | Ser | Ile | Ser | Thr | Ala | Tyr | |
| 65 | | | | | 70 | | | | | 75 | | | | | 80 | |
| ctg | cag | tgg | agc | agc | ctg | aag | gcc | tcg | gac | acc | gcc | atg | tat | tac | tgt | 288 |
| Leu | Gln | Trp | Ser | Ser | Leu | Lys | Ala | Ser | Asp | Thr | Ala | Met | Tyr | Tyr | Cys | |
| | | | | 85 | | | | | 90 | | | | | 95 | | |
| gcg | aga | ctc | cga | ggc | ccc | tat | tac | gat | ttt | tgg | aat | ggc | tat | cgg | gag | 336 |
| Ala | Arg | Leu | Arg | Gly | Pro | Tyr | Tyr | Asp | Phe | Trp | Asn | Gly | Tyr | Arg | Glu | |
| | | | 100 | | | | | 105 | | | | | 110 | | | |
| aca | cat | gat | gct | ttt | aat | gtg | tgg | ggc | caa | ggg | aca | atg | gtc | acc | gtc | 384 |
| Thr | His | Asp | Ala | Phe | Asn | Val | Trp | Gly | Gln | Gly | Thr | Met | Val | Thr | Val | |
| | | 115 | | | | | 120 | | | | | 125 | | | | |
| tcg | agc | ggt | acg | ggc | ggt | tca | ggc | gga | acc | ggc | agc | ggc | act | ggc | ggg | 432 |
| Ser | Ser | Gly | Thr | Gly | Gly | Ser | Gly | Gly | Thr | Gly | Ser | Gly | Thr | Gly | Gly | |
| 130 | | | | | 135 | | | | | 140 | | | | | | |
| tcg | acg | gat | gtt | gtg | atg | act | cag | tct | cca | gac | tcc | ctg | gct | gtg | tct | 480 |
| Ser | Thr | Asp | Val | Val | Met | Thr | Gln | Ser | Pro | Asp | Ser | Leu | Ala | Val | Ser | |
| 145 | | | | | 150 | | | | | 155 | | | | | 160 | |
| ctg | ggc | gag | agg | gcc | acc | atc | aac | tgc | aag | tcc | agc | cag | aat | att | tta | 528 |
| Leu | Gly | Glu | Arg | Ala | Thr | Ile | Asn | Cys | Lys | Ser | Ser | Gln | Asn | Ile | Leu | |
| | | | | 165 | | | | | 170 | | | | | 175 | | |
| gac | aac | tcc | gac | aat | aag | aac | ttc | tta | gct | tgg | tac | cag | cag | aaa | cca | 576 |
| Asp | Asn | Ser | Asp | Asn | Lys | Asn | Phe | Leu | Ala | Trp | Tyr | Gln | Gln | Lys | Pro | |
| | | | 180 | | | | | 185 | | | | | 190 | | | |
| gga | cag | cct | cct | aaa | ttg | ctc | att | tac | tgg | gca | tct | gcc | cgg | gag | tcc | 624 |
| Gly | Gln | Pro | Pro | Lys | Leu | Leu | Ile | Tyr | Trp | Ala | Ser | Ala | Arg | Glu | Ser | |
| | | 195 | | | | | 200 | | | | | 205 | | | | |
| ggg | gtc | cct | gac | cga | ttc | agt | ggc | agc | ggg | tct | ggg | aca | gat | ttc | act | 672 |
| Gly | Val | Pro | Asp | Arg | Phe | Ser | Gly | Ser | Gly | Ser | Gly | Thr | Asp | Phe | Thr | |
| | 210 | | | | | 215 | | | | | 220 | | | | | |
| ctc | acc | atc | agc | agc | ctg | cag | gct | gaa | gat | gtg | gca | ctt | tat | tac | tgt | 720 |
| Leu | Thr | Ile | Ser | Ser | Leu | Gln | Ala | Glu | Asp | Val | Ala | Leu | Tyr | Tyr | Cys | |
| 225 | | | | | 230 | | | | | 235 | | | | | 240 | |
| cag | caa | tat | tat | aat | act | ccc | atc | acc | ttc | ggt | caa | ggg | aca | cga | ctg | 768 |
| Gln | Gln | Tyr | Tyr | Asn | Thr | Pro | Ile | Thr | Phe | Gly | Gln | Gly | Thr | Arg | Leu | |
| | | | | 245 | | | | | 250 | | | | | 255 | | |
| gag | att | aaa | cgt | | | | | | | | | | | | | 780 |

```
Glu Ile Lys Arg
            260

<210> SEQ ID NO 78
<211> LENGTH: 260
<212> TYPE: PRT
<213> ORGANISM: Artificial sequence
<220> FEATURE:
<223> OTHER INFORMATION: SC04-361

<400> SEQUENCE: 78

Glu Val Gln Leu Val Gln Ser Gly Ala Glu Val Lys Lys Pro Gly Glu
1               5                   10                  15

Ser Leu Lys Ile Ser Cys Lys Ala Ser Gly Phe Ser Phe Ser Thr Tyr
            20                  25                  30

Trp Ile Gly Trp Val Arg Gln Met Pro Gly Lys Gly Leu Glu Trp Met
        35                  40                  45

Gly Ile Ile Tyr Pro Ala Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Arg Gly Pro Tyr Tyr Asp Phe Trp Asn Gly Tyr Arg Glu
            100                 105                 110

Thr His Asp Ala Phe Asn Val Trp Gly Gln Gly Thr Met Val Thr Val
        115                 120                 125

Ser Ser Gly Thr Gly Gly Ser Gly Gly Thr Gly Ser Gly Thr Gly Gly
    130                 135                 140

Ser Thr Asp Val Val Met Thr Gln Ser Pro Asp Ser Leu Ala Val Ser
145                 150                 155                 160

Leu Gly Glu Arg Ala Thr Ile Asn Cys Lys Ser Ser Gln Asn Ile Leu
                165                 170                 175

Asp Asn Ser Asp Asn Lys Asn Phe Leu Ala Trp Tyr Gln Gln Lys Pro
            180                 185                 190

Gly Gln Pro Pro Lys Leu Leu Ile Tyr Trp Ala Ser Ala Arg Glu Ser
        195                 200                 205

Gly Val Pro Asp Arg Phe Ser Gly Ser Gly Ser Gly Thr Asp Phe Thr
    210                 215                 220

Leu Thr Ile Ser Ser Leu Gln Ala Glu Asp Val Ala Leu Tyr Tyr Cys
225                 230                 235                 240

Gln Gln Tyr Tyr Asn Thr Pro Ile Thr Phe Gly Gln Gly Thr Arg Leu
                245                 250                 255

Glu Ile Lys Arg
            260

<210> SEQ ID NO 79
<211> LENGTH: 774
<212> TYPE: DNA
<213> ORGANISM: Artificial sequence
<220> FEATURE:
<223> OTHER INFORMATION: SC04-374
<220> FEATURE:
<221> NAME/KEY: CDS
<222> LOCATION: (1)..(774)

<400> SEQUENCE: 79 cag gtc acc ttg aag gag tct ggt cct acg ctg gtg aaa ccc aca cag    48
Gln Val Thr Leu Lys Glu Ser Gly Pro Thr Leu Val Lys Pro Thr Gln
```

```
                  1               5               10              15
acc ctc acg ttg acc tgc acc ttc tct ggg ttc tca ctc agc act agt     96
Thr Leu Thr Leu Thr Cys Thr Phe Ser Gly Phe Ser Leu Ser Thr Ser
                20              25              30 gga gtg ggt gtg ggc tgg atc cgt cag ccc cca gga aag gcc ctg gag    144
Gly Val Gly Val Gly Trp Ile Arg Gln Pro Pro Gly Lys Ala Leu Glu
            35              40              45 tgg ctt gca gtc att tat tgg aat gat gat aag ctc tac agg cca tct    192
Trp Leu Ala Val Ile Tyr Trp Asn Asp Asp Lys Leu Tyr Arg Pro Ser
        50              55              60 ctg aag agc agg ctc acc atc acc aag gac acc tcc aaa aac cag gtg    240
Leu Lys Ser Arg Leu Thr Ile Thr Lys Asp Thr Ser Lys Asn Gln Val
65              70              75              80 gtc ctt aca atg acc aag atg gac cct gtg gac aca gcc aca tat tac    288
Val Leu Thr Met Thr Lys Met Asp Pro Val Asp Thr Ala Thr Tyr Tyr
                85              90              95 tgt gca cac aga cac cgt tac tat gat att agt ggt tat tac cgt ctc    336
Cys Ala His Arg His Arg Tyr Tyr Asp Ile Ser Gly Tyr Tyr Arg Leu
            100             105             110 ttc tct gat gct ttt gat atc tgg ggc caa ggg aca atg gtc acc gtc    384
Phe Ser Asp Ala Phe Asp Ile Trp Gly Gln Gly Thr Met Val Thr Val
        115             120             125 tcg agc ggt acg ggc ggt tca ggc gga acc ggc agc ggc act ggc ggg    432
Ser Ser Gly Thr Gly Gly Ser Gly Gly Thr Gly Ser Gly Thr Gly Gly
    130             135             140 tcg acg cag tct gtc gtg acg cag ccg ccc tca gtg tct ggg gcc cca    480
Ser Thr Gln Ser Val Val Thr Gln Pro Pro Ser Val Ser Gly Ala Pro
145             150             155             160 ggg cag agg gtc acc atc tcc tgc act ggg agc agc tcc aac atc ggg    528
Gly Gln Arg Val Thr Ile Ser Cys Thr Gly Ser Ser Ser Asn Ile Gly
                165             170             175 gca ggt tat gat gta cac tgg tac cag cag ctt cca gga aca gcc ccc    576
Ala Gly Tyr Asp Val His Trp Tyr Gln Gln Leu Pro Gly Thr Ala Pro
            180             185             190 aaa ctc ctc atc tat ggt aac agc aat cgg ccc tca ggg gtc cct gac    624
Lys Leu Leu Ile Tyr Gly Asn Ser Asn Arg Pro Ser Gly Val Pro Asp
        195             200             205 cga ttc tct ggc tcc aag tct ggc acc tca gcc tcc ctg gcc atc act    672
Arg Phe Ser Gly Ser Lys Ser Gly Thr Ser Ala Ser Leu Ala Ile Thr
    210             215             220 ggg ctc cag gct gag gat gag gct gat tat tac tgc cag tcc tat gac    720
Gly Leu Gln Ala Glu Asp Glu Ala Asp Tyr Tyr Cys Gln Ser Tyr Asp
225             230             235             240 agc agc ttg agt ggt tcg gtg ttc ggc gga ggg acc aag ctg acc gtc    768
Ser Ser Leu Ser Gly Ser Val Phe Gly Gly Gly Thr Lys Leu Thr Val
                245             250             255 cta ggt                                                             774
Leu Gly
```

<210> SEQ ID NO 80
<211> LENGTH: 258
<212> TYPE: PRT
<213> ORGANISM: Artificial sequence
<220> FEATURE:
<223> OTHER INFORMATION: SC04-374

<400> SEQUENCE: 80

```
Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
```

```
                20                  25                  30
Gly Val Gly Val Gly Trp Ile Arg Gln Pro Pro Gly Lys Ala Leu Glu
            35                  40                  45

Trp Leu Ala Val Ile Tyr Trp Asn Asp Asp Lys Leu Tyr Arg Pro Ser
 50                  55                  60

Leu Lys Ser Arg Leu Thr Ile Thr Lys Asp Thr Ser Lys Asn Gln Val
 65                  70                  75                  80

Val Leu Thr Met Thr Lys Met Asp Pro Val Asp Thr Ala Thr Tyr Tyr
                85                  90                  95

Cys Ala His Arg His Arg Tyr Tyr Asp Ile Ser Gly Tyr Tyr Arg Leu
                100                 105                 110

Phe Ser Asp Ala Phe Asp Ile Trp Gly Gln Gly Thr Met Val Thr Val
                115                 120                 125

Ser Ser Gly Thr Gly Gly Ser Gly Gly Thr Gly Ser Gly Thr Gly Gly
                130                 135                 140

Ser Thr Gln Ser Val Val Thr Gln Pro Pro Ser Val Ser Gly Ala Pro
145                 150                 155                 160

Gly Gln Arg Val Thr Ile Ser Cys Thr Gly Ser Ser Asn Ile Gly
                165                 170                 175

Ala Gly Tyr Asp Val His Trp Tyr Gln Gln Leu Pro Gly Thr Ala Pro
                180                 185                 190

Lys Leu Leu Ile Tyr Gly Asn Ser Asn Arg Pro Ser Gly Val Pro Asp
                195                 200                 205

Arg Phe Ser Gly Ser Lys Ser Gly Thr Ser Ala Ser Leu Ala Ile Thr
210                 215                 220

Gly Leu Gln Ala Glu Asp Glu Ala Asp Tyr Tyr Cys Gln Ser Tyr Asp
225                 230                 235                 240

Ser Ser Leu Ser Gly Ser Val Phe Gly Gly Gly Thr Lys Leu Thr Val
                245                 250                 255

Leu Gly
```

<210> SEQ ID NO 81
<211> LENGTH: 24
<212> TYPE: DNA
<213> ORGANISM: Artificial sequence
<220> FEATURE:
<223> OTHER INFORMATION: Primer HuCkappa

<400> SEQUENCE: 81
acactctccc ctgttgaagc tctt                                    24

<210> SEQ ID NO 82
<211> LENGTH: 23
<212> TYPE: DNA
<213> ORGANISM: Artificial sequence
<220> FEATURE:
<223> OTHER INFORMATION: Primer HuClambda2

<400> SEQUENCE: 82
tgaacattct gtaggggcca ctg                                     23

<210> SEQ ID NO 83
<211> LENGTH: 23
<212> TYPE: DNA
<213> ORGANISM: Artificial sequence
<220> FEATURE:
<223> OTHER INFORMATION: Primer HuClambda7

<400> SEQUENCE: 83

-continued

```
agagcattct gcaggggcca ctg                                              23

<210> SEQ ID NO 84
<211> LENGTH: 4941
<212> TYPE: DNA
<213> ORGANISM: Artificial sequence
<220> FEATURE:
<223> OTHER INFORMATION: Vector PDV-C06

<400> SEQUENCE: 84
aagcttgcat gcaaattcta tttcaaggag acagtcataa tgaaatacct attgcctacg        60
gcagccgctg gattgttatt actcgcggcc cagccggcca tggccgaggt gtttgactaa       120
tggggcgcgc tcagggaac cctggtcacc gtctcgagcg gtacgggcgg ttcaggcgga        180
accggcagcg gcactggcgg gtcgacggaa attgtgctca cagtctcc agccaccctg         240 tctttgtctc cagggaaag agccaccctc tcctgcaggg ccagtcagag tgttagcagc        300
tacttagcct ggtaccaaca gaaacctggc caggctccca ggctcctcat ctatgatgca       360
tccaacaggg ccactggcat cccagccagg ttcagtggca gtgggtctgg gacagacttc       420
actctcacca tcagcagcct agagcctgaa gattttgcag tttattactg tcagcagcgt       480
agcaactggc ctccggcttt cggcggaggg accaaggtgg agatcaaacg tgcggccgca       540
catcatcatc accatcacgg ggccgcatat accgatattg aaatgaaccg cctgggcaaa       600
ggggccgcat agactgttga agttgtttta gcaaaacctc atacagaaaa ttcatttact       660
aacgtctgga agacgacaa aactttagat cgttacgcta actatgaggg ctgtctgtgg       720
aatgctacag gcgttgtggt ttgtactggt gacgaaactc agtgttacgg tacatgggtt       780
cctattgggc ttgctatccc tgaaaatgag ggtggtggct ctgagggtgg cggttctgag       840
ggtggcggtt ctgagggtgg cggtactaaa cctcctgagt acggtgatac acctattccg       900
ggctatactt atatcaaccc tctcgacggc acttatccgc tggtactga gcaaaacccc        960 gctaatccta atccttctct tgaggagtct cagcctctta atactttcat gtttcagaat      1020
aataggttcc gaaataggca gggtgcatta actgtttata cgggcactgt tactcaaggc      1080
actgaccccg ttaaaactta ttaccagtac actcctgtat catcaaaagc catgtatgac      1140
gcttactgga acgtaaatt cagagactgc gcttttccatt ctggctttaa tgaggatcca      1200
ttcgtttgtg aatatcaagg ccaatcgtct gacctgcctc aacctcctgt caatgctggc      1260
ggcggctctg gtggtggttc tggtggcggc tctgagggtg cggctctga gggtggcggt      1320 tctgagggtg cggctctga gggtggcggt tccggtggcg ctccggttc cggtgatttt       1380 gattatgaaa aaatggcaaa cgctaataag gggctatga ccgaaaatgc cgatgaaaac       1440
gcgctacagt ctgacgctaa aggcaaactt gattctgtcg ctactgatta cggtgctgct      1500
atcgatggtt tcattggtga cgtttccggc cttgctaatg gtaatggtgc tactggtgat      1560
tttgctggct ctaattccca aatggctcaa gtcggtgacg gtgataattc acctttaatg      1620
aataatttcc gtcaatatt tccttctttg cctcagtcgg ttgaatgtcg cccttatgtc       1680
tttggcgctg gtaaaccata tgaattttct attgattgtg acaaaataaa cttattccgt      1740
ggtgtctttg cgtttctttt atatgttgcc acctttatgt atgtattttc gacgtttgct      1800
aacatactgc gtaataagga gtcttaataa gaattcactg gccgtcgttt tacaacgtcg      1860
tgactgggaa aaccctggcg ttacccaact taatcgcctt gcagcacatc ccctttcgc       1920 cagctggcgt aatagcgaag aggcccgcac cgatcgccct tcccaacagt tgcgcagcct      1980
```

```
gaatggcgaa tggcgcctga tgcggtattt tctccttacg catctgtgcg gtatttcaca    2040
ccgcatacgt caaagcaacc atagtacgcg ccctgtagcg gcgcattaag cgcggcgggt    2100
gtggtggtta cgcgcagcgt gaccgctaca cttgccagcg ccctagcgcc cgctcctttc    2160
gctttcttcc cttcctttct cgccacgttc gccggctttc cccgtcaagc tctaaatcgg    2220
gggctccctt tagggttccg atttagtgct ttacggcacc tcgacccaa aaaacttgat     2280 ttgggtgatg gttcacgtag tgggccatcg ccctgataga cggttttcg ccctttgacg     2340 ttggagtcca cgttctttaa tagtggactc ttgttccaaa ctggaacaac actcaaccct    2400
atctcgggct attcttttga tttataaggg attttgccga tttcggccta ttggttaaaa    2460
aatgagctga tttaacaaaa atttaacgcg aattttaaca aaatattaac gtttacaatt    2520
ttatggtgca ctctcagtac aatctgctct gatgccgcat agttaagcca gccccgacac    2580
ccgccaacac ccgctgacgc gccctgacgg gcttgtctgc tcccggcatc cgcttacaga    2640
caagctgtga ccgtctccgg gagctgcatg tgtcagaggt tttcaccgtc atcaccgaaa    2700
cgcgcgagac gaaagggcct cgtgatacgc ctatttttat aggttaatgt catgataata    2760
atggtttctt agacgtcagg tggcactttt cggggaaatg tgcgcggaac cctatttgt     2820 ttattttct aaatacattc aaatatgtat ccgctcatga acaataaccc ctgataaatg     2880
cttcaataat attgaaaaag gaagagtatg agtattcaac atttccgtgt cgcccttatt    2940
cccttttttg cggcattttg ccttcctgtt tttgctcacc cagaaacgct ggtgaaagta    3000
aaagatgctg aagatcagtt gggtgcacga gtggttaca tcgaactgga tctcaacagc     3060
ggtaagatcc ttgagagttt tcgccccgaa gaacgttttc caatgatgag cacttttaaa    3120
gttctgctat gtggcgcggt attatcccgt attgacgccg ggcaagagca actcggtcgc    3180
cgcatacact attctcagaa tgacttggtt gagtactcac cagtcacaga aaagcatctt    3240
acggatggca tgacagtaag agaattatgc agtgctgcca taaccatgag tgataacact    3300
gcggccaact tacttctgac aacgatcgga ggaccgaagg agctaaccgc ttttttgcac    3360
aacatggggg atcatgtaac tcgccttgat cgttgggaac cggagctgaa tgaagccata    3420
ccaaacgacg agcgtgacac cacgatgcct gtagcaatgg caacaacgtt gcgcaaacta    3480
ttaactggcg aactacttac tctagcttcc cggcaacaat taatagactg gatggaggcg    3540
gataaagttg caggaccact tctgcgctcg gcccttccgg ctggctggtt tattgctgat    3600
aaatctggag ccggtgagcg tgggtctcgc ggtatcattg cagcactggg gccagatggt    3660
aagccctccc gtatcgtagt tatctacacg acggggagtc aggcaactat ggatgaacga    3720
aatagacaga tcgctgagat aggtgcctca ctgattaagc attggtaact gtcagaccaa    3780
gtttactcat atatacttta gattgattta aaacttcatt tttaatttaa aaggatctag    3840
gtgaagatcc tttttgataa tctcatgacc aaaatccctt aacgtgagtt ttcgttccac    3900
tgagcgtcag accccgtaga aaagatcaaa ggatcttctt gagatccttt ttttctgcgc    3960
gtaatctgct gcttgcaaac aaaaaaacca ccgctaccag cggtggtttg tttgccggat    4020
caagagctac caactctttt tccgaaggta actggcttca gcagagcgca gataccaaat    4080
actgtccttc tagtgtagcc gtagttaggc caccacttca agaactctgt agcaccgcct    4140
acatacctcg ctctgctaat cctgttacca gtggctgctg ccagtggcga taagtcgtgt    4200
cttaccgggt tggactcaag acgatagtta ccggataagg cgcagcggtc gggctgaacg    4260
gggggttcgt gcacacagcc cagcttggag cgaacgacct acaccgaact gagatacccta   4320 cagcgtgagc tatgagaaag cgccacgctt cccgaaggga gaaaggcgga caggtatccg    4380
```

-continued

```
gtaagcggca gggtcggaac aggagagcgc acgagggagc ttccaggggg aaacgcctgg    4440
tatctttata gtcctgtcgg gtttcgccac ctctgacttg agcgtcgatt tttgtgatgc    4500
tcgtcagggg ggcggagcct atggaaaaac gccagcaacg cggcctttttt acggttcctg   4560 gccttttgct ggccttttgc tcacatgttc tttcctgcgt tatcccctga ttctgtggat    4620
aaccgtatta ccgcctttga gtgagctgat accgctcgcc gcagccgaac gaccgagcgc    4680
agcgagtcag tgagcgagga agcggaagag cgcccaatac gcaaaccgcc tctccccgcg    4740
cgttggccga ttcattaatg cagctggcac gacaggtttc ccgactggaa agcgggcagt    4800
gagcgcaacg caattaatgt gagttagctc actcattagg caccccaggc tttacacttt    4860
atgcttccgg ctcgtatgtt gtgtggaatt gtgagcggat aacaatttca cacaggaaac    4920
agctatgacc atgattacgc c                                              4941
```

<210> SEQ ID NO 85
<211> LENGTH: 24
<212> TYPE: DNA
<213> ORGANISM: Artificial sequence
<220> FEATURE:
<223> OTHER INFORMATION: Primer HuCIgG

<400> SEQUENCE: 85

```
gtccaccttg gtgttgctgg gctt                                             24
```

<210> SEQ ID NO 86
<211> LENGTH: 669
<212> TYPE: PRT
<213> ORGANISM: West Nile virus

<400> SEQUENCE: 86

```
Met Val Thr Leu Ser Asn Phe Gln Gly Lys Val Met Met Thr Val Asn
1               5                   10                  15

Ala Thr Asp Val Thr Asp Val Ile Thr Ile Pro Thr Ala Ala Gly Lys
            20                  25                  30

Asn Leu Cys Ile Val Arg Ala Met Asp Val Gly Tyr Met Cys Asp Asp
        35                  40                  45

Thr Ile Thr Tyr Glu Cys Pro Val Leu Ser Ala Gly Asn Asp Pro Glu
    50                  55                  60

Asp Ile Asp Cys Trp Cys Thr Lys Ser Ala Val Tyr Val Arg Tyr Gly
65                  70                  75                  80

Arg Cys Thr Lys Thr Arg His Ser Arg Arg Ser Arg Arg Ser Leu Thr
                85                  90                  95

Val Gln Thr His Gly Glu Ser Thr Leu Ala Asn Lys Lys Gly Ala Trp
            100                 105                 110

Met Asp Ser Thr Lys Ala Thr Arg Tyr Leu Val Lys Thr Glu Ser Trp
        115                 120                 125

Ile Leu Arg Asn Pro Gly Tyr Ala Leu Val Ala Ala Val Ile Gly Trp
    130                 135                 140

Met Leu Gly Ser Asn Thr Met Gln Arg Val Val Phe Val Val Leu Leu
145                 150                 155                 160

Leu Leu Val Ala Pro Ala Tyr Ser Phe Asn Cys Leu Gly Met Ser Asn
                165                 170                 175

Arg Asp Phe Leu Glu Gly Val Ser Gly Ala Thr Trp Val Asp Leu Val
            180                 185                 190

Leu Glu Gly Asp Ser Cys Val Thr Ile Met Ser Lys Asp Lys Pro Thr
        195                 200                 205
```

-continued

```
Ile Asp Val Lys Met Met Asn Met Glu Ala Ala Asn Leu Ala Glu Val
210                 215                 220
Arg Ser Tyr Cys Tyr Leu Ala Thr Val Ser Asp Leu Ser Thr Lys Ala
225                 230                 235                 240
Ala Cys Pro Thr Met Gly Glu Ala His Asn Asp Lys Arg Ala Asp Pro
                245                 250                 255
Ala Phe Val Cys Arg Gln Gly Val Val Asp Arg Gly Trp Gly Asn Gly
                260                 265                 270
Cys Gly Leu Phe Gly Lys Gly Ser Ile Asp Thr Cys Ala Lys Phe Ala
                275                 280                 285
Cys Ser Thr Lys Ala Ile Gly Arg Thr Ile Leu Lys Glu Asn Ile Lys
290                 295                 300
Tyr Glu Val Ala Ile Phe Val His Gly Pro Thr Thr Val Glu Ser His
305                 310                 315                 320
Gly Asn Tyr Ser Thr Gln Val Gly Ala Thr Gln Ala Gly Arg Phe Ser
                325                 330                 335
Ile Thr Pro Ala Ala Pro Ser Tyr Thr Leu Lys Leu Gly Glu Tyr Gly
                340                 345                 350
Glu Val Thr Val Asp Cys Glu Pro Arg Ser Gly Ile Asp Thr Asn Ala
                355                 360                 365
Tyr Tyr Val Met Thr Val Gly Thr Lys Thr Phe Leu Val His Arg Glu
370                 375                 380
Trp Phe Met Asp Leu Asn Leu Pro Trp Ser Ser Ala Gly Ser Thr Val
385                 390                 395                 400
Trp Arg Asn Arg Glu Thr Leu Met Glu Phe Glu Glu Pro His Ala Thr
                405                 410                 415
Lys Gln Ser Val Ile Ala Leu Gly Ser Gln Glu Gly Ala Leu His Gln
                420                 425                 430
Ala Leu Ala Gly Ala Ile Pro Val Glu Phe Ser Ser Asn Thr Val Lys
                435                 440                 445
Leu Thr Ser Gly His Leu Lys Cys Arg Val Lys Met Glu Lys Leu Gln
450                 455                 460
Leu Lys Gly Thr Thr Tyr Gly Val Cys Ser Lys Ala Phe Lys Phe Leu
465                 470                 475                 480
Gly Thr Pro Ala Asp Thr Gly His Gly Thr Val Val Leu Glu Leu Gln
                485                 490                 495
Tyr Thr Gly Thr Asp Gly Pro Cys Lys Val Pro Ile Ser Ser Val Ala
                500                 505                 510
Ser Leu Asn Asp Leu Thr Pro Val Gly Arg Leu Val Thr Val Asn Pro
                515                 520                 525
Phe Val Ser Val Ala Thr Ala Asn Ala Lys Val Leu Ile Glu Leu Glu
530                 535                 540
Pro Pro Phe Gly Asp Ser Tyr Ile Val Val Gly Arg Gly Glu Gln Gln
545                 550                 555                 560
Ile Asn His His Trp His Lys Ser Gly Ser Ser Ile Gly Lys Ala Phe
                565                 570                 575
Thr Thr Thr Leu Lys Gly Ala Gln Arg Leu Ala Ala Leu Gly Asp Thr
                580                 585                 590
Ala Trp Asp Phe Gly Ser Val Gly Gly Val Phe Thr Ser Val Gly Lys
                595                 600                 605
Ala Val His Gln Val Phe Gly Gly Ala Phe Arg Ser Leu Phe Gly Gly
                610                 615                 620
```

-continued

Met Ser Trp Ile Thr Gln Gly Leu Leu Gly Ala Leu Leu Leu Trp Met
625 630 635 640

Gly Ile Asn Ala Arg Asp Arg Ser Ile Ala Leu Thr Phe Leu Ala Val
645 650 655

Gly Gly Val Leu Leu Phe Leu Ser Val Asn Val His Ala
660 665

<210> SEQ ID NO 87
<211> LENGTH: 23
<212> TYPE: DNA
<213> ORGANISM: Artificial sequence
<220> FEATURE:
<223> OTHER INFORMATION: Primer CMV-Spe

<400> SEQUENCE: 87
ccatgttgac attgattatt gac 23

<210> SEQ ID NO 88
<211> LENGTH: 26
<212> TYPE: DNA
<213> ORGANISM: Artificial sequence
<220> FEATURE:
<223> OTHER INFORMATION: Primer WNV-E-95 REV

<400> SEQUENCE: 88
gctctagact tgccgatgct gctgcc 26

<210> SEQ ID NO 89
<211> LENGTH: 40
<212> TYPE: DNA
<213> ORGANISM: Artificial sequence
<220> FEATURE:
<223> OTHER INFORMATION: Primer clefsmaquwnv

<400> SEQUENCE: 89
ggaattcagc atggcccagg tgaccctgag caacttccag 40

<210> SEQ ID NO 90
<211> LENGTH: 26
<212> TYPE: DNA
<213> ORGANISM: Artificial sequence
<220> FEATURE:
<223> OTHER INFORMATION: Primer reverse WNVmychis

<400> SEQUENCE: 90
gactagtcaa ctcaatggtg atggtg 26

<210> SEQ ID NO 91
<211> LENGTH: 6760
<212> TYPE: DNA
<213> ORGANISM: Artificial sequence
<220> FEATURE:
<223> OTHER INFORMATION: Vector pSyn-C18-HCgamma1

<400> SEQUENCE: 91
ctagcaccaa gggccccagc gtgttccccc tggcccccag cagcaagagc accagcggcg 60
gcacagccgc cctgggctgc ctggtgaagg actacttccc cgagcccgtg accgtgagct 120
ggaacagcgg cgccttgacc agcggcgtgc acaccttccc cgccgtgctg cagagcagcg 180
gcctgtacag cctgagcagc gtggtgaccg tgcccagcag cagcctgggc acccagacct 240
acatctgcaa cgtgaaccac aagcccagca acaccaaggt ggacaaacgc gtggagccca 300
agagctgcga caagacccac acctgccccc cctgccctgc ccccgagctg ctgggcggac 360

-continued

| | |
|---|---|
| cctccgtgtt cctgttcccc cccaagccca aggacaccct catgatcagc cggaccccg | 420 |
| aggtgacctg cgtggtggtg gacgtgagcc acgaggaccc cgaggtgaag ttcaactggt | 480 |
| acgtggacgg cgtggaggtg cacaacgcca agaccaagcc ccgggaggag cagtacaaca | 540 |
| gcacctaccg ggtggtgagc gtgctcaccg tgctgcacca ggactggctg aacggcaagg | 600 |
| agtacaagtg caaggtgagc aacaaggccc tgcctgcccc catcgagaag accatcagca | 660 |
| aggccaaggg ccagccccgg gagccccagg tgtacaccct gcccccagc cgggaggaga | 720 |
| tgaccaagaa ccaggtgtcc ctcacctgtc tggtgaaggg cttctacccc agcgacatcg | 780 |
| ccgtggagtg ggagagcaac ggccagcccg agaacaacta caagaccacc cccctgtgc | 840 |
| tggacagcga cggcagcttc ttcctgtaca gcaagctcac cgtggacaag agccggtggc | 900 |
| agcagggcaa cgtgttcagc tgcagcgtga tgcacgaggc cctgcacaac cactacaccc | 960 |
| agaagagcct gagcctgagc cccggcaagt gataatctag agggccgtt taaacccgct | 1020 |
| gatcagcctc gactgtgcct tctagttgcc agccatctgt tgtttgcccc tccccgtgc | 1080 |
| cttccttgac cctggaaggt gccactccca ctgtcctttc ctaataaaat gaggaaattg | 1140 |
| catcgcattg tctgagtagg tgtcattcta ttctgggggg tgggtgggg caggacagca | 1200 |
| agggggagga ttgggaagac aatagcaggc atgctgggga tgcggtgggc tctatggctt | 1260 |
| ctgaggcgga aagaaccagc tggggctcta ggggggtatcc ccacgcgccc tgtagcggcg | 1320 |
| cattaagcgc ggcgggtgtg tggttacgc gcagcgtgac cgctacactt gccagcgccc | 1380 |
| tagcgcccgc tcctttcgct ttcttcccct cctttctcgc cacgttcgcc ggctttcccc | 1440 |
| gtcaagctct aaatcggggg ctcccttag gttccgatt tagtgcttta cggcacctcg | 1500 |
| accccaaaaa acttgattag ggtgatggtt cacgtagtgg gccatcgccc tgatagacgg | 1560 |
| tttttcgccc tttgacgttg gagtccacgt tctttaatag tggactcttg ttccaaactg | 1620 |
| gaacaacact caaccctatc tcggtctatt cttttgattt ataagggatt ttgccgattt | 1680 |
| cggcctattg gttaaaaaat gagctgattt aacaaaaatt taacgcgaat taattctgtg | 1740 |
| gaatgtgtgt cagttagggt gtggaaagtc cccaggctcc ccagcaggca gaagtatgca | 1800 |
| aagcatgcat ctcaattagt cagcaaccag gtgtggaaag tccccaggct ccccagcagg | 1860 |
| cagaagtatg caaagcatgc atctcaatta gtcagcaacc atagtcccgc ccctaactcc | 1920 |
| gcccatcccg cccctaactc cgcccagttc cgcccattct ccgccccatg ctgactaat | 1980 |
| tttttttatt tatgcagagg ccgaggccgc ctctgcctct gagctattcc agaagtagtg | 2040 |
| aggaggcttt tttggaggcc taggcttttg caaaaagctc ccgggagctt gtatatccat | 2100 |
| tttcggatct gatcaagaga caggatgagg atcgtttcgc atgattgaac aagatggatt | 2160 |
| gcacgcaggt tctccggccg cttgggtgga gaggctattc ggctatgact gggcacaaca | 2220 |
| gacaatcggc tgctctgatg ccgccgtgtt ccggctgtca gcgcaggggc gcccggttct | 2280 |
| ttttgtcaag accgacctgt ccggtgccct gaatgaactg caggacgagg cagcgcggct | 2340 |
| atcgtggctg gccacgacgg gcgttccttg cgcagctgtg ctcgacgttg tcactgaagc | 2400 |
| gggaagggac tggctgctat tgggcgaagt gccggggcag gatctcctgt catctcacct | 2460 |
| tgctcctgcc gagaaagtat ccatcatggc tgatgcaatg cggcggctgc atacgcttga | 2520 |
| tccggctacc tgcccattcg accaccaagc gaaacatcgc atcgagcgag cacgtactcg | 2580 |
| gatggaagcc ggtcttgtcg atcaggatga tctggacgaa gagcatcagg ggctcgcgcc | 2640 |
| agccgaactg ttcgccaggc tcaaggcgcg catgcccgac ggcgaggatc tcgtcgtgac | 2700 |
| ccatggcgat gcctgcttgc cgaatatcat ggtggaaaat ggccgctttt ctggattcat | 2760 |

```
cgactgtggc cggctgggtg tggcggaccg ctatcaggac atagcgttgg ctacccgtga    2820
tattgctgaa gagcttggcg gcgaatgggc tgaccgcttc ctcgtgcttt acggtatcgc    2880
cgctcccgat tcgcagcgca tcgccttcta tcgccttctt gacgagttct tctgagcggg    2940
actctggggt tcgaaatgac cgaccaagcg acgcccaacc tgccatcacg agatttcgat    3000
tccaccgccg ccttctatga aaggttgggc ttcggaatcg ttttccggga cgccggctgg    3060
atgatcctcc agcgcgggga tctcatgctg gagttcttcg cccaccccaa cttgtttatt    3120
gcagcttata atggttacaa ataaagcaat agcatcacaa atttcacaaa taaagcattt    3180
ttttcactgc attctagttg tggtttgtcc aaactcatca atgtatctta tcatgtctgt    3240
ataccgtcga cctctagcta gagcttggcg taatcatggt catagctgtt tcctgtgtga    3300
aattgttatc cgctcacaat tccacacaac atacgagccg aagcataaa gtgtaaagcc    3360 tggggtgcct aatgagtgag ctaactcaca ttaattgcgt tgcgctcact gcccgctttc    3420
cagtcgggaa acctgtcgtg ccagctgcat taatgaatcg gccaacgcgc ggggagaggc    3480
ggtttgcgta ttgggcgctc ttccgcttcc tcgctcactg actcgctgcg ctcggtcgtt    3540
cggctgcggc gagcggtatc agctcactca aaggcggtaa tacggttatc cacagaatca    3600
ggggataacg caggaaagaa catgtgagca aaaggccagc aaaaggccag gaaccgtaaa    3660
aaggccgcgt tgctggcgtt tttccatagg ctccgccccc ctgacgagca tcacaaaaat    3720
cgacgctcaa gtcagaggtg gcgaaacccg acaggactat aaagatacca ggcgtttccc    3780
cctggaagct ccctcgtgcg ctctcctgtt ccgaccctgc cgcttaccgg atacctgtcc    3840
gcctttctcc cttcgggaag cgtggcgctt tctcatagct cacgctgtag gtatctcagt    3900
tcggtgtagg tcgttcgctc caagctgggc tgtgtgcacg aaccccccgt tcagcccgac    3960
cgctgcgcct tatccggtaa ctatcgtctt gagtccaacc cggtaagaca cgacttatcg    4020
ccactggcag cagccactgg taacaggatt agcagagcga ggtatgtagg cggtgctaca    4080
gagttcttga agtggtggcc taactacggc tacactagaa gaacagtatt tggtatctgc    4140
gctctgctga agccagttac cttcggaaaa agagttggta gctcttgatc cggcaaacaa    4200
accaccgctg gtagcggttt ttttgtttgc aagcagcaga ttacgcgcag aaaaaaagga    4260
tctcaagaag atcctttgat cttttctacg gggtctgacg ctcagtggaa cgaaaactca    4320
cgttaaggga ttttggtcat gagattatca aaaaggatct tcacctagat ccttttaaat    4380 taaaatgaa gttttaaatc aatctaaagt atatatgagt aaacttggtc tgacagttac    4440
caatgcttaa tcagtgaggc acctatctca gcgatctgtc tatttcgttc atccatagtt    4500
gcctgactcc ccgtcgtgta gataactacg atacgggagg gcttaccatc tggccccagt    4560
gctgcaatga taccgcgaga cccacgctca ccggctccag atttatcagc aataaaccag    4620
ccagccggaa gggccgagcg cagaagtggt cctgcaactt tatccgcctc catccagtct    4680
attaattgtt gccgggaagc tagagtaagt agttcgccag ttaatagttt gcgcaacgtt    4740
gttgccattg ctacaggcat cgtggtgtca cgctcgtcgt ttggtatggc ttcattcagc    4800
tccggttccc aacgatcaag gcgagttaca tgatccccca tgttgtgcaa aaaagcggtt    4860
agctccttcg gtcctccgat cgttgtcaga agtaagttgg ccgcagtgtt atcactcatg    4920
gttatggcag cactgcataa ttctcttact gtcatgccat ccgtaagatg cttttctgtg    4980
actggtgagt actcaaccaa gtcattctga gaatagtgta tgcggcgacc gagttgctct    5040
tgcccggcgt caatacggga taataccgcg ccacatagca gaactttaaa agtgctcatc    5100
```

-continued

```
attggaaaac gttcttcggg gcgaaaactc tcaaggatct taccgctgtt gagatccagt    5160
tcgatgtaac ccactcgtgc acccaactga tcttcagcat cttttacttt caccagcgtt    5220
tctgggtgag caaaaacagg aaggcaaaat gccgcaaaaa agggaataag ggcgacacgg    5280
aaatgttgaa tactcatact cttccttttt caatattatt gaagcattta tcagggttat    5340
tgtctcatga gcggatacat atttgaatgt atttagaaaa ataaacaaat aggggttccg    5400
cgcacatttc cccgaaaagt gccacctgac gtcgacggat cgggagatct cccgatcccc    5460
tatggtgcac tctcagtaca atctgctctg atgccgcata gttaagccag tatctgctcc    5520
ctgcttgtgt gttggaggtc gctgagtagt gcgcgagcaa aatttaagct acaacaaggc    5580
aaggcttgac cgacaattgc atgaagaatc tgcttagggt taggcgtttt gcgctgcttc    5640
gctaggtggt caatattggc cattagccat attattcatt ggttatatag cataaatcaa    5700
tattggctat tggccattgc atacgttgta tccatatcat aatatgtaca tttatattgg    5760
ctcatgtcca acattaccgc catgttgaca ttgattattg actagttatt aatagtaatc    5820
aattacgggg tcattagttc atagcccata tatggagttc cgcgttacat aacttacggt    5880
aaatggcccg cctggctgac cgcccaacga ccccgccca ttgacgtcaa taatgacgta    5940
tgttcccata gtaacgccaa tagggacttt ccattgacgt caatgggtgg agtatttacg    6000
gtaaactgcc cacttggcag tacatcaagt gtatcatatg ccaagtacgc ccctattga    6060 cgtcaatgac ggtaaatggc ccgcctggca ttatgcccag tacatgacct tatgggactt    6120
tcctacttgg cagtacatct acgtattagt catcgctatt accatggtga tgcggttttg    6180
gcagtacatc aatgggcgtg gatagcggtt tgactcacgg ggatttccaa gtctccaccc    6240
cattgacgtc aatgggagtt tgttttggca ccaaaatcaa cgggactttc caaaatgtcg    6300
taacaactcc gccccattga cgcaaatggg cggtaggcgt gtacggtggg aggtctatat    6360
aagcagagct cgtttagtga accgtcagat cgcctggaga cgccatccac gctgttttga    6420
cctccataga agacaccggg accgatccag cctccgcggc cgggaacggt gcattggaag    6480
ctggcctgga tggcctgact ctcttaggta gccttgcaga agttggtcgt gaggcactgg    6540
gcaggtaagt atcaaggtta agacaggt ttaaggagat caatagaaac tgggcttgtc    6600
gagacagaga agactcttgc gtttctgata ggcacctatt ggtcttactg acatccactt    6660
tgcctttctc tccacaggtg tccactccca gttcaattac agctcgccac catggcctgc    6720
cccggcttcc tgtgggccct ggtgatcagc acctgcctgg                           6760
```

<210> SEQ ID NO 92
<211> LENGTH: 6267
<212> TYPE: DNA
<213> ORGANISM: Artificial sequence
<220> FEATURE:
<223> OTHER INFORMATION: Vector pSyn-C05-Ckappa

<400> SEQUENCE: 92

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgttaa ttaacatgaa    180
gaatctgctt agggttaggc gttttgcgct gcttcgctag gtggtcaata ttggccatta    240
gccatattat tcattggtta tatagcataa atcaatattg gctattggcc attgcatacg    300
ttgtatccat atcataatat gtacatttat attggctcat gtccaacatt accgccatgt    360
tgacattgat tattgactag ttattaatag taatcaatta cggggtcatt agttcatagc    420
```

-continued

```
ccatatatgg agttccgcgt tacataactt acggtaaatg ccccgcctgg ctgaccgccc      480
aacgaccccc gcccattgac gtcaataatg acgtatgttc ccatagtaac gccaataggg      540
actttccatt gacgtcaatg ggtggagtat ttacggtaaa ctgcccactt ggcagtacat      600
caagtgtatc atatgccaag tacgccccct attgacgtca atgacggtaa atggcccgcc      660
tggcattatg cccagtacat gaccttatgg gactttccta cttggcagta catctacgta      720
ttagtcatcg ctattaccat ggtgatgcgg ttttggcagt acatcaatgg gcgtggatag      780
cggtttgact cacggggatt tccaagtctc cacccccattg acgtcaatgg gagtttgttt      840
tggcaccaaa atcaacggga ctttccaaaa tgtcgtaaca actccgcccc attgacgcaa      900
atgggcggta ggcgtgtacg gtgggaggtc tatataagca gagctcgttt agtgaaccgt      960
cagatcgcct ggagacgcca tccacgctgt tttgacctcc atagaagaca ccgggaccga     1020
tccagcctcc gcggccggga acgtgcatt ggaatcgatg actctcttag gtagccttgc      1080
agaagttggt cgtgaggcac tgggcaggta agtatcaagg ttacaagaca ggtttaagga     1140
gatcaataga aactgggctt gtcgagacag agaagactct tgcgtttctg ataggcacct     1200
attggtctta ctgacatcca ctttgccttt ctctccacag gtgtccactc ccagttcaat     1260
tacagctcgc caccatggcc tgccccggct cctgtgggc cctggtgatc agcacctgcc      1320
tcgagttcag cggccctaag cggaccgtgg ccgctcccag cgtgttcatc ttccccccct     1380
ccgacgagca gctgaagagc ggcaccgcca gcgtggtgtg cctgctgaac aacttctacc     1440
cccgggaggc caaggtgcag tggaaggtgg acaacgccct gcagagcggc aacagccagg     1500
agagcgtgac cgagcaggac agcaaggact ccacctacag cctgagcagc accctcaccc     1560
tgagcaaggc cgactacgag aagcacaagg tgtacgcctg cgaggtgacc caccagggcc     1620
tgagcagccc cgtgaccaag agcttcaacc ggggcgagtg ttaatagact aagtttaaa     1680
ccgctgatca gcctcgactg tgccttctag ttgccagcca tctgttgttt gcccctcccc     1740
cgtgccttcc ttgaccctgg aaggtgccac tcccactgtc ctttcctaat aaaatgagga     1800
aattgcatcg cattgtctga gtaggtgtca ttctattctg gggggtgggg tgggcagga      1860
cagcaagggg gaggattggg aagacaatag caggcatgct ggggatgcgg tgggctctat     1920
ggcttctgag gcgaaagaa ccagctgggg ctctaggggg tatccccacg cgccctgtag      1980
cggcgcatta agcgcggcgg gtgtggtggt tacgcgcagc gtgaccgcta cacttgccag     2040
cgccctagcg cccgctcctt tcgctttctt cccttccttt ctcgccacgt tcgccggctt     2100
tccccgtcaa gctctaaatc ggggggctccc tttagggttc cgatttagtg ctttacggca     2160
cctcgacccc aaaaaacttg attagggtga tggttcacgt agtgggccat cgccctgata     2220
gacggttttt cgccctttga cgttggagtc acgttctttt aatagtggac tcttgttcca     2280
aactggaaca acactcaacc ctatctcggt ctattctttt gatttataag ggattttggc     2340
catttcggcc tattggttaa aaaatgagct gatttaacaa aaatttaacg cgaattaatt     2400
ctgtggaatg tgtgtcagtt agggtgtgga aagtccccag gctccccagc aggcagaagt     2460
atgcaaagca tgcatctcaa ttagtcagca accaggtgtg gaaagtcccc aggctcccca     2520
gcaggcagaa gtatgcaaag catgcatctc aattagtcag caaccatagt cccgccccta     2580
actccgccca tcccgcccct aactccgccc agttccgccc attctccgcc ccatggctga     2640
ctaatttttt ttatttatgc agaggccgag gccgcctctg cctctgagct attccagaag     2700
tagtgaggag gcttttttgg aggcctaggc ttttgcaaaa agctcccggg agcttgtata     2760
```

-continued

```
tccattttcg gatctgatca gcacgtgatg aaaaagcctg aactcaccgc gacgtctgtc    2820
gagaagtttc tgatcgaaaa gttcgacagc gtctccgacc tgatgcagct ctcggagggc    2880
gaagaatctc gtgctttcag cttcgatgta ggagggcgtg gatatgtcct gcgggtaaat    2940
agctgcgccg atggtttcta caaagatcgt tatgtttatc ggcactttgc atcggccgcg    3000
ctcccgattc cggaagtgct tgacattggg gaattcagcg agagcctgac ctattgcatc    3060
tcccgccgtg cacagggtgt cacgttgcaa gacctgcctg aaaccgaact gcccgctgtt    3120
ctgcagccgg tcgcggaggc catggatgcg atcgctgcgg ccgatcttag ccagacgagc    3180
gggttcggcc cattcggacc acaaggaatc ggtcaataca ctacatggcg tgatttcata    3240
tgcgcgattg ctgatcccca tgtgtatcac tggcaaactg tgatggacga caccgtcagt    3300
gcgtccgtcg cgcaggctct cgatgagctg atgctttggg ccgaggactg ccccgaagtc    3360
cggcacctcg tgcacgcgga tttcggctcc aacaatgtcc tgacggacaa tggccgcata    3420
acagcggtca ttgactggag cgaggcgatg ttcggggatt cccaatacga ggtcgccaac    3480
atcttcttct ggaggccgtg gttggcttgt atggagcagc agacgcgcta cttcgagcgg    3540
aggcatccgg agcttgcagg atcgccgcgg ctccgggcgt atatgctccg cattggtctt    3600
gaccaactct atcagagctt ggttgacggc aatttcgatg atgcagcttg ggcgcagggt    3660
cgatgcgacg caatcgtccg atccggagcc gggactgtcg ggcgtacaca aatcgcccgc    3720
agaagcgcgg ccgtctggac cgatggctgt gtagaagtac tcgccgatag tggaaaccga    3780
cgccccagca ctcgtccgag ggcaaaggaa tagcacgtgc tacgagattt cgattccacc    3840
gccgccttct atgaaaggtt gggcttcgga atcgttttcc gggacgccgg ctggatgatc    3900
ctccagcgcg gggatctcat gctggagttc ttcgcccacc ccaacttgtt tattgcagct    3960
tataatggtt acaaataaag caatagcatc acaaatttca caaataaagc atttttttca    4020
ctgcattcta gttgtggttt gtccaaactc atcaatgtat cttatcatgt ctgtataccg    4080
tcgacctcta gctagagctt ggcgtaatca tggtcatagc tgtttcctgt gtgaaattgt    4140
tatccgctca caattccaca acatacga gccggaagca taagtgtaa agcctggggt    4200
gcctaatgag tgagctaact cacattaatt gcgttgcgct cactgcccgc tttccagtcg    4260
ggaaacctgt cgtgccagct gcattaatga atcggccaac gcgcggggag aggcggtttg    4320
cgtattgggc gctcttccgc ttcctcgctc actgactcgc tgcgctcggt cgttcggctg    4380
cggcgagcgg tatcagctca ctcaaaggcg gtaatacggt tatccacaga atcaggggat    4440
aacgcaggaa agaacatgtg agcaaaaggc cagcaaaagg ccaggaaccg taaaaaggcc    4500
gcgttgctgg cgttttccca taggctccgc cccctgacg agcatcacaa aaatcgacgc    4560
tcaagtcaga ggtggcgaaa cccgacagga ctataaagat accaggcgtt ccccctgga    4620
agctccctcg tgcgctctcc tgttccgacc ctgccgctta ccggatacct gtccgccttt    4680
ctcccttcgg aagcgtggc gctttctcat agctcacgct gtaggtatct cagttcggtg    4740
taggtcgttc gctccaagct gggctgtgtg cacgaacccc ccgttcagcc cgaccgctgc    4800
gccttatccg gtaactatcg tcttgagtcc aacccggtaa gacacgactt atcgccactg    4860
gcagcagcca ctggtaacag gattagcaga gcgaggtatg taggcggtgc tacagagttc    4920
ttgaagtggt ggcctaacta cggctacact agaagaacag tatttggtat ctgcgctctg    4980
ctgaagccag ttaccttcgg aaaaagagtt ggtagctctt gatccggcaa caaaccacc    5040
gctggtagcg gtttttttgt ttgcaagcag cagattacgc gcagaaaaaa aggatctcaa    5100
gaagatcctt tgatctttc tacggggtct gacgctcagt ggaacgaaaa ctcacgttaa    5160
```

```
gggattttgg tcatgagatt atcaaaaagg atcttcacct agatccttt  aaattaaaaa    5220 tgaagtttta aatcaatcta agtatatat  gagtaaactt ggtctgacag ttaccaatgc    5280
ttaatcagtg aggcacctat ctcagcgatc tgtctatttc gttcatccat agttgcctga    5340
ctccccgtcg tgtagataac tacgatacgg gagggcttac catctggccc cagtgctgca    5400
atgataccgc gagacccacg ctcaccggct ccagatttat cagcaataaa ccagccagcc    5460
ggaagggccg agcgcagaag tggtcctgca actttatccg cctccatcca gtctattaat    5520
tgttgccggg aagctagagt aagtagttcg ccagttaata gtttgcgcaa cgttgttgcc    5580
attgctacag gcatcgtggt gtcacgctcg tcgtttggta tggcttcatt cagctccggt    5640
tcccaacgat caaggcgagt tacatgatcc cccatgttgt gcaaaaaagc ggttagctcc    5700
ttcggtcctc cgatcgttgt cagaagtaag ttggccgcag tgttatcact catggttatg    5760
gcagcactgc ataattctct tactgtcatg ccatccgtaa gatgcttttc tgtgactggt    5820
gagtactcaa ccaagtcatt ctgagaatag tgtatgcggc gaccgagttg ctcttgcccg    5880
gcgtcaatac gggataatac cgcgccacat agcagaactt taaaagtgct catcattgga    5940
aaacgttctt cggggcgaaa actctcaagg atcttaccgc tgttgagatc cagttcgatg    6000
taacccactc gtgcacccaa ctgatcttca gcatctttta ctttcaccag cgtttctggg    6060
tgagcaaaaa caggaaggca aaatgccgca aaaaagggaa taagggcgac acggaaatgt    6120
tgaatactca tactcttcct ttttcaatat tattgaagca tttatcaggg ttattgtctc    6180
atgagcggat acatatttga atgtatttag aaaaataaac aatagggggt tccgcgcaca    6240
tttccccgaa aagtgccacc tgacgtc                                       6267

<210> SEQ ID NO 93
<211> LENGTH: 6283
<212> TYPE: DNA
<213> ORGANISM: Artificial sequence
<220> FEATURE:
<223> OTHER INFORMATION: Vector pSyn-C04-Clambda

<400> SEQUENCE: 93
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgttaa ttaacatgaa    180
gaatctgctt agggttaggc gttttgcgct gcttcgctag gtggtcaata ttggccatta    240
gccatattat tcattggtta tatagcataa atcaatattg gctattggcc attgcatacg    300
ttgtatccat atcataatat gtacatttat attggctcat gtccaacatt accgccatgt    360
tgacattgat tattgactag ttattaatag taatcaatta cggggtcatt agttcatagc    420
ccatatatgg agttccgcgt tacataactt acggtaaatg gcccgcctgg ctgaccgccc    480
aacgaccccc gcccattgac gtcaataatg acgtatgttc ccatagtaac gccaataggg    540
actttccatt gacgtcaatg ggtggagtat ttacggtaaa ctgcccactt ggcagtacat    600
caagtgtatc atatgccaag tacgccccct attgacgtca atgacggtaa atggcccgcc    660
tggcattatg cccagtacat gaccttatgg gactttccta cttggcagta catctacgta    720
ttagtcatcg ctattaccat ggtgatgcgg ttttggcagt acatcaatgg gcgtggatag    780
cggtttgact cacggggatt tccaagtctc cacccattg  acgtcaatgg gagtttgttt    840
tggcaccaaa atcaacggga ctttccaaaa tgtcgtaaca actccgcccc attgacgcaa    900
```

-continued

| | | | | | |
|---|---|---|---|---|---|
| atgggcggta | ggcgtgtacg | gtgggaggtc | tatataagca | gagctcgttt | agtgaaccgt | 960 |
| cagatcgcct | ggagacgcca | tccacgctgt | tttgacctcc | atagaagaca | ccgggaccga | 1020 |
| tccagcctcc | gcggccggga | acggtgcatt | ggaatcgatg | actctcttag | gtagccttgc | 1080 |
| agaagttggt | cgtgaggcac | tgggcaggta | agtatcaagg | ttacaagaca | ggtttaagga | 1140 |
| gatcaataga | aactgggctt | gtcgagacag | agaagactct | tgcgtttctg | ataggcacct | 1200 |
| attggtctta | ctgacatcca | ctttgccttt | ctctccacag | gtgtccactc | ccagttcaat | 1260 |
| tacagctcgc | caccatggcc | tgccccggct | tcctgtgggc | cctggtgatc | agcacctgcc | 1320 |
| tcgagatccc | cggaccgcgg | ccgcaagctt | accgtgctgg | gccagcccaa | ggccgctccc | 1380 |
| agcgtgaccc | tgttcccccc | ctcctccgag | gagctgcagg | ccaacaaggc | caccctggtg | 1440 |
| tgcctcatca | gcgacttcta | ccctggcgcc | gtgaccgtgg | cctggaaggc | cgacagcagc | 1500 |
| cccgtgaagg | ccggcgtgga | gaccaccacc | cccagcaagc | agagcaacaa | caagtacgcc | 1560 |
| gccagcagct | acctgagcct | cacccccgag | cagtggaaga | gccaccggag | ctacagctgc | 1620 |
| caggtgaccc | acgagggcag | caccgtggag | aagaccgtgg | cccccaccga | gtgcagctaa | 1680 |
| tagacttaag | tttaaaccgc | tgatcagcct | cgactgtgcc | ttctagttgc | cagccatctg | 1740 |
| ttgtttgccc | ctcccccgtg | ccttccttga | ccctggaagg | tgccactccc | actgtccttt | 1800 |
| cctaataaaa | tgaggaaatt | gcatcgcatt | gtctgagtag | gtgtcattct | attctggggg | 1860 |
| gtggggtggg | gcaggacagc | aaggggggagg | attgggaaga | caatagcagg | catgctgggg | 1920 |
| atgcggtggg | ctctatggct | tctgaggcgg | aaagaaccag | ctggggctct | aggggggtatc | 1980 |
| cccacgcgcc | ctgtagcggc | gcattaagcg | cggcgggtgt | ggtggttacg | cgcagcgtga | 2040 |
| ccgctacact | tgccagcgcc | ctagcgcccg | ctcctttcgc | tttcttccct | tcctttctcg | 2100 |
| ccacgttcgc | cggctttccc | cgtcaagctc | taaatcgggg | gctcccttta | gggttccgat | 2160 |
| ttagtgcttt | acggcacctc | gaccccaaaa | aacttgatta | gggtgatggt | tcacgtagtg | 2220 |
| ggccatcgcc | ctgatagacg | gttttttcgcc | ctttgacgtt | ggagtccacg | ttctttaata | 2280 |
| gtggactctt | gttccaaact | ggaacaacac | tcaaccctat | ctcggtctat | tcttttgatt | 2340 |
| tataagggat | tttggccatt | tcggcctatt | ggttaaaaaa | tgagctgatt | taacaaaaat | 2400 |
| ttaacgcgaa | ttaattctgt | ggaatgtgtg | tcagttaggg | tgtggaaagt | ccccaggctc | 2460 |
| cccagcaggc | agaagtatgc | aaagcatgca | tctcaattag | tcagcaacca | ggtgtggaaa | 2520 |
| gtccccaggc | tccccagcag | gcagaagtat | gcaaagcatg | catctcaatt | agtcagcaac | 2580 |
| catagtcccg | cccctaactc | cgcccatccc | gcccctaact | ccgcccagtt | ccgcccattc | 2640 |
| tccgccccat | ggctgactaa | ttttttttat | ttatgcagag | gccgaggccg | cctctgcctc | 2700 |
| tgagctattc | cagaagtagt | gaggaggctt | ttttggaggc | ctaggctttt | gcaaaaagct | 2760 |
| cccgggagct | tgtatatcca | ttttcggatc | tgatcagcac | gtgatgaaaa | agcctgaact | 2820 |
| caccgcgacg | tctgtcgaga | agtttctgat | cgaaaagttc | gacagcgtct | ccgacctgat | 2880 |
| gcagctctcg | gagggcgaag | aatctcgtgc | tttcagcttc | gatgtaggag | ggcgtggata | 2940 |
| tgtcctgcgg | gtaaatagct | gcgccgatgg | tttctacaaa | gatcgttatg | tttatcggca | 3000 |
| ctttgcatcg | gccgcgctcc | cgattccgga | agtgcttgac | attggggaat | tcagcgagag | 3060 |
| cctgaccctat | tgcatctccc | gccgtgcaca | gggtgtcacg | ttgcaagacc | tgcctgaaac | 3120 |
| cgaactgccc | gctgttctgc | agccggtcgc | ggaggccatg | gatgcgatcg | ctgcggccga | 3180 |
| tcttagccag | acgagcgggt | tcggcccatt | cggaccgcaa | ggaatcggtc | aatacactac | 3240 |
| atggcgtgat | ttcatatgcg | cgattgctga | tccccatgtg | tatcactggc | aaactgtgat | 3300 |

```
ggacgacacc gtcagtgcgt ccgtcgcgca ggctctcgat gagctgatgc tttgggccga   3360
ggactgcccc gaagtccggc acctcgtgca cgcggatttc ggctccaaca atgtcctgac   3420
ggacaatggc cgcataacag cggtcattga ctggagcgag gcgatgttcg gggattccca   3480
atacgaggtc gccaacatct tcttctggag gccgtggttg gcttgtatgg agcagcagac   3540
gcgctacttc gagcggaggc atccggagct tgcaggatcg ccgcggctcc gggcgtatat   3600
gctccgcatt ggtcttgacc aactctatca gagcttggtt gacggcaatt tcgatgatgc   3660
agcttgggcg cagggtcgat gcgacgcaat cgtccgatcc ggagccggga ctgtcgggcg   3720
tacacaaatc gcccgcagaa gcgcggccgt ctggaccgat ggctgtgtag aagtactcgc   3780
cgatagtgga aaccgacgcc ccagcactcg tccgagggca aaggaatagc acgtgctacg   3840
agatttcgat tccaccgccg ccttctatga aaggttgggc ttcggaatcg ttttccggga   3900
cgccggctgg atgatcctcc agcgcgggga tctcatgctg gagttcttcg cccacccccaa  3960 cttgtttatt gcagcttata atggttacaa ataaagcaat agcatcacaa atttcacaaa   4020
taaagcattt ttttcactgc attctagttg tggtttgtcc aaactcatca atgtatctta   4080
tcatgtctgt ataccgtcga cctctagcta gagcttggcg taatcatggt catagctgtt   4140
tcctgtgtga aattgttatc cgctcacaat tccacacaac atacgagccg gaagcataaa   4200
gtgtaaagcc tggggtgcct aatgagtgag ctaactcaca ttaattgcgt tgcgctcact   4260
gcccgctttc cagtcgggaa acctgtcgtg ccagctgcat taatgaatcg gccaacgcgc   4320
ggggagaggc ggtttgcgta ttgggcgctc ttccgcttcc tcgctcactg actcgctgcg   4380
ctcggtcgtt cggctgcggc gagcggtatc agctcactca aaggcggtaa tacggttatc   4440
cacagaatca ggggataacg caggaaagaa catgtgagca aaaggccagc aaaaggccag   4500
gaaccgtaaa aaggccgcgt tgctggcgtt tttccatagg ctccgccccc ctgacgagca   4560
tcacaaaaat cgacgctcaa gtcagaggtg gcgaaacccg acaggactat aaagatacca   4620
ggcgtttccc cctggaagct ccctcgtgcg ctctcctgtt ccgaccctgc cgcttaccgg   4680
atacctgtcc gcctttctcc cttcgggaag cgtggcgctt tctcatagct cacgctgtag   4740
gtatctcagt tcggtgtagg tcgttcgctc caagctgggc tgtgtgcacg aaccccccgt   4800
tcagcccgac cgctgcgcct tatccggtaa ctatcgtctt gagtccaacc cggtaagaca   4860
cgacttatcg ccactggcag cagccactgg taacaggatt agcagagcga ggtatgtagg   4920
cggtgctaca gagttcttga agtggtggcc taactacggc tacactagaa gaacagtatt   4980
tggtatctgc gctctgctga agccagttac cttcggaaaa agagttggta gctcttgatc   5040
cggcaaacaa accaccgctg gtagcggttt ttttgtttgc aagcagcaga ttacgcgcag   5100
aaaaaaagga tctcaagaag atcctttgat cttttctacg gggtctgacg ctcagtggaa   5160
cgaaaactca cgttaaggga ttttggtcat gagattatca aaaaggatct tcacctagat   5220
ccttttaaat taaaaatgaa gttttaaatc aatctaaagt atatatgagt aaacttggtc   5280
tgacagttac caatgcttaa tcagtgaggc acctatctca gcgatctgtc tatttcgttc   5340
atccatagtt gcctgactcc ccgtcgtgta gataactacg atacgggagg gcttaccatc   5400
tggccccagt gctgcaatga taccgcgaga cccacgctca ccggctccag atttatcagc   5460
aataaaccag ccagccggaa gggccgagcg cagaagtggt cctgcaactt tatccgcctc   5520
catccagtct attaattgtt gccgggaagc tagagtaagt agttcgccag ttaatagttt   5580
gcgcaacgtt gttgccattg ctacaggcat cgtggtgtca cgctcgtcgt ttggtatggc   5640
```

```
ttcattcagc tccggttccc aacgatcaag gcgagttaca tgatccccca tgttgtgcaa    5700
aaaagcggtt agctccttcg gtcctccgat cgttgtcaga agtaagttgg ccgcagtgtt    5760
atcactcatg gttatggcag cactgcataa ttctcttact gtcatgccat ccgtaagatg    5820
cttttctgtg actggtgagt actcaaccaa gtcattctga gaatagtgta tgcggcgacc    5880
gagttgctct tgcccggcgt caatacggga taataccgcg ccacatagca gaactttaaa    5940
agtgctcatc attggaaaac gttcttcggg gcgaaaactc tcaaggatct taccgctgtt    6000
gagatccagt tcgatgtaac ccactcgtgc acccaactga tcttcagcat cttttacttt    6060
caccagcgtt tctgggtgag caaaaacagg aaggcaaaat gccgcaaaaa agggaataag    6120
ggcgacacgg aaatgttgaa tactcatact cttccttttt caatattatt gaagcattta    6180
tcagggttat tgtctcatga gcggatacat atttgaatgt atttagaaaa ataaacaaat    6240
aggggttccg cgcacatttc cccgaaaagt gccacctgac gtc                      6283
```

<210> SEQ ID NO 94
<211> LENGTH: 47
<212> TYPE: DNA
<213> ORGANISM: Artificial sequence
<220> FEATURE:
<223> OTHER INFORMATION: Oligonucleotide 5K-G

<400> SEQUENCE: 94
acctgtctcg agttttccat ggctgacatc gtgatgaccc agtctcc                   47

<210> SEQ ID NO 95
<211> LENGTH: 42
<212> TYPE: DNA
<213> ORGANISM: Artificial sequence
<220> FEATURE:
<223> OTHER INFORMATION: Oligonucleotide sy3K-F

<400> SEQUENCE: 95
gctgggggcg gccacggtcc gcttgatctc caccttggtc cc                        42

<210> SEQ ID NO 96
<211> LENGTH: 44
<212> TYPE: DNA
<213> ORGANISM: Artificial sequence
<220> FEATURE:
<223> OTHER INFORMATION: Oligonucleotide 5K-B

<400> SEQUENCE: 96
acctgtctcg agttttccat ggctgacatc cagatgaccc agtc                      44

<210> SEQ ID NO 97
<211> LENGTH: 49
<212> TYPE: DNA
<213> ORGANISM: Artificial sequence
<220> FEATURE:
<223> OTHER INFORMATION: Oligonucleotide 5K-J

<400> SEQUENCE: 97
acctgtctcg agttttccat ggctgacatc gtgatgaccc agtctccag                 49

<210> SEQ ID NO 98
<211> LENGTH: 52
<212> TYPE: DNA
<213> ORGANISM: Artificial sequence
<220> FEATURE:
<223> OTHER INFORMATION: Oligonucleotide 5L-B

<400> SEQUENCE: 98

```
acctgtctcg agttttccat ggctcagtcc gccctgaccc agccccgctc ag        52
```

<210> SEQ ID NO 99
<211> LENGTH: 28
<212> TYPE: DNA
<213> ORGANISM: Artificial sequence
<220> FEATURE:
<223> OTHER INFORMATION: Oligonucleotide sy3L-E

<400> SEQUENCE: 99

```
ccagcacggt aagcttggtc ccagttcc                                    28
```

<210> SEQ ID NO 100
<211> LENGTH: 44
<212> TYPE: DNA
<213> ORGANISM: Artificial sequence
<220> FEATURE:
<223> OTHER INFORMATION: Oligonucleotide 5L-G

<400> SEQUENCE: 100

```
acctgtctcg agttttccat ggcttcctac gtgctgactc agcc                  44
```

<210> SEQ ID NO 101
<211> LENGTH: 28
<212> TYPE: DNA
<213> ORGANISM: Artificial sequence
<220> FEATURE:
<223> OTHER INFORMATION: Oligonucleotide sy3L-Cmod

<400> SEQUENCE: 101

```
ccagcacggt aagcttggtg cctccgcc                                    28
```

<210> SEQ ID NO 102
<211> LENGTH: 52
<212> TYPE: DNA
<213> ORGANISM: Artificial sequence
<220> FEATURE:
<223> OTHER INFORMATION: Oligonucleotide 5L-C

<400> SEQUENCE: 102

```
acctgtctcg agttttccat ggctcagtcc gtgctgaccc agcctccctc ag         52
```

<210> SEQ ID NO 103
<211> LENGTH: 47
<212> TYPE: DNA
<213> ORGANISM: Artificial sequence
<220> FEATURE:
<223> OTHER INFORMATION: Oligonucleotide 5H-H

<400> SEQUENCE: 103

```
acctgtcttg aattctccat ggccgaggtg cagctggtgc agtctgg               47
```

<210> SEQ ID NO 104
<211> LENGTH: 47
<212> TYPE: DNA
<213> ORGANISM: Artificial sequence
<220> FEATURE:
<223> OTHER INFORMATION: Oligonucleotide sy3H-A

<400> SEQUENCE: 104

```
gcccttggtg ctagcgctgg agacggtcac cagggtgccc tggcccc               47
```

<210> SEQ ID NO 105
<211> LENGTH: 47
<212> TYPE: DNA

<213> ORGANISM: Artificial sequence
<220> FEATURE:
<223> OTHER INFORMATION: Oligonucleotide sy3H-C

<400> SEQUENCE: 105
gcccttggtg ctagcgctgg agacggtcac ggtggtgccc tggcccc        47

<210> SEQ ID NO 106
<211> LENGTH: 47
<212> TYPE: DNA
<213> ORGANISM: Artificial sequence
<220> FEATURE:
<223> OTHER INFORMATION: Oligonucleotide 5H-C

<400> SEQUENCE: 106
acctgtcttg aattctccat ggcccaggtg cagctggtgg agtctgg        47

<210> SEQ ID NO 107
<211> LENGTH: 47
<212> TYPE: DNA
<213> ORGANISM: Artificial sequence
<220> FEATURE:
<223> OTHER INFORMATION: Oligonucleotide 5H-A

<400> SEQUENCE: 107
acctgtcttg aattctccat ggcccaggtg cagctggtgc agtctgg        47

<210> SEQ ID NO 108
<211> LENGTH: 47
<212> TYPE: DNA
<213> ORGANISM: Artificial sequence
<220> FEATURE:
<223> OTHER INFORMATION: Oligonucleotide 5H-N

<400> SEQUENCE: 108
acctgtcttg aattctccat ggcccagatc accttgaagg agtctgg        47

<210> SEQ ID NO 109
<211> LENGTH: 47
<212> TYPE: DNA
<213> ORGANISM: Artificial sequence
<220> FEATURE:
<223> OTHER INFORMATION: Oligonucleotide sy3H-D

<400> SEQUENCE: 109
gcccttggtg ctagcgctgg acacggtcac catggtgccc tggcccc        47

<210> SEQ ID NO 110
<211> LENGTH: 10515
<212> TYPE: DNA
<213> ORGANISM: Artificial sequence
<220> FEATURE:
<223> OTHER INFORMATION: pIg-C911-HCgamma1
<220> FEATURE:
<221> NAME/KEY: misc_feature
<222> LOCATION: (1326)..(5076)
<223> OTHER INFORMATION: Stuffer

<400> SEQUENCE: 110
tcgacggatc gggagatctc ccgatcccct atggtgcact ctcagtacaa tctgctctga     60
tgccgcatag ttaagccagt atctgctccc tgcttgtgtg ttggaggtcg ctgagtagtg    120
cgcgagcaaa atttaagcta caacaaggca aggcttgacc gacaattgca tgaagaatct    180
gcttagggtt aggcgttttg cgctgcttcg ctaggtggtc aatattggcc attagccata    240
ttattcattg gttatatagc ataaatcaat attggctatt ggccattgca tacgttgtat    300

```
ccatatcata atatgtacat ttatattggc tcatgtccaa cattaccgcc atgttgacat    360
tgattattga ctagttatta atagtaatca attacggggt cattagttca tagcccatat    420
atggagttcc gcgttacata acttacggta aatggcccgc ctggctgacc gcccaacgac    480
ccccgcccat tgacgtcaat aatgacgtat gttcccatag taacgccaat agggactttc    540
cattgacgtc aatgggtgga gtatttacgg taaactgccc acttggcagt acatcaagtg    600
tatcatatgc caagtacgcc ccctattgac gtcaatgacg gtaaatggcc cgcctggcat    660
tatgcccagt acatgacctt atgggacttt cctacttggc agtacatcta cgtattagtc    720
atcgctatta ccatggtgat gcggttttgg cagtacatca atgggcgtgg atagcggttt    780
gactcacggg gatttccaag tctccacccc attgacgtca atgggagttt gttttggcac    840
caaaatcaac gggactttcc aaaatgtcgt aacaactccg ccccattgac gcaaatgggc    900
ggtaggcgtg tacggtggga ggtctatata agcagagctc gtttagtgaa ccgtcagatc    960
gcctggagac gccatccacg ctgttttgac ctccatagaa gacaccggga ccgatccagc   1020
ctccgcggcc gggaacggtg cattggaagc tggcctggat atcctgactc tcttaggtag   1080
ccttgcagaa gttggtcgtg aggcactggg caggtaagta tcaaggttac aagacaggtt   1140
taaggagatc aatagaaact gggcttgtcg agacagagaa gactcttgcg tttctgatag   1200
gcacctattg gtcttactga catccacttt gcctttctct ccacaggtgt ccactcccag   1260
ttcaattaca gctcgccacc atgggatgga gctgtatcat cctcttcttg gtactgctgc   1320
tgcccagcc ggccagtgac cttgaccggt gcaccacttt tgatgatgtt caagctccta   1380
attacactca acatacttca tctatgaggg gggtttacta tcctgatgaa atttttagat   1440
cggacactct ttatttaact caggatttat ttcttccatt ttattctaat gttacagggt   1500
ttcatactat taatcatacg tttggcaacc ctgtcatacc ttttaaggat ggtatttatt   1560
ttgctgccac agagaaatca aatgttgtcc gtggttgggt ttttggttct accatgaaca   1620
acaagtcaca gtcggtgatt attattaaca attctactaa tgttgttata cgagcatgta   1680
actttgaatt gtgtgacaac cctttctttg ctgtttctaa acccatgggt acacagacac   1740
atactatgat attcgataat gcatttaatt gcactttcga gtacatatct gatgcctttt   1800
cgcttgatgt ttcagaaaag tcaggtaatt ttaaacactt acgagagttt gtgtttaaaa   1860
ataaagatgg gtttctctat gtttataagg gctatcaacc tatagatgta gttcgtgatc   1920
taccttctgg ttttaacact tgaaaccta tttttaagtt gcctcttggt attaacatta   1980
caaattttag agccattctt acagccttt cacctgctca agacatttgg ggcacgtcag   2040
ctgcagccta ttttgttggc tatttaaagc caactacatt tatgctcaag tatgatgaaa   2100
atggtacaat cacagatgct gttgattgtt ctcaaaatcc acttgctgaa ctcaaatgct   2160
ctgttaagag ctttgagatt gacaaaggaa tttaccagac tctaattttc agggttgttc   2220
cctcaggaga tgttgtgaga ttccctaata ttacaaactt gtgtccttt ggagaggttt   2280
ttaatgctac taaattccct tctgtctatg catgggagag aaaaaaaatt tctaattgtg   2340
ttgctgatta ctctgtgctc tacaactcaa catttttttc aacctttaag tgctatggcg   2400
tttctgccac taagttgaat gatctttgct tctccaatgt ctatgcagat tcttttgtag   2460
tcaagggaga tgatgtaaga caaatagcgc aggacaaac tggtgttatt gctgattata   2520
attataaatt gccagatgat ttcatgggtt gtgtccttgc ttggaatact aggaacattg   2580
atgctacttc aactggtaat tataattata aatataggta tcttagacat ggcaagctta   2640
```

```
ggcccttga gagagacata tctaatgtgc ctttctcccc tgatggcaaa ccttgcaccc    2700
cacctgctct taattgttat tggccattaa atgattatgg tttttacacc actactggca    2760
ttggctacca accttacaga gttgtagtac tttcttttga acttttaaat gcaccggcca    2820
cggtttgtgg accaaaatta tccactgacc ttattaagaa ccagtgtgtc aattttaatt    2880
ttaatggact cactggtact ggtgtgttaa ctccttcttc aaagagattt caaccatttc    2940
aacaatttgg ccgtgatgtt tctgatttca ctgattccgt tcgagatcct aaaacatctg    3000
aaatattaga catttcacct tgctcttttg ggggtgtaag tgtaattaca cctggaacaa    3060
atgcttcatc tgaagttgct gttctatatc aagatgttaa ctgcactgat gtttctacag    3120
caattcatgc agatcaactc acaccagctt ggcgcatata ttctactgga aacaatgtat    3180
tccagactca ggcaggctgt cttataggag ctgagcatgt cgacacttct tatgagtgcg    3240
acattcctat tggagctggc atttgtgcta gttaccatac agtttcttta ttacgtagta    3300
ctagccaaaa atctattgtg gcttatacta tgtctttagg tgctgatagt tcaattgctt    3360
actctaataa caccattgct atacctacta acttttcaat tagcattact acagaagtaa    3420
tgcctgtttc tatggctaaa acctccgtag attgtaatat gtacatctgc ggagattcta    3480
ctgaatgtgc taatttgctt ctccaatatg gtagcttttg cacacaacta aatcgtgcac    3540
tctcaggtat tgctgctgaa caggatcgca acacacgtga agtgttcgct caagtcaaac    3600
aaatgtacaa accccaact tgaaatatt ttggtggttt taatttttca caatattac     3660 ctgaccctct aaagccaact aagaggtctt ttattgagga cttgctcttt aataaggtga    3720
cactcgctga tgctggcttc atgaagcaat atggcgaatg cctaggtgat attaatgcta    3780
gagatctcat ttgtgcgcag aagttcaatg gacttacagt gttgccacct ctgctcactg    3840
atgatatgat tgctgcctac actgctgctc tagttagtgg tactgccact gctggatgga    3900
catttggtgc tggcgctgct cttcaaatac cttttgctat gcaaatggca tataggttca    3960
atggcattgg agttacccaa aatgttctct atgagaacca aaaacaaatc gccaaccaat    4020
ttaacaaggc gattagtcaa attcaagaat cacttacaac aacatcaact gcattgggca    4080
agctgcaaga cgttgttaac cagaatgctc aagcattaaa cacacttgtt aaacaactta    4140
gctctaattt tggtgcaatt tcaagtgtgc taaatgatat cctttcgcga cttgataaag    4200
tcgaggcgga ggtacaaatt gacaggttaa ttacaggcag acttcaaagc cttcaaacct    4260
atgtaacaca acaactaatc agggctgctg aaatcagggc ttctgctaat cttgctgcta    4320
ctaaaatgtc tgagtgtgtt cttggacaat caaaaagagt tgacttttgt ggaaagggct    4380
accaccttat gtccttccca caagcagccc cgcatggtgt tgtcttccta catgtcacgt    4440
atgtgccatc ccaggagagg aacttcacca cagcgccagc aatttgtcat gaaggcaaag    4500
catacttccc tcgtgaaggt gttttttgtg ttaatggcac ttcttggttt attacacaga    4560
ggaacttctt ttctccacaa ataattacta cagacaatac atttgtctca ggaaattgtg    4620
atgtcgttat tggcatcatt aacaacacag tttatgatcc tctgcaacct gagcttgact    4680
cattcaaaga agagctggac aagtacttca aaaatcatac atcaccagat gttgattttg    4740
gcgacatttc aggcattaac gcttctgtcg tcaacattca aaaagaaatt gaccgcctca    4800
atgaggtcgc taaaaattta aatgaatcac tcattgacct tcaagaactg ggaaaatatg    4860
agcaatatat taaatggcct ctcgacgaac aaaaactcat ctcagaagag gatctgaatg    4920
ctgtgggcca ggacacgcag gaggtcatcg tggtgccaca ctccttgccc tttaaggtgg    4980
tggtgatctc agccatcctg gccctggtgg tgctcaccat catctcccta atcatcctca    5040
```

```
tcatgctttg gcagaagaag ccacgttagg cggccgctcg agtgctagca ccaagggccc    5100
cagcgtgttc ccctggccc ccagcagcaa gagcaccagc ggcggcacag ccgccctggg    5160
ctgcctggtg aaggactact tccccgagcc cgtgaccgtg agctggaaca gcggcgcctt    5220
gaccagcggc gtgcacacct tccccgccgt gctgcagagc agcggcctgt acagcctgag    5280
cagcgtggtg accgtgccca gcagcagcct gggcacccag acctacatct gcaacgtgaa    5340
ccacaagccc agcaacacca aggtggacaa gcgcgtggag cccaagagct gcgacaagac    5400
ccacacctgc ccccctgcc ctgccccga gctgctgggc ggaccctccg tgttcctgtt    5460 ccccccaag cccaaggaca ccctcatgat cagccggacc cccgaggtga cctgcgtggt    5520
ggtggacgtg agccacgagg accccgaggt gaagttcaac tggtacgtgg acggcgtgga    5580
ggtgcacaac gccaagacca gccccgggga ggagcagtac aacagcaccc tccgggtggt    5640
gagcgtgctc accgtgctgc accaggactg gctgaacggc aaggagtaca agtgcaaggt    5700
gagcaacaag gccctgcctg cccccatcga gaagaccatc agcaaggcca agggccagcc    5760
ccgggagccc caggtgtaca ccctgccccc cagcagggag gagatgacca gaaccaggt    5820 gtccctcacc tgtctggtga agggcttcta ccccagcgac atcgccgtgg agtgggagag    5880
caacggccag cccgagaaca actacaagac caccccccct gtgctggaca gcgacggcag    5940
cttcttcctg tacagcaagc tcaccgtgga caagagccgg tggcagcagg gcaacgtgtt    6000
cagctgcagc gtgatgcacg aggccctgca caaccactac acccagaaga gcctgagcct    6060
gagccccggc aagtgataat ctagagggcc cgtttaaacc cgctgatcag cctcgactgt    6120
gccttctagt tgccagccat ctgttgtttg cccctccccc gtgccttcct tgaccctgga    6180
aggtgccact cccactgtcc tttcctaata aaatgaggaa attgcatcgc attgtctgag    6240
taggtgtcat tctattctgg gggtgggt gggcaggac agcaagggg aggattggga    6300 agacaatagc aggcatgctg gggatgcggt gggctctatg gcttctgagg cggaaagaac    6360
cagctggggc tctagggggt atccccacgc gccctgtagc ggcgcattaa gcgcggcggg    6420
tgtggtggtt acgcgcagcg tgaccgctac acttgccagc gccctagcgc ccgctccttt    6480
cgctttcttc ccttccttc tcgccacgtt cgccggcttt ccccgtcaag ctctaaatcg    6540
ggggctccct ttagggttcc gatttagtgc tttacggcac ctcgacccca aaaaacttga    6600
ttagggtgat ggttcacgta gtgggccatc gccctgatag acggtttttc gccctttgac    6660
gttggagtcc acgttcttta atagtggact cttgttccaa actggaacaa cactcaaccc    6720
tatctcggtc tattcttttg atttataagg gattttgccg atttcggcct attggttaaa    6780
aaatgagctg atttaacaaa aatttaacgc gaattaattc tgtggaatgt gtgtcagtta    6840
gggtgtggaa agtccccagg ctccccagca ggcagaagta tgcaaagcat gcatctcaat    6900
tagtcagcaa ccaggtgtgg aaagtcccca ggctccccag caggcagaag tatgcaaagc    6960
atgcatctca attagtcagc aaccatagtc cgcccctaa ctccgcccat cccgcccta    7020 actccgccca gttccgccca ttctccgccc catggctgac taattttttt tatttatgca    7080
gaggccgagg ccgcctctgc ctctgagcta ttccagaagt agtgaggagg cttttttgga    7140
ggcctaggct tttgcaaaaa gctcccggga gcttgtatat ccattttcgg atctgatcaa    7200
gagacaggat gaggatcgtt tcgcatgatt gaacaagatg gattgcacgc aggttctccg    7260
gccgcttggg tggagaggct attcggctat gactgggcac aacagacaat cggctgctct    7320
gatgccgccg tgttccggct gtcagcgcag gggcgcccgg ttcttttgt caagaccgac    7380
```

```
ctgtccggtg ccctgaatga actgcaggac gaggcagcgc ggctatcgtg gctggccacg    7440
acgggcgttc cttgcgcagc tgtgctcgac gttgtcactg aagcgggaag ggactggctg    7500
ctattgggcg aagtgccggg gcaggatctc ctgtcatctc accttgctcc tgccagaaaa    7560
gtatccatca tggctgatgc aatgcggcgg ctgcatacgc ttgatccggc tacctgccca    7620
ttcgaccacc aagcgaaaca tcgcatcgag cgagcacgta ctcggatgga agccggtctt    7680
gtcgatcagg atgatctgga cgaagagcat caggggctcg cgccagccga actgttcgcc    7740
aggctcaagg cgcgcatgcc cgacggcgag gatctcgtcg tgacccatgg cgatgcctgc    7800
ttgccgaata tcatggtgga aaatggccgc ttttctggat tcatcgactg tggccggctg    7860
ggtgtggcgg accgctatca ggacatagcg ttggctaccc gtgatattgc tgaagagctt    7920
ggcggcgaat gggctgaccg cttcctcgtg ctttacggta tcgccgctcc cgattcgcag    7980
cgcatcgcct tctatcgcct tcttgacgag ttcttctgag cgggactctg gggttcgaaa    8040
tgaccgacca agcgacgccc aacctgccat cacgagattt cgattccacc gccgccttct    8100
atgaaaggtt gggcttcgga atcgttttcc gggacgccgg ctggatgatc ctccagcgcg    8160
gggatctcat gctggagttc ttcgcccacc ccaacttgtt tattgcagct tataatggtt    8220
acaaataaag caatagcatc acaaatttca caaataaagc atttttttca ctgcattcta    8280
gttgtggttt gtccaaactc atcaatgtat cttatcatgt ctgtataccg tcgacctcta    8340
gctagagctt ggcgtaatca tggtcatagc tgtttcctgt gtgaaattgt tatccgctca    8400
caattccaca acatacga gccggaagca taaagtgtaa agcctggggt gcctaatgag    8460
tgagctaact cacattaatt gcgttgcgct cactgcccgc tttccagtcg ggaaacctgt    8520
cgtgccagct gcattaatga atcggccaac gcgcggggag aggcggtttg cgtattgggc    8580
gctcttccgc ttcctcgctc actgactcgc tgcgctcggt cgttcggctg cggcgagcgg    8640
tatcagctca ctcaaaggcg gtaatacggt tatccacaga atcaggggat aacgcaggaa    8700
agaacatgtg agcaaaaggc cagcaaaagg ccaggaaccg taaaaaggcc gcgttgctgg    8760
cgttttccca taggctccgc cccctgacg agcatcacaa aaatcgacgc tcaagtcaga    8820
ggtggcgaaa cccgacagga ctataaagat accaggcgtt tccccctgga agctccctcg    8880
tgcgctctcc tgttccgacc ctgccgctta ccggatacct gtccgccttt ctcccttcgg    8940
aagcgtggc gctttctcat agctcacgct gtaggtatct cagttcggtg taggtcgttc    9000
gctccaagct gggctgtgtg cacgaacccc ccgttcagcc cgaccgctgc gccttatccg    9060
gtaactatcg tcttgagtcc aacccggtaa gacacgactt atcgccactg gcagcagcca    9120
ctggtaacag gattagcaga gcgaggtatg taggcggtgc tacagagttc ttgaagtggt    9180
ggcctaacta cggctacact agaagaacag tatttggtat ctgcgctctg ctgaagccag    9240
ttaccttcgg aaaaagagtt ggtagctctt gatccggcaa acaaaccacc gctggtagcg    9300
gtttttttgt ttgcaagcag cagattacgc gcagaaaaaa aggatctcaa gaagatcctt    9360
tgatcttttc tacgggtct gacgctcagt ggaacgaaaa ctcacgttaa gggattttgg    9420
tcatgagatt atcaaaaagg atcttcacct agatcctttt aaattaaaaa tgaagtttta    9480
aatcaatcta agtatatat gagtaaactt ggtctgacag ttaccaatgc ttaatcagtg    9540
aggcaccctat ctcagcgatc tgtctatttc gttcatccat agttgcctga ctccccgtcg    9600
tgtagataac tacgatacgg gagggcttac catctggccc cagtgctgca atgataccgc    9660
gagacccacg ctcaccggct ccagatttat cagcaataaa ccagccagcc ggaagggccg    9720
agcgcagaag tggtcctgca actttatccg cctccatcca gtctattaat tgttgccggg    9780
```

-continued

| | |
|---|---|
| aagctagagt aagtagttcg ccagttaata gtttgcgcaa cgttgttgcc attgctacag | 9840 |
| gcatcgtggt gtcacgctcg tcgtttggta tggcttcatt cagctccggt tcccaacgat | 9900 |
| caaggcgagt tacatgatcc cccatgttgt gcaaaaaagc ggttagctcc ttcggtcctc | 9960 |
| cgatcgttgt cagaagtaag ttggccgcag tgttatcact catggttatg gcagcactgc | 10020 |
| ataattctct tactgtcatg ccatccgtaa gatgcttttc tgtgactggt gagtactcaa | 10080 |
| ccaagtcatt ctgagaatag tgtatgcggc gaccgagttg ctcttgcccg cgtcaatac | 10140 |
| gggataatac cgcgccacat agcagaactt taaaagtgct catcattgga aaacgttctt | 10200 |
| cggggcgaaa actctcaagg atcttaccgc tgttgagatc cagttcgatg taacccactc | 10260 |
| gtgcacccaa ctgatcttca gcatctttta ctttcaccag cgtttctggg tgagcaaaaa | 10320 |
| caggaaggca aaatgccgca aaaaagggaa taaggcgac acggaaatgt tgaatactca | 10380 |
| tactcttcct ttttcaatat tattgaagca tttatcaggg ttattgtctc atgagcggat | 10440 |
| acatatttga atgtatttag aaaaataaac aatagggggt tccgcgcaca tttccccgaa | 10500 |
| aagtgccacc tgacg | 10515 |

<210> SEQ ID NO 111
<211> LENGTH: 8777
<212> TYPE: DNA
<213> ORGANISM: Artificial sequence
<220> FEATURE:
<223> OTHER INFORMATION: pIg-C909-Ckappa
<220> FEATURE:
<221> NAME/KEY: misc_feature
<222> LOCATION: (1328)..(3860)

<400> SEQUENCE: 111

| | |
|---|---|
| tcgacggatc gggagatctc ccgatcccct atggtgcact ctcagtacaa tctgctctga | 60 |
| tgccgcatag ttaagccagt atctgctccc tgcttgtgtg ttggaggtcg ctgagtagtg | 120 |
| cgcgagcaaa atttaagcta caacaaggca aggcttgacc gacaattgtt aattaacatg | 180 |
| aagaatctgc ttagggttag gcgttttgcg ctgcttcgct aggtggtcaa tattggccat | 240 |
| tagccatatt attcattggt tatatagcat aaatcaatat tggctattgg ccattgcata | 300 |
| cgttgtatcc atatcataat atgtacattt atattggctc atgtccaaca ttaccgccat | 360 |
| gttgacattg attattgact agttattaat agtaatcaat tacggggtca ttagttcata | 420 |
| gcccatatat ggagttccgc gttacataac ttacggtaaa tggcccgcct ggctgaccgc | 480 |
| ccaacgaccc ccgcccattg acgtcaataa tgacgtatgt tcccatagta acgccaatag | 540 |
| ggactttcca ttgacgtcaa tgggtggagt atttacggta aactgcccac ttggcagtac | 600 |
| atcaagtgta tcatatgcca gtacgcccc ctattgacgt caatgacggt aaatggcccg | 660 |
| cctggcatta tgcccagtac atgaccttat gggactttcc tacttggcag tacatctacg | 720 |
| tattagtcat cgctattacc atggtgatgc ggttttggca gtacatcaat gggcgtggat | 780 |
| agcggtttga ctcacgggga tttccaagtc tccaccccat tgacgtcaat gggagtttgt | 840 |
| tttggcacca aaatcaacgg gactttccaa aatgtcgtaa caactccgcc ccattgacgc | 900 |
| aaatgggcgg taggcgtgta cggtgggagg tctatataag cagagctcgt ttagtgaacc | 960 |
| gtcagatcgc ctggagacgc catccacgct gttttgacct ccatagaaga cacgggacc | 1020 |
| gatccagcct ccgcggccgg gaacggtgca ttggaatcga tgactctctt aggtagcctt | 1080 |
| gcagaagttg gtcgtgaggc actgggcagg taagtatcaa ggttacaaga caggtttaag | 1140 |
| gagatcaata gaaactgggc ttgtcgagac agagaagact cttgcgtttc tgataggcac | 1200 |

```
ctattggtct tactgacatc cactttgcct ttctctccac aggtgtccac tcccagttca    1260
attacagctc gccaccatgc ggctgcccgc ccagctgctg ggccttctca tgctgtgggt    1320
gcccgcctcg agatctatcg atgcatgcca tggtaccaag cttgccacca tgagcagcag    1380
ctcttggctg ctgctgagcc tggtggccgt gacagccgcc cagagcacca tcgaggagca    1440
ggccaagacc ttcctggaca gttcaacca cgaggccgag gacctgttct accagagcag    1500
cctggccagc tggaactaca acaccaacat caccgaggag aacgtgcaga acatgaacaa    1560
cgccggcgac aagtggagcg ccttcctgaa ggagcagagc cactggccc agatgtaccc    1620
cctgcaggag atccagaacc tgaccgtgaa gctgcagctg caggccctgc agcagaacgg    1680
cagcagcgtg ctgagcgagg acaagagcaa gcggctgaac accatcctga acaccatgtc    1740
caccatctac agcaccggca agtgtgcaa ccccgacaac ccccaggagt gcctgctgct    1800
ggagcccggc ctgaacgaga tcatggccaa cagcctggac tacaacgagc ggctgtgggc    1860
ctgggagagc tggcggagcg aagtgggcaa gcagctgcgg cccctgtacg aggagtacgt    1920
ggtgctgaag aacgagatgg ccagggccaa ccactacgag gactacgcg actactggag    1980
aggcgactac gaagtgaacg gcgtggacgg ctacgactac agcagaggcc agctgatcga    2040
ggacgtggag cacaccttcg aggagatcaa gcctctgtac gagcacctgc acgcctacgt    2100
gcgggccaag ctgatgaacg cctacccag ctacatcagc cccatcggct gcctgccgc    2160
ccacctgctg ggcgacatgt ggggccggtt ctggaccaac ctgtacagcc tgaccgtgcc    2220
cttcggccag aagcccaaca tcgacgtgac cgacgccatg gtggaccagg cctgggacgc    2280
ccagcggatc ttcaaggagg ccgagaagtt cttcgtgagc gtgggcctgc ccaacatgac    2340
ccagggcttt tgggagaaca gcatgctgac cgaccccggc aatgtgcaga aggccgtgtg    2400
ccacccacc gcctgggacc tgggcaaggg cgacttccgg atcctgatgt gcaccaaagt    2460
gaccatggac gacttcctga ccgcccacca cgagatgggc cacatccagt acgacatggc    2520
ctacgccgcc cagccttcc tgctgcggaa cggcgccaac gagggctttc acgaggccgt    2580
gggcgagatc atgagcctga cgccgccac ccccaagcac ctgaagagca tcggcctgct    2640
gagccccgac ttccaggagg acaacgagac cgagatcaac ttcctgctga gcaggccct    2700
gaccatcgtg ggcaccctgc ccttcaccta catgctggaa agtggcggt ggatggtgtt    2760
taagggcgag atccccaagg accagtggat gaagaagtgg tgggagatga gcgggagat    2820
cgtgggcgtg gtggagcccg tgccccacga cgagacctac tgcgaccccg ccagcctgtt    2880
ccacgtgagc aacgactact ccttcatccg gtactacacc cggaccctgt accagttcca    2940
gttccaggag gccctgtgcc aggccgccaa gcacagggc cccctgcaca gtgcgacat    3000
cagcaacagc accgaggccg acagaaact gttcaacatg ctgcggctgg gcaagagcga    3060
gccctggacc ctgccctgg agaatgtggt gggcgccaag aacatgaatg tgcgcccct    3120
gctgaactac ttcgagcccc tgttcacctg gctgaaggac cagaacaaga acagcttcgt    3180
gggctggagc accgactgga gccctacgc cgaccagagc atcaaagtgc ggatcagcct    3240
gaagagcgcc ctgggcgaca ggcctacga gtggaacgac aacgagatgt acctgttccg    3300
gagcagcgtg gcctatgcca tgcggcagta cttcctgaaa gtgaagaacc agatgatcct    3360
gttcggcgag gaggacgtga gagtggccaa cctgaagccc ggatcagct tcaacttctt    3420
cgtgaccgcc cccaagaacg tgagcgacat catcccccgg accgaagtgg agaaggccat    3480
ccggatgagc cggagccgga tcaacgacgc cttccggctg aacgacaact ccctggagtt    3540
```

-continued

```
cctgggcatc cagcccaccc tgggccctcc caaccagccc cccgtgagca tctggctgat    3600
cgtgtttggc gtggtgatgg gcgtgatcgt ggtgggaatc gtgatcctga tcttcaccgg    3660
catccgggac cggaagaaga agaacaaggc ccggagcggc gagaacccct acgccagcat    3720
cgatatcagc aagggcgaga acaaccccgg cttccagaac accgacgacg tgcagaccag    3780
cttctgataa tctagaacga gctcgaattc gaagcttctg cagacgcgtc gacgtcatat    3840
ggatccgata tcgccgtggc ggccgcaccc agcgtgttca tcttcccccc ctccgacgag    3900
cagctgaaga gcggcaccgc cagcgtggtg tgcctgctga caacttcta cccccgggag    3960
gccaaggtgc agtggaaggt ggacaacgcc ctgcagagcg gcaacagcca ggagagcgtg    4020
accgagcagg acagcaagga ctccacctac agcctgagca gcaccctcac cctgagcaag    4080
gccgactacg agaagcacaa ggtgtacgcc tgcgaggtga cccaccaggg cctgagcagc    4140
cccgtgacca gagcttcaa ccggggcgag tgttaataga cttaagttta aaccgctgat     4200
cagcctcgac tgtgccttct agttgccagc catctgttgt ttgcccctcc ccgtgccttt    4260
ccttgaccct ggaaggtgcc actcccactg tcctttccta ataaaatgag gaaattgcat    4320
cgcattgtct gagtaggtgt cattctattc tggggggtgg ggtggggcag gacagcaagg    4380
gggaggattg ggaagacaat agcaggcatg ctggggatgc ggtgggctct atggcttctg    4440
aggcggaaag aaccagctgg ggctctaggg gtatcccca cgcgcccgt agcggcgcat      4500
taagcgcggc gggtgtggtg gttacgcgca gcgtgaccgc tacacttgcc agcgccctag   4560
cgcccgctcc tttcgctttc ttcccttcct ttctcgccac gttcgccggc tttccccgtc    4620
aagctctaaa tcggggctc cctttagggt tccgatttag tgctttacgg cacctcgacc     4680
ccaaaaaact tgattagggt gatggttcac gtagtgggcc atcgccctga tagacggttt    4740
ttcgcccttt gacgttggag tccacgttct ttaatagtgg actcttgttc caaactggaa    4800
caacactcaa ccctatctcg gtctattctt ttgatttata aggattttg gccatttcgg     4860
cctattggtt aaaaaatgag ctgatttaac aaaaatttaa cgcgaattaa ttctgtggaa    4920
tgtgtgtcag ttagggtgtg gaaagtcccc aggctcccca gcaggcagaa gtatgcaaag    4980
catgcatctc aattagtcag caaccaggtg tggaaagtcc ccaggctccc cagcaggcag    5040
aagtatgcaa agcatgcatc tcaattagtc agcaaccata gtcccgcccc taactccgcc    5100
catcccgccc ctaactccgc ccagttccgc ccattctccg ccccatggct gactaatttt    5160
tttttattat gcagaggccg aggccgcctc tgcctctgag ctattccaga agtagtgagg    5220
aggctttttt ggaggcctag gcttttgcaa aaagctcccg ggagcttgta tatccatttt    5280
cggatctgat cagcacgtga tgaaaaagcc tgaactcacc gcgacgtctg tcgagaagtt    5340
tctgatcgaa aagttcgaca gcgtctccga cctgatgcag ctctcggagg gcgaagaatc    5400
tcgtgctttc agcttcgatg taggagggcg tggatatgtc ctgcgggtaa atagctgcgc    5460
cgatggtttc tacaaagatc gttatgttta tcggcacttt gcatcggccg cgctcccgat    5520
tccggaagtg cttgacattg gggaattcag cgagagcctg acctattgca tctcccgccg    5580
tgcacaggg gtcacgttgc aagacctgcc tgaaaccgaa ctgcccgctg ttctgcagcc     5640
ggtcgcggag gccatggatg cgatcgctgc ggccgatctt agccagacga gcgggttcgg    5700
cccattcgga ccacaaggaa tcggtcaata cactacatgg cgtgatttca tatgcgcgat    5760
tgctgatccc catgtgtatc actggcaaac tgtgatggac gacaccgtca gtgcgtccgt    5820
cgcgcaggct ctcgatgagc tgatgctttg ggccgaggac tgccccgaag tccggcacct    5880
cgtgcacgcg gatttcggct ccaacaatgt cctgacggac aatggccgca taacagcggt    5940
```

```
cattgactgg agcgaggcga tgttcgggga ttcccaatac gaggtcgcca acatcttctt    6000
ctggaggccg tggttggctt gtatggagca gcagacgcgc tacttcgagc ggaggcatcc    6060
ggagcttgca ggatcgccgc ggctccgggc gtatatgctc cgcattggtc ttgaccaact    6120
ctatcagagc ttggttgacg gcaatttcga tgatgcagct tgggcgcagg gtcgatgcga    6180
cgcaatcgtc cgatccggag ccgggactgt cgggcgtaca caaatcgccc gcagaagcgc    6240
ggccgtctgg accgatggct gtgtagaagt actcgccgat agtggaaacc gacgcccag     6300 cactcgtccg agggcaaagg aatagcacgt gctacgagat ttcgattcca ccgccgcctt    6360
ctatgaaagg ttgggcttcg gaatcgtttt ccgggacgcc ggctggatga tcctccagcg    6420
cggggatctc atgctggagt tcttcgccca ccccaacttg tttattgcag cttataatgg    6480
ttacaaataa agcaatagca tcacaaattt cacaaataaa gcattttttt cactgcattc    6540
tagttgtggt ttgtccaaac tcatcaatgt atcttatcat gtctgtatac cgtcgacctc    6600
tagctagagc ttggcgtaat catggtcata gctgtttcct gtgtgaaatt gttatccgct    6660
cacaattcca cacaacatac gagccggaag cataaagtgt aaagcctggg gtgcctaatg    6720
agtgagctaa ctcacattaa ttgcgttgcg ctcactgccc gctttccagt cgggaaacct    6780
gtcgtgccag ctgcattaat gaatcggcca acgcgcgggg agaggcggtt tgcgtattgg    6840
gcgctcttcc gcttcctcgc tcactgactc gctgcgctcg tcgttcggc tgcggcgagc     6900 ggtatcagct cactcaaagg cggtaatacg gttatccaca gaatcagggg ataacgcagg    6960
aaagaacatg tgagcaaaag gccagcaaaa ggccaggaac cgtaaaaagg ccgcgttgct    7020
ggcgtttttc cataggctcc gcccccctga cgagcatcac aaaaatcgac gctcaagtca    7080
gaggtggcga aacccgacag gactataaag ataccaggcg tttccccctg gaagctccct    7140
cgtgcgctct cctgttccga ccctgccgct taccggatac ctgtccgcct ttctcccttc    7200
gggaagcgtg gcgctttctc atagctcacg ctgtaggtat ctcagttcgg tgtaggtcgt    7260
tcgctccaag ctgggctgtg tgcacgaacc ccccgttcag cccgaccgct gcgccttatc    7320
cggtaactat cgtcttgagt ccaacccggt aagacacgac ttatcgccac tggcagcagc    7380
cactggtaac aggattagca gagcgaggta tgtaggcggt gctacagagt tcttgaagtg    7440
gtggcctaac tacggctaca ctagaagaac agtatttggt atctgcgctc tgctgaagcc    7500
agttaccttc ggaaaaagag ttggtagctc ttgatccggc aaacaaacca ccgctggtag    7560
cggtgttttt gtttgcaagc agcagattac gcgcagaaaa aaggatctc aagaagatcc      7620 tttgatcttt tctacggggt ctgacgctca gtggaacgaa aactcacgtt aagggatttt    7680
ggtcatgaga ttatcaaaaa ggatcttcac ctagatcctt ttaaattaaa aatgaagttt    7740
taaatcaatc taaagtatat atgagtaaac ttggtctgac agttaccaat gcttaatcag    7800
tgaggcacct atctcagcga tctgtctatt tcgttcatcc atagttgcct gactccccgt    7860
cgtgtagata actacgatac gggagggctt accatctggc cccagtgctg caatgatacc    7920
gcgagaccca cgctcaccgg ctccagattt atcagcaata accagccag ccggaagggc      7980 cgagcgcaga agtggtcctg caactttatc cgcctccatc cagtctatta attgttgccg    8040
ggaagctaga gtaagtagtt cgccagttaa tagtttcgc aacgttgttg ccattgctac      8100
aggcatcgtg gtgtcacgct cgtcgtttgg tatggcttca ttcagctccg gttcccaacg    8160
atcaaggcga gttacatgat cccccatgtt gtgcaaaaaa gcggttagct ccttcggtcc    8220
tccgatcgtt gtcagaagta agttggccgc agtgttatca ctcatggtta tggcagcact    8280
```

-continued

```
gcataattct cttactgtca tgccatccgt aagatgcttt tctgtgactg gtgagtactc    8340
aaccaagtca ttctgagaat agtgtatgcg gcgaccgagt tgctcttgcc cggcgtcaat    8400
acgggataat accgcgccac atagcagaac tttaaaagtg ctcatcattg gaaaacgttc    8460 ttcgggcga aaactctcaa ggatcttacc gctgttgaga tccagttcga tgtaacccac     8520
tcgtgcaccc aactgatctt cagcatcttt tactttcacc agcgtttctg ggtgagcaaa    8580
aacaggaagg caaaatgccg caaaaaaggg aataagggcg acacggaaat gttgaatact    8640
catactcttc cttttttcaat attattgaag catttatcag ggttattgtc tcatgagcgg   8700
atacatattt gaatgtattt agaaaaataa acaaatagg gttccgcgca catttccccg     8760
aaaagtgcca cctgacg                                                    8777
```

<210> SEQ ID NO 112  
<211> LENGTH: 1356  
<212> TYPE: DNA  
<213> ORGANISM: Artificial sequence  
<220> FEATURE:  
<223> OTHER INFORMATION: Heavy chain CR4271  
<220> FEATURE:  
<221> NAME/KEY: CDS  
<222> LOCATION: (1)..(1356)

<400> SEQUENCE: 112

```
gag gtg cag ctg gtg cag tct gga gca gag gtg aaa aag ccc ggg gag        48
Glu Val Gln Leu Val Gln Ser Gly Ala Glu Val Lys Lys Pro Gly Glu
1               5                   10                  15 tct ctg agg att tcc tgt aag ggt tct gga tac acc ttt aac aat tat       96
Ser Leu Arg Ile Ser Cys Lys Gly Ser Gly Tyr Thr Phe Asn Asn Tyr
            20                  25                  30 tgg atc ggc tgg gtg cgc cag atg ccc ggg aaa ggc ctg gag tgg atg      144
Trp Ile Gly Trp Val Arg Gln Met Pro Gly Lys Gly Leu Glu Trp Met
        35                  40                  45 ggg atc atc tat cct ggt gac tct gat acc aga tac agc ccg tcc gtc      192
Gly Ile Ile Tyr Pro Gly Asp Ser Asp Thr Arg Tyr Ser Pro Ser Val
    50                  55                  60 caa ggc cac gtc acc atc tca gcc gac aag tcc atc aac acc gcc tac      240
Gln Gly His Val Thr Ile Ser Ala Asp Lys Ser Ile Asn Thr Ala Tyr
65                  70                  75                  80 ctg cag tgg agc agc ctg aag gcc tcg gac acc gcc gtg tat tac tgt      288
Leu Gln Trp Ser Ser Leu Lys Ala Ser Asp Thr Ala Val Tyr Tyr Cys
                85                  90                  95 gcg aga cgg cct gga tac gac tat gga ttt tac tac ttt gac tac tgg      336
Ala Arg Arg Pro Gly Tyr Asp Tyr Gly Phe Tyr Tyr Phe Asp Tyr Trp
            100                 105                 110 ggc cag ggc acc ctg gtg acc gtc tcc agc gct agc acc aag ggc ccc      384
Gly Gln Gly Thr Leu Val Thr Val Ser Ser Ala Ser Thr Lys Gly Pro
        115                 120                 125 agc gtg ttc ccc ctg gcc ccc agc agc aag agc acc agc ggc ggc aca      432
Ser Val Phe Pro Leu Ala Pro Ser Ser Lys Ser Thr Ser Gly Gly Thr
    130                 135                 140 gcc gcc ctg ggc tgc ctg gtg aag gac tac ttc ccc gag ccc gtg acc      480
Ala Ala Leu Gly Cys Leu Val Lys Asp Tyr Phe Pro Glu Pro Val Thr
145                 150                 155                 160 gtg agc tgg aac agc ggc gcc ttg acc agc ggc gtg cac acc ttc ccc      528
Val Ser Trp Asn Ser Gly Ala Leu Thr Ser Gly Val His Thr Phe Pro
                165                 170                 175 gcc gtg ctg cag agc agc ggc ctg tac agc ctg agc agc gtg gtg acc      576
Ala Val Leu Gln Ser Ser Gly Leu Tyr Ser Leu Ser Ser Val Val Thr
            180                 185                 190
```

```
gtg ccc agc agc agc ctg ggc acc cag acc tac atc tgc aac gtg aac         624
Val Pro Ser Ser Ser Leu Gly Thr Gln Thr Tyr Ile Cys Asn Val Asn
        195                 200                 205 cac aag ccc agc aac acc aag gtg gac aaa cgc gtg gag ccc aag agc         672
His Lys Pro Ser Asn Thr Lys Val Asp Lys Arg Val Glu Pro Lys Ser
    210                 215                 220 tgc gac aag acc cac acc tgc ccc ccc tgc cct gcc ccc gag ctg ctg         720
Cys Asp Lys Thr His Thr Cys Pro Pro Cys Pro Ala Pro Glu Leu Leu
225                 230                 235                 240 ggc gga ccc tcc gtg ttc ctg ttc ccc ccc aag ccc aag gac acc ctc         768
Gly Gly Pro Ser Val Phe Leu Phe Pro Pro Lys Pro Lys Asp Thr Leu
                245                 250                 255 atg atc agc cgg acc ccc gag gtg acc tgc gtg gtg gtg gac gtg agc         816
Met Ile Ser Arg Thr Pro Glu Val Thr Cys Val Val Val Asp Val Ser
            260                 265                 270 cac gag gac ccc gag gtg aag ttc aac tgg tac gtg gac ggc gtg gag         864
His Glu Asp Pro Glu Val Lys Phe Asn Trp Tyr Val Asp Gly Val Glu
        275                 280                 285 gtg cac aac gcc aag acc aag ccc cgg gag gag cag tac aac agc acc         912
Val His Asn Ala Lys Thr Lys Pro Arg Glu Glu Gln Tyr Asn Ser Thr
    290                 295                 300 tac cgg gtg gtg agc gtg ctc acc gtg ctg cac cag gac tgg ctg aac         960
Tyr Arg Val Val Ser Val Leu Thr Val Leu His Gln Asp Trp Leu Asn
305                 310                 315                 320 ggc aag gag tac aag tgc aag gtg agc aac aag gcc ctg cct gcc ccc        1008
Gly Lys Glu Tyr Lys Cys Lys Val Ser Asn Lys Ala Leu Pro Ala Pro
                325                 330                 335 atc gag aag acc atc agc aag gcc aag ggc cag ccc cgg gag ccc cag        1056
Ile Glu Lys Thr Ile Ser Lys Ala Lys Gly Gln Pro Arg Glu Pro Gln
            340                 345                 350 gtg tac acc ctg ccc ccc agc cgg gag gag atg acc aag aac cag gtg        1104
Val Tyr Thr Leu Pro Pro Ser Arg Glu Glu Met Thr Lys Asn Gln Val
        355                 360                 365 tcc ctc acc tgt ctg gtg aag ggc ttc tac ccc agc gac atc gcc gtg        1152
Ser Leu Thr Cys Leu Val Lys Gly Phe Tyr Pro Ser Asp Ile Ala Val
    370                 375                 380 gag tgg gag agc aac ggc cag ccc gag aac aac tac aag acc acc ccc        1200
Glu Trp Glu Ser Asn Gly Gln Pro Glu Asn Asn Tyr Lys Thr Thr Pro
385                 390                 395                 400 cct gtg ctg gac agc gac ggc agc ttc ttc ctg tac agc aag ctc acc        1248
Pro Val Leu Asp Ser Asp Gly Ser Phe Phe Leu Tyr Ser Lys Leu Thr
                405                 410                 415 gtg gac aag agc cgg tgg cag cag ggc aac gtg ttc agc tgc agc gtg        1296
Val Asp Lys Ser Arg Trp Gln Gln Gly Asn Val Phe Ser Cys Ser Val
            420                 425                 430 atg cac gag gcc ctg cac aac cac tac acc cag aag agc ctg agc ctg        1344
Met His Glu Ala Leu His Asn His Tyr Thr Gln Lys Ser Leu Ser Leu
        435                 440                 445 agc ccc ggc aag                                                        1356
Ser Pro Gly Lys
    450
```

<210> SEQ ID NO 113
<211> LENGTH: 452
<212> TYPE: PRT
<213> ORGANISM: Artificial sequence
<220> FEATURE:
<223> OTHER INFORMATION: Heavy chain CR4271

<400> SEQUENCE: 113

Glu Val Gln Leu Val Gln Ser Gly Ala Glu Val Lys Lys Pro Gly Glu

```
1               5                   10                  15
Ser Leu Arg Ile Ser Cys Lys Gly Ser Gly Tyr Thr Phe Asn Asn Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Val
        50                  55                  60

Gln Gly His Val Thr Ile Ser Ala Asp Lys Ser Ile Asn Thr Ala Tyr
65                  70                  75                  80

Leu Gln Trp Ser Ser Leu Lys Ala Ser Asp Thr Ala Val Tyr Tyr Cys
                85                  90                  95

Ala Arg Arg Pro Gly Tyr Asp Tyr Gly Phe Tyr Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430
```

Met His Glu Ala Leu His Asn His Tyr Thr Gln Lys Ser Leu Ser Leu
        435                 440                 445

Ser Pro Gly Lys
    450

<210> SEQ ID NO 114
<211> LENGTH: 1380
<212> TYPE: DNA
<213> ORGANISM: Artificial sequence
<220> FEATURE:
<223> OTHER INFORMATION: Heavy chain CR4274
<220> FEATURE:
<221> NAME/KEY: CDS
<222> LOCATION: (1)..(1380)

<400> SEQUENCE: 114

| | | | | | | | | | | | | | | | | |
|---|---|---|---|---|---|---|---|---|---|---|---|---|---|---|---|---|---|
| gag | gtg | cag | ctg | gtg | cag | tct | gga | gca | gag | gtg | aaa | aag | ccc | ggg | gag | | 48 |
| Glu | Val | Gln | Leu | Val | Gln | Ser | Gly | Ala | Glu | Val | Lys | Lys | Pro | Gly | Glu | | |
| 1 | | | | 5 | | | | | 10 | | | | | 15 | | | |
| tct | ctg | aag | atc | tcc | tgt | aag | ggt | tct | gga | tac | agc | ttt | acc | agc | tac | | 96 |
| Ser | Leu | Lys | Ile | Ser | Cys | Lys | Gly | Ser | Gly | Tyr | Ser | Phe | Thr | Ser | Tyr | | |
| | | | 20 | | | | | 25 | | | | | 30 | | | | |
| tgg | atc | ggc | tgg | gtg | cgc | cag | atg | ccc | ggg | aaa | ggc | ctg | gag | tgg | atg | | 144 |
| Trp | Ile | Gly | Trp | Val | Arg | Gln | Met | Pro | Gly | Lys | Gly | Leu | Glu | Trp | Met | | |
| | | 35 | | | | | 40 | | | | | 45 | | | | | |
| ggc | atc | atc | tat | cct | ggt | gac | tct | gat | acc | aga | tac | agc | ccg | tcc | ttc | | 192 |
| Gly | Ile | Ile | Tyr | Pro | Gly | Asp | Ser | Asp | Thr | Arg | Tyr | Ser | Pro | Ser | Phe | | |
| | 50 | | | | | 55 | | | | | 60 | | | | | | |
| caa | ggc | cag | gtc | acc | atc | tca | gcc | gac | agg | tcc | atc | agc | acc | gcc | tac | | 240 |
| Gln | Gly | Gln | Val | Thr | Ile | Ser | Ala | Asp | Arg | Ser | Ile | Ser | Thr | Ala | Tyr | | |
| 65 | | | | | 70 | | | | | 75 | | | | | 80 | | |
| ctg | cag | tgg | agc | agc | ctg | aag | gcc | tcg | gac | acc | gcc | atg | tat | tac | tgt | | 288 |
| Leu | Gln | Trp | Ser | Ser | Leu | Lys | Ala | Ser | Asp | Thr | Ala | Met | Tyr | Tyr | Cys | | |
| | | | | 85 | | | | | 90 | | | | | 95 | | | |
| gcg | aga | ctc | cga | ggc | ccc | tat | tac | gat | ttt | tgg | aat | ggc | tat | cgg | gag | | 336 |
| Ala | Arg | Leu | Arg | Gly | Pro | Tyr | Tyr | Asp | Phe | Trp | Asn | Gly | Tyr | Arg | Glu | | |
| | | | 100 | | | | | 105 | | | | | 110 | | | | |
| aca | cat | gat | gct | ttt | aat | gtg | tgg | ggc | cag | ggc | acc | acc | gtg | acc | gtc | | 384 |
| Thr | His | Asp | Ala | Phe | Asn | Val | Trp | Gly | Gln | Gly | Thr | Thr | Val | Thr | Val | | |
| | | 115 | | | | | 120 | | | | | 125 | | | | | |
| tcc | agc | gct | agc | acc | aag | ggc | ccc | agc | gtg | ttc | ccc | ctg | gcc | ccc | agc | | 432 |
| Ser | Ser | Ala | Ser | Thr | Lys | Gly | Pro | Ser | Val | Phe | Pro | Leu | Ala | Pro | Ser | | |
| 130 | | | | | 135 | | | | | 140 | | | | | | | |
| agc | aag | agc | acc | agc | ggc | ggc | aca | gcc | gcc | ctg | ggc | tgc | ctg | gtg | aag | | 480 |
| Ser | Lys | Ser | Thr | Ser | Gly | Gly | Thr | Ala | Ala | Leu | Gly | Cys | Leu | Val | Lys | | |
| 145 | | | | | 150 | | | | | 155 | | | | | 160 | | |
| gac | tac | ttc | ccc | gag | ccc | gtg | acc | gtg | agc | tgg | aac | agc | ggc | gcc | ttg | | 528 |
| Asp | Tyr | Phe | Pro | Glu | Pro | Val | Thr | Val | Ser | Trp | Asn | Ser | Gly | Ala | Leu | | |
| | | | | 165 | | | | | 170 | | | | | 175 | | | |
| acc | agc | ggc | gtg | cac | acc | ttc | ccc | gcc | gtg | ctg | cag | agc | agc | ggc | ctg | | 576 |
| Thr | Ser | Gly | Val | His | Thr | Phe | Pro | Ala | Val | Leu | Gln | Ser | Ser | Gly | Leu | | |
| | | | 180 | | | | | 185 | | | | | 190 | | | | |
| tac | agc | ctg | agc | agc | gtg | gtg | acc | gtg | ccc | agc | agc | agc | ctg | ggc | acc | | 624 |
| Tyr | Ser | Leu | Ser | Ser | Val | Val | Thr | Val | Pro | Ser | Ser | Ser | Leu | Gly | Thr | | |
| | | | | 195 | | | | | 200 | | | | | 205 | | | |
| cag | acc | tac | atc | tgc | aac | gtg | aac | cac | aag | ccc | agc | aac | acc | aag | gtg | | 672 |
| Gln | Thr | Tyr | Ile | Cys | Asn | Val | Asn | His | Lys | Pro | Ser | Asn | Thr | Lys | Val | | |
| | | 210 | | | | | 215 | | | | | 220 | | | | | |
| gac | aaa | cgc | gtg | gag | ccc | aag | agc | tgc | gac | aag | acc | cac | acc | tgc | ccc | | 720 |
| Asp | Lys | Arg | Val | Glu | Pro | Lys | Ser | Cys | Asp | Lys | Thr | His | Thr | Cys | Pro | | |
| 225 | | | | | 230 | | | | | 235 | | | | | 240 | | |

-continued

```
ccc tgc cct gcc ccc gag ctg ctg ggc gga ccc tcc gtg ttc ctg ttc         768
Pro Cys Pro Ala Pro Glu Leu Leu Gly Gly Pro Ser Val Phe Leu Phe
                245                 250                 255 ccc ccc aag ccc aag gac acc ctc atg atc agc cgg acc ccc gag gtg         816
Pro Pro Lys Pro Lys Asp Thr Leu Met Ile Ser Arg Thr Pro Glu Val
            260                 265                 270 acc tgc gtg gtg gtg gac gtg agc cac gag gac ccc gag gtg aag ttc         864
Thr Cys Val Val Val Asp Val Ser His Glu Asp Pro Glu Val Lys Phe
            275                 280                 285 aac tgg tac gtg gac ggc gtg gag gtg cac aac gcc aag acc aag ccc         912
Asn Trp Tyr Val Asp Gly Val Glu Val His Asn Ala Lys Thr Lys Pro
        290                 295                 300 cgg gag gag cag tac aac agc acc tac cgg gtg gtg agc gtg ctc acc         960
Arg Glu Glu Gln Tyr Asn Ser Thr Tyr Arg Val Val Ser Val Leu Thr
305                 310                 315                 320 gtg ctg cac cag gac tgg ctg aac ggc aag gag tac aag tgc aag gtg        1008
Val Leu His Gln Asp Trp Leu Asn Gly Lys Glu Tyr Lys Cys Lys Val
                325                 330                 335 agc aac aag gcc ctg cct gcc ccc atc gag aag acc atc agc aag gcc        1056
Ser Asn Lys Ala Leu Pro Ala Pro Ile Glu Lys Thr Ile Ser Lys Ala
            340                 345                 350 aag ggc cag ccc cgg gag ccc cag gtg tac acc ctg ccc ccc agc cgg        1104
Lys Gly Gln Pro Arg Glu Pro Gln Val Tyr Thr Leu Pro Pro Ser Arg
            355                 360                 365 gag gag atg acc aag aac cag gtg tcc ctc acc tgt ctg gtg aag ggc        1152
Glu Glu Met Thr Lys Asn Gln Val Ser Leu Thr Cys Leu Val Lys Gly
        370                 375                 380 ttc tac ccc agc gac atc gcc gtg gag tgg gag agc aac ggc cag ccc        1200
Phe Tyr Pro Ser Asp Ile Ala Val Glu Trp Glu Ser Asn Gly Gln Pro
385                 390                 395                 400 gag aac aac tac aag acc acc ccc cct gtg ctg gac agc gac ggc agc        1248
Glu Asn Asn Tyr Lys Thr Thr Pro Pro Val Leu Asp Ser Asp Gly Ser
                405                 410                 415 ttc ttc ctg tac agc aag ctc acc gtg gac aag agc cgg tgg cag cag        1296
Phe Phe Leu Tyr Ser Lys Leu Thr Val Asp Lys Ser Arg Trp Gln Gln
            420                 425                 430 ggc aac gtg ttc agc tgc agc gtg atg cac gag gcc ctg cac aac cac        1344
Gly Asn Val Phe Ser Cys Ser Val Met His Glu Ala Leu His Asn His
            435                 440                 445 tac acc cag aag agc ctg agc ctg agc ccc ggc aag                        1380
Tyr Thr Gln Lys Ser Leu Ser Leu Ser Pro Gly Lys
        450                 455                 460
```

<210> SEQ ID NO 115
<211> LENGTH: 460
<212> TYPE: PRT
<213> ORGANISM: Artificial sequence
<220> FEATURE:
<223> OTHER INFORMATION: Heavy chain CR4274

<400> SEQUENCE: 115

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60
```

```
Gln Gly Gln Val Thr Ile Ser Ala Asp Arg Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu Arg Gly Pro Tyr Tyr Asp Phe Trp Asn Gly Tyr Arg Glu
            100                 105                 110

Thr His Asp Ala Phe Asn Val Trp Gly Gln Gly Thr Thr Val Thr Val
        115                 120                 125

Ser Ser Ala Ser Thr Lys Gly Pro Ser Val Phe Pro Leu Ala Pro Ser
130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Arg Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
450                 455                 460

<210> SEQ ID NO 116
<211> LENGTH: 1380
<212> TYPE: DNA
```

```
<213> ORGANISM: Artificial sequence
<220> FEATURE:
<223> OTHER INFORMATION: Heavy chain CR4283
<220> FEATURE:
<221> NAME/KEY: CDS
<222> LOCATION: (1)..(1380)

<400> SEQUENCE: 116 gag gtg cag ctg gtg cag tct gga gca gag gtg aaa aag tcc ggg gag      48
Glu Val Gln Leu Val Gln Ser Gly Ala Glu Val Lys Lys Ser Gly Glu
1               5                   10                  15 tct ctg aag atc tcc tgt aag ggt tct gga tac acc ttt aat acc tac      96
Ser Leu Lys Ile Ser Cys Lys Gly Ser Gly Tyr Thr Phe Asn Thr Tyr
            20                  25                  30 tgg atc ggc tgg gtg cgc cag atg ccc ggg aaa ggc ctg gag tgg atg     144
Trp Ile Gly Trp Val Arg Gln Met Pro Gly Lys Gly Leu Glu Trp Met
        35                  40                  45 ggg atc att tat cct ggt gac tct gat acc ata tac agc ccg tcc ttc     192
Gly Ile Ile Tyr Pro Gly Asp Ser Asp Thr Ile Tyr Ser Pro Ser Phe
    50                  55                  60 caa ggc cag gtc acc atc tca gcc gac aag tcc atc agc acc gcc tac     240
Gln Gly Gln Val Thr Ile Ser Ala Asp Lys Ser Ile Ser Thr Ala Tyr
65                  70                  75                  80 ctg cag tgg agc agc ctg aag gcc tcg gac agc gcc atg tat tac tgt     288
Leu Gln Trp Ser Ser Leu Lys Ala Ser Asp Ser Ala Met Tyr Tyr Cys
                85                  90                  95 gcg aga ctt acc ttt cga cgt gga tat agt ggc tcc gat tcg ttt ctc     336
Ala Arg Leu Thr Phe Arg Arg Gly Tyr Ser Gly Ser Asp Ser Phe Leu
            100                 105                 110 cct ccg ggg gac ttt gac tac tgg ggc cag ggc acc ctg gtg acc gtc     384
Pro Pro Gly Asp Phe Asp Tyr Trp Gly Gln Gly Thr Leu Val Thr Val
        115                 120                 125 tcc agc gct agc acc aag ggc ccc agc gtg ttc ccc ctg gcc ccc agc     432
Ser Ser Ala Ser Thr Lys Gly Pro Ser Val Phe Pro Leu Ala Pro Ser
    130                 135                 140 agc aag agc acc agc ggc ggc aca gcc gcc ctg ggc tgc ctg gtg aag     480
Ser Lys Ser Thr Ser Gly Gly Thr Ala Ala Leu Gly Cys Leu Val Lys
145                 150                 155                 160 gac tac ttc ccc gag ccc gtg acc gtg agc tgg aac agc ggc gcc ttg     528
Asp Tyr Phe Pro Glu Pro Val Thr Val Ser Trp Asn Ser Gly Ala Leu
                165                 170                 175 acc agc ggc gtg cac acc ttc ccc gcc gtg ctg cag agc agc ggc ctg     576
Thr Ser Gly Val His Thr Phe Pro Ala Val Leu Gln Ser Ser Gly Leu
            180                 185                 190 tac agc ctg agc agc gtg gtg acc gtg ccc agc agc agc ctg ggc acc     624
Tyr Ser Leu Ser Ser Val Val Thr Val Pro Ser Ser Ser Leu Gly Thr
        195                 200                 205 cag acc tac atc tgc aac gtg aac cac aag ccc agc aac acc aag gtg     672
Gln Thr Tyr Ile Cys Asn Val Asn His Lys Pro Ser Asn Thr Lys Val
    210                 215                 220 gac aaa cgc gtg gag ccc aag agc tgc gac aag acc cac acc tgc ccc     720
Asp Lys Arg Val Glu Pro Lys Ser Cys Asp Lys Thr His Thr Cys Pro
225                 230                 235                 240 ccc tgc cct gcc ccc gag ctg ctg ggc gga ccc tcc gtg ttc ctg ttc     768
Pro Cys Pro Ala Pro Glu Leu Leu Gly Gly Pro Ser Val Phe Leu Phe
                245                 250                 255 ccc ccc aag ccc aag gac acc ctc atg atc agc cgg acc ccc gag gtg     816
Pro Pro Lys Pro Lys Asp Thr Leu Met Ile Ser Arg Thr Pro Glu Val
            260                 265                 270 acc tgc gtg gtg gtg gac gtg agc cac gag gac ccc gag gtg aag ttc     864
Thr Cys Val Val Val Asp Val Ser His Glu Asp Pro Glu Val Lys Phe
```

```
                      275                 280                 285
aac tgg tac gtg gac ggc gtg gag gtg cac aac gcc aag acc aag ccc         912
Asn Trp Tyr Val Asp Gly Val Glu Val His Asn Ala Lys Thr Lys Pro
    290                 295                 300 cgg gag gag cag tac aac agc acc tac cgg gtg gtg agc gtg ctc acc         960
Arg Glu Glu Gln Tyr Asn Ser Thr Tyr Arg Val Val Ser Val Leu Thr
305                 310                 315                 320 gtg ctg cac cag gac tgg ctg aac ggc aag gag tac aag tgc aag gtg        1008
Val Leu His Gln Asp Trp Leu Asn Gly Lys Glu Tyr Lys Cys Lys Val
                325                 330                 335 agc aac aag gcc ctg cct gcc ccc atc gag aag acc atc agc aag gcc        1056
Ser Asn Lys Ala Leu Pro Ala Pro Ile Glu Lys Thr Ile Ser Lys Ala
            340                 345                 350 aag ggc cag ccc cgg gag ccc cag gtg tac acc ctg ccc ccc agc cgg        1104
Lys Gly Gln Pro Arg Glu Pro Gln Val Tyr Thr Leu Pro Pro Ser Arg
        355                 360                 365 gag gag atg acc aag aac cag gtg tcc ctc acc tgt ctg gtg aag ggc        1152
Glu Glu Met Thr Lys Asn Gln Val Ser Leu Thr Cys Leu Val Lys Gly
    370                 375                 380 ttc tac ccc agc gac atc gcc gtg gag tgg gag agc aac ggc cag ccc        1200
Phe Tyr Pro Ser Asp Ile Ala Val Glu Trp Glu Ser Asn Gly Gln Pro
385                 390                 395                 400 gag aac aac tac aag acc acc ccc cct gtg ctg gac agc gac ggc agc        1248
Glu Asn Asn Tyr Lys Thr Thr Pro Pro Val Leu Asp Ser Asp Gly Ser
                405                 410                 415 ttc ttc ctg tac agc aag ctc acc gtg gac aag agc cgg tgg cag cag        1296
Phe Phe Leu Tyr Ser Lys Leu Thr Val Asp Lys Ser Arg Trp Gln Gln
            420                 425                 430 ggc aac gtg ttc agc tgc agc gtg atg cac gag gcc ctg cac aac cac        1344
Gly Asn Val Phe Ser Cys Ser Val Met His Glu Ala Leu His Asn His
        435                 440                 445 tac acc cag aag agc ctg agc ctg agc ccc ggc aag                        1380
Tyr Thr Gln Lys Ser Leu Ser Leu Ser Pro Gly Lys
    450                 455                 460

<210> SEQ ID NO 117
<211> LENGTH: 460
<212> TYPE: PRT
<213> ORGANISM: Artificial sequence
<220> FEATURE:
<223> OTHER INFORMATION: Heavy chain CR4283

<400> SEQUENCE: 117

Glu Val Gln Leu Val Gln Ser Gly Ala Glu Val Lys Lys Ser Gly Glu
1               5                   10                  15

Ser Leu Lys Ile Ser Cys Lys Gly Ser Gly Tyr Thr Phe Asn Thr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Ile Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Ser Ala Met Tyr Tyr Cys
                85                  90                  95

Ala Arg Leu Thr Phe Arg Arg Gly Tyr Ser Gly Ser Asp Ser Phe Leu
            100                 105                 110

Pro Pro Gly Asp Phe Asp Tyr Trp Gly Gln Gly Thr Leu Val Thr Val
        115                 120                 125
```

```
Ser Ser Ala Ser Thr Lys Gly Pro Ser Val Phe Pro Leu Ala Pro Ser
130                 135                 140
Ser Lys Ser Thr Ser Gly Gly Thr Ala Ala Leu Gly Cys Leu Val Lys
145                 150                 155                 160
Asp Tyr Phe Pro Glu Pro Val Thr Val Ser Trp Asn Ser Gly Ala Leu
            165                 170                 175
Thr Ser Gly Val His Thr Phe Pro Ala Val Leu Gln Ser Ser Gly Leu
            180                 185                 190
Tyr Ser Leu Ser Ser Val Val Thr Val Pro Ser Ser Ser Leu Gly Thr
        195                 200                 205
Gln Thr Tyr Ile Cys Asn Val Asn His Lys Pro Ser Asn Thr Lys Val
    210                 215                 220
Asp Lys Arg Val Glu Pro Lys Ser Cys Asp Lys Thr His Thr Cys Pro
225                 230                 235                 240
Pro Cys Pro Ala Pro Glu Leu Leu Gly Gly Pro Ser Val Phe Leu Phe
            245                 250                 255
Pro Pro Lys Pro Lys Asp Thr Leu Met Ile Ser Arg Thr Pro Glu Val
            260                 265                 270
Thr Cys Val Val Val Asp Val Ser His Glu Asp Pro Glu Val Lys Phe
        275                 280                 285
Asn Trp Tyr Val Asp Gly Val Glu Val His Asn Ala Lys Thr Lys Pro
    290                 295                 300
Arg Glu Glu Gln Tyr Asn Ser Thr Tyr Arg Val Val Ser Val Leu Thr
305                 310                 315                 320
Val Leu His Gln Asp Trp Leu Asn Gly Lys Glu Tyr Lys Cys Lys Val
            325                 330                 335
Ser Asn Lys Ala Leu Pro Ala Pro Ile Glu Lys Thr Ile Ser Lys Ala
            340                 345                 350
Lys Gly Gln Pro Arg Glu Pro Gln Val Tyr Thr Leu Pro Pro Ser Arg
        355                 360                 365
Glu Glu Met Thr Lys Asn Gln Val Ser Leu Thr Cys Leu Val Lys Gly
    370                 375                 380
Phe Tyr Pro Ser Asp Ile Ala Val Glu Trp Glu Ser Asn Gly Gln Pro
385                 390                 395                 400
Glu Asn Asn Tyr Lys Thr Thr Pro Pro Val Leu Asp Ser Asp Gly Ser
            405                 410                 415
Phe Phe Leu Tyr Ser Lys Leu Thr Val Asp Lys Ser Arg Trp Gln Gln
            420                 425                 430
Gly Asn Val Phe Ser Cys Ser Val Met His Glu Ala Leu His Asn His
        435                 440                 445
Tyr Thr Gln Lys Ser Leu Ser Leu Ser Pro Gly Lys
    450                 455                 460

<210> SEQ ID NO 118
<211> LENGTH: 1365
<212> TYPE: DNA
<213> ORGANISM: Artificial sequence
<220> FEATURE:
<223> OTHER INFORMATION: Heavy chain CR4289
<220> FEATURE:
<221> NAME/KEY: CDS
<222> LOCATION: (1)..(1365)

<400> SEQUENCE: 118 gag gtg cag ctg gtg cag tct gga gca gag gtg aaa aag ccc ggg gag    48
Glu Val Gln Leu Val Gln Ser Gly Ala Glu Val Lys Lys Pro Gly Glu
```

-continued

```
1               5                    10                   15 tct ctg agg atc tcc tgt aag ggt tct gga tac agc ttt acc agt aac        96
Ser Leu Arg Ile Ser Cys Lys Gly Ser Gly Tyr Ser Phe Thr Ser Asn
             20                  25                  30 tgg atc acc tgg gtg cgc cag atg ccc ggg aaa ggc ctg gag tgg atg       144
Trp Ile Thr Trp Val Arg Gln Met Pro Gly Lys Gly Leu Glu Trp Met
         35                  40                  45 ggg agg att gat cct agt gac tct tat acc aac tac agc ccg tcc ttc       192
Gly Arg Ile Asp Pro Ser Asp Ser Tyr Thr Asn Tyr Ser Pro Ser Phe
     50                  55                  60 caa ggc cac gtc acc atc tca gct gac aag tcc atc agc act gcc tac       240
Gln Gly His Val Thr Ile Ser Ala Asp Lys Ser Ile Ser Thr Ala Tyr
65                  70                  75                  80 ctg cag tgg agc agc ctg aag gcc tcg gac acc gcc atg tat tac tgt       288
Leu Gln Trp Ser Ser Leu Lys Ala Ser Asp Thr Ala Met Tyr Tyr Cys
                 85                  90                  95 gcg aga gac gta gtt ggg gtg gga gct tcc gac tac tat tat tac atg       336
Ala Arg Asp Val Val Gly Val Gly Ala Ser Asp Tyr Tyr Tyr Tyr Met
             100                 105                 110 gac gtc tgg ggc cag ggc acc acc gtg acc gtc tcc agc gct agc acc       384
Asp Val Trp Gly Gln Gly Thr Thr Val Thr Val Ser Ser Ala Ser Thr
         115                 120                 125 aag ggc ccc agc gtg ttc ccc ctg gcc ccc agc agc aag agc acc agc       432
Lys Gly Pro Ser Val Phe Pro Leu Ala Pro Ser Ser Lys Ser Thr Ser
     130                 135                 140 ggc ggc aca gcc gcc ctg ggc tgc ctg gtg aag gac tac ttc ccc gag       480
Gly Gly Thr Ala Ala Leu Gly Cys Leu Val Lys Asp Tyr Phe Pro Glu
145                 150                 155                 160 ccc gtg acc gtg agc tgg aac agc ggc gcc ttg acc agc ggc gtg cac       528
Pro Val Thr Val Ser Trp Asn Ser Gly Ala Leu Thr Ser Gly Val His
                 165                 170                 175 acc ttc ccc gcc gtg ctg cag agc agc ggc ctg tac agc ctg agc agc       576
Thr Phe Pro Ala Val Leu Gln Ser Ser Gly Leu Tyr Ser Leu Ser Ser
             180                 185                 190 gtg gtg acc gtg ccc agc agc agc ctg ggc acc cag acc tac atc tgc       624
Val Val Thr Val Pro Ser Ser Ser Leu Gly Thr Gln Thr Tyr Ile Cys
         195                 200                 205 aac gtg aac cac aag ccc agc aac acc aag gtg gac aaa cgc gtg gag       672
Asn Val Asn His Lys Pro Ser Asn Thr Lys Val Asp Lys Arg Val Glu
     210                 215                 220 ccc aag agc tgc gac aag acc cac acc tgc ccc ccc tgc cct gcc ccc       720
Pro Lys Ser Cys Asp Lys Thr His Thr Cys Pro Pro Cys Pro Ala Pro
225                 230                 235                 240 gag ctg ctg ggc gga ccc tcc gtg ttc ctg ttc ccc ccc aag ccc aag       768
Glu Leu Leu Gly Gly Pro Ser Val Phe Leu Phe Pro Pro Lys Pro Lys
                 245                 250                 255 gac acc ctc atg atc agc cgg acc ccc gag gtg acc tgc gtg gtg gtg       816
Asp Thr Leu Met Ile Ser Arg Thr Pro Glu Val Thr Cys Val Val Val
             260                 265                 270 gac gtg agc cac gag gac ccc gag gtg aag ttc aac tgg tac gtg gac       864
Asp Val Ser His Glu Asp Pro Glu Val Lys Phe Asn Trp Tyr Val Asp
         275                 280                 285 ggc gtg gag gtg cac aac gcc aag acc aag ccc cgg gag gag cag tac       912
Gly Val Glu Val His Asn Ala Lys Thr Lys Pro Arg Glu Glu Gln Tyr
     290                 295                 300 aac agc acc tac cgg gtg gtg agc gtg ctc acc gtg ctg cac cag gac       960
Asn Ser Thr Tyr Arg Val Val Ser Val Leu Thr Val Leu His Gln Asp
305                 310                 315                 320 tgg ctg aac ggc aag gag tac aag tgc aag gtg agc aac aag gcc ctg      1008
```

```
Trp Leu Asn Gly Lys Glu Tyr Lys Cys Lys Val Ser Asn Lys Ala Leu
            325                 330                 335 cct gcc ccc atc gag aag acc atc agc aag gcc aag ggc cag ccc cgg    1056
Pro Ala Pro Ile Glu Lys Thr Ile Ser Lys Ala Lys Gly Gln Pro Arg
            340                 345                 350 gag ccc cag gtg tac acc ctg ccc cca agc cgg gag gag atg acc aag    1104
Glu Pro Gln Val Tyr Thr Leu Pro Pro Ser Arg Glu Glu Met Thr Lys
            355                 360                 365 aac cag gtg tcc ctc acc tgt ctg gtg aag ggc ttc tac ccc agc gac    1152
Asn Gln Val Ser Leu Thr Cys Leu Val Lys Gly Phe Tyr Pro Ser Asp
        370                 375                 380 atc gcc gtg gag tgg gag agc aac ggc cag ccc gag aac aac tac aag    1200
Ile Ala Val Glu Trp Glu Ser Asn Gly Gln Pro Glu Asn Asn Tyr Lys
385                 390                 395                 400 acc acc ccc cct gtg ctg gac agc gac ggc agc ttc ttc ctg tac agc    1248
Thr Thr Pro Pro Val Leu Asp Ser Asp Gly Ser Phe Phe Leu Tyr Ser
                405                 410                 415 aag ctc acc gtg gac aag agc cgg tgg cag cag ggc aac gtg ttc agc    1296
Lys Leu Thr Val Asp Lys Ser Arg Trp Gln Gln Gly Asn Val Phe Ser
            420                 425                 430 tgc agc gtg atg cac gag gcc ctg cac aac cac tac acc cag aag agc    1344
Cys Ser Val Met His Glu Ala Leu His Asn His Tyr Thr Gln Lys Ser
            435                 440                 445 ctg agc ctg agc ccc ggc aag                                         1365
Leu Ser Leu Ser Pro Gly Lys
        450                 455

<210> SEQ ID NO 119
<211> LENGTH: 455
<212> TYPE: PRT
<213> ORGANISM: Artificial sequence
<220> FEATURE:
<223> OTHER INFORMATION: Heavy chain CR4289

<400> SEQUENCE: 119

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Asn
            20                  25                  30

Trp Ile Thr Trp Val Arg Gln Met Pro Gly Lys Gly Leu Glu Trp Met
        35                  40                  45

Gly Arg Ile Asp Pro Ser Asp Ser Tyr Thr Asn Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Val Val Gly Val Gly Ala Ser Asp Tyr Tyr Tyr Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
```

```
                    180                 185                 190
Val Val Thr Val Pro Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 120
<211> LENGTH: 1362
<212> TYPE: DNA
<213> ORGANISM: Artificial sequence
<220> FEATURE:
<223> OTHER INFORMATION: Heavy chain CR4299
<220> FEATURE:
<221> NAME/KEY: CDS
<222> LOCATION: (1)..(1362)

<400> SEQUENCE: 120 cag gtg cag ctg gtg gag tct ggg gga ggc gtg gtc cag cct ggg agg      48
Gln Val Gln Leu Val Glu Ser Gly Gly Gly Val Val Gln Pro Gly Arg
1               5                   10                  15 tcc ctg aga ctc tcc tgt gca gcc tct gga ttc acc ttc agt ggc tat      96
Ser Leu Arg Leu Ser Cys Ala Ala Ser Gly Phe Thr Phe Ser Gly Tyr
            20                  25                  30 gct atg cac tgg gtc cgc cag gct cca ggc aag ggg cta gac tgg gtg     144
Ala Met His Trp Val Arg Gln Ala Pro Gly Lys Gly Leu Asp Trp Val
        35                  40                  45 gca gtt ata tca tat gat gga agt gaa aaa tat tcc gcc gac tct gtg     192
```

```
                Ala Val Ile Ser Tyr Asp Gly Ser Glu Lys Tyr Ser Ala Asp Ser Val
                         50              55                  60 aag ggc cgg ttc acc atc tcc aga gac aat tcc aag aac acg ctc tat            240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tat tgt            288
Leu Gln Met Asn Ser Leu Arg Ala Glu Asp Thr Ala Val Tyr Tyr Cys
                    85                  90                  95 gcg aaa gag tcc ggg gga cct ata tgg tac aag tac tac ggc gtg gac            336
Ala Lys Glu Ser Gly Gly Pro Ile Trp Tyr Lys Tyr Tyr Gly Val Asp
                100                 105                 110 gtc tgg ggc cag ggc acc acc gtg acc gtc tcc agc gct agc acc aag            384
Val Trp Gly Gln Gly Thr Thr Val Thr Val Ser Ser Ala Ser Thr Lys
            115                 120                 125 ggc ccc agc gtg ttc ccc ctg gcc ccc agc agc aag agc acc agc ggc            432
Gly Pro Ser Val Phe Pro Leu Ala Pro Ser Ser Lys Ser Thr Ser Gly
        130                 135                 140 ggc aca gcc gcc ctg ggc tgc ctg gtg aag gac tac ttc ccc gag ccc            480
Gly Thr Ala Ala Leu Gly Cys Leu Val Lys Asp Tyr Phe Pro Glu Pro
145                 150                 155                 160 gtg acc gtg agc tgg aac agc ggc gcc ttg acc agc ggc gtg cac acc            528
Val Thr Val Ser Trp Asn Ser Gly Ala Leu Thr Ser Gly Val His Thr
                165                 170                 175 ttc ccc gcc gtg ctg cag agc agc ggc ctg tac agc ctg agc agc gtg            576
Phe Pro Ala Val Leu Gln Ser Ser Gly Leu Tyr Ser Leu Ser Ser Val
                180                 185                 190 gtg acc gtg ccc agc agc agc ctg ggc acc cag acc tac atc tgc aac            624
Val Thr Val Pro Ser Ser Ser Leu Gly Thr Gln Thr Tyr Ile Cys Asn
            195                 200                 205 gtg aac cac aag ccc agc aac acc aag gtg gac aaa cgc gtg gag ccc            672
Val Asn His Lys Pro Ser Asn Thr Lys Val Asp Lys Arg Val Glu Pro
210                 215                 220 aag agc tgc gac aag acc cac acc tgc ccc ccc tgc cct gcc ccc gag            720
Lys Ser Cys Asp Lys Thr His Thr Cys Pro Pro Cys Pro Ala Pro Glu
225                 230                 235                 240 ctg ctg ggc gga ccc tcc gtg ttc ctg ttc ccc ccc aag ccc aag gac            768
Leu Leu Gly Gly Pro Ser Val Phe Leu Phe Pro Pro Lys Pro Lys Asp
                245                 250                 255 acc ctc atg atc agc cgg acc ccc gag gtg acc tgc gtg gtg gtg gac            816
Thr Leu Met Ile Ser Arg Thr Pro Glu Val Thr Cys Val Val Val Asp
                260                 265                 270 gtg agc cac gag gac ccc gag gtg aag ttc aac tgg tac gtg gac ggc            864
Val Ser His Glu Asp Pro Glu Val Lys Phe Asn Trp Tyr Val Asp Gly
            275                 280                 285 gtg gag gtg cac aac gcc aag acc aag ccc cgg gag gag cag tac aac            912
Val Glu Val His Asn Ala Lys Thr Lys Pro Arg Glu Glu Gln Tyr Asn
        290                 295                 300 agc acc tac cgg gtg gtg agc gtg ctc acc gtg ctg cac cag gac tgg            960
Ser Thr Tyr Arg Val Val Ser Val Leu Thr Val Leu His Gln Asp Trp
305                 310                 315                 320 ctg aac ggc aag gag tac aag tgc aag gtg agc aac aag gcc ctg cct           1008
Leu Asn Gly Lys Glu Tyr Lys Cys Lys Val Ser Asn Lys Ala Leu Pro
                325                 330                 335 gcc ccc atc gag aag acc atc agc aag gcc aag ggc cag ccc cgg gag           1056
Ala Pro Ile Glu Lys Thr Ile Ser Lys Ala Lys Gly Gln Pro Arg Glu
                340                 345                 350 ccc cag gtg tac acc ctg ccc ccc agc cgg gag gag atg acc aag aac           1104
Pro Gln Val Tyr Thr Leu Pro Pro Ser Arg Glu Glu Met Thr Lys Asn
            355                 360                 365
```

-continued

```
cag gtg tcc ctc acc tgt ctg gtg aag ggc ttc tac ccc agc gac atc     1152
Gln Val Ser Leu Thr Cys Leu Val Lys Gly Phe Tyr Pro Ser Asp Ile
    370                 375                 380 gcc gtg gag tgg gag agc aac ggc cag ccc gag aac aac tac aag acc     1200
Ala Val Glu Trp Glu Ser Asn Gly Gln Pro Glu Asn Asn Tyr Lys Thr
385                 390                 395                 400 acc ccc cct gtg ctg gac agc gac ggc agc ttc ttc ctg tac agc aag     1248
Thr Pro Pro Val Leu Asp Ser Asp Gly Ser Phe Phe Leu Tyr Ser Lys
                405                 410                 415 ctc acc gtg gac aag agc cgg tgg cag cag ggc aac gtg ttc agc tgc     1296
Leu Thr Val Asp Lys Ser Arg Trp Gln Gln Gly Asn Val Phe Ser Cys
            420                 425                 430 agc gtg atg cac gag gcc ctg cac aac cac tac acc cag aag agc ctg     1344
Ser Val Met His Glu Ala Leu His Asn His Tyr Thr Gln Lys Ser Leu
        435                 440                 445 agc ctg agc ccc ggc aag                                             1362
Ser Leu Ser Pro Gly Lys
    450

<210> SEQ ID NO 121
<211> LENGTH: 454
<212> TYPE: PRT
<213> ORGANISM: Artificial sequence
<220> FEATURE:
<223> OTHER INFORMATION: Heavy chain CR4299

<400> SEQUENCE: 121

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Ala Met His Trp Val Arg Gln Ala Pro Gly Lys Gly Leu Asp Trp Val
        35                  40                  45

Ala Val Ile Ser Tyr Asp Gly Ser Glu Lys Tyr Ser Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Ser Gly Gly Pro Ile Trp Tyr Lys Tyr Tyr Gly Val Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240
```

```
Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 122
<211> LENGTH: 1347
<212> TYPE: DNA
<213> ORGANISM: Artificial sequence
<220> FEATURE:
<223> OTHER INFORMATION: Heavy chain CR4311
<220> FEATURE:
<221> NAME/KEY: CDS
<222> LOCATION: (1)..(1347)

<400> SEQUENCE: 122 cag gtg cag ctg gtg gag tct ggg gga ggc gtg gtc cag cct ggc agg    48
Gln Val Gln Leu Val Glu Ser Gly Gly Gly Val Val Gln Pro Gly Arg
1               5                   10                  15 tcc ctg aga ctc tcc tgt gta gcc tct gga ttc acc ttc agt aag gac    96
Ser Leu Arg Leu Ser Cys Val Ala Ser Gly Phe Thr Phe Ser Lys Asp
            20                  25                  30 gct atg cac tgg gtc cgc cag gct cca ggc aag ggg cta gag tgg gtg   144
Ala Met His Trp Val Arg Gln Ala Pro Gly Lys Gly Leu Glu Trp Val
        35                  40                  45 gca gtt ata tca tat gat gga agt gat aaa cac tac gca gac tcc gtg   192
Ala Val Ile Ser Tyr Asp Gly Ser Asp Lys His Tyr Ala Asp Ser Val
    50                  55                  60 aag ggc cga gtc acc atc tcc aga gac aat tcc agg aaa acg ctg tat   240
Lys Gly Arg Val Thr Ile Ser Arg Asp Asn Ser Arg Lys Thr Leu Tyr
65                  70                  75                  80 ctg cga atg gac agc ctg aga gct gag gac acg gct cta tat tac tgt   288
Leu Arg Met Asp Ser Leu Arg Ala Glu Asp Thr Ala Leu Tyr Tyr Cys
                85                  90                  95
```

```
gcg aga gga tac aac tct ggt cat tac ttt gac tac tgg ggc cag ggc        336
Ala Arg Gly Tyr Asn Ser Gly His Tyr Phe Asp Tyr Trp Gly Gln Gly
            100                 105                 110 acc ctg gtg acc gtc tcc agc gct agc acc aag ggc ccc agc gtg ttc        384
Thr Leu Val Thr Val Ser Ser Ala Ser Thr Lys Gly Pro Ser Val Phe
    115                 120                 125 ccc ctg gcc ccc agc agc aag agc acc agc ggc ggc aca gcc gcc ctg        432
Pro Leu Ala Pro Ser Ser Lys Ser Thr Ser Gly Gly Thr Ala Ala Leu
130                 135                 140 ggc tgc ctg gtg aag gac tac ttc ccc gag ccc gtg acc gtg agc tgg        480
Gly Cys Leu Val Lys Asp Tyr Phe Pro Glu Pro Val Thr Val Ser Trp
145                 150                 155                 160 aac agc ggc gcc ttg acc agc ggc gtg cac acc ttc ccc gcc gtg ctg        528
Asn Ser Gly Ala Leu Thr Ser Gly Val His Thr Phe Pro Ala Val Leu
                165                 170                 175 cag agc agc ggc ctg tac agc ctg agc agc gtg gtg acc gtg ccc agc        576
Gln Ser Ser Gly Leu Tyr Ser Leu Ser Ser Val Val Thr Val Pro Ser
            180                 185                 190 agc agc ctg ggc acc cag acc tac atc tgc aac gtg aac cac aag ccc        624
Ser Ser Leu Gly Thr Gln Thr Tyr Ile Cys Asn Val Asn His Lys Pro
        195                 200                 205 agc aac acc aag gtg gac aaa cgc gtg gag ccc aag agc tgc gac aag        672
Ser Asn Thr Lys Val Asp Lys Arg Val Glu Pro Lys Ser Cys Asp Lys
    210                 215                 220 acc cac acc tgc ccc ccc tgc cct gcc ccc gag ctg ctg ggc gga ccc        720
Thr His Thr Cys Pro Pro Cys Pro Ala Pro Glu Leu Leu Gly Gly Pro
225                 230                 235                 240 tcc gtg ttc ctg ttc ccc ccc aag ccc aag gac acc ctc atg atc agc        768
Ser Val Phe Leu Phe Pro Pro Lys Pro Lys Asp Thr Leu Met Ile Ser
                245                 250                 255 cgg acc ccc gag gtg acc tgc gtg gtg gtg gac gtg agc cac gag gac        816
Arg Thr Pro Glu Val Thr Cys Val Val Val Asp Val Ser His Glu Asp
            260                 265                 270 ccc gag gtg aag ttc aac tgg tac gtg gac ggc gtg gag gtg cac aac        864
Pro Glu Val Lys Phe Asn Trp Tyr Val Asp Gly Val Glu Val His Asn
        275                 280                 285 gcc aag acc aag ccc cgg gag gag cag tac aac agc acc tac cgg gtg        912
Ala Lys Thr Lys Pro Arg Glu Glu Gln Tyr Asn Ser Thr Tyr Arg Val
    290                 295                 300 gtg agc gtg ctc acc gtg ctg cac cag gac tgg ctg aac ggc aag gag        960
Val Ser Val Leu Thr Val Leu His Gln Asp Trp Leu Asn Gly Lys Glu
305                 310                 315                 320 tac aag tgc aag gtg agc aac aag gcc ctg cct gcc ccc atc gag aag       1008
Tyr Lys Cys Lys Val Ser Asn Lys Ala Leu Pro Ala Pro Ile Glu Lys
                325                 330                 335 acc atc agc aag gcc aag ggc cag ccc cgg gag ccc cag gtg tac acc       1056
Thr Ile Ser Lys Ala Lys Gly Gln Pro Arg Glu Pro Gln Val Tyr Thr
            340                 345                 350 ctg ccc ccc agc cgg gag gag atg acc aag aac cag gtg tcc ctc acc       1104
Leu Pro Pro Ser Arg Glu Glu Met Thr Lys Asn Gln Val Ser Leu Thr
        355                 360                 365 tgt ctg gtg aag ggc ttc tac ccc agc gac atc gcc gtg gag tgg gag       1152
Cys Leu Val Lys Gly Phe Tyr Pro Ser Asp Ile Ala Val Glu Trp Glu
    370                 375                 380 agc aac ggc cag ccc gag aac aac tac aag acc acc ccc cct gtg ctg       1200
Ser Asn Gly Gln Pro Glu Asn Asn Tyr Lys Thr Thr Pro Pro Val Leu
385                 390                 395                 400 gac agc gac ggc agc ttc ttc ctg tac agc aag ctc acc gtg gac aag       1248
Asp Ser Asp Gly Ser Phe Phe Leu Tyr Ser Lys Leu Thr Val Asp Lys
                405                 410                 415
```

-continued

```
agc cgg tgg cag cag ggc aac gtg ttc agc tgc agc gtg atg cac gag      1296
Ser Arg Trp Gln Gln Gly Asn Val Phe Ser Cys Ser Val Met His Glu
        420                 425                 430 gcc ctg cac aac cac tac acc cag aag agc ctg agc ctg agc ccc ggc      1344
Ala Leu His Asn His Tyr Thr Gln Lys Ser Leu Ser Leu Ser Pro Gly
            435                 440                 445 aag                                                                   1347
Lys

<210> SEQ ID NO 123
<211> LENGTH: 449
<212> TYPE: PRT
<213> ORGANISM: Artificial sequence
<220> FEATURE:
<223> OTHER INFORMATION: Heavy chain CR4311

<400> SEQUENCE: 123

Gln Val Gln Leu Val Glu Ser Gly Gly Val Val Gln Pro Gly Arg
1               5                   10                  15

Ser Leu Arg Leu Ser Cys Val Ala Ser Gly Phe Thr Phe Ser Lys Asp
            20                  25                  30

Ala Met His Trp Val Arg Gln Ala Pro Gly Lys Gly Leu Glu Trp Val
        35                  40                  45

Ala Val Ile Ser Tyr Asp Gly Ser Asp Lys His Tyr Ala Asp Ser Val
    50                  55                  60

Lys Gly Arg Val Thr Ile Ser Arg Asp Asn Ser Arg Lys Thr Leu Tyr
65                  70                  75                  80

Leu Arg Met Asp Ser Leu Arg Ala Glu Asp Thr Ala Leu Tyr Tyr Cys
                85                  90                  95

Ala Arg Gly Tyr Asn Ser Gly His Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 124
<211> LENGTH: 1341
<212> TYPE: DNA
<213> ORGANISM: Artificial sequence
<220> FEATURE:
<223> OTHER INFORMATION: Heavy chain CR4325
<220> FEATURE:
<221> NAME/KEY: CDS
<222> LOCATION: (1)..(1341)

<400> SEQUENCE: 124 cag gtg cag ctg gtg cag tct ggg gct gag gtg aag aag cct ggg tcc    48
Gln Val Gln Leu Val Gln Ser Gly Ala Glu Val Lys Lys Pro Gly Ser
1               5                   10                  15 tcg gtg aag gtc tcc tgc aag gct tct gga gac acc ttc agc agt tat    96
Ser Val Lys Val Ser Cys Lys Ala Ser Gly Asp Thr Phe Ser Ser Tyr
            20                  25                  30 gct atc agc tgg gtg cga cag gcc cct gga caa ggg ctt gag tgg atg   144
Ala Ile Ser Trp Val Arg Gln Ala Pro Gly Gln Gly Leu Glu Trp Met
        35                  40                  45 gga ggg atc ttt ggt aca gca agc tac gca cag aag ttc cag gtc aga   192
Gly Gly Ile Phe Gly Thr Ala Ser Tyr Ala Gln Lys Phe Gln Gly Arg
    50                  55                  60 gtc acg att acc gcg gac gaa tcc acg agc aca gcc tac atg gag ctg   240
Val Thr Ile Thr Ala Asp Glu Ser Thr Ser Thr Ala Tyr Met Glu Leu
65                  70                  75                  80 agc agc ctg aga tct gag gac acg gcc gtg tat tac tgt gcg aga gga   288
Ser Ser Leu Arg Ser Glu Asp Thr Ala Val Tyr Tyr Cys Ala Arg Gly
                85                  90                  95 ggg atg gct aca aca ccg gga ctt gac tac tgg ggc cag ggc acc ctg   336
Gly Met Ala Thr Thr Pro Gly Leu Asp Tyr Trp Gly Gln Gly Thr Leu
            100                 105                 110 gtg acc gtc tcc agc gct agc acc aag ggc ccc agc gtg ttc ccc ctg   384
Val Thr Val Ser Ser Ala Ser Thr Lys Gly Pro Ser Val Phe Pro Leu
        115                 120                 125 gcc ccc agc agc aag agc acc agc ggc ggc aca gcc gcc ctg ggc tgc   432
Ala Pro Ser Ser Lys Ser Thr Ser Gly Gly Thr Ala Ala Leu Gly Cys
    130                 135                 140 ctg gtg aag gac tac ttc ccc gag ccc gtg acc gtg agc tgg aac agc   480
```

```
                                                                                          -continued Leu Val Lys Asp Tyr Phe Pro Glu Pro Val Thr Val Ser Trp Asn Ser
145                 150                 155                 160 ggc gcc ttg acc agc ggc gtg cac acc ttc ccc gcc gtg ctg cag agc          528
Gly Ala Leu Thr Ser Gly Val His Thr Phe Pro Ala Val Leu Gln Ser
                165                 170                 175 agc ggc ctg tac agc ctg agc agc gtg gtg acc gtg ccc agc agc agc          576
Ser Gly Leu Tyr Ser Leu Ser Ser Val Val Thr Val Pro Ser Ser Ser
            180                 185                 190 ctg ggc acc cag acc tac atc tgc aac gtg aac cac aag ccc agc aac          624
Leu Gly Thr Gln Thr Tyr Ile Cys Asn Val Asn His Lys Pro Ser Asn
        195                 200                 205 acc aag gtg gac aaa cgc gtg gag ccc aag agc tgc gac aag acc cac          672
Thr Lys Val Asp Lys Arg Val Glu Pro Lys Ser Cys Asp Lys Thr His
    210                 215                 220 acc tgc ccc ccc tgc cct gcc ccc gag ctg ctg gga gga ccc tcc gtg          720
Thr Cys Pro Pro Cys Pro Ala Pro Glu Leu Leu Gly Gly Pro Ser Val
225                 230                 235                 240 ttc ctg ttc ccc ccc aag ccc aag gac acc ctc atg atc agc cgg acc          768
Phe Leu Phe Pro Pro Lys Pro Lys Asp Thr Leu Met Ile Ser Arg Thr
                245                 250                 255 ccc gag gtg acc tgc gtg gtg gtg gac gtg agc cac gag gac ccc gag          816
Pro Glu Val Thr Cys Val Val Val Asp Val Ser His Glu Asp Pro Glu
            260                 265                 270 gtg aag ttc aac tgg tac gtg gac ggc gtg gag gtg cac aac gcc aag          864
Val Lys Phe Asn Trp Tyr Val Asp Gly Val Glu Val His Asn Ala Lys
        275                 280                 285 acc aag ccc cgg gag gag cag tac aac agc acc tac cgg gtg gtg agc          912
Thr Lys Pro Arg Glu Glu Gln Tyr Asn Ser Thr Tyr Arg Val Val Ser
    290                 295                 300 gtg ctc acc gtg ctg cac cag gac tgg ctg aac ggc aag gag tac aag          960
Val Leu Thr Val Leu His Gln Asp Trp Leu Asn Gly Lys Glu Tyr Lys
305                 310                 315                 320 tgc aag gtg agc aac aag gcc ctg cct gcc ccc atc gag aag acc atc         1008
Cys Lys Val Ser Asn Lys Ala Leu Pro Ala Pro Ile Glu Lys Thr Ile
                325                 330                 335 agc aag gcc aag ggc cag ccc cgg gag ccc cag gtg tac acc ctg ccc         1056
Ser Lys Ala Lys Gly Gln Pro Arg Glu Pro Gln Val Tyr Thr Leu Pro
            340                 345                 350 ccc agc cgg gag gag atg acc aag aac cag gtg tcc ctc acc tgt ctg         1104
Pro Ser Arg Glu Glu Met Thr Lys Asn Gln Val Ser Leu Thr Cys Leu
        355                 360                 365 gtg aag ggc ttc tac ccc agc gac atc gcc gtg gag tgg gag agc aac         1152
Val Lys Gly Phe Tyr Pro Ser Asp Ile Ala Val Glu Trp Glu Ser Asn
    370                 375                 380 ggc cag ccc gag aac aac tac aag acc acc ccc cct gtg ctg gac agc         1200
Gly Gln Pro Glu Asn Asn Tyr Lys Thr Thr Pro Pro Val Leu Asp Ser
385                 390                 395                 400 gac ggc agc ttc ttc ctg tac agc aag ctc acc gtg gac aag agc cgg         1248
Asp Gly Ser Phe Phe Leu Tyr Ser Lys Leu Thr Val Asp Lys Ser Arg
                405                 410                 415 tgg cag cag ggc aac gtg ttc agc tgc agc gtg atg cac gag gcc ctg         1296
Trp Gln Gln Gly Asn Val Phe Ser Cys Ser Val Met His Glu Ala Leu
            420                 425                 430 cac aac cac tac acc cag aag agc ctg agc ctg agc ccc ggc aag             1341
His Asn His Tyr Thr Gln Lys Ser Leu Ser Leu Ser Pro Gly Lys
        435                 440                 445

<210> SEQ ID NO 125
<211> LENGTH: 447
<212> TYPE: PRT
```

-continued

<213> ORGANISM: Artificial sequence
<220> FEATURE:
<223> OTHER INFORMATION: Heavy chain CR4325

<400> SEQUENCE: 125

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ser |
| 1 | | | | 5 | | | | | 10 | | | | | 15 | |
| Ser | Val | Lys | Val | Ser | Cys | Lys | Ala | Ser | Gly | Asp | Thr | Phe | Ser | Ser | Tyr |
| | | | 20 | | | | | 25 | | | | | 30 | | |
| Ala | Ile | Ser | Trp | Val | Arg | Gln | Ala | Pro | Gly | Gln | Gly | Leu | Glu | Trp | Met |
| | | 35 | | | | | 40 | | | | | 45 | | | |
| Gly | Gly | Ile | Phe | Gly | Thr | Ala | Ser | Tyr | Ala | Gln | Lys | Phe | Gln | Gly | Arg |
| | 50 | | | | | 55 | | | | | 60 | | | | |
| Val | Thr | Ile | Thr | Ala | Asp | Glu | Ser | Thr | Ser | Thr | Ala | Tyr | Met | Glu | Leu |
| 65 | | | | | 70 | | | | | 75 | | | | | 80 |
| Ser | Ser | Leu | Arg | Ser | Glu | Asp | Thr | Ala | Val | Tyr | Tyr | Cys | Ala | Arg | Gly |
| | | | | 85 | | | | | 90 | | | | | 95 | |
| Gly | Met | Ala | Thr | Thr | Pro | Gly | Leu | Asp | Tyr | Trp | Gly | Gln | Gly | Thr | Leu |
| | | | 100 | | | | | 105 | | | | | 110 | | |
| Val | Thr | Val | Ser | Ser | Ala | Ser | Thr | Lys | Gly | Pro | Ser | Val | Phe | Pro | Leu |
| | | 115 | | | | | 120 | | | | | 125 | | | |
| Ala | Pro | Ser | Ser | Lys | Ser | Thr | Ser | Gly | Gly | Thr | Ala | Ala | Leu | Gly | Cys |
| | 130 | | | | | 135 | | | | | 140 | | | | |
| Leu | Val | Lys | Asp | Tyr | Phe | Pro | Glu | Pro | Val | Thr | Val | Ser | Trp | Asn | Ser |
| 145 | | | | | 150 | | | | | 155 | | | | | 160 |
| Gly | Ala | Leu | Thr | Ser | Gly | Val | His | Thr | Phe | Pro | Ala | Val | Leu | Gln | Ser |
| | | | | 165 | | | | | 170 | | | | | 175 | |
| Ser | Gly | Leu | Tyr | Ser | Leu | Ser | Ser | Val | Val | Thr | Val | Pro | Ser | Ser | Ser |
| | | | 180 | | | | | 185 | | | | | 190 | | |
| Leu | Gly | Thr | Gln | Thr | Tyr | Ile | Cys | Asn | Val | Asn | His | Lys | Pro | Ser | Asn |
| | | 195 | | | | | 200 | | | | | 205 | | | |
| Thr | Lys | Val | Asp | Lys | Arg | Val | Glu | Pro | Lys | Ser | Cys | Asp | Lys | Thr | His |
| | 210 | | | | | 215 | | | | | 220 | | | | |
| Thr | Cys | Pro | Pro | Cys | Pro | Ala | Pro | Glu | Leu | Leu | Gly | Gly | Pro | Ser | Val |
| 225 | | | | | 230 | | | | | 235 | | | | | 240 |
| Phe | Leu | Phe | Pro | Pro | Lys | Pro | Lys | Asp | Thr | Leu | Met | Ile | Ser | Arg | Thr |
| | | | | 245 | | | | | 250 | | | | | 255 | |
| Pro | Glu | Val | Thr | Cys | Val | Val | Val | Asp | Val | Ser | His | Glu | Asp | Pro | Glu |
| | | | 260 | | | | | 265 | | | | | 270 | | |
| Val | Lys | Phe | Asn | Trp | Tyr | Val | Asp | Gly | Val | Glu | Val | His | Asn | Ala | Lys |
| | | 275 | | | | | 280 | | | | | 285 | | | |
| Thr | Lys | Pro | Arg | Glu | Glu | Gln | Tyr | Asn | Ser | Thr | Tyr | Arg | Val | Val | Ser |
| | 290 | | | | | 295 | | | | | 300 | | | | |
| Val | Leu | Thr | Val | Leu | His | Gln | Asp | Trp | Leu | Asn | Gly | Lys | Glu | Tyr | Lys |
| 305 | | | | | 310 | | | | | 315 | | | | | 320 |
| Cys | Lys | Val | Ser | Asn | Lys | Ala | Leu | Pro | Ala | Pro | Ile | Glu | Lys | Thr | Ile |
| | | | | 325 | | | | | 330 | | | | | 335 | |
| Ser | Lys | Ala | Lys | Gly | Gln | Pro | Arg | Glu | Pro | Gln | Val | Tyr | Thr | Leu | Pro |
| | | | 340 | | | | | 345 | | | | | 350 | | |
| Pro | Ser | Arg | Glu | Glu | Met | Thr | Lys | Asn | Gln | Val | Ser | Leu | Thr | Cys | Leu |
| | | 355 | | | | | 360 | | | | | 365 | | | |
| Val | Lys | Gly | Phe | Tyr | Pro | Ser | Asp | Ile | Ala | Val | Glu | Trp | Glu | Ser | Asn |
| | 370 | | | | | 375 | | | | | 380 | | | | |
| Gly | Gln | Pro | Glu | Asn | Asn | Tyr | Lys | Thr | Thr | Pro | Pro | Val | Leu | Asp | Ser |

-continued

```
                385                 390                 395                 400
Asp Gly Ser Phe Phe Leu Tyr Ser Lys Leu Thr Val Asp Lys Ser Arg
                405                 410                 415

Trp Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 126
<211> LENGTH: 1371
<212> TYPE: DNA
<213> ORGANISM: Artificial sequence
<220> FEATURE:
<223> OTHER INFORMATION: Heavy chain CR4353
<220> FEATURE:
<221> NAME/KEY: CDS
<222> LOCATION: (1)..(1371)

<400> SEQUENCE: 126 cag gtg cag ctg gtg gag tct ggg gga ggc gtg gtc cag cct ggg agg        48
Gln Val Gln Leu Val Glu Ser Gly Gly Gly Val Val Gln Pro Gly Arg
1               5                   10                  15 tcc ctg aga ctc tcc tgt gca gcc tct gga ttc acc ttc agt aat tat        96
Ser Leu Arg Leu Ser Cys Ala Ala Ser Gly Phe Thr Phe Ser Asn Tyr
            20                  25                  30 gct atg cac tgg gtc cgc cag gct cca ggc aag ggg cta gag tgg gtg       144
Ala Met His Trp Val Arg Gln Ala Pro Gly Lys Gly Leu Glu Trp Val
        35                  40                  45 gca gtt ata tca tat gat gga ggt aat aaa tac tac gca gac tcc gtg       192
Ala Val Ile Ser Tyr Asp Gly Gly Asn Lys Tyr Tyr Ala Asp Ser Val
    50                  55                  60 aag ggc cga ttc acc atg tcc aga gac aat tcc aag aac acg ctg tat       240
Lys Gly Arg Phe Thr Met Ser Arg Asp Asn Ser Lys Asn Thr Leu Tyr
65                  70                  75                  80 ctg caa atg aac agc ctg aga gct gag gac acg gct gtg tat tat tgt       288
Leu Gln Met Asn Ser Leu Arg Ala Glu Asp Thr Ala Val Tyr Tyr Cys
                85                  90                  95 gcg aga gat ttt tgg agt ggt tac tca atg gta gac tcc tac tac tac       336
Ala Arg Asp Phe Trp Ser Gly Tyr Ser Met Val Asp Ser Tyr Tyr Tyr
            100                 105                 110 tac atg gac gtg tgg ggc cag ggc acc acc gtg acc gtc tcc agc gct       384
Tyr Met Asp Val Trp Gly Gln Gly Thr Thr Val Thr Val Ser Ser Ala
        115                 120                 125 agc acc aag ggc ccc agc gtg ttc ccc ctg gcc ccc agc agc aag agc       432
Ser Thr Lys Gly Pro Ser Val Phe Pro Leu Ala Pro Ser Ser Lys Ser
    130                 135                 140 acc agc ggc ggc aca gcc gcc ctg ggc tgc ctg gtg aag gac tac ttc       480
Thr Ser Gly Gly Thr Ala Ala Leu Gly Cys Leu Val Lys Asp Tyr Phe
145                 150                 155                 160 ccc gag ccc gtg acc gtg agc tgg aac agc ggc gcc ttg acc agc ggc       528
Pro Glu Pro Val Thr Val Ser Trp Asn Ser Gly Ala Leu Thr Ser Gly
                165                 170                 175 gtg cac acc ttc ccc gcc gtg ctg cag agc agc ggc ctg tac agc ctg       576
Val His Thr Phe Pro Ala Val Leu Gln Ser Ser Gly Leu Tyr Ser Leu
            180                 185                 190 agc agc gtg gtg acc gtg ccc agc agc agc ctg ggc acc cag acc tac       624
Ser Ser Val Val Thr Val Pro Ser Ser Ser Leu Gly Thr Gln Thr Tyr
        195                 200                 205 atc tgc aac gtg aac cac aag ccc agc aac acc aag gtg gac aaa cgc       672
Ile Cys Asn Val Asn His Lys Pro Ser Asn Thr Lys Val Asp Lys Arg
    210                 215                 220
```

```
gtg gag ccc aag agc tgc gac aag acc cac acc tgc ccc ccc tgc cct        720
Val Glu Pro Lys Ser Cys Asp Lys Thr His Thr Cys Pro Pro Cys Pro
225                 230                 235                 240 gcc ccc gag ctg ctg ggc gga ccc tcc gtg ttc ctg ttc ccc ccc aag        768
Ala Pro Glu Leu Leu Gly Gly Pro Ser Val Phe Leu Phe Pro Pro Lys
                245                 250                 255 ccc aag gac acc ctc atg atc agc cgg acc ccc gag gtg acc tgc gtg        816
Pro Lys Asp Thr Leu Met Ile Ser Arg Thr Pro Glu Val Thr Cys Val
            260                 265                 270 gtg gtg gac gtg agc cac gag gac ccc gag gtg aag ttc aac tgg tac        864
Val Val Asp Val Ser His Glu Asp Pro Glu Val Lys Phe Asn Trp Tyr
        275                 280                 285 gtg gac ggc gtg gag gtg cac aac gcc aag acc aag ccc cgg gag gag        912
Val Asp Gly Val Glu Val His Asn Ala Lys Thr Lys Pro Arg Glu Glu
    290                 295                 300 cag tac aac agc acc tac cgg gtg gtg agc gtg ctc acc gtg ctg cac        960
Gln Tyr Asn Ser Thr Tyr Arg Val Val Ser Val Leu Thr Val Leu His
305                 310                 315                 320 cag gac tgg ctg aac ggc aag gag tac aag tgc aag gtg agc aac aag       1008
Gln Asp Trp Leu Asn Gly Lys Glu Tyr Lys Cys Lys Val Ser Asn Lys
                325                 330                 335 gcc ctg cct gcc ccc atc gag aag acc atc agc aag gcc aag ggc cag       1056
Ala Leu Pro Ala Pro Ile Glu Lys Thr Ile Ser Lys Ala Lys Gly Gln
                340                 345                 350 ccc cgg gag ccc cag gtg tac acc ctg ccc ccc agc cgg gag gag atg       1104
Pro Arg Glu Pro Gln Val Tyr Thr Leu Pro Pro Ser Arg Glu Glu Met
            355                 360                 365 acc aag aac cag gtg tcc ctc acc tgt ctg gtg aag ggc ttc tac ccc       1152
Thr Lys Asn Gln Val Ser Leu Thr Cys Leu Val Lys Gly Phe Tyr Pro
        370                 375                 380 agc gac atc gcc gtg gag tgg gag agc aac ggc cag ccc gag aac aac       1200
Ser Asp Ile Ala Val Glu Trp Glu Ser Asn Gly Gln Pro Glu Asn Asn
385                 390                 395                 400 tac aag acc acc ccc cct gtg ctg gac agc gac ggc agc ttc ttc ctg       1248
Tyr Lys Thr Thr Pro Pro Val Leu Asp Ser Asp Gly Ser Phe Phe Leu
                405                 410                 415 tac agc aag ctc acc gtg gac aag agc cgg tgg cag cag ggc aac gtg       1296
Tyr Ser Lys Leu Thr Val Asp Lys Ser Arg Trp Gln Gln Gly Asn Val
                420                 425                 430 ttc agc tgc agc gtg atg cac gag gcc ctg cac aac cac tac acc cag       1344
Phe Ser Cys Ser Val Met His Glu Ala Leu His Asn His Tyr Thr Gln
            435                 440                 445 aag agc ctg agc ctg agc ccc ggc aag                                   1371
Lys Ser Leu Ser Leu Ser Pro Gly Lys
450                 455

<210> SEQ ID NO 127
<211> LENGTH: 457
<212> TYPE: PRT
<213> ORGANISM: Artificial sequence
<220> FEATURE:
<223> OTHER INFORMATION: Heavy chain CR4353

<400> SEQUENCE: 127

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Trp Val
        35                  40                  45
```

```
Ala Val Ile Ser Tyr Asp Gly Gly Asn Lys Tyr Tyr Ala Asp Ser Val
         50                  55                  60

Lys Gly Arg Phe Thr Met Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Phe Trp Ser Gly Tyr Ser Met Val Asp Ser Tyr Tyr Tyr
            100                 105                 110

Tyr Met Asp Val Trp Gly Gln Gly Thr Thr Val Thr Val Ser Ser Ala
            115                 120                 125

Ser Thr Lys Gly Pro Ser Val Phe Pro Leu Ala Pro Ser Ser Lys Ser
        130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
450                 455
```

<210> SEQ ID NO 128
<211> LENGTH: 1380
<212> TYPE: DNA
<213> ORGANISM: Artificial sequence
<220> FEATURE:
<223> OTHER INFORMATION: Heavy chain CR4361
<220> FEATURE:
<221> NAME/KEY: CDS
<222> LOCATION: (1)..(1380)

<400> SEQUENCE: 128

| | | | | | | | | | | | | | | | | |
|---|---|---|---|---|---|---|---|---|---|---|---|---|---|---|---|---|
| gag | gtg | cag | ctg | gtg | cag | tct | gga | gca | gaa | gtg | aaa | aag | ccc | ggg | gag | 48 |
| Glu | Val | Gln | Leu | Val | Gln | Ser | Gly | Ala | Glu | Val | Lys | Lys | Pro | Gly | Glu | |
| 1 | | | | 5 | | | | | 10 | | | | | 15 | | |

| tct | ctg | aag | atc | tcc | tgt | aag | gcc | tct | gga | ttc | agc | ttt | agc | acc | tat | 96 |
|---|---|---|---|---|---|---|---|---|---|---|---|---|---|---|---|---|
| Ser | Leu | Lys | Ile | Ser | Cys | Lys | Ala | Ser | Gly | Phe | Ser | Phe | Ser | Thr | Tyr | |
| | | 20 | | | | | 25 | | | | | 30 | | | | |

| tgg | atc | ggc | tgg | gta | cgc | cag | atg | ccc | ggg | aaa | ggc | ctg | gag | tgg | atg | 144 |
|---|---|---|---|---|---|---|---|---|---|---|---|---|---|---|---|---|
| Trp | Ile | Gly | Trp | Val | Arg | Gln | Met | Pro | Gly | Lys | Gly | Leu | Glu | Trp | Met | |
| | | | 35 | | | | | 40 | | | | | 45 | | | |

| ggg | atc | atc | tat | cct | gct | gac | tct | gat | acc | aga | tac | agc | ccg | tcc | ttc | 192 |
|---|---|---|---|---|---|---|---|---|---|---|---|---|---|---|---|---|
| Gly | Ile | Ile | Tyr | Pro | Ala | Asp | Ser | Asp | Thr | Arg | Tyr | Ser | Pro | Ser | Phe | |
| 50 | | | | | 55 | | | | | 60 | | | | | | |

| caa | ggc | cag | gtc | acc | atc | tca | gcc | gac | aag | tcc | atc | agc | acc | gcc | tac | 240 |
|---|---|---|---|---|---|---|---|---|---|---|---|---|---|---|---|---|
| Gln | Gly | Gln | Val | Thr | Ile | Ser | Ala | Asp | Lys | Ser | Ile | Ser | Thr | Ala | Tyr | |
| 65 | | | | 70 | | | | | 75 | | | | | 80 | | |

| ctg | cag | tgg | agc | agc | ctg | aag | gcc | tcg | gac | acc | gcc | atg | tat | tac | tgt | 288 |
|---|---|---|---|---|---|---|---|---|---|---|---|---|---|---|---|---|
| Leu | Gln | Trp | Ser | Ser | Leu | Lys | Ala | Ser | Asp | Thr | Ala | Met | Tyr | Tyr | Cys | |
| | | | | 85 | | | | | 90 | | | | | 95 | | |

| gcg | aga | ctc | cga | ggc | ccc | tat | tac | gat | ttt | tgg | aat | ggc | tat | cgg | gag | 336 |
|---|---|---|---|---|---|---|---|---|---|---|---|---|---|---|---|---|
| Ala | Arg | Leu | Arg | Gly | Pro | Tyr | Tyr | Asp | Phe | Trp | Asn | Gly | Tyr | Arg | Glu | |
| | | | 100 | | | | | 105 | | | | | 110 | | | |

| aca | cat | gat | gct | ttt | aat | gtg | tgg | ggc | cag | ggc | acc | atg | gtg | acc | gtg | 384 |
|---|---|---|---|---|---|---|---|---|---|---|---|---|---|---|---|---|
| Thr | His | Asp | Ala | Phe | Asn | Val | Trp | Gly | Gln | Gly | Thr | Met | Val | Thr | Val | |
| | | 115 | | | | | 120 | | | | | 125 | | | | |

| tcc | agc | gct | agc | acc | aag | ggc | ccc | agc | gtg | ttc | ccc | ctg | gcc | ccc | agc | 432 |
|---|---|---|---|---|---|---|---|---|---|---|---|---|---|---|---|---|
| Ser | Ser | Ala | Ser | Thr | Lys | Gly | Pro | Ser | Val | Phe | Pro | Leu | Ala | Pro | Ser | |
| 130 | | | | | 135 | | | | | 140 | | | | | | |

| agc | aag | agc | acc | agc | ggc | ggc | aca | gcc | gcc | ctg | ggc | tgc | ctg | gtg | aag | 480 |
|---|---|---|---|---|---|---|---|---|---|---|---|---|---|---|---|---|
| Ser | Lys | Ser | Thr | Ser | Gly | Gly | Thr | Ala | Ala | Leu | Gly | Cys | Leu | Val | Lys | |
| 145 | | | | 150 | | | | | 155 | | | | | 160 | | |

| gac | tac | ttc | ccc | gag | ccc | gtg | acc | gtg | agc | tgg | aac | agc | ggc | gcc | ttg | 528 |
|---|---|---|---|---|---|---|---|---|---|---|---|---|---|---|---|---|
| Asp | Tyr | Phe | Pro | Glu | Pro | Val | Thr | Val | Ser | Trp | Asn | Ser | Gly | Ala | Leu | |
| | | | | 165 | | | | | 170 | | | | | 175 | | |

| acc | agc | ggc | gtg | cac | acc | ttc | ccc | gcc | gtg | ctg | cag | agc | agc | ggc | ctg | 576 |
|---|---|---|---|---|---|---|---|---|---|---|---|---|---|---|---|---|
| Thr | Ser | Gly | Val | His | Thr | Phe | Pro | Ala | Val | Leu | Gln | Ser | Ser | Gly | Leu | |
| | | | 180 | | | | | 185 | | | | | 190 | | | |

| tac | agc | ctg | agc | agc | gtg | gtg | acc | gtg | ccc | agc | agc | agc | ctg | ggc | acc | 624 |
|---|---|---|---|---|---|---|---|---|---|---|---|---|---|---|---|---|
| Tyr | Ser | Leu | Ser | Ser | Val | Val | Thr | Val | Pro | Ser | Ser | Ser | Leu | Gly | Thr | |
| | | 195 | | | | | 200 | | | | | 205 | | | | |

| cag | acc | tac | atc | tgc | aac | gtg | aac | cac | aag | ccc | agc | aac | acc | aag | gtg | 672 |
|---|---|---|---|---|---|---|---|---|---|---|---|---|---|---|---|---|
| Gln | Thr | Tyr | Ile | Cys | Asn | Val | Asn | His | Lys | Pro | Ser | Asn | Thr | Lys | Val | |
| 210 | | | | | 215 | | | | | 220 | | | | | | |

| gac | aaa | cgc | gtg | gag | ccc | aag | agc | tgc | gac | aag | acc | cac | acc | tgc | ccc | 720 |
|---|---|---|---|---|---|---|---|---|---|---|---|---|---|---|---|---|
| Asp | Lys | Arg | Val | Glu | Pro | Lys | Ser | Cys | Asp | Lys | Thr | His | Thr | Cys | Pro | |
| 225 | | | | 230 | | | | | 235 | | | | | 240 | | |

| ccc | tgc | cct | gcc | ccc | gag | ctg | ctg | ggc | gga | ccc | tcc | gtg | ttc | ctg | ttc | 768 |
|---|---|---|---|---|---|---|---|---|---|---|---|---|---|---|---|---|
| Pro | Cys | Pro | Ala | Pro | Glu | Leu | Leu | Gly | Gly | Pro | Ser | Val | Phe | Leu | Phe | |
| | | | | 245 | | | | | 250 | | | | | 255 | | |

| ccc | ccc | aag | ccc | aag | gac | acc | ctc | atg | atc | agc | cgg | acc | ccc | gag | gtg | 816 |
|---|---|---|---|---|---|---|---|---|---|---|---|---|---|---|---|---|
| Pro | Pro | Lys | Pro | Lys | Asp | Thr | Leu | Met | Ile | Ser | Arg | Thr | Pro | Glu | Val | |

-continued

```
                       260                 265                 270
acc tgc gtg gtg gtg gac gtg agc cac gag gac ccc gag gtg aag ttc      864
Thr Cys Val Val Val Asp Val Ser His Glu Asp Pro Glu Val Lys Phe
        275                 280                 285 aac tgg tac gtg gac ggc gtg gag gtg cac aac gcc aag acc aag ccc      912
Asn Trp Tyr Val Asp Gly Val Glu Val His Asn Ala Lys Thr Lys Pro
    290                 295                 300 cgg gag gag cag tac aac agc acc tac cgg gtg gtg agc gtg ctc acc      960
Arg Glu Glu Gln Tyr Asn Ser Thr Tyr Arg Val Val Ser Val Leu Thr
305                 310                 315                 320 gtg ctg cac cag gac tgg ctg aac ggc aag gag tac aag tgc aag gtg     1008
Val Leu His Gln Asp Trp Leu Asn Gly Lys Glu Tyr Lys Cys Lys Val
            325                 330                 335 agc aac aag gcc ctg cct gcc ccc atc gag aag acc atc agc aag gcc     1056
Ser Asn Lys Ala Leu Pro Ala Pro Ile Glu Lys Thr Ile Ser Lys Ala
                340                 345                 350 aag ggc cag ccc cgg gag ccc cag gtg tac acc ctg ccc ccc agc cgg     1104
Lys Gly Gln Pro Arg Glu Pro Gln Val Tyr Thr Leu Pro Pro Ser Arg
                    355                 360                 365 gag gag atg acc aag aac cag gtg tcc ctc acc tgt ctg gtg aag ggc     1152
Glu Glu Met Thr Lys Asn Gln Val Ser Leu Thr Cys Leu Val Lys Gly
    370                 375                 380 ttc tac ccc agc gac atc gcc gtg gag tgg gag agc aac ggc cag ccc     1200
Phe Tyr Pro Ser Asp Ile Ala Val Glu Trp Glu Ser Asn Gly Gln Pro
385                 390                 395                 400 gag aac aac tac aag acc acc ccc cct gtg ctg gac agc gac ggc agc     1248
Glu Asn Asn Tyr Lys Thr Thr Pro Pro Val Leu Asp Ser Asp Gly Ser
                405                 410                 415 ttc ttc ctg tac agc aag ctc acc gtg gac aag agc cgg tgg cag cag     1296
Phe Phe Leu Tyr Ser Lys Leu Thr Val Asp Lys Ser Arg Trp Gln Gln
                    420                 425                 430 ggc aac gtg ttc agc tgc agc gtg atg cac gag gcc ctg cac aac cac     1344
Gly Asn Val Phe Ser Cys Ser Val Met His Glu Ala Leu His Asn His
        435                 440                 445 tac acc cag aag agc ctg agc ctg agc ccc ggc aag                     1380
Tyr Thr Gln Lys Ser Leu Ser Leu Ser Pro Gly Lys
    450                 455                 460
```

<210> SEQ ID NO 129
<211> LENGTH: 460
<212> TYPE: PRT
<213> ORGANISM: Artificial sequence
<220> FEATURE:
<223> OTHER INFORMATION: Heavy chain CR4361

<400> SEQUENCE: 129

```
Glu Val Gln Leu Val Gln Ser Gly Ala Glu Val Lys Lys Pro Gly Glu
1               5                   10                  15

Ser Leu Lys Ile Ser Cys Lys Ala Ser Gly Phe Ser Phe Ser Thr Tyr
            20                  25                  30

Trp Ile Gly Trp Val Arg Gln Met Pro Gly Lys Gly Leu Glu Trp Met
        35                  40                  45

Gly Ile Ile Tyr Pro Ala Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Arg Gly Pro Tyr Tyr Asp Phe Trp Asn Gly Tyr Arg Glu
```

```
                100                 105                 110
Thr His Asp Ala Phe Asn Val Trp Gly Gln Gly Thr Met Val Thr Val
        115                 120                 125

Ser Ser Ala Ser Thr Lys Gly Pro Ser Val Phe Pro Leu Ala Pro Ser
130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Arg Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460

<210> SEQ ID NO 130
<211> LENGTH: 1380
<212> TYPE: DNA
<213> ORGANISM: Artificial sequence
<220> FEATURE:
<223> OTHER INFORMATION: Heavy chain CR4374
<220> FEATURE:
<221> NAME/KEY: CDS
<222> LOCATION: (1)..(1380)
```

<400> SEQUENCE: 130

| | | | | | | | | | | | | | | | | |
|---|---|---|---|---|---|---|---|---|---|---|---|---|---|---|---|---|
| cag | atc | acc | ttg | aag | gag | tct | ggt | cct | acg | ctg | gtg | aaa | ccc | aca | cag | 48 |
| Gln | Ile | Thr | Leu | Lys | Glu | Ser | Gly | Pro | Thr | Leu | Val | Lys | Pro | Thr | Gln | |
| 1 | | | | 5 | | | | | 10 | | | | | 15 | | |
| acc | ctc | acg | ttg | acc | tgc | acc | ttc | tct | ggg | ttc | tca | ctc | agc | act | agt | 96 |
| Thr | Leu | Thr | Leu | Thr | Cys | Thr | Phe | Ser | Gly | Phe | Ser | Leu | Ser | Thr | Ser | |
| | | | 20 | | | | | 25 | | | | | 30 | | | |
| gga | gtg | ggt | gtg | ggc | tgg | atc | cgt | cag | ccc | cca | gga | aag | gcc | ctg | gag | 144 |
| Gly | Val | Gly | Val | Gly | Trp | Ile | Arg | Gln | Pro | Pro | Gly | Lys | Ala | Leu | Glu | |
| | | 35 | | | | | 40 | | | | | 45 | | | | |
| tgg | ctt | gca | gtc | att | tat | tgg | aat | gat | gat | aag | ctc | tac | agg | cca | tct | 192 |
| Trp | Leu | Ala | Val | Ile | Tyr | Trp | Asn | Asp | Asp | Lys | Leu | Tyr | Arg | Pro | Ser | |
| 50 | | | | | 55 | | | | | 60 | | | | | | |
| ctg | aag | agc | agg | ctc | acc | atc | acc | aag | gac | acc | tcc | aaa | aac | cag | gtg | 240 |
| Leu | Lys | Ser | Arg | Leu | Thr | Ile | Thr | Lys | Asp | Thr | Ser | Lys | Asn | Gln | Val | |
| 65 | | | | 70 | | | | | 75 | | | | | 80 | | |
| gtc | ctt | aca | atg | acc | aag | atg | gac | cct | gtg | gac | aca | gcc | aca | tat | tac | 288 |
| Val | Leu | Thr | Met | Thr | Lys | Met | Asp | Pro | Val | Asp | Thr | Ala | Thr | Tyr | Tyr | |
| | | | | 85 | | | | | 90 | | | | | 95 | | |
| tgt | gca | cac | aga | cac | cgt | tac | tat | gat | att | agt | ggt | tat | tac | cgt | ctc | 336 |
| Cys | Ala | His | Arg | His | Arg | Tyr | Tyr | Asp | Ile | Ser | Gly | Tyr | Tyr | Arg | Leu | |
| | | | 100 | | | | | 105 | | | | | 110 | | | |
| ttc | tct | gat | gct | ttt | gat | atc | tgg | ggc | cag | ggc | acc | atg | gtc | acc | gtg | 384 |
| Phe | Ser | Asp | Ala | Phe | Asp | Ile | Trp | Gly | Gln | Gly | Thr | Met | Val | Thr | Val | |
| | | 115 | | | | | 120 | | | | | 125 | | | | |
| tcc | agc | gct | agc | acc | aag | ggc | ccc | agc | gtg | ttc | ccc | ctg | gcc | ccc | agc | 432 |
| Ser | Ser | Ala | Ser | Thr | Lys | Gly | Pro | Ser | Val | Phe | Pro | Leu | Ala | Pro | Ser | |
| 130 | | | | | 135 | | | | | 140 | | | | | | |
| agc | aag | agc | acc | agc | ggc | ggc | aca | gcc | gcc | ctg | ggc | tgc | ctg | gtg | aag | 480 |
| Ser | Lys | Ser | Thr | Ser | Gly | Gly | Thr | Ala | Ala | Leu | Gly | Cys | Leu | Val | Lys | |
| 145 | | | | 150 | | | | | 155 | | | | | 160 | | |
| gac | tac | ttc | ccc | gag | ccc | gtg | acc | gtg | agc | tgg | aac | agc | ggc | gcc | ttg | 528 |
| Asp | Tyr | Phe | Pro | Glu | Pro | Val | Thr | Val | Ser | Trp | Asn | Ser | Gly | Ala | Leu | |
| | | | | 165 | | | | | 170 | | | | | 175 | | |
| acc | agc | ggc | gtg | cac | acc | ttc | ccc | gcc | gtg | ctg | cag | agc | agc | ggc | ctg | 576 |
| Thr | Ser | Gly | Val | His | Thr | Phe | Pro | Ala | Val | Leu | Gln | Ser | Ser | Gly | Leu | |
| | | | 180 | | | | | 185 | | | | | 190 | | | |
| tac | agc | ctg | agc | agc | gtg | gtg | acc | gtg | ccc | agc | agc | agc | ctg | ggc | acc | 624 |
| Tyr | Ser | Leu | Ser | Ser | Val | Val | Thr | Val | Pro | Ser | Ser | Ser | Leu | Gly | Thr | |
| | | 195 | | | | | 200 | | | | | 205 | | | | |
| cag | acc | tac | atc | tgc | aac | gtg | aac | cac | aag | ccc | agc | aac | acc | aag | gtg | 672 |
| Gln | Thr | Tyr | Ile | Cys | Asn | Val | Asn | His | Lys | Pro | Ser | Asn | Thr | Lys | Val | |
| | 210 | | | | | 215 | | | | | 220 | | | | | |
| gac | aaa | cgc | gtg | gag | ccc | aag | agc | tgc | gac | aag | acc | cac | acc | tgc | ccc | 720 |
| Asp | Lys | Arg | Val | Glu | Pro | Lys | Ser | Cys | Asp | Lys | Thr | His | Thr | Cys | Pro | |
| 225 | | | | | 230 | | | | | 235 | | | | | 240 | |
| ccc | tgc | cct | gcc | ccc | gag | ctg | ctg | ggc | gga | ccc | tcc | gtg | ttc | ctg | ttc | 768 |
| Pro | Cys | Pro | Ala | Pro | Glu | Leu | Leu | Gly | Gly | Pro | Ser | Val | Phe | Leu | Phe | |
| | | | 245 | | | | | 250 | | | | | 255 | | | |
| ccc | ccc | aag | ccc | aag | gac | acc | ctc | atg | atc | agc | cgg | acc | ccc | gag | gtg | 816 |
| Pro | Pro | Lys | Pro | Lys | Asp | Thr | Leu | Met | Ile | Ser | Arg | Thr | Pro | Glu | Val | |
| | | 260 | | | | | 265 | | | | | 270 | | | | |
| acc | tgc | gtg | gtg | gtg | gac | gtg | agc | cac | gag | gac | ccc | gag | gtg | aag | ttc | 864 |
| Thr | Cys | Val | Val | Val | Asp | Val | Ser | His | Glu | Asp | Pro | Glu | Val | Lys | Phe | |
| | 275 | | | | | 280 | | | | | 285 | | | | | |
| aac | tgg | tac | gtg | gac | ggc | gtg | gag | gtg | cac | aac | gcc | aag | acc | aag | ccc | 912 |
| Asn | Trp | Tyr | Val | Asp | Gly | Val | Glu | Val | His | Asn | Ala | Lys | Thr | Lys | Pro | |
| 290 | | | | | 295 | | | | | 300 | | | | | | |
| cgg | gag | gag | cag | tac | aac | agc | acc | tac | cgg | gtg | gtg | agc | gtg | ctc | acc | 960 |

```
Arg Glu Glu Gln Tyr Asn Ser Thr Tyr Arg Val Val Ser Val Leu Thr
305                 310                 315                 320 gtg ctg cac cag gac tgg ctg aac ggc aag gag tac aag tgc aag gtg      1008
Val Leu His Gln Asp Trp Leu Asn Gly Lys Glu Tyr Lys Cys Lys Val
                325                 330                 335 agc aac aag gcc ctg cct gcc ccc atc gag aag acc atc agc aag gcc      1056
Ser Asn Lys Ala Leu Pro Ala Pro Ile Glu Lys Thr Ile Ser Lys Ala
            340                 345                 350 aag ggc cag ccc cgg gag ccc cag gtg tac acc ctg ccc ccc agc cgg      1104
Lys Gly Gln Pro Arg Glu Pro Gln Val Tyr Thr Leu Pro Pro Ser Arg
        355                 360                 365 gag gag atg acc aag aac cag gtg tcc ctc acc tgt ctg gtg aag ggc      1152
Glu Glu Met Thr Lys Asn Gln Val Ser Leu Thr Cys Leu Val Lys Gly
    370                 375                 380 ttc tac ccc agc gac atc gcc gtg gag tgg gag agc aac ggc cag ccc      1200
Phe Tyr Pro Ser Asp Ile Ala Val Glu Trp Glu Ser Asn Gly Gln Pro
385                 390                 395                 400 gag aac aac tac aag acc acc ccc cct gtg ctg gac agc gac ggc agc      1248
Glu Asn Asn Tyr Lys Thr Thr Pro Pro Val Leu Asp Ser Asp Gly Ser
                405                 410                 415 ttc ttc ctg tac agc aag ctc acc gtg gac aag agc cgg tgg cag cag      1296
Phe Phe Leu Tyr Ser Lys Leu Thr Val Asp Lys Ser Arg Trp Gln Gln
            420                 425                 430 ggc aac gtg ttc agc tgc agc gtg atg cac gag gcc ctg cac aac cac      1344
Gly Asn Val Phe Ser Cys Ser Val Met His Glu Ala Leu His Asn His
        435                 440                 445 tac acc cag aag agc ctg agc ctg agc ccc ggc aag                      1380
Tyr Thr Gln Lys Ser Leu Ser Leu Ser Pro Gly Lys
    450                 455                 460

<210> SEQ ID NO 131
<211> LENGTH: 460
<212> TYPE: PRT
<213> ORGANISM: Artificial sequence
<220> FEATURE:
<223> OTHER INFORMATION: Heavy chain CR4374

<400> SEQUENCE: 131

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Val Gly Val Gly Trp Ile Arg Gln Pro Pro Gly Lys Ala Leu Glu
            35                  40                  45

Trp Leu Ala Val Ile Tyr Trp Asn Asp Asp Lys Leu Tyr Arg Pro Ser
        50                  55                  60

Leu Lys Ser Arg Leu Thr Ile Thr Lys Asp Thr Ser Lys Asn Gln Val
65                  70                  75                  80

Val Leu Thr Met Thr Lys Met Asp Pro Val Asp Thr Ala Thr Tyr Tyr
                85                  90                  95

Cys Ala His Arg His Arg Tyr Tyr Asp Ile Ser Gly Tyr Tyr Arg Leu
            100                 105                 110

Phe Ser Asp Ala Phe Asp Ile Trp Gly Gln Gly Thr Met Val Thr Val
        115                 120                 125

Ser Ser Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160
```

| | | | | | | | | | | | | |
|---|---|---|---|---|---|---|---|---|---|---|---|---|
|Asp|Tyr|Phe|Pro|Glu|Pro|Val|Thr|Val|Ser|Trp|Asn|Ser|Gly|Ala|Leu|

```
Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Leu Gly Thr
        195                 200                 205

Gln Thr Tyr Ile Cys Asn Val Asn His Lys Pro Ser Asn Thr Lys Val
    210                 215                 220

Asp Lys Arg Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
450                 455                 460
```

<210> SEQ ID NO 132
<211> LENGTH: 648
<212> TYPE: DNA
<213> ORGANISM: Artificial sequence
<220> FEATURE:
<223> OTHER INFORMATION: Light chain CR4271
<220> FEATURE:
<221> NAME/KEY: CDS
<222> LOCATION: (1)..(648)

<400> SEQUENCE: 132

```
cag tcc gcc ctg acc cag ccc cgc tca gtg tcc ggg tct cct gga cag      48
Gln Ser Ala Leu Thr Gln Pro Arg Ser Val Ser Gly Ser Pro Gly Gln
1               5                   10                  15 tca gtc acc atc tcc tgc act gga acc agc agt gat gtt ggt ggt tat      96
Ser Val Thr Ile Ser Cys Thr Gly Thr Ser Ser Asp Val Gly Gly Tyr
            20                  25                  30 aac tat gtc tcc tgg tac caa cat cac cca ggc aaa gcc ccc aaa ctc     144
```

```
Asn Tyr Val Ser Trp Tyr Gln His His Pro Gly Lys Ala Pro Lys Leu
        35                  40                  45 atg att tat gat gtc agt aat cgg ccc tta ggg gtt tct aat cgc ttc      192
Met Ile Tyr Asp Val Ser Asn Arg Pro Leu Gly Val Ser Asn Arg Phe
 50                  55                  60 tct ggc tcc aag tct ggc aac acg gcc tcc ctg acc atc tct ggg ctc      240
Ser Gly Ser Lys Ser Gly Asn Thr Ala Ser Leu Thr Ile Ser Gly Leu
 65                  70                  75                  80 cag gct gag gac gag gct gat tat tac tgc agc tca tat aca agc agc      288
Gln Ala Glu Asp Glu Ala Asp Tyr Tyr Cys Ser Ser Tyr Thr Ser Ser
                 85                  90                  95 agc act tat gtc ttc gga act ggg acc aag ctt acc gtc ctg ggc cag      336
Ser Thr Tyr Val Phe Gly Thr Gly Thr Lys Leu Thr Val Leu Gly Gln
            100                 105                 110 ccc aag gcc gct ccc agc gtg acc ctg ttc ccc ccc tcc tcc gag gag      384
Pro Lys Ala Ala Pro Ser Val Thr Leu Phe Pro Pro Ser Ser Glu Glu
            115                 120                 125 ctg cag gcc aac aag gcc acc ctg gtg tgc ctc atc agc gac ttc tac      432
Leu Gln Ala Asn Lys Ala Thr Leu Val Cys Leu Ile Ser Asp Phe Tyr
130                 135                 140 cct ggc gcc gtg acc gtg gcc tgg aag gcc gac agc agc ccc gtg aag      480
Pro Gly Ala Val Thr Val Ala Trp Lys Ala Asp Ser Ser Pro Val Lys
145                 150                 155                 160 gcc ggc gtg gag acc acc acc ccc agc aag cag agc aac aac aag tac      528
Ala Gly Val Glu Thr Thr Thr Pro Ser Lys Gln Ser Asn Asn Lys Tyr
                165                 170                 175 gcc gcc agc agc tac ctg agc ctc acc ccc gag cag tgg aag agc cac      576
Ala Ala Ser Ser Tyr Leu Ser Leu Thr Pro Glu Gln Trp Lys Ser His
            180                 185                 190 cgg agc tac agc tgc cag gtg acc cac gag ggc agc acc gtg gag aag      624
Arg Ser Tyr Ser Cys Gln Val Thr His Glu Gly Ser Thr Val Glu Lys
            195                 200                 205 acc gtg gcc ccc acc gag tgc agc                                      648
Thr Val Ala Pro Thr Glu Cys Ser
            210                 215

<210> SEQ ID NO 133
<211> LENGTH: 216
<212> TYPE: PRT
<213> ORGANISM: Artificial sequence
<220> FEATURE:
<223> OTHER INFORMATION: Light chain CR4271

<400> SEQUENCE: 133

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln His His Pro Gly Lys Ala Pro Lys Leu
        35                  40                  45

Met Ile Tyr Asp Val Ser Asn Arg Pro Leu Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Tyr Val Phe Gly Thr Gly Thr Lys Leu Thr Val Leu Gly Gln
            100                 105                 110

Pro Lys Ala Ala Pro Ser Val Thr Leu Phe Pro Pro Ser Ser Glu Glu
```

```
                 115                 120                 125
Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
            195                 200                 205

Thr Val Ala Pro Thr Glu Cys Ser
        210                 215

<210> SEQ ID NO 134
<211> LENGTH: 660
<212> TYPE: DNA
<213> ORGANISM: Artificial sequence
<220> FEATURE:
<223> OTHER INFORMATION: Light chain CR4274
<220> FEATURE:
<221> NAME/KEY: CDS
<222> LOCATION: (1)..(660)

<400> SEQUENCE: 134 gac atc gtg atg acc cag tct cca gac tcc ctg gct gtg tct ctg ggc      48
Asp Ile Val Met Thr Gln Ser Pro Asp Ser Leu Ala Val Ser Leu Gly
1               5                   10                  15 gag agg gcc acc atc aac tgc aag tcc agc cag agt gtt tta tac agc      96
Glu Arg Ala Thr Ile Asn Cys Lys Ser Ser Gln Ser Val Leu Tyr Ser
                20                  25                  30 tcc aac aat aag aac tac tta gct tgg tac cag cag aaa cca gga cag     144
Ser Asn Asn Lys Asn Tyr Leu Ala Trp Tyr Gln Gln Lys Pro Gly Gln
            35                  40                  45 cct cct aag ctg ctc att tac tgg gca tct acc cgg gaa tcc ggg gtc     192
Pro Pro Lys Leu Leu Ile Tyr Trp Ala Ser Thr Arg Glu Ser Gly Val
        50                  55                  60 cct gac cga ttc agt ggc agc ggg tct ggg aca gat ttc act ctc acc     240
Pro Asp Arg Phe Ser Gly Ser Gly Ser Gly Thr Asp Phe Thr Leu Thr
65                  70                  75                  80 atc agc agc ctg cag gct gaa gat gtg gca gtt tat tat tgt cag caa     288
Ile Ser Ser Leu Gln Ala Glu Asp Val Ala Val Tyr Tyr Cys Gln Gln
                85                  90                  95 tat tat agt act cct ccg act ttc ggc gga ggg acc aag gtg gag atc     336
Tyr Tyr Ser Thr Pro Pro Thr Phe Gly Gly Gly Thr Lys Val Glu Ile
                100                 105                 110 aag cgg acc gtg gcc gct ccc agc gtg ttc atc ttc ccc ccc tcc gac     384
Lys Arg Thr Val Ala Ala Pro Ser Val Phe Ile Phe Pro Pro Ser Asp
            115                 120                 125 gag cag ctg aag agc ggc acc gcc agc gtg gtg tgc ctg ctg aac aac     432
Glu Gln Leu Lys Ser Gly Thr Ala Ser Val Val Cys Leu Leu Asn Asn
        130                 135                 140 ttc tac ccc cgg gag gcc aag gtg cag tgg aag gtg gac aac gcc ctg     480
Phe Tyr Pro Arg Glu Ala Lys Val Gln Trp Lys Val Asp Asn Ala Leu
145                 150                 155                 160 cag agc ggc aac agc cag gag agc gtg acc gag cag gac agc aag gac     528
Gln Ser Gly Asn Ser Gln Glu Ser Val Thr Glu Gln Asp Ser Lys Asp
                165                 170                 175 tcc acc tac agc ctg agc agc acc ctc acc ctg agc aag gcc gac tac     576
Ser Thr Tyr Ser Leu Ser Ser Thr Leu Thr Leu Ser Lys Ala Asp Tyr
```

```
                    180              185              190
gag aag cac aag gtg tac gcc tgc gag gtg acc cac cag ggc ctg agc      624
Glu Lys His Lys Val Tyr Ala Cys Glu Val Thr His Gln Gly Leu Ser
        195              200              205 agc ccc gtg acc aag agc ttc aac cgg ggc gag tgt                      660
Ser Pro Val Thr Lys Ser Phe Asn Arg Gly Glu Cys
    210              215              220
```

<210> SEQ ID NO 135
<211> LENGTH: 220
<212> TYPE: PRT
<213> ORGANISM: Artificial sequence
<220> FEATURE:
<223> OTHER INFORMATION: Light chain CR4274

<400> SEQUENCE: 135

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 136
<211> LENGTH: 636
<212> TYPE: DNA
<213> ORGANISM: Artificial sequence
<220> FEATURE:
<223> OTHER INFORMATION: Light chain CR4283
<220> FEATURE:
<221> NAME/KEY: CDS
<222> LOCATION: (1)..(636)

<400> SEQUENCE: 136

```
gac atc cag atg acc cag tct cct tcc acc ctg tct gca tct gta gga      48
Asp Ile Gln Met Thr Gln Ser Pro Ser Thr Leu Ser Ala Ser Val Gly
1               5                   10                  15
```

```
gac aga gtc acc atc act tgc cgg gcc agt cag agt att agt agc tgg      96
Asp Arg Val Thr Ile Thr Cys Arg Ala Ser Gln Ser Ile Ser Ser Trp
        20                  25                  30 ttg gcc tgg tat cag cag aaa cca ggg aaa gcc cct aat ctc ctg atc     144
Leu Ala Trp Tyr Gln Gln Lys Pro Gly Lys Ala Pro Asn Leu Leu Ile
    35                  40                  45 tat gct gca tcc agt ttg caa agt ggg gtc cca tca agg ttc agc ggc     192
Tyr Ala Ala Ser Ser Leu Gln Ser Gly Val Pro Ser Arg Phe Ser Gly
50                  55                  60 agt gga tct ggg aca gat ttc act ctc acc atc agc agc ctg cag cct     240
Ser Gly Ser Gly Thr Asp Phe Thr Leu Thr Ile Ser Ser Leu Gln Pro
65                  70                  75                  80 gat gac tct gca act tat tac tgc caa cag tat aat act tat ccc ctc     288
Asp Asp Ser Ala Thr Tyr Tyr Cys Gln Gln Tyr Asn Thr Tyr Pro Leu
                85                  90                  95 act ttc ggg acc aag gtg gag atc aag cgg acc gtg gcc gct ccc agc     336
Thr Phe Gly Thr Lys Val Glu Ile Lys Arg Thr Val Ala Ala Pro Ser
            100                 105                 110 gtg ttc atc ttc ccc ccc tcc gac gag cag ctg aag agc ggc acc gcc     384
Val Phe Ile Phe Pro Pro Ser Asp Glu Gln Leu Lys Ser Gly Thr Ala
        115                 120                 125 agc gtg gtg tgc ctg ctg aac aac ttc tac ccc cgg gag gcc aag gtg     432
Ser Val Val Cys Leu Leu Asn Asn Phe Tyr Pro Arg Glu Ala Lys Val
    130                 135                 140 cag tgg aag gtg gac aac gcc ctg cag agc ggc aac agc cag gag agc     480
Gln Trp Lys Val Asp Asn Ala Leu Gln Ser Gly Asn Ser Gln Glu Ser
145                 150                 155                 160 gtg acc gag cag gac agc aag gac tcc acc tac agc ctg agc agc acc     528
Val Thr Glu Gln Asp Ser Lys Asp Ser Thr Tyr Ser Leu Ser Ser Thr
                165                 170                 175 ctc acc ctg agc aag gcc gac tac gag aag cac aag gtg tac gcc tgc     576
Leu Thr Leu Ser Lys Ala Asp Tyr Glu Lys His Lys Val Tyr Ala Cys
            180                 185                 190 gag gtg acc cac cag ggc ctg agc agc ccc gtg acc aag agc ttc aac     624
Glu Val Thr His Gln Gly Leu Ser Ser Pro Val Thr Lys Ser Phe Asn
        195                 200                 205 cgg ggc gag tgt                                                     636
Arg Gly Glu Cys
    210
```

<210> SEQ ID NO 137
<211> LENGTH: 212
<212> TYPE: PRT
<213> ORGANISM: Artificial sequence
<220> FEATURE:
<223> OTHER INFORMATION: Light chain CR4283

<400> SEQUENCE: 137

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Ser Ala Thr Tyr Tyr Cys Gln Gln Tyr Asn Thr Tyr Pro Leu
                85                  90                  95
```

```
Thr Phe Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210
```

<210> SEQ ID NO 138
<211> LENGTH: 651
<212> TYPE: DNA
<213> ORGANISM: Artificial sequence
<220> FEATURE:
<223> OTHER INFORMATION: Light chain CR4289
<220> FEATURE:
<221> NAME/KEY: CDS
<222> LOCATION: (1)..(651)

<400> SEQUENCE: 138

```
tcg acg gaa att gtg ttg acg cag tct cca ggc acc ctg tct ttg tct      48
Ser Thr Glu Ile Val Leu Thr Gln Ser Pro Gly Thr Leu Ser Leu Ser
1               5                   10                  15 cca ggg gaa aca gcc acc ctc tcc tgc agg acc agt cag agt gtt agt      96
Pro Gly Glu Thr Ala Thr Leu Ser Cys Arg Thr Ser Gln Ser Val Ser
            20                  25                  30 agc agc tac tta ggc tgg tac cag cag aaa cct ggc cag gct ccc agg     144
Ser Ser Tyr Leu Gly Trp Tyr Gln Gln Lys Pro Gly Gln Ala Pro Arg
        35                  40                  45 ctc ctc atc tat ggt gca tcc atc agg gcc act ggc atc cca gcc agg     192
Leu Leu Ile Tyr Gly Ala Ser Ile Arg Ala Thr Gly Ile Pro Ala Arg
    50                  55                  60 ttc agt ggc agt ggg tct ggg aca gag ttc act ctc acc atc gac agc     240
Phe Ser Gly Ser Gly Ser Gly Thr Glu Phe Thr Leu Thr Ile Asp Ser
65                  70                  75                  80 cta cag tct gaa gat ttt gca gtt tat tac tgt cag cag tat aat aac     288
Leu Gln Ser Glu Asp Phe Ala Val Tyr Tyr Cys Gln Gln Tyr Asn Asn
                85                  90                  95 tgg cct ccg atc acc ttc ggc caa ggg aca cga ctg gag att aaa cgt     336
Trp Pro Pro Ile Thr Phe Gly Gln Gly Thr Arg Leu Glu Ile Lys Arg
            100                 105                 110 gcg gcc gca ccc agc gtg ttc atc ttc ccc ccc tcc gac gag cag ctg     384
Ala Ala Ala Pro Ser Val Phe Ile Phe Pro Pro Ser Asp Glu Gln Leu
        115                 120                 125 aag agc ggc acc gcc agc gtg gtg tgc ctg ctg aac aac ttc tac ccc     432
Lys Ser Gly Thr Ala Ser Val Val Cys Leu Leu Asn Asn Phe Tyr Pro
    130                 135                 140 cgg gag gcc aag gtg cag tgg aag gtg gac aac gcc ctg cag agc ggc     480
Arg Glu Ala Lys Val Gln Trp Lys Val Asp Asn Ala Leu Gln Ser Gly
145                 150                 155                 160 aac agc cag gag agc gtg acc gag cag gac agc aag gac tcc acc tac     528
```

```
Asn Ser Gln Glu Ser Val Thr Glu Gln Asp Ser Lys Asp Ser Thr Tyr
                165                 170                 175 agc ctg agc agc acc ctc acc ctg agc aag gcc gac tac gag aag cac        576
Ser Leu Ser Ser Thr Leu Thr Leu Ser Lys Ala Asp Tyr Glu Lys His
            180                 185                 190 aag gtg tac gcc tgc gag gtg acc cac cag ggc ctg agc agc ccc gtg        624
Lys Val Tyr Ala Cys Glu Val Thr His Gln Gly Leu Ser Ser Pro Val
        195                 200                 205 acc aag agc ttc aac cgg ggc gag tgt                                    651
Thr Lys Ser Phe Asn Arg Gly Glu Cys
    210                 215
```

<210> SEQ ID NO 139
<211> LENGTH: 217
<212> TYPE: PRT
<213> ORGANISM: Artificial sequence
<220> FEATURE:
<223> OTHER INFORMATION: Light chain CR4289

<400> SEQUENCE: 139

```
Ser Thr Glu Ile Val Leu Thr Gln Ser Pro Gly Thr Leu Ser Leu Ser
1               5                   10                  15

Pro Gly Glu Thr Ala Thr Leu Ser Cys Arg Thr Ser Gln Ser Val Ser
            20                  25                  30

Ser Ser Tyr Leu Gly Trp Tyr Gln Gln Lys Pro Gly Gln Ala Pro Arg
        35                  40                  45

Leu Leu Ile Tyr Gly Ala Ser Ile Arg Ala Thr Gly Ile Pro Ala Arg
    50                  55                  60

Phe Ser Gly Ser Gly Ser Gly Thr Glu Phe Thr Leu Thr Ile Asp Ser
65                  70                  75                  80

Leu Gln Ser Glu Asp Phe Ala Val Tyr Tyr Cys Gln Gln Tyr Asn Asn
                85                  90                  95

Trp Pro Pro Ile Thr Phe Gly Gln Gly Thr Arg Leu Glu Ile Lys Arg
            100                 105                 110

Ala Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 140
<211> LENGTH: 648
<212> TYPE: DNA
<213> ORGANISM: Artificial sequence
<220> FEATURE:
<223> OTHER INFORMATION: Light chain CR4299
<220> FEATURE:
<221> NAME/KEY: CDS
<222> LOCATION: (1)..(648)

<400> SEQUENCE: 140

```
tcc tac gtg ctg act cag cca ccc tcg ctg tct gca gcc ccc agg cag      48
Ser Tyr Val Leu Thr Gln Pro Pro Ser Leu Ser Ala Ala Pro Arg Gln
 1               5                  10                  15 agg gtc acc atc tcc tgt tct gga agc agc tcc aat atc gga aat tat      96
Arg Val Thr Ile Ser Cys Ser Gly Ser Ser Ser Asn Ile Gly Asn Tyr
                20                  25                  30 ggt gtg aac tgg tac cag cag ctc cca gga aag gct ccc aaa ctc ctc     144
Gly Val Asn Trp Tyr Gln Gln Leu Pro Gly Lys Ala Pro Lys Leu Leu
            35                  40                  45 atc tat tat gat gat ctg ctg ccc tca ggg gtc tct gac cga ttc tct     192
Ile Tyr Tyr Asp Asp Leu Leu Pro Ser Gly Val Ser Asp Arg Phe Ser
        50                  55                  60 ggc tcc aag tct ggc acc tca gcc tcc ctg gcc atc agt ggg ctc cag     240
Gly Ser Lys Ser Gly Thr Ser Ala Ser Leu Ala Ile Ser Gly Leu Gln
65                  70                  75                  80 tct gag gat gaa ggt gat tat tac tgt gca gcg tgg gat gac acc cta     288
Ser Glu Asp Glu Gly Asp Tyr Tyr Cys Ala Ala Trp Asp Asp Thr Leu
                85                  90                  95 agt gct tgg gtg ttc ggc gga ggc acc aag ctt acc gtc ctg ggc cag     336
Ser Ala Trp Val Phe Gly Gly Gly Thr Lys Leu Thr Val Leu Gly Gln
            100                 105                 110 ccc aag gcc gct ccc agc gtg acc ctg ttc ccc ccc tcc tcc gag gag     384
Pro Lys Ala Ala Pro Ser Val Thr Leu Phe Pro Pro Ser Ser Glu Glu
        115                 120                 125 ctg cag gcc aac aag gcc acc ctg gtg tgc ctc atc agc gac ttc tac     432
Leu Gln Ala Asn Lys Ala Thr Leu Val Cys Leu Ile Ser Asp Phe Tyr
    130                 135                 140 cct ggc gcc gtg acc gtg gcc tgg aag gcc gac agc agc ccc gtg aag     480
Pro Gly Ala Val Thr Val Ala Trp Lys Ala Asp Ser Ser Pro Val Lys
145                 150                 155                 160 gcc ggc gtg gag acc acc acc ccc agc aag cag agc aac aac aag tac     528
Ala Gly Val Glu Thr Thr Thr Pro Ser Lys Gln Ser Asn Asn Lys Tyr
                165                 170                 175 gcc gcc agc agc tac ctg agc ctc acc ccc gag cag tgg aag agc cac     576
Ala Ala Ser Ser Tyr Leu Ser Leu Thr Pro Glu Gln Trp Lys Ser His
            180                 185                 190 cgg agc tac agc tgc cag gtg acc cac gag ggc agc acc gtg gag aag     624
Arg Ser Tyr Ser Cys Gln Val Thr His Glu Gly Ser Thr Val Glu Lys
        195                 200                 205 acc gtg gcc ccc acc gag tgc agc                                     648
Thr Val Ala Pro Thr Glu Cys Ser
    210                 215

<210> SEQ ID NO 141
<211> LENGTH: 216
<212> TYPE: PRT
<213> ORGANISM: Artificial sequence
<220> FEATURE:
<223> OTHER INFORMATION: Light chain CR4299

<400> SEQUENCE: 141

Ser Tyr Val Leu Thr Gln Pro Pro Ser Leu Ser Ala Ala Pro Arg Gln
 1               5                  10                  15

Arg Val Thr Ile Ser Cys Ser Gly Ser Ser Ser Asn Ile Gly Asn Tyr
                20                  25                  30

Gly Val Asn Trp Tyr Gln Gln Leu Pro Gly Lys Ala Pro Lys Leu Leu
            35                  40                  45

Ile Tyr Tyr Asp Asp Leu Leu Pro Ser Gly Val Ser Asp Arg Phe Ser
        50                  55                  60
```

```
Gly Ser Lys Ser Gly Thr Ser Ala Ser Leu Ala Ile Ser Gly Leu Gln
 65                  70                  75                  80

Ser Glu Asp Glu Gly Asp Tyr Tyr Cys Ala Ala Trp Asp Asp Thr Leu
                 85                  90                  95

Ser Ala Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 142
<211> LENGTH: 648
<212> TYPE: DNA
<213> ORGANISM: Artificial sequence
<220> FEATURE:
<223> OTHER INFORMATION: Light chain CR4311
<220> FEATURE:
<221> NAME/KEY: CDS
<222> LOCATION: (1)..(648)

<400> SEQUENCE: 142 cag tcc gtg ctg acc cag cct ccc tca gtg tct gcg gcc cca gga cag      48
Gln Ser Val Leu Thr Gln Pro Pro Ser Val Ser Ala Ala Pro Gly Gln
 1               5                  10                  15 aag gtc acc atc tcc tgc tct gga acc agc tcc aat att ggg gat aat      96
Lys Val Thr Ile Ser Cys Ser Gly Thr Ser Ser Asn Ile Gly Asp Asn
            20                  25                  30 tat gta tcc tgg tac cag cac ctc cca gga aca gcc ccc aaa ctc ctc     144
Tyr Val Ser Trp Tyr Gln His Leu Pro Gly Thr Ala Pro Lys Leu Leu
        35                  40                  45 att tat gac aat aat aag cga ccc tca ggg att cct gac cga ttc tct     192
Ile Tyr Asp Asn Asn Lys Arg Pro Ser Gly Ile Pro Asp Arg Phe Ser
    50                  55                  60 ggc tcc aag tct ggc acg tca gcc acc ctg ggc gtc acc gga ctc cag     240
Gly Ser Lys Ser Gly Thr Ser Ala Thr Leu Gly Val Thr Gly Leu Gln
 65                  70                  75                  80 act ggg gac gag gcc gat tat tac tgc gga aca tgg gat agc agc ctg     288
Thr Gly Asp Glu Ala Asp Tyr Tyr Cys Gly Thr Trp Asp Ser Ser Leu
                 85                  90                  95 act gct gtg gtc ttc ggc gga ggc acc aag ctt acc gtc ctg ggc cag     336
Thr Ala Val Val Phe Gly Gly Gly Thr Lys Leu Thr Val Leu Gly Gln
            100                 105                 110 ccc aag gcc gct ccc agc gtg acc ctg ttc ccc ccc tcc tcc gag gag     384
Pro Lys Ala Ala Pro Ser Val Thr Leu Phe Pro Pro Ser Ser Glu Glu
        115                 120                 125 ctg cag gcc aac aag gcc acc ctg gtg tgc ctc atc agc gac ttc tac     432
Leu Gln Ala Asn Lys Ala Thr Leu Val Cys Leu Ile Ser Asp Phe Tyr
    130                 135                 140
```

```
cct ggc gcc gtg acc gtg gcc tgg aag gcc gac agc agc ccc gtg aag       480
Pro Gly Ala Val Thr Val Ala Trp Lys Ala Asp Ser Ser Pro Val Lys
145                 150                 155                 160 gcc ggc gtg gag acc acc acc ccc agc aag cag agc aac aac aag tac       528
Ala Gly Val Glu Thr Thr Thr Pro Ser Lys Gln Ser Asn Asn Lys Tyr
                165                 170                 175 gcc gcc agc agc tac ctg agc ctc acc ccc gag cag tgg aag agc cac       576
Ala Ala Ser Ser Tyr Leu Ser Leu Thr Pro Glu Gln Trp Lys Ser His
            180                 185                 190 cgg agc tac agc tgc cag gtg acc cac gag ggc agc acc gtg gag aag       624
Arg Ser Tyr Ser Cys Gln Val Thr His Glu Gly Ser Thr Val Glu Lys
        195                 200                 205 acc gtg gcc ccc acc gag tgc agc                                       648
Thr Val Ala Pro Thr Glu Cys Ser
    210                 215

<210> SEQ ID NO 143
<211> LENGTH: 216
<212> TYPE: PRT
<213> ORGANISM: Artificial sequence
<220> FEATURE:
<223> OTHER INFORMATION: Light chain CR4311

<400> SEQUENCE: 143

Gln Ser Val Leu Thr Gln Pro Pro Ser Val Ser Ala Ala Pro Gly Gln
1               5                   10                  15

Lys Val Thr Ile Ser Cys Ser Gly Thr Ser Ser Asn Ile Gly Asp Asn
            20                  25                  30

Tyr Val Ser Trp Tyr Gln His Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Val Thr Gly Leu Gln
65                  70                  75                  80

Thr Gly Asp Glu Ala Asp Tyr Tyr Cys Gly Thr Trp Asp Ser Ser Leu
                85                  90                  95

Thr Ala Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 144
<211> LENGTH: 654
<212> TYPE: DNA
<213> ORGANISM: Artificial sequence
<220> FEATURE:
<223> OTHER INFORMATION: Light chain CR4325
```

-continued

```
<220> FEATURE:
<221> NAME/KEY: CDS
<222> LOCATION: (1)..(654)

<400> SEQUENCE: 144 gac atc gtg atg acc cag tct cca gac tcc ctg gct gtg tct ctg ggc         48
Asp Ile Val Met Thr Gln Ser Pro Asp Ser Leu Ala Val Ser Leu Gly
  1               5                  10                  15 gag agg gcc acc atc aac tgc aag tcc agc cag agt gtt tta tac agc         96
Glu Arg Ala Thr Ile Asn Cys Lys Ser Ser Gln Ser Val Leu Tyr Ser
             20                  25                  30 tcc aac aat aag aac tac tta gct tgg tac cag cag aaa cca gga cag        144
Ser Asn Asn Lys Asn Tyr Leu Ala Trp Tyr Gln Gln Lys Pro Gly Gln
         35                  40                  45 cct cct aag ctg ctc att tac tgg gca tct acc cgg gaa tcc ggg gtc        192
Pro Pro Lys Leu Leu Ile Tyr Trp Ala Ser Thr Arg Glu Ser Gly Val
     50                  55                  60 cct gac cga ttc agt ggc agc ggg tct ggg aca gat ttc act ctc acc        240
Pro Asp Arg Phe Ser Gly Ser Gly Ser Gly Thr Asp Phe Thr Leu Thr
 65                  70                  75                  80 atc agc agc ctg cag gct gaa gat gtg gca gtt tat tac tgt cag caa        288
Ile Ser Ser Leu Gln Ala Glu Asp Val Ala Val Tyr Tyr Cys Gln Gln
                 85                  90                  95 tat tat agt acc ccg ttg acg ttc ggg acc aag gtg gag atc aag cgg        336
Tyr Tyr Ser Thr Pro Leu Thr Phe Gly Thr Lys Val Glu Ile Lys Arg
            100                 105                 110 acc gtg gcc gct ccc agc gtg ttc atc ttc ccc ccc tcc gac gag cag        384
Thr Val Ala Ala Pro Ser Val Phe Ile Phe Pro Pro Ser Asp Glu Gln
        115                 120                 125 ctg aag agc ggc acc gcc agc gtg gtg tgc ctg ctg aac aac ttc tac        432
Leu Lys Ser Gly Thr Ala Ser Val Val Cys Leu Leu Asn Asn Phe Tyr
    130                 135                 140 ccc cgg gag gcc aag gtg cag tgg aag gtg gac aac gcc ctg cag agc        480
Pro Arg Glu Ala Lys Val Gln Trp Lys Val Asp Asn Ala Leu Gln Ser
145                 150                 155                 160 ggc aac agc cag gag agc gtg acc gag cag gac agc aag gac tcc acc        528
Gly Asn Ser Gln Glu Ser Val Thr Glu Gln Asp Ser Lys Asp Ser Thr
                165                 170                 175 tac agc ctg agc agc acc ctc acc ctg agc aag gcc gac tac gag aag        576
Tyr Ser Leu Ser Ser Thr Leu Thr Leu Ser Lys Ala Asp Tyr Glu Lys
            180                 185                 190 cac aag gtg tac gcc tgc gag gtg acc cac cag ggc ctg agc agc ccc        624
His Lys Val Tyr Ala Cys Glu Val Thr His Gln Gly Leu Ser Ser Pro
        195                 200                 205 gtg acc aag agc ttc aac cgg ggc gag tgt                                654
Val Thr Lys Ser Phe Asn Arg Gly Glu Cys
    210                 215

<210> SEQ ID NO 145
<211> LENGTH: 218
<212> TYPE: PRT
<213> ORGANISM: Artificial sequence
<220> FEATURE:
<223> OTHER INFORMATION: Light chain CR4325

<400> SEQUENCE: 145

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Val Leu Tyr Ser
             20                  25                  30

Ser Asn Asn Lys Asn Tyr Leu Ala Trp Tyr Gln Gln Lys Pro Gly Gln
```

```
                35                  40                  45
Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 146
<211> LENGTH: 645
<212> TYPE: DNA
<213> ORGANISM: Artificial sequence
<220> FEATURE:
<223> OTHER INFORMATION: Light chain CR4353
<220> FEATURE:
<221> NAME/KEY: CDS
<222> LOCATION: (1)..(645)

<400> SEQUENCE: 146 tcg acg gaa acg aca ctc acg cag tcc cca ggc acc ctg tct ttg tct      48
Ser Thr Glu Thr Thr Leu Thr Gln Ser Pro Gly Thr Leu Ser Leu Ser
1               5                   10                  15 ccc ggg gaa aga gcc acc ctc tcc tgc aga gcc agt cag agt gtt agc      96
Pro Gly Glu Arg Ala Thr Leu Ser Cys Arg Ala Ser Gln Ser Val Ser
                20                  25                  30 aac acc ttc tta gcc tgg tac cag cag aaa cct ggc cag gct ccc agg     144
Asn Thr Phe Leu Ala Trp Tyr Gln Gln Lys Pro Gly Gln Ala Pro Arg
            35                  40                  45 ctc ctc atc tat ggt gca tcc agc agg gcc act ggc atc cca gac agg     192
Leu Leu Ile Tyr Gly Ala Ser Ser Arg Ala Thr Gly Ile Pro Asp Arg
        50                  55                  60 ttc agt ggc agt ggg tct ggg aca gac ttc act ctc acc atc agc aga     240
Phe Ser Gly Ser Gly Ser Gly Thr Asp Phe Thr Leu Thr Ile Ser Arg
65                  70                  75                  80 ctg gag cct gaa gat ttt gca gcg tat tac tgt cag cag tat ggt agc     288
Leu Glu Pro Glu Asp Phe Ala Ala Tyr Tyr Cys Gln Gln Tyr Gly Ser
                85                  90                  95 tcg ctc act ttc ggc cct ggg acc aaa gtg gat atc aaa cgt gcg gcc     336
Ser Leu Thr Phe Gly Pro Gly Thr Lys Val Asp Ile Lys Arg Ala Ala
            100                 105                 110 gca ccc agc gtg ttc atc ttc ccc ccc tcc gac gag cag ctg aag agc     384
Ala Pro Ser Val Phe Ile Phe Pro Pro Ser Asp Glu Gln Leu Lys Ser
        115                 120                 125
```

```
ggc acc gcc agc gtg gtg tgc ctg ctg aac aac ttc tac ccc cgg gag      432
Gly Thr Ala Ser Val Val Cys Leu Leu Asn Asn Phe Tyr Pro Arg Glu
    130                 135                 140 gcc aag gtg cag tgg aag gtg gac aac gcc ctg cag agc ggc aac agc      480
Ala Lys Val Gln Trp Lys Val Asp Asn Ala Leu Gln Ser Gly Asn Ser
145                 150                 155                 160 cag gag agc gtg acc gag cag gac agc aag gac tcc acc tac agc ctg      528
Gln Glu Ser Val Thr Glu Gln Asp Ser Lys Asp Ser Thr Tyr Ser Leu
                165                 170                 175 agc agc acc ctc acc ctg agc aag gcc gac tac gag aag cac aag gtg      576
Ser Ser Thr Leu Thr Leu Ser Lys Ala Asp Tyr Glu Lys His Lys Val
        180                 185                 190 tac gcc tgc gag gtg acc cac cag ggc ctg agc agc ccc gtg acc aag      624
Tyr Ala Cys Glu Val Thr His Gln Gly Leu Ser Ser Pro Val Thr Lys
    195                 200                 205 agc ttc aac cgg ggc gag tgt                                          645
Ser Phe Asn Arg Gly Glu Cys
210                 215

<210> SEQ ID NO 147
<211> LENGTH: 215
<212> TYPE: PRT
<213> ORGANISM: Artificial sequence
<220> FEATURE:
<223> OTHER INFORMATION: Light chain CR4353

<400> SEQUENCE: 147

Ser Thr Glu Thr Thr Leu Thr Gln Ser Pro Gly Thr Leu Ser Leu Ser
1               5                   10                  15

Pro Gly Glu Arg Ala Thr Leu Ser Cys Arg Ala Ser Gln Ser Val Ser
            20                  25                  30

Asn Thr Phe Leu Ala Trp Tyr Gln Gln Lys Pro Gly Gln Ala Pro Arg
        35                  40                  45

Leu Leu Ile Tyr Gly Ala Ser Ser Arg Ala Thr Gly Ile Pro Asp Arg
    50                  55                  60

Phe Ser Gly Ser Gly Ser Gly Thr Asp Phe Thr Leu Thr Ile Ser Arg
65                  70                  75                  80

Leu Glu Pro Glu Asp Phe Ala Ala Tyr Tyr Cys Gln Gln Tyr Gly Ser
                85                  90                  95

Ser Leu Thr Phe Gly Pro Gly Thr Lys Val Asp Ile Lys Arg Ala Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 148
```

<211> LENGTH: 663
<212> TYPE: DNA
<213> ORGANISM: Artificial sequence
<220> FEATURE:
<223> OTHER INFORMATION: Light chain CR4361
<220> FEATURE:
<221> NAME/KEY: CDS
<222> LOCATION: (1)..(663)

<400> SEQUENCE: 148

| tcg | acg | gat | gtt | gtg | atg | act | cag | tct | cca | gac | tcc | ctg | gct | gtg | tct | 48 |
|---|---|---|---|---|---|---|---|---|---|---|---|---|---|---|---|---|
| Ser | Thr | Asp | Val | Val | Met | Thr | Gln | Ser | Pro | Asp | Ser | Leu | Ala | Val | Ser | |
| 1 | | | | 5 | | | | | 10 | | | | | 15 | | |

| ctg | ggc | gag | agg | gcc | acc | atc | aac | tgc | aag | tcc | agc | cag | aat | att | tta | 96 |
|---|---|---|---|---|---|---|---|---|---|---|---|---|---|---|---|---|
| Leu | Gly | Glu | Arg | Ala | Thr | Ile | Asn | Cys | Lys | Ser | Ser | Gln | Asn | Ile | Leu | |
| | | | 20 | | | | | 25 | | | | | 30 | | | |

| gac | aac | tcc | gac | aat | aag | aac | ttc | tta | gct | tgg | tac | cag | cag | aaa | cca | 144 |
|---|---|---|---|---|---|---|---|---|---|---|---|---|---|---|---|---|
| Asp | Asn | Ser | Asp | Asn | Lys | Asn | Phe | Leu | Ala | Trp | Tyr | Gln | Gln | Lys | Pro | |
| | | 35 | | | | | 40 | | | | | 45 | | | | |

| gga | cag | cct | cct | aaa | ttg | ctc | att | tac | tgg | gca | tct | gcc | cgg | gag | tcc | 192 |
|---|---|---|---|---|---|---|---|---|---|---|---|---|---|---|---|---|
| Gly | Gln | Pro | Pro | Lys | Leu | Leu | Ile | Tyr | Trp | Ala | Ser | Ala | Arg | Glu | Ser | |
| | 50 | | | | | 55 | | | | | 60 | | | | | |

| ggg | gtc | cct | gac | cga | ttc | agt | ggc | agc | ggg | tct | ggg | aca | gat | ttc | act | 240 |
|---|---|---|---|---|---|---|---|---|---|---|---|---|---|---|---|---|
| Gly | Val | Pro | Asp | Arg | Phe | Ser | Gly | Ser | Gly | Ser | Gly | Thr | Asp | Phe | Thr | |
| 65 | | | | | 70 | | | | | 75 | | | | | 80 | |

| ctc | acc | atc | agc | agc | ctg | cag | gct | gaa | gat | gtg | gca | ctt | tat | tac | tgt | 288 |
|---|---|---|---|---|---|---|---|---|---|---|---|---|---|---|---|---|
| Leu | Thr | Ile | Ser | Ser | Leu | Gln | Ala | Glu | Asp | Val | Ala | Leu | Tyr | Tyr | Cys | |
| | | | | 85 | | | | | 90 | | | | | 95 | | |

| cag | caa | tat | tat | aat | act | ccc | atc | acc | ttc | ggt | caa | ggg | aca | cga | ctg | 336 |
|---|---|---|---|---|---|---|---|---|---|---|---|---|---|---|---|---|
| Gln | Gln | Tyr | Tyr | Asn | Thr | Pro | Ile | Thr | Phe | Gly | Gln | Gly | Thr | Arg | Leu | |
| | | | 100 | | | | | 105 | | | | | 110 | | | |

| gag | att | aaa | cgt | gcg | gcc | gca | ccc | agc | gtg | ttc | atc | ttc | ccc | ccc | tcc | 384 |
|---|---|---|---|---|---|---|---|---|---|---|---|---|---|---|---|---|
| Glu | Ile | Lys | Arg | Ala | Ala | Ala | Pro | Ser | Val | Phe | Ile | Phe | Pro | Pro | Ser | |
| | | 115 | | | | | 120 | | | | | 125 | | | | |

| gac | gag | cag | ctg | aag | agc | ggc | acc | gcc | agc | gtg | gtg | tgc | ctg | ctg | aac | 432 |
|---|---|---|---|---|---|---|---|---|---|---|---|---|---|---|---|---|
| Asp | Glu | Gln | Leu | Lys | Ser | Gly | Thr | Ala | Ser | Val | Val | Cys | Leu | Leu | Asn | |
| | 130 | | | | | 135 | | | | | 140 | | | | | |

| aac | ttc | tac | ccc | cgg | gag | gcc | aag | gtg | cag | tgg | aag | gtg | gac | aac | gcc | 480 |
|---|---|---|---|---|---|---|---|---|---|---|---|---|---|---|---|---|
| Asn | Phe | Tyr | Pro | Arg | Glu | Ala | Lys | Val | Gln | Trp | Lys | Val | Asp | Asn | Ala | |
| 145 | | | | | 150 | | | | | 155 | | | | | 160 | |

| ctg | cag | agc | ggc | aac | agc | cag | gag | agc | gtg | acc | gag | cag | gac | agc | aag | 528 |
|---|---|---|---|---|---|---|---|---|---|---|---|---|---|---|---|---|
| Leu | Gln | Ser | Gly | Asn | Ser | Gln | Glu | Ser | Val | Thr | Glu | Gln | Asp | Ser | Lys | |
| | | | | 165 | | | | | 170 | | | | | 175 | | |

| gac | tcc | acc | tac | agc | ctg | agc | agc | acc | ctc | acc | ctg | agc | aag | gcc | gac | 576 |
|---|---|---|---|---|---|---|---|---|---|---|---|---|---|---|---|---|
| Asp | Ser | Thr | Tyr | Ser | Leu | Ser | Ser | Thr | Leu | Thr | Leu | Ser | Lys | Ala | Asp | |
| | | | 180 | | | | | 185 | | | | | 190 | | | |

| tac | gag | aag | cac | aag | gtg | tac | gcc | tgc | gag | gtg | acc | cac | cag | ggc | ctg | 624 |
|---|---|---|---|---|---|---|---|---|---|---|---|---|---|---|---|---|
| Tyr | Glu | Lys | His | Lys | Val | Tyr | Ala | Cys | Glu | Val | Thr | His | Gln | Gly | Leu | |
| | | 195 | | | | | 200 | | | | | 205 | | | | |

| agc | agc | ccc | gtg | acc | aag | agc | ttc | aac | cgg | ggc | gag | tgt | | | | 663 |
|---|---|---|---|---|---|---|---|---|---|---|---|---|---|---|---|---|
| Ser | Ser | Pro | Val | Thr | Lys | Ser | Phe | Asn | Arg | Gly | Glu | Cys | | | | |
| | 210 | | | | | 215 | | | | | 220 | | | | | |

<210> SEQ ID NO 149
<211> LENGTH: 221
<212> TYPE: PRT
<213> ORGANISM: Artificial sequence
<220> FEATURE:
<223> OTHER INFORMATION: Light chain CR4361

<400> SEQUENCE: 149

| Ser | Thr | Asp | Val | Val | Met | Thr | Gln | Ser | Pro | Asp | Ser | Leu | Ala | Val | Ser |
|---|---|---|---|---|---|---|---|---|---|---|---|---|---|---|---|
| 1 | | | | 5 | | | | | 10 | | | | | 15 | |

```
Leu Gly Glu Arg Ala Thr Ile Asn Cys Lys Ser Ser Gln Asn Ile Leu
            20                  25                  30

Asp Asn Ser Asp Asn Lys Asn Phe Leu Ala Trp Tyr Gln Gln Lys Pro
        35                  40                  45

Gly Gln Pro Pro Lys Leu Leu Ile Tyr Trp Ala Ser Ala Arg Glu Ser
    50                  55                  60

Gly Val Pro Asp Arg Phe Ser Gly Ser Gly Ser Gly Thr Asp Phe Thr
65                  70                  75                  80

Leu Thr Ile Ser Ser Leu Gln Ala Glu Asp Val Ala Leu Tyr Tyr Cys
                85                  90                  95

Gln Gln Tyr Tyr Asn Thr Pro Ile Thr Phe Gly Gln Gly Thr Arg Leu
            100                 105                 110

Glu Ile Lys Arg Ala Ala Ala Pro Ser Val Phe Ile Phe Pro Pro Ser
        115                 120                 125

Asp Glu Gln Leu Lys Ser Gly Thr Ala Ser Val Val Cys Leu Leu Asn
130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Val Tyr Ala Cys Glu Val Thr His Gln Gly Leu
        195                 200                 205

Ser Ser Pro Val Thr Lys Ser Phe Asn Arg Gly Glu Cys
    210                 215                 220

<210> SEQ ID NO 150
<211> LENGTH: 651
<212> TYPE: DNA
<213> ORGANISM: Artificial sequence
<220> FEATURE:
<223> OTHER INFORMATION: Light chain CR4374
<220> FEATURE:
<221> NAME/KEY: CDS
<222> LOCATION: (1)..(651)

<400> SEQUENCE: 150 cag tcc gtg ctg acc cag cct ccc tca gtg tct ggg gcc cca ggg cag      48
Gln Ser Val Leu Thr Gln Pro Pro Ser Val Ser Gly Ala Pro Gly Gln
1               5                   10                  15 agg gtc acc atc tcc tgc act ggg agc agc tcc aac atc ggg gca ggt      96
Arg Val Thr Ile Ser Cys Thr Gly Ser Ser Ser Asn Ile Gly Ala Gly
            20                  25                  30 tat gat gta cac tgg tac cag cag ctt cca gga aca gcc ccc aaa ctc     144
Tyr Asp Val His Trp Tyr Gln Gln Leu Pro Gly Thr Ala Pro Lys Leu
        35                  40                  45 ctc atc tat ggt aac agc aat cgg ccc tca ggg gtc cct gac cga ttc     192
Leu Ile Tyr Gly Asn Ser Asn Arg Pro Ser Gly Val Pro Asp Arg Phe
    50                  55                  60 tct ggc tcc aag tct ggc acc tca gcc tcc ctg gcc atc act ggg ctc     240
Ser Gly Ser Lys Ser Gly Thr Ser Ala Ser Leu Ala Ile Thr Gly Leu
65                  70                  75                  80 cag gct gag gat gag gct gat tat tac tgc cag tcc tat gac agc agc     288
Gln Ala Glu Asp Glu Ala Asp Tyr Tyr Cys Gln Ser Tyr Asp Ser Ser
                85                  90                  95 ttg agt ggt tcg gtg ttc ggc gga ggc acc aag ctt acc gtg ctg ggc     336
Leu Ser Gly Ser Val Phe Gly Gly Gly Thr Lys Leu Thr Val Leu Gly
```

```
            100                 105                 110
cag ccc aag gcc gct ccc agc gtg acc ctg ttc ccc ccc tcc tcc gag      384
Gln Pro Lys Ala Ala Pro Ser Val Thr Leu Phe Pro Pro Ser Ser Glu
        115                 120                 125 gag ctg cag gcc aac aag gcc acc ctg gtg tgc ctc atc agc gac ttc      432
Glu Leu Gln Ala Asn Lys Ala Thr Leu Val Cys Leu Ile Ser Asp Phe
    130                 135                 140 tac cct ggc gcc gtg acc gtg gcc tgg aag gcc gac agc agc ccc gtg      480
Tyr Pro Gly Ala Val Thr Val Ala Trp Lys Ala Asp Ser Ser Pro Val
145                 150                 155                 160 aag gcc ggc gtg gag acc acc acc ccc agc aag cag agc aac aac aag      528
Lys Ala Gly Val Glu Thr Thr Thr Pro Ser Lys Gln Ser Asn Asn Lys
                165                 170                 175 tac gcc gcc agc agc tac ctg agc ctc acc ccc gag cag tgg aag agc      576
Tyr Ala Ala Ser Ser Tyr Leu Ser Leu Thr Pro Glu Gln Trp Lys Ser
            180                 185                 190 cac cgg agc tac agc tgc cag gtg acc cac gag ggc agc acc gtg gag      624
His Arg Ser Tyr Ser Cys Gln Val Thr His Glu Gly Ser Thr Val Glu
        195                 200                 205 aag acc gtg gcc ccc acc gag tgc agc                                   651
Lys Thr Val Ala Pro Thr Glu Cys Ser
    210                 215

<210> SEQ ID NO 151
<211> LENGTH: 217
<212> TYPE: PRT
<213> ORGANISM: Artificial sequence
<220> FEATURE:
<223> OTHER INFORMATION: Light chain CR4374

<400> SEQUENCE: 151

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205
```

```
Lys Thr Val Ala Pro Thr Glu Cys Ser
    210                 215
```

<210> SEQ ID NO 152
<211> LENGTH: 23
<212> TYPE: DNA
<213> ORGANISM: Artificial sequence
<220> FEATURE:
<223> OTHER INFORMATION: HuVlambda1A

<400> SEQUENCE: 152
cagtctgtgc tgactcagcc acc                                              23

<210> SEQ ID NO 153
<211> LENGTH: 23
<212> TYPE: DNA
<213> ORGANISM: Artificial sequence
<220> FEATURE:
<223> OTHER INFORMATION: HuVlambda1B

<400> SEQUENCE: 153
cagtctgtgy tgacgcagcc gcc                                              23

<210> SEQ ID NO 154
<211> LENGTH: 23
<212> TYPE: DNA
<213> ORGANISM: Artificial sequence
<220> FEATURE:
<223> OTHER INFORMATION: HuVlambda1C

<400> SEQUENCE: 154
cagtctgtcg tgacgcagcc gcc                                              23

<210> SEQ ID NO 155
<211> LENGTH: 21
<212> TYPE: DNA
<213> ORGANISM: Artificial sequence
<220> FEATURE:
<223> OTHER INFORMATION: HuVlambda2

<400> SEQUENCE: 155
cartctgccc tgactcagcc t                                                21

<210> SEQ ID NO 156
<211> LENGTH: 23
<212> TYPE: DNA
<213> ORGANISM: Artificial sequence
<220> FEATURE:
<223> OTHER INFORMATION: HuVlambda3A

<400> SEQUENCE: 156
tcctatgwgc tgactcagcc acc                                              23

<210> SEQ ID NO 157
<211> LENGTH: 23
<212> TYPE: DNA
<213> ORGANISM: Artificial sequence
<220> FEATURE:
<223> OTHER INFORMATION: HuVlambda3B

<400> SEQUENCE: 157
tcttctgagc tgactcagga ccc                                              23

<210> SEQ ID NO 158
<211> LENGTH: 23
<212> TYPE: DNA

<210> SEQ ID NO 159
<211> LENGTH: 23
<212> TYPE: DNA
<213> ORGANISM: Artificial sequence
<220> FEATURE:
<223> OTHER INFORMATION: HuVlambda4

<400> SEQUENCE: 158
cacgttatac tgactcaacc gcc                                           23

<210> SEQ ID NO 159
<211> LENGTH: 23
<212> TYPE: DNA
<213> ORGANISM: Artificial sequence
<220> FEATURE:
<223> OTHER INFORMATION: HuVlambda5

<400> SEQUENCE: 159
caggctgtgc tgactcagcc gtc                                           23

<210> SEQ ID NO 160
<211> LENGTH: 23
<212> TYPE: DNA
<213> ORGANISM: Artificial sequence
<220> FEATURE:
<223> OTHER INFORMATION: HuVlambda6

<400> SEQUENCE: 160
aattttatgc tgactcagcc cca                                           23

<210> SEQ ID NO 161
<211> LENGTH: 23
<212> TYPE: DNA
<213> ORGANISM: Artificial sequence
<220> FEATURE:
<223> OTHER INFORMATION: HuVlambda7/8

<400> SEQUENCE: 161
cagrctgtgg tgacycagga gcc                                           23

<210> SEQ ID NO 162
<211> LENGTH: 23
<212> TYPE: DNA
<213> ORGANISM: Artificial sequence
<220> FEATURE:
<223> OTHER INFORMATION: HuVlambda9

<400> SEQUENCE: 162
cwgcctgtgc tgactcagcc mcc                                           23

<210> SEQ ID NO 163
<211> LENGTH: 23
<212> TYPE: DNA
<213> ORGANISM: Artificial sequence
<220> FEATURE:
<223> OTHER INFORMATION: HuVkappa1B

<400> SEQUENCE: 163
gacatccagw tgacccagtc tcc                                           23

<210> SEQ ID NO 164
<211> LENGTH: 23
<212> TYPE: DNA
<213> ORGANISM: Artificial sequence
<220> FEATURE:
<223> OTHER INFORMATION: HuVkappa2

<400> SEQUENCE: 164
gatgttgtga tgactcagtc tcc                                           23

<210> SEQ ID NO 165
<211> LENGTH: 23
<212> TYPE: DNA
<213> ORGANISM: Artificial sequence
<220> FEATURE:
<223> OTHER INFORMATION: HuVkappa3

<400> SEQUENCE: 165
gaaattgtgw tgacrcagtc tcc                                              23

<210> SEQ ID NO 166
<211> LENGTH: 23
<212> TYPE: DNA
<213> ORGANISM: Artificial sequence
<220> FEATURE:
<223> OTHER INFORMATION: HuVkappa4

<400> SEQUENCE: 166
gatattgtga tgacccacac tcc                                              23

<210> SEQ ID NO 167
<211> LENGTH: 23
<212> TYPE: DNA
<213> ORGANISM: Artificial sequence
<220> FEATURE:
<223> OTHER INFORMATION: HuVkappa5

<400> SEQUENCE: 167
gaaacgacac tcacgcagtc tcc                                              23

<210> SEQ ID NO 168
<211> LENGTH: 23
<212> TYPE: DNA
<213> ORGANISM: Artificial sequence
<220> FEATURE:
<223> OTHER INFORMATION: HuVkappa6

<400> SEQUENCE: 168
gaaattgtgc tgactcagtc tcc                                              23

<210> SEQ ID NO 169
<211> LENGTH: 41
<212> TYPE: DNA
<213> ORGANISM: Artificial sequence
<220> FEATURE:
<223> OTHER INFORMATION: HuVkappa1B-SalI

<400> SEQUENCE: 169
tgagcacaca ggtcgacgga catccagwtg acccagtctc c                          41

<210> SEQ ID NO 170
<211> LENGTH: 41
<212> TYPE: DNA
<213> ORGANISM: Artificial sequence
<220> FEATURE:
<223> OTHER INFORMATION: HuVkappa2-SalI

<400> SEQUENCE: 170
tgagcacaca ggtcgacgga tgttgtgatg actcagtctc c                          41

<210> SEQ ID NO 171
<211> LENGTH: 41
<212> TYPE: DNA
<213> ORGANISM: Artificial sequence
<220> FEATURE:

<223> OTHER INFORMATION: HuVkappa3B-SalI

<400> SEQUENCE: 171
tgagcacaca ggtcgacgga aattgtgwtg acrcagtctc c                    41

<210> SEQ ID NO 172
<211> LENGTH: 41
<212> TYPE: DNA
<213> ORGANISM: Artificial sequence
<220> FEATURE:
<223> OTHER INFORMATION: HuVkappa4B-SalI

<400> SEQUENCE: 172
tgagcacaca ggtcgacgga tattgtgatg acccacactc c                    41

<210> SEQ ID NO 173
<211> LENGTH: 41
<212> TYPE: DNA
<213> ORGANISM: Artificial sequence
<220> FEATURE:
<223> OTHER INFORMATION: HuVkappa5-SalI

<400> SEQUENCE: 173
tgagcacaca ggtcgacgga aacgacactc acgcagtctc c                    41

<210> SEQ ID NO 174
<211> LENGTH: 41
<212> TYPE: DNA
<213> ORGANISM: Artificial sequence
<220> FEATURE:
<223> OTHER INFORMATION: HuVkappa6-SalI

<400> SEQUENCE: 174
tgagcacaca ggtcgacgga aattgtgctg actcagtctc c                    41

<210> SEQ ID NO 175
<211> LENGTH: 48
<212> TYPE: DNA
<213> ORGANISM: Artificial sequence
<220> FEATURE:
<223> OTHER INFORMATION: HuJkappa1-NotI

<400> SEQUENCE: 175
gagtcattct cgacttgcgg ccgcacgttt gatttccacc ttggtccc             48

<210> SEQ ID NO 176
<211> LENGTH: 48
<212> TYPE: DNA
<213> ORGANISM: Artificial sequence
<220> FEATURE:
<223> OTHER INFORMATION: HuJkappa2-NotI

<400> SEQUENCE: 176
gagtcattct cgacttgcgg ccgcacgttt gatctccagc ttggtccc             48

<210> SEQ ID NO 177
<211> LENGTH: 48
<212> TYPE: DNA
<213> ORGANISM: Artificial sequence
<220> FEATURE:
<223> OTHER INFORMATION: HuJkappa3-NotI

<400> SEQUENCE: 177
gagtcattct cgacttgcgg ccgcacgttt gatatccact ttggtccc             48

<210> SEQ ID NO 178
<211> LENGTH: 48
<212> TYPE: DNA
<213> ORGANISM: Artificial sequence
<220> FEATURE:
<223> OTHER INFORMATION: HuJkappa4-NotI

<400> SEQUENCE: 178
gagtcattct cgacttgcgg ccgcacgttt gatctccacc ttggtccc                48

<210> SEQ ID NO 179
<211> LENGTH: 48
<212> TYPE: DNA
<213> ORGANISM: Artificial sequence
<220> FEATURE:
<223> OTHER INFORMATION: HuJkappa5-NotI

<400> SEQUENCE: 179
gagtcattct cgacttgcgg ccgcacgttt aatctccagt cgtgtccc                48

<210> SEQ ID NO 180
<211> LENGTH: 41
<212> TYPE: DNA
<213> ORGANISM: Artificial sequence
<220> FEATURE:
<223> OTHER INFORMATION: HuVlambda1A-SalI

<400> SEQUENCE: 180
tgagcacaca ggtcgacgca gtctgtgctg actcagccac c                       41

<210> SEQ ID NO 181
<211> LENGTH: 41
<212> TYPE: DNA
<213> ORGANISM: Artificial sequence
<220> FEATURE:
<223> OTHER INFORMATION: HuVlambda1B-SalI

<400> SEQUENCE: 181
tgagcacaca ggtcgacgca gtctgtgytg acgcagccgc c                       41

<210> SEQ ID NO 182
<211> LENGTH: 41
<212> TYPE: DNA
<213> ORGANISM: Artificial sequence
<220> FEATURE:
<223> OTHER INFORMATION: HuVlambda1C-SalI

<400> SEQUENCE: 182
tgagcacaca ggtcgacgca gtctgtcgtg acgcagccgc c                       41

<210> SEQ ID NO 183
<211> LENGTH: 39
<212> TYPE: DNA
<213> ORGANISM: Artificial sequence
<220> FEATURE:
<223> OTHER INFORMATION: HuVlambda2-SalI

<400> SEQUENCE: 183
tgagcacaca ggtcgacgca rtctgccctg actcagcct                          39

<210> SEQ ID NO 184
<211> LENGTH: 41
<212> TYPE: DNA
<213> ORGANISM: Artificial sequence
<220> FEATURE:
<223> OTHER INFORMATION: HuVlambda3A-SalI

```
<400> SEQUENCE: 184
tgagcacaca ggtcgacgtc ctatgwgctg actcagccac c        41

<210> SEQ ID NO 185
<211> LENGTH: 41
<212> TYPE: DNA
<213> ORGANISM: Artificial sequence
<220> FEATURE:
<223> OTHER INFORMATION: HuVlambda3B-SalI

<400> SEQUENCE: 185
tgagcacaca ggtcgacgtc ttctgagctg actcaggacc c        41

<210> SEQ ID NO 186
<211> LENGTH: 41
<212> TYPE: DNA
<213> ORGANISM: Artificial sequence
<220> FEATURE:
<223> OTHER INFORMATION: HuVlambda4-SalI

<400> SEQUENCE: 186
tgagcacaca ggtcgacgca cgttatactg actcaaccgc c        41

<210> SEQ ID NO 187
<211> LENGTH: 41
<212> TYPE: DNA
<213> ORGANISM: Artificial sequence
<220> FEATURE:
<223> OTHER INFORMATION: HuVlambda5-SalI

<400> SEQUENCE: 187
tgagcacaca ggtcgacgca ggctgtgctg actcagccgt c        41

<210> SEQ ID NO 188
<211> LENGTH: 41
<212> TYPE: DNA
<213> ORGANISM: Artificial sequence
<220> FEATURE:
<223> OTHER INFORMATION: HuVlambda6-SalI

<400> SEQUENCE: 188
tgagcacaca ggtcgacgaa ttttatgctg actcagcccc a        41

<210> SEQ ID NO 189
<211> LENGTH: 41
<212> TYPE: DNA
<213> ORGANISM: Artificial sequence
<220> FEATURE:
<223> OTHER INFORMATION: HuVlambda7/8-SalI

<400> SEQUENCE: 189
tgagcacaca ggtcgacgca grctgtggtg acycaggagc c        41

<210> SEQ ID NO 190
<211> LENGTH: 41
<212> TYPE: DNA
<213> ORGANISM: Artificial sequence
<220> FEATURE:
<223> OTHER INFORMATION: HuVlambda9-SalI

<400> SEQUENCE: 190
tgagcacaca ggtcgacgcw gcctgtgctg actcagccmc c        41

<210> SEQ ID NO 191
<211> LENGTH: 48
```

<210> SEQ ID NO 191
<211> LENGTH: 48
<212> TYPE: DNA
<213> ORGANISM: Artificial sequence
<220> FEATURE:
<223> OTHER INFORMATION: HuJlambda1-NotI

<400> SEQUENCE: 191
gagtcattct cgacttgcgg ccgcacctag gacggtgacc ttggtccc                48

<210> SEQ ID NO 192
<211> LENGTH: 48
<212> TYPE: DNA
<213> ORGANISM: Artificial sequence
<220> FEATURE:
<223> OTHER INFORMATION: HuJlambda2/3-NotI

<400> SEQUENCE: 192
gagtcattct cgacttgcgg ccgcacctag gacggtcagc ttggtccc                48

<210> SEQ ID NO 193
<211> LENGTH: 48
<212> TYPE: DNA
<213> ORGANISM: Artificial sequence
<220> FEATURE:
<223> OTHER INFORMATION: HuJlambda4/5-NotI

<400> SEQUENCE: 193
gagtcattct cgacttgcgg ccgcacytaa aacggtgagc tgggtccc                48

<210> SEQ ID NO 194
<211> LENGTH: 23
<212> TYPE: DNA
<213> ORGANISM: Artificial sequence
<220> FEATURE:
<223> OTHER INFORMATION: HuVH1B/7A

<400> SEQUENCE: 194
cagrtgcagc tggtgcartc tgg                                           23

<210> SEQ ID NO 195
<211> LENGTH: 23
<212> TYPE: DNA
<213> ORGANISM: Artificial sequence
<220> FEATURE:
<223> OTHER INFORMATION: HuVH1C

<400> SEQUENCE: 195
saggtccagc tggtrcagtc tgg                                           23

<210> SEQ ID NO 196
<211> LENGTH: 23
<212> TYPE: DNA
<213> ORGANISM: Artificial sequence
<220> FEATURE:
<223> OTHER INFORMATION: HuVH2B

<400> SEQUENCE: 196
saggtgcagc tggtggagtc tgg                                           23

<210> SEQ ID NO 197
<211> LENGTH: 23
<212> TYPE: DNA
<213> ORGANISM: Artificial sequence
<220> FEATURE:
<223> OTHER INFORMATION: HuVH3B

<400> SEQUENCE: 197

```
saggtgcagc tggtggagtc tgg                                              23
```

<210> SEQ ID NO 198
<211> LENGTH: 23
<212> TYPE: DNA
<213> ORGANISM: Artificial sequence
<220> FEATURE:
<223> OTHER INFORMATION: HuVH3C

<400> SEQUENCE: 198

```
gaggtgcagc tggtggagwc ygg                                              23
```

<210> SEQ ID NO 199
<211> LENGTH: 23
<212> TYPE: DNA
<213> ORGANISM: Artificial sequence
<220> FEATURE:
<223> OTHER INFORMATION: HuVH4B

<400> SEQUENCE: 199

```
caggtgcagc tacagcagtg ggg                                              23
```

<210> SEQ ID NO 200
<211> LENGTH: 23
<212> TYPE: DNA
<213> ORGANISM: Artificial sequence
<220> FEATURE:
<223> OTHER INFORMATION: HuVH4C

<400> SEQUENCE: 200

```
cagstgcagc tgcaggagtc sgg                                              23
```

<210> SEQ ID NO 201
<211> LENGTH: 23
<212> TYPE: DNA
<213> ORGANISM: Artificial sequence
<220> FEATURE:
<223> OTHER INFORMATION: HuVH5B

<400> SEQUENCE: 201

```
gargtgcagc tggtgcagtc tgg                                              23
```

<210> SEQ ID NO 202
<211> LENGTH: 23
<212> TYPE: DNA
<213> ORGANISM: Artificial sequence
<220> FEATURE:
<223> OTHER INFORMATION: HuVH6A

<400> SEQUENCE: 202

```
caggtacagc tgcagcagtc agg                                              23
```

<210> SEQ ID NO 203
<211> LENGTH: 56
<212> TYPE: DNA
<213> ORGANISM: Artificial sequence
<220> FEATURE:
<223> OTHER INFORMATION: HuVH1B/7A-SfiI

<400> SEQUENCE: 203

```
gtcctcgcaa ctgcggccca gccggccatg gcccagrtgc agctggtgca rtctgg         56
```

<210> SEQ ID NO 204
<211> LENGTH: 56
<212> TYPE: DNA
<213> ORGANISM: Artificial sequence

```
<220> FEATURE:
<223> OTHER INFORMATION: HuVH1C-SfiI

<400> SEQUENCE: 204
gtcctcgcaa ctgcggccca gccggccatg gccsaggtcc agctggtrca gtctgg      56

<210> SEQ ID NO 205
<211> LENGTH: 56
<212> TYPE: DNA
<213> ORGANISM: Artificial sequence
<220> FEATURE:
<223> OTHER INFORMATION: HuVH2B-SfiI

<400> SEQUENCE: 205
gtcctcgcaa ctgcggccca gccggccatg gcccagrtca ccttgaagga gtctgg      56

<210> SEQ ID NO 206
<211> LENGTH: 56
<212> TYPE: DNA
<213> ORGANISM: Artificial sequence
<220> FEATURE:
<223> OTHER INFORMATION: HuVH3B-SfiI

<400> SEQUENCE: 206
gtcctcgcaa ctgcggccca gccggccatg gccsaggtgc agctggtgga gtctgg      56

<210> SEQ ID NO 207
<211> LENGTH: 56
<212> TYPE: DNA
<213> ORGANISM: Artificial sequence
<220> FEATURE:
<223> OTHER INFORMATION: HuVH3C-SfiI

<400> SEQUENCE: 207
gtcctcgcaa ctgcggccca gccggccatg gccgaggtgc agctggtgga gwcygg      56

<210> SEQ ID NO 208
<211> LENGTH: 56
<212> TYPE: DNA
<213> ORGANISM: Artificial sequence
<220> FEATURE:
<223> OTHER INFORMATION: HuVH4B-SfiI

<400> SEQUENCE: 208
gtcctcgcaa ctgcggccca gccggccatg gcccaggtgc agctacagca gtgggg      56

<210> SEQ ID NO 209
<211> LENGTH: 56
<212> TYPE: DNA
<213> ORGANISM: Artificial sequence
<220> FEATURE:
<223> OTHER INFORMATION: HuVH4C-SfiI

<400> SEQUENCE: 209
gtcctcgcaa ctgcggccca gccggccatg gcccagstgc agctgcagga gtcsgg      56

<210> SEQ ID NO 210
<211> LENGTH: 56
<212> TYPE: DNA
<213> ORGANISM: Artificial sequence
<220> FEATURE:
<223> OTHER INFORMATION: HuVH5B-SfiI

<400> SEQUENCE: 210
gtcctcgcaa ctgcggccca gccggccatg gccgargtgc agctggtgca gtctgg      56
```

```
<210> SEQ ID NO 211
<211> LENGTH: 56
<212> TYPE: DNA
<213> ORGANISM: Artificial sequence
<220> FEATURE:
<223> OTHER INFORMATION: HuVH6A-SfiI

<400> SEQUENCE: 211
gtcctcgcaa ctgcggccca gccggccatg gcccaggtac agctgcagca gtcagg        56

<210> SEQ ID NO 212
<211> LENGTH: 36
<212> TYPE: DNA
<213> ORGANISM: Artificial sequence
<220> FEATURE:
<223> OTHER INFORMATION: HuJH1/2-XhoI

<400> SEQUENCE: 212
gagtcattct cgactcgaga cggtgaccag ggtgcc        36

<210> SEQ ID NO 213
<211> LENGTH: 36
<212> TYPE: DNA
<213> ORGANISM: Artificial sequence
<220> FEATURE:
<223> OTHER INFORMATION: HuJH3-XhoI

<400> SEQUENCE: 213
gagtcattct cgactcgaga cggtgaccat tgtccc        36

<210> SEQ ID NO 214
<211> LENGTH: 36
<212> TYPE: DNA
<213> ORGANISM: Artificial sequence
<220> FEATURE:
<223> OTHER INFORMATION: HuJH4/5-XhoI

<400> SEQUENCE: 214
gagtcattct cgactcgaga cggtgaccag ggttcc        36

<210> SEQ ID NO 215
<211> LENGTH: 36
<212> TYPE: DNA
<213> ORGANISM: Artificial sequence
<220> FEATURE:
<223> OTHER INFORMATION: HuJH6-XhoI

<400> SEQUENCE: 215
gagtcattct cgactcgaga cggtgaccgt ggtccc        36

<210> SEQ ID NO 216
<211> LENGTH: 5855
<212> TYPE: DNA
<213> ORGANISM: Artificial sequence
<220> FEATURE:
<223> OTHER INFORMATION: Vector pCR-IgM

<400> SEQUENCE: 216
gttctttcct gcgttatccc ctgattctgt ggataaccgt attaccgcct ttgagtgagc        60
tgataccgct cgccgcagcc gaacgaccga gcgcagcgag tcagtgagcg aggaagcgga       120
agagcgccca atacgcaaac cgcctctccc cgcgcgttgg ccgattcatt aatgcagctg       180
gcacgacagg tttcccgact ggaaagcggg cagtgagcgc aacgcaatta atgtgagtta       240
gctcactcat taggcacccc aggctttaca ctttatgctt ccggctcgta tgttgtgtgg       300
```

-continued

```
aattgtgagc ggataacaat ttcacacagg aaacagctat gaccatgatt acgccaagct    360
cagaattaac cctcactaaa gggactagtc ctgcaggttt aaacgaattc gcccttcagg    420
gagtgctagc gccccaaccc ttttccccct cgtctcctgt gagaattccc cgtcggatac    480
gagcagcgtg gccgttggct gcctcgcaca ggacttcctt cccgactcca tcactttctc    540
ctggaaatac aagaacaact ctgacatcag cagcacccgg ggcttcccat cagtcctgag    600
agggggcaag tacgcagcca cctcacaggt gctgctgcct tccaaggacg tcatgcaggg    660
cacagacgaa cacgtggtgt gcaaagtcca gcacccccaac ggcaacaaag aaaagaacgt    720
gcctcttcca ggtgagggcc gggcccagcc accgggacag agagggagcc gaaggggcg    780 ggagtggcgg gcaccgggct gacacgtgtc cctcactgca gtgattgctg agctgcctcc    840
caaagtgagc gtcttcgtcc cacccgcga cggcttcttc ggcaaccccc gcaagtccaa    900
gctcatctgc caggccacgg gtttcagtcc ccggcagatt caggtgtcct ggctgcgcga    960
ggggaagcag gtgggtctg gcgtcaccac ggaccaggtg caggctgagg ccaaagagtc    1020
tgggcccacg acctacaagg tgaccagcac actgaccatc aaagagagcg actggctcag    1080
ccagagcatg ttcacctgcc gcgtggatca caggggcctg accttccagc agaatgcgtc    1140
ctccatgtgt gtccccggtg agtgacctgt ccccaggggc agcacccacc gacacacagg    1200
ggtccactcg ggtctggcat cgccacccc ggatgcagcc atctactccc tgagccttgg    1260
cttcccagag cggccaaggg caggggctcg gcgcggcagga cccctgggct cggcagaggc    1320
agttgctact ctttgggtgg gaaccatgcc tccgcccaca tccacacctg ccccacctct    1380
gactcccttc tcttgactcc agatcaagac acagccatcc gggtcttcgc catcccccca    1440
tcctttgcca gcatcttcct caccaagtcc accaagttga cctgcctggt cacagacctg    1500
accacctatg acagcgtgac catctcctgg acccgccaga atggcgaagc tgtgaaaacc    1560
cacaccaaca tctccgagag ccaccccaat gccactttca cgccgtggg tgaggccagc    1620 atctgcgagg atgactggaa ttccggggag aggttcacgt gcaccgtgac ccacacagac    1680 ctgcccctcgc cactgaagca gaccatctcc cggcccaagg gtaggcccca ctcttgcccc    1740
tcttcctgca ctccctggga cctcccttgg cctctggggc atggtggaaa gcacccctca    1800
ctcccccgtt gtctgggcaa ctggggaaaa ggggactcaa ccccagccca caggctggtc    1860
cccccactgc cccgccctca ccaccatctc tgttcacagg ggtggccctg cacaggcccg    1920
atgtctactt gctgccacca gcccgggagc agctgaacct gcgggagtcg gccaccatca    1980
cgtgcctggt gacgggcttc tctcccgcgg acgtcttcgt gcagtggatg cagaggggc    2040 agcccttgtc cccggagaag tatgtgacca gcgcccaat gcctgagccc caggcccag    2100 gccggtactt cgcccacagc atcctgaccg tgtccgaaga ggaatggaac acgggggaga    2160
cctacacctg cgtggtggcc catgaggccc tgcccaacag ggtcaccgag aggaccgtgg    2220
acaagtccac cggtaaaccc accctgtaca acgtgtccct ggtcatgtcc gacacagctg    2280
gcacctgcta ctgatgatct agatctagaa cacaaaggc gaattcgcgg ccgctaaatt    2340
caattcgccc tatagtgagt cgtattacaa ttcactggcc gtcgttttac aacgtcgtga    2400
ctgggaaaac cctggcgtta cccaacttaa tcgccttgca gcacatcccc ctttcgccag    2460
ctggcgtaat agcgaagagg cccgcaccga tcgcccttcc caacagttgc gcagcctata    2520
cgtacggcag tttaaggttt acacctataa aagagagagc cgttatcgtc tgtttgtgga    2580
tgtacagagt gatattattg acacgccggg gcgacggatg gtgatccccc tggccagtgc    2640
```

```
acgtctgctg tcagataaag tctcccgtga actttacccg gtggtgcata tcggggatga    2700
aagctggcgc atgatgacca ccgatatggc cagtgtgccg gtctccgtta tcggggaaga    2760
agtggctgat ctcagccacc gcgaaaatga catcaaaaac gccattaacc tgatgttctg    2820
gggaatataa atgtcaggca tgagattatc aaaaaggatc ttcacctaga tccttttcac    2880
gtagaaagcc agtccgcaga aacggtgctg accccggatg aatgtcagct actgggctat    2940
ctggacaagg gaaaacgcaa gcgcaaagag aaagcaggta gcttgcagtg ggcttacatg    3000
gcgatagcta gactgggcgg ttttatggac agcaagcgaa ccggaattgc cagctggggc    3060
gccctctggt aaggttggga agccctgcaa agtaaactgg atggctttct cgccgccaag    3120
gatctgatgg cgcaggggat caagctctga tcaagagaca ggatgaggat cgtttcgcat    3180
gattgaacaa gatggattgc acgcaggttc tccggccgct tgggtggaga ggctattcgg    3240
ctatgactgg gcacaacaga caatcggctg ctctgatgcc gccgtgttcc ggctgtcagc    3300 gcagggcgc ccggttcttt ttgtcaagac cgacctgtcc ggtgccctga atgaactgca    3360
agacgaggca gcgcggctat cgtggctggc cacgacgggc gttccttgcg cagctgtgct    3420
cgacgttgtc actgaagcgg gaagggactg gctgctattg ggcgaagtgc cggggcagga    3480
tctcctgtca tctcaccttg ctcctgccga gaaagtatcc atcatggctg atgcaatgcg    3540
gcggctgcat acgcttgatc cggctacctg cccattcgac caccaagcga acatcgcat    3600 cgagcgagca cgtactcgga tggaagccgg tcttgtcgat caggatgatc tggacgaaga    3660
gcatcagggg ctcgcgccag ccgaactgtt cgccaggctc aaggcgagca tgcccgacgg    3720
cgaggatctc gtcgtgaccc atggcgatgc ctgcttgccg aatatcatgg tggaaaatgg    3780
ccgcttttct ggattcatcg actgtggccg gctgggtgtg gcggaccgct atcaggacat    3840
agcgttggct acccgtgata ttgctgaaga gcttggcggc gaatgggctg accgcttcct    3900
cgtgctttac ggtatcgccg ctcccgattc gcagcgcatc gccttctatc gccttcttga    3960
cgagttcttc tgaattatta cgcttacaa tttcctgatg cggtattttc tccttacgca    4020
tctgtgcggt atttcacacc gcatacaggt ggcactttc ggggaaatgt gcgcggaacc    4080
cctatttgtt tattttctta aatacattca aatatgtatc cgctcatgag acaataaccc    4140
tgataaatgc ttcaataata ttgaaaaagg aagagtatga gtattcaaca tttccgtgtc    4200
gcccttattc ccttttttgc ggcattttgc cttcctgttt ttgctcaccc agaaacgctg    4260
gtgaaagtaa aagatgctga agatcagttg ggtgcacgag tgggttacat cgaactggat    4320
ctcaacagcg gtaagatcct tgagagtttt cgccccgaag aacgttttcc aatgatgagc    4380
acttttaaag ttctgctatg tggcgcggta ttatcccgta ttgacgccgg gcaagagcaa    4440
ctcggtcgcc gcatacacta ttctcagaat gacttggttg agtactcacc agtcacagaa    4500
aagcatctta cggatggcat gacagtaaga gaattatgca gtgctgccat aaccatgagt    4560
gataacactg cggccaactt acttctgaca acgatcggag gaccgaagga gctaaccgct    4620
tttttgcaca acatggggga tcatgtaact cgccttgatc gttgggaacc ggagctgaat    4680
gaagccatac caaacgacga gcgtgacacc acgatgcctg tagcaatggc aacaacgttg    4740
cgcaaactat taactggcga actacttact ctagcttccc ggcaacaatt aatagactgg    4800
atggaggcga taaagttgc aggaccactt ctgcgctcgg cccttccggc tggctggttt    4860
attgctgata atctggagc cggtgagcgt gggtctcgcg gtatcattgc agcactgggg    4920
ccagatggta agccctcccg tatcgtagtt atctacacga cggggagtca ggcaactatg    4980
gatgaacgaa atagacagat cgctgagata ggtgcctcac tgattaagca ttggtaactg    5040
```

```
tcagaccaag tttactcata tatactttag attgatttaa aacttcattt ttaatttaaa      5100
aggatctagg tgaagatcct ttttgataat ctcatgacca aaatcccctta acgtgagttt     5160 tcgttccact gagcgtcaga ccccgtagaa aagatcaaag gatcttcttg agatcctttt     5220
tttctgcgcg taatctgctg cttgcaaaca aaaaaccac cgctaccagc ggtggtttgt      5280
ttgccggatc aagagctacc aactcttttt ccgaaggtaa ctggcttcag cagagcgcag     5340
ataccaaata ctgtccttct agtgtagccg tagttaggcc accacttcaa gaactctgta    5400
gcaccgccta catacctcgc tctgctaatc ctgttaccag tggctgctgc cagtggcgat    5460
aagtcgtgtc ttaccgggtt ggactcaaga cgatagttac cggataaggc gcagcggtcg    5520
ggctgaacgg ggggttcgtg cacacagccc agcttggagc gaacgaccta caccgaactg    5580
agatacctac agcgtgagct atgagaaagc gccacgcttc ccgaagggag aaaggcggac    5640
aggtatccgg taagcggcag ggtcggaaca ggagagcgca cgagggagct tccaggggga    5700
aacgcctggt atctttatag tcctgtcggg tttcgccacc tctgacttga gcgtcgattt    5760
ttgtgatgct cgtcaggggg gcggagccta tggaaaaacg ccagcaacgc ggccttttta    5820
cggttcctgg cttttgctg gccttttgct cacat                                5855

<210> SEQ ID NO 217
<211> LENGTH: 2257
<212> TYPE: DNA
<213> ORGANISM: Artificial sequence
<220> FEATURE:
<223> OTHER INFORMATION: Heavy chain CRM4374
<220> FEATURE:
<221> NAME/KEY: Intron
<222> LOCATION: (697)..(786)
<220> FEATURE:
<221> NAME/KEY: Intron
<222> LOCATION: (1589)..(1867)
<220> FEATURE:
<221> NAME/KEY: Intron
<222> LOCATION: (1123)..(1366)

<400> SEQUENCE: 217
cagatcacct tgaaggagtc tggtcctacg ctggtgaaac ccacacagac cctcacgttg      60
acctgcacct tctctgggtt ctcactcagc actagtggag tgggtgtggg ctggatccgt     120
cagcccccag gaaaggccct ggagtggctt gcagtcattt attggaatga tgataagctc    180
tacaggccat ctctgaagag caggctcacc atcaccaagg acacctccaa aaaccaggtg    240
gtccttacaa tgaccaagat ggaccctgtg acacagcca catattactg tgcacacaga     300
caccgttact atgatattag tggttattac cgtctcttct ctgatgcttt tgatatctgg    360
ggccagggca ccatggtgac cgtgtccagc gctagcgccc caacccttt cccccctcgtc    420 tcctgtgaga attccccgtc ggatacgagc agcgtggccg ttggctgcct cgcacaggac    480
ttccttcccg actccatcac tttctcctgg aaatacaaga acaactctga catcagcagc    540 acccgggggct tcccatcagt cctgagaggg ggcaagtacg cagccacctc acaggtgctg    600
ctgccttcca aggacgtcat gcagggcaca gacgaacacg tggtgtgcaa agtccagcac    660
cccaacggca caaagaaaaa gaacgtgcct cttccaggtg agggccgggc ccagccaccg    720
ggacagagag ggagccgaag ggggcgggag tggcgggcac cgggctgaca cgtgtccctc    780
actgcagtga ttgctgagct gcctcccaaa gtgagcgtct tcgtcccacc ccgcgacggc    840
ttcttcggca accccgcaa gtccaagctc atctgccagg ccacgggttt cagtcccgg     900 cagattcagg tgtcctggct gcgcgagggg aagcaggtgg ggtctggcgt caccacggac    960
```

```
caggtgcagg ctgaggccaa agagtctggg cccacgacct acaaggtgac cagcacactg    1020
accatcaaag agagcgactg gctcagccag agcatgttca cctgccgcgt ggatcacagg    1080
ggcctgacct tccagcagaa tgcgtcctcc atgtgtgtcc ccggtgagtg acctgtcccc    1140
aggggcagca cccaccgaca cacaggggtc cactcgggtc tggcattcgc caccccggat    1200
gcagccatct actccctgag ccttggcttc cagagcggc caagggcagg ggctcgggcg     1260
gcaggacccc tgggctcggc agaggcagtt gctactcttt gggtgggaac catgcctccg    1320
cccacatcca cacctgcccc acctctgact cccttctctt gactccagat caagacacag    1380
ccatccgggt cttcgccatc ccccatcct  ttgccagcat cttcctcacc aagtccacca    1440
agttgacctg cctggtcaca gacctgacca cctatgacag cgtgaccatc tcctggaccc    1500
gccagaatgg cgaagctgtg aaaacccaca ccaacatctc cgagagccac cccaatgcca    1560
ctttcagcgc cgtgggtgag gccagcatct gcgaggatga ctggaattcc ggggagaggt    1620
tcacgtgcac cgtgacccac acagacctgc cctcgccact gaagcagacc atctcccggc    1680
ccaagggtag gccccactct tgcccctctt cctgcactcc ctgggacctc ccttggcctc    1740
tggggcatgg tggaaagcac ccctcactcc cccgttgtct gggcaactgg ggaaaagggg    1800
actcaacccc agcccacagg ctggtccccc cactgccccg ccctcaccac catctctgtt    1860 cacagggtg gccctgcaca ggcccgatgt ctacttgctg ccaccagccc gggagcagct     1920
gaacctgcgg gagtcggcca ccatcacgtg cctggtgacg ggcttctctc ccgcggacgt    1980
cttcgtgcag tggatgcaga ggggggcagcc cttgtccccg gagaagtatg tgaccagcgc   2040
cccaatgcct gagccccagg ccccaggccg gtacttcgcc cacagcatcc tgaccgtgtc    2100
cgaagaggaa tggaacacgg gggagaccta cacctgcgtg gtggcccatg aggccctgcc    2160
caacagggtc accgagagga ccgtggacaa gtccaccggt aaacccaccc tgtacaacgt    2220
gtccctggtc atgtccgaca cagctggcac ctgctac                             2257
```

<210> SEQ ID NO 218
<211> LENGTH: 581
<212> TYPE: PRT
<213> ORGANISM: Artificial sequence
<220> FEATURE:
<223> OTHER INFORMATION: Heavy chain CRM4374

<400> SEQUENCE: 218

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Val Gly Val Gly Trp Ile Arg Gln Pro Pro Gly Lys Ala Leu Glu
            35                  40                  45

Trp Leu Ala Val Ile Tyr Trp Asn Asp Asp Lys Leu Tyr Arg Pro Ser
        50                  55                  60

Leu Lys Ser Arg Leu Thr Ile Thr Lys Asp Thr Ser Lys Asn Gln Val
65                  70                  75                  80

Val Leu Thr Met Thr Lys Met Asp Pro Val Asp Thr Ala Thr Tyr Tyr
                85                  90                  95

Cys Ala His Arg His Arg Tyr Tyr Asp Ile Ser Gly Tyr Tyr Arg Leu
                100                 105                 110

Phe Ser Asp Ala Phe Asp Ile Trp Gly Gln Gly Thr Met Val Thr Val
            115                 120                 125
```

```
Ser Ser Ala Ser Ala Pro Thr Leu Phe Pro Leu Val Ser Cys Glu Asn
    130                 135                 140

Ser Pro Ser Asp Thr Ser Ser Val Ala Val Gly Cys Leu Ala Gln Asp
145                 150                 155                 160

Phe Leu Pro Asp Ser Ile Thr Phe Ser Trp Lys Tyr Lys Asn Asn Ser
                165                 170                 175

Asp Ile Ser Ser Thr Arg Gly Phe Pro Ser Val Leu Arg Gly Gly Lys
            180                 185                 190

Tyr Ala Ala Thr Ser Gln Val Leu Leu Pro Ser Lys Asp Val Met Gln
        195                 200                 205

Gly Thr Asp Glu His Val Val Cys Lys Val Gln His Pro Asn Gly Asn
    210                 215                 220

Lys Glu Lys Asn Val Pro Leu Pro Val Ile Ala Glu Leu Pro Pro Lys
225                 230                 235                 240

Val Ser Val Phe Val Pro Pro Arg Asp Gly Phe Phe Gly Asn Pro Arg
                245                 250                 255

Lys Ser Lys Leu Ile Cys Gln Ala Thr Gly Phe Ser Pro Arg Gln Ile
            260                 265                 270

Gln Val Ser Trp Leu Arg Glu Gly Lys Gln Val Gly Ser Gly Val Thr
        275                 280                 285

Thr Asp Gln Val Gln Ala Glu Ala Lys Glu Ser Gly Pro Thr Thr Tyr
    290                 295                 300

Lys Val Thr Ser Thr Leu Thr Ile Lys Glu Ser Asp Trp Leu Ser Gln
305                 310                 315                 320

Ser Met Phe Thr Cys Arg Val Asp His Arg Gly Leu Thr Phe Gln Gln
                325                 330                 335

Asn Ala Ser Ser Met Cys Val Pro Asp Gln Asp Thr Ala Ile Arg Val
            340                 345                 350

Phe Ala Ile Pro Pro Ser Phe Ala Ser Ile Phe Leu Thr Lys Ser Thr
        355                 360                 365

Lys Leu Thr Cys Leu Val Thr Asp Leu Thr Thr Tyr Asp Ser Val Thr
370                 375                 380

Ile Ser Trp Thr Arg Gln Asn Gly Glu Ala Val Lys Thr His Thr Asn
385                 390                 395                 400

Ile Ser Glu Ser His Pro Asn Ala Thr Phe Ser Ala Val Gly Glu Ala
                405                 410                 415

Ser Ile Cys Glu Asp Asp Trp Asn Ser Gly Glu Arg Phe Thr Cys Thr
            420                 425                 430

Val Thr His Thr Asp Leu Pro Ser Pro Leu Lys Gln Thr Ile Ser Arg
        435                 440                 445

Pro Lys Gly Val Ala Leu His Arg Pro Asp Val Tyr Leu Leu Pro Pro
450                 455                 460

Ala Arg Glu Gln Leu Asn Leu Arg Glu Ser Ala Thr Ile Thr Cys Leu
465                 470                 475                 480

Val Thr Gly Phe Ser Pro Ala Asp Val Phe Val Gln Trp Met Gln Arg
                485                 490                 495

Gly Gln Pro Leu Ser Pro Glu Lys Tyr Val Thr Ser Ala Pro Met Pro
            500                 505                 510

Glu Pro Gln Ala Pro Gly Arg Tyr Phe Ala His Ser Ile Leu Thr Val
        515                 520                 525

Ser Glu Glu Glu Trp Asn Thr Gly Glu Thr Tyr Thr Cys Val Val Ala
530                 535                 540

His Glu Ala Leu Pro Asn Arg Val Thr Glu Arg Thr Val Asp Lys Ser
```

```
                545                 550                 555                 560
        Thr Gly Lys Pro Thr Leu Tyr Asn Val Ser Leu Val Met Ser Asp Thr
                            565                 570                 575

Ala Gly Thr Cys Tyr
                580

<210> SEQ ID NO 219
<211> LENGTH: 8792
<212> TYPE: DNA
<213> ORGANISM: Artificial sequence
<220> FEATURE:
<223> OTHER INFORMATION: Vector pIg-C910-Clambda

<400> SEQUENCE: 219
tcgacggatc gggagatctc ccgatcccct atggtgcact ctcagtacaa tctgctctga      60
tgccgcatag ttaagccagt atctgctccc tgcttgtgtg ttggaggtcg ctgagtagtg     120
cgcgagcaaa atttaagcta caacaaggca aggcttgacc acaattgtt aattaacatg      180 aagaatctgc ttagggttag gcgttttgcg ctgcttcgct aggtggtcaa tattggccat     240
tagccatatt attcattggt tatatagcat aaatcaatat tggctattgg ccattgcata     300
cgttgtatcc atatcataat atgtacattt atattggctc atgtccaaca ttaccgccat     360
gttgacattg attattgact agttattaat agtaatcaat tacggggtca ttagttcata     420
gcccatatat ggagttccgc gttacataac ttacggtaaa tggcccgcct ggctgaccgc     480
ccaacgaccc ccgcccattg acgtcaataa tgacgtatgt tcccatagta acgccaatag     540
ggactttcca ttgacgtcaa tgggtggagt atttacggta aactgcccac ttggcagtac     600
atcaagtgta tcatatgcca agtacgcccc ctattgacgt caatgacggt aaatggcccg     660
cctggcatta tgcccagtac atgaccttat gggactttcc tacttggcag tacatctacg     720
tattagtcat cgctattacc atggtgatgc ggttttggca gtacatcaat gggcgtggat     780
agcggtttga ctcacgggga tttccaagtc tccaccccat tgacgtcaat gggagtttgt     840
tttggcacca aaatcaacgg gactttccaa aatgtcgtaa caactccgcc ccattgacgc     900
aaatgggcgg taggcgtgta cggtgggagg tctatataag cagagctcgt ttagtgaacc     960
gtcagatcgc ctggagacgc catccacgct gttttgacct ccatagaaga caccgggacc    1020
gatccagcct ccgcggccgg gaacggtgca ttggaatcga tgactctctt aggtagcctt    1080
gcagaagttg gtcgtgaggc actgggcagg taagtatcaa ggttacaaga caggtttaag    1140
gagatcaata gaaactgggc ttgtcgagac agagaagact cttgcgtttc tgataggcac    1200
ctattggtct tactgacatc cactttgcct ttctctccac aggtgtccac tcccagttca    1260
attacagctc gccaccatgc ggttctccgc tcagctgctg gccttctgg tgctgtggat      1320 tcccggcgtc tcgagatcta tcgatgcatg ccatggtacc aagcttgcca ccatgagcag    1380
cagctcttgg ctgctgctga gcctggtggc cgtgacagcc gcccagagca ccatcgagga    1440
gcaggccaag accttcctgg acaagttcaa ccacgaggcc gaggacctgt tctaccagag    1500
cagcctggcc agctggaact acaacaccaa catcaccgag gagaacgtgc agaacatgaa    1560
caacgccggc gacaagtgga gcgccttcct gaaggagcag agcacactgg cccagatgta    1620
ccccctgcag gagatccaga acctgaccgt gaagctgcag ctgcaggccc tgcagcagaa    1680
cggcagcagc gtgctgagcg aggacaagag caagcggctg aacaccatcc tgaacaccat    1740
gtccaccatc tacagcaccg gcaaagtgtg caaccccgac aacccccagg agtgcctgct    1800
gctggagccc ggcctgaacg agatcatggc caacagcctg gactacaacg agcggctgtg    1860
```

```
ggcctgggag agctggcgga gcgaagtggg caagcagctg cggcccctgt acgaggagta    1920
cgtggtgctg aagaacgaga tggccagggc caaccactac gaggactacg gcgactactg    1980
gagaggcgac tacagaagtga acggcgtgga cggctacgac tacagcagag gccagctgat    2040
cgaggacgtg gagcacacct tcgaggagat caagcctctg tacgagcacc tgcacgccta    2100
cgtgcgggcc aagctgatga acgcctaccc cagctacatc agccccatcg gctgcctgcc    2160
cgcccacctg ctgggcgaca tgtggggccg gttctggacc aacctgtaca gcctgaccgt    2220
gcccttcggc cagaagccca acatcgacgt gaccgacgcc atggtggacc aggcctggga    2280
cgcccagcgg atcttcaagg aggccgagaa gttcttcgtg agcgtgggcc tgcccaacat    2340
gacccagggc ttttgggaga acagcatgct gaccgacccc ggcaatgtgc agaaggccgt    2400
gtgccacccc accgcctggg acctgggcaa gggcgacttc cggatcctga tgtgcaccaa    2460
agtgaccatg gacgacttcc tgaccgccca ccacgagatg gccacatcc agtacgacat    2520 ggcctacgcc gcccagccct tcctgctgcg gaacggcgcc aacgagggct tcacgaggc    2580 cgtgggcgag atcatgagcc tgagcgccgc caccccaag cacctgaaga gcatcggcct    2640
gctgagcccc gacttccagg aggacaacga gaccgagatc aacttcctgc tgaagcaggc    2700
cctgaccatc gtgggcaccc tgcccttcac ctacatgctg agaagtggc ggtggatggt    2760 gtttaagggc gagatcccca aggaccagtg gatgaagaag tggtgggaga tgaagcggga    2820
gatcgtgggc gtggtggagc ccgtgcccca cgacgagacc tactgcgacc ccgccagcct    2880
gttccacgtg agcaacgact actccttcat ccggtactac acccggaccc tgtaccagtt    2940
ccagttccag gaggccctgt gccaggccgc caagcacgag ggccccctgc acaagtgcga    3000
catcagcaac agcaccgagg ccggacagaa actgttcaac atgctgcggc tgggcaagag    3060
cgagccctgg accctggccc tggagaatgt ggtgggcgcc aagaacatga atgtgcgccc    3120
cctgctgaac tacttcgagc ccctgttcac ctggctgaag accagaaca agaacagctt    3180 cgtgggctgg agcaccgact ggagcccta cgccgaccag agcatcaaag tgcggatcag    3240
cctgaagagc gccctgggcg acaaggccta cgagtggaac gacaacgaga tgtacctgtt    3300
ccggagcagc gtggcctatg ccatgcggca gtacttcctg aaagtgaaga accagatgat    3360
cctgttcggc gaggaggacg tgagagtggc caacctgaag ccccggatca gcttcaactt    3420
cttcgtgacc gccccaaga acgtgagcga catcatcccc cggaccgaag tggagaaggc    3480
catccggatg agccggagcc ggatcaacga cgccttccgg ctgaacgaca actccctgga    3540
gttcctgggc atccagccca ccctgggccc tcccaaccag cccccgtga gcatctggct    3600 gatcgtgttt ggcgtggtga tgggcgtgat cgtggtggga atcgtgatcc tgatcttcac    3660
cggcatccgg accggaaga agaagaacaa ggcccggagc ggcgagaacc cctacgccag    3720
catcgatatc agcaagggcg agaacaaccc cggcttccag aacaccgacg acgtgcagac    3780
cagcttctga taatctagaa cgagctcgaa ttcgaagctt ctgcagacgc gtcgacgtca    3840
tatggatccg atatcgccgt ggcggccgca ggccagccca aggccgctcc cagcgtgacc    3900
ctgttccccc cctcctccga ggagctgcag gccaacaagg ccaccctggt gtgcctcatc    3960
agcgacttct accctggcgc cgtgaccgtg gcctggaagg ccgacagcag ccccgtgaag    4020
gccggcgtgg agaccaccac ccccagcaag cagagcaaca caagtacgc cgccagcagc    4080 tacctgagcc tcaccccga gcagtggaag agccaccgga gctacagctg ccaggtgacc    4140
cacgagggca gcaccgtgga gaagaccgtg gcccccaccg agtgcagcta atagacttaa    4200
```

```
gtttaaaccg ctgatcagcc tcgactgtgc cttctagttg ccagccatct gttgtttgcc    4260
cctcccccgt gccttccttg accctggaag gtgccactcc cactgtcctt tcctaataaa    4320
atgaggaaat tgcatcgcat tgtctgagta ggtgtcattc tattctgggg ggtggggtgg    4380
ggcaggacag caaggggag gattgggaag acaatagcag gcatgctggg gatgcggtgg    4440
gctctatggc ttctgaggcg gaaagaacca gctgggctc tagggggtat ccccacgcgc    4500
cctgtagcgg cgcattaagc gcggcgggtg tggtggttac gcgcagcgtg accgctacac    4560
ttgccagcgc cctagcgccc gctcctttcg ctttcttccc ttcctttctc gccacgttcg    4620
ccggctttcc ccgtcaagct ctaaatcggg gctcccttt agggttccga tttagtgctt    4680
tacggcacct cgaccccaaa aaacttgatt agggtgatgg ttcacgtagt gggccatcgc    4740
cctgatagac ggttttcgc cctttgacgt tggagtccac gttctttaat agtggactct    4800
tgttccaaac tggaacaaca ctcaaccta tctcggtcta ttcttttgat ttataaggga    4860
ttttggccat ttcggcctat tggttaaaaa atgagctgat ttaacaaaaa tttaacgcga    4920
attaattctg tggaatgtgt gtcagttagg gtgtggaaag tccccaggct ccccagcagg    4980
cagaagtatg caaagcatgc atctcaatta gtcagcaacc aggtgtggaa agtccccagg    5040
ctccccagca ggcagaagta tgcaaagcat gcatctcaat tagtcagcaa ccatagtccc    5100
gcccctaact ccgcccatcc cgccctaac tccgcccagt tccgcccatt ctccgcccca    5160
tggctgacta atttttttta tttatgcaga ggccgaggcc gcctctgcct ctgagctatt    5220
ccagaagtag tgaggaggct ttttggagg cctaggcttt tgcaaaaagc tcccgggagc    5280
ttgtatatcc attttcggat ctgatcagca cgtgatgaaa aagcctgaac tcaccgcgac    5340
gtctgtcgag aagtttctga tcgaaaagtt cgacagcgtc tccgacctga tgcagctctc    5400
ggagggcgaa gaatctcgtg ctttcagctt cgatgtagga gggcgtggat atgtcctgcg    5460
ggtaaatagc tgcgccgatg gtttctacaa agatcgttat gtttatcggc actttgcatc    5520
ggccgcgctc ccgattccgg aagtgcttga cattgggaa ttcagcgaga gcctgaccta    5580
ttgcatctcc cgccgtgcac agggtgtcac gttgcaagac ctgcctgaaa ccgaactgcc    5640
cgctgttctg cagccggtcg cggaggccat ggatgcgatc gctgcggccg atcttagcca    5700
gacgagcggg ttcggcccat tcggaccgca aggaatcggt caatacacta catggcgtga    5760
tttcatatgc gcgattgctg atccccatgt gtatcactgg caaactgtga tggacgacac    5820
cgtcagtgcg tccgtcgcgc aggctctcga tgagctgatg ctttgggccg aggactgccc    5880
cgaagtccgg cacctcgtgc acgcggattt cggctccaac aatgtcctga cggacaatgg    5940
ccgcataaca gcggtcattg actggagcga ggcgatgttc ggggattccc aatacgaggt    6000
cgccaacatc ttcttctgga ggccgtggtt ggcttgtatg gagcagcaga cgcgctactt    6060
cgagcggagg catccggagc ttgcaggatc gccgcggctc cgggcgtata tgctccgcat    6120
tggtcttgac caactctatc agagcttggt tgacggcaat ttcgatgatg cagcttgggc    6180
gcagggtcga tgcgacgcaa tcgtccgatc cggagccggg actgtcgggc gtacacaaat    6240
cgcccgcaga agcgcggccg tctggaccga tggctgtgta aagtactcg ccgatagtgg    6300 aaaccgacgc cccagcactc gtccgagggc aaaggaatag cacgtgctac gagatttcga    6360
ttccaccgcc gccttctatg aaaggttggg cttcggaatc gttttccggg acgccggctg    6420
gatgatcctc cagcgcgggg atctcatgct ggagttcttc gcccacccca acttgtttat    6480
tgcagcttat aatggttaca aataaagcaa tagcatcaca aatttcacaa ataaagcatt    6540
tttttcactg cattctagtt gtggtttgtc caaactcatc aatgtatctt atcatgtctg    6600
```

-continued

```
tataccgtcg acctctagct agagcttggc gtaatcatgg tcatagctgt ttcctgtgtg    6660
aaattgttat ccgctcacaa ttccacacaa catacgagcc ggaagcataa agtgtaaagc    6720
ctggggtgcc taatgagtga gctaactcac attaattgcg ttgcgctcac tgcccgcttt    6780
ccagtcggga aacctgtcgt gccagctgca ttaatgaatc ggccaacgcg cggggagagg    6840
cggtttgcgt attgggcgct cttccgcttc ctcgctcact gactcgctgc gctcggtcgt    6900
tcggctgcgg cgagcggtat cagctcactc aaaggcggta atacggttat ccacagaatc    6960
aggggataac gcaggaaaga acatgtgagc aaaaggccag caaaaggcca ggaaccgtaa    7020
aaaggccgcg ttgctggcgt ttttccatag gctccgcccc cctgacgagc atcacaaaaa    7080
tcgacgctca agtcagaggt ggcgaaaccc gacaggacta taaagatacc aggcgtttcc    7140
ccctggaagc tccctcgtgc gctctcctgt tccgaccctg ccgcttaccg gatacctgtc    7200
cgcctttctc ccttcgggaa gcgtggcgct ttctcatagc tcacgctgta ggtatctcag    7260
ttcggtgtag gtcgttcgct ccaagctggg ctgtgtgcac gaaccccccg ttcagcccga    7320
ccgctgcgcc ttatccggta actatcgtct tgagtccaac ccgtaagac acgacttatc     7380 gccactggca gcagccactg gtaacaggat tagcagagcg aggtatgtag gcggtgctac    7440
agagttcttg aagtggtggc ctaactacgc tacactaga agaacagtat ttggtatctg     7500
cgctctgctg aagccagtta ccttcggaaa aagagttggt agctcttgat ccggcaaaca    7560
aaccaccgct ggtagcggtt ttttgtttg caagcagcag attacgcgca gaaaaaagg      7620 atctcaagaa gatcctttga tcttttctac ggggtctgac gctcagtgga acgaaaactc    7680
acgttaaggg attttggtca tgagattatc aaaaaggatc ttcacctaga tccttttaaa    7740
ttaaaaatga agttttaaat caatctaaag tatatatgag taaacttggt ctgacagtta    7800
ccaatgctta atcagtgagg cacctatctc agcgatctgt ctatttcgtt catccatagt    7860
tgcctgactc cccgtcgtgt agataactac gatacgggag ggcttaccat ctggccccag    7920
tgctgcaatg ataccgcgag acccacgctc accggctcca gatttatcag caataaacca    7980
gccagccgga agggccgagc gcagaagtgg tcctgcaact ttatccgcct ccatccagtc    8040
tattaattgt tgccgggaag ctagagtaag tagttcgcca gttaatagtt tgcgcaacgt    8100
tgttgccatt gctacaggca tcgtggtgtc acgctcgtcg tttggtatgg cttcattcag    8160
ctccggttcc caacgatcaa ggcgagttac atgatccccc atgttgtgca aaaaagcggt    8220
tagctccttc ggtcctccga tcgttgtcag aagtaagttg gccgcagtgt tatcactcat    8280
ggttatggca gcactgcata attctcttac tgtcatgcca tccgtaagat gcttttctgt    8340
gactggtgag tactcaacca agtcattctg agaatagtgt atgcggcgac cgagttgctc    8400
ttgcccggcg tcaatacggg ataataccgc gccacatagc agaactttaa aagtgctcat    8460
cattggaaaa cgttcttcgg ggcgaaaact ctcaaggatc ttaccgctgt tgagatccag    8520
ttcgatgtaa cccactcgtg cacccaactg atcttcagca tcttttactt tcaccagcgt    8580
ttctgggtga gcaaaaacag gaaggcaaaa tgccgcaaaa aagggaataa gggcgacacg    8640
gaaatgttga atactcatac tcttcctttt tcaatattat tgaagcattt atcagggtta    8700
ttgtctcatg agcggataca tatttgaatg tatttagaaa aataaacaaa taggggttcc    8760
gcgcacattt ccccgaaaag tgccacctga cg                                  8792
```

<210> SEQ ID NO 220
<211> LENGTH: 663
<212> TYPE: DNA

<213> ORGANISM: Artificial sequence
<220> FEATURE:
<223> OTHER INFORMATION: Light chain of CR5074
<220> FEATURE:
<221> NAME/KEY: CDS
<222> LOCATION: (1)..(663)

<400> SEQUENCE: 220

```
cag tct gtg ttg acg cag ccg ccc tca gtg tct ggg gcc cca ggg cag      48
Gln Ser Val Leu Thr Gln Pro Pro Ser Val Ser Gly Ala Pro Gly Gln
1               5                   10                  15 agg gtc acc atc tcc tgc act ggg agc agc tcc aac atc ggg aca ggt      96
Arg Val Thr Ile Ser Cys Thr Gly Ser Ser Ser Asn Ile Gly Thr Gly
                20                  25                  30 tat gat gta cac tgg tac cag cag ctt cca gga aca gcc ccc aaa ctc     144
Tyr Asp Val His Trp Tyr Gln Gln Leu Pro Gly Thr Ala Pro Lys Leu
            35                  40                  45 ctc atc tat gct gac acc aat cgg ccc tca ggg gtc cct gac cga ttc     192
Leu Ile Tyr Ala Asp Thr Asn Arg Pro Ser Gly Val Pro Asp Arg Phe
        50                  55                  60 tct ggc tcc aag tct ggc acc tca gcc tcc ctg gcc atc act ggg gtc     240
Ser Gly Ser Lys Ser Gly Thr Ser Ala Ser Leu Ala Ile Thr Gly Val
65                  70                  75                  80 cag gct gag gat gag gct gat tat tac tgc cag tcc tat gac acc agc     288
Gln Ala Glu Asp Glu Ala Asp Tyr Tyr Cys Gln Ser Tyr Asp Thr Ser
                85                  90                  95 ctg act ggt tgg gtg ttc ggc gga ggg acc aag gtc acc gtc cta ggt     336
Leu Thr Gly Trp Val Phe Gly Gly Gly Thr Lys Val Thr Val Leu Gly
                100                 105                 110 gcg gcc gca ggc cag ccc aag gcc gct ccc agc gtg acc ctg ttc ccc     384
Ala Ala Ala Gly Gln Pro Lys Ala Ala Pro Ser Val Thr Leu Phe Pro
            115                 120                 125 ccc tcc tcc gag gag ctg cag gcc aac aag gcc acc ctg gtg tgc ctc     432
Pro Ser Ser Glu Glu Leu Gln Ala Asn Lys Ala Thr Leu Val Cys Leu
        130                 135                 140 atc agc gac ttc tac cct ggc gcc gtg acc gtg gcc tgg aag gcc gac     480
Ile Ser Asp Phe Tyr Pro Gly Ala Val Thr Val Ala Trp Lys Ala Asp
145                 150                 155                 160 agc agc ccc gtg aag gcc ggc gtg gag acc acc acc ccc agc aag cag     528
Ser Ser Pro Val Lys Ala Gly Val Glu Thr Thr Thr Pro Ser Lys Gln
                165                 170                 175 agc aac aac aag tac gcc gcc agc agc tac ctg agc ctc acc ccc gag     576
Ser Asn Asn Lys Tyr Ala Ala Ser Ser Tyr Leu Ser Leu Thr Pro Glu
                180                 185                 190 cag tgg aag agc cac cgg agc tac agc tgc cag gtg acc cac gag ggc     624
Gln Trp Lys Ser His Arg Ser Tyr Ser Cys Gln Val Thr His Glu Gly
            195                 200                 205 agc acc gtg gag aag acc gtg gcc ccc acc gag tgc agc                  663
Ser Thr Val Glu Lys Thr Val Ala Pro Thr Glu Cys Ser
        210                 215                 220
```

<210> SEQ ID NO 221
<211> LENGTH: 221
<212> TYPE: PRT
<213> ORGANISM: Artificial sequence
<220> FEATURE:
<223> OTHER INFORMATION: Light chain of CR5074

<400> SEQUENCE: 221

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Thr Gly
```

```
                20                  25                  30
Tyr Asp Val His Trp Tyr Gln Gln Leu Pro Gly Thr Ala Pro Lys Leu
         35                  40                  45

Leu Ile Tyr Ala Asp Thr Asn Arg Pro Ser Gly Val Pro Asp Arg Phe
 50                  55                  60

Ser Gly Ser Lys Ser Gly Thr Ser Ala Ser Leu Ala Ile Thr Gly Val
 65                  70                  75                  80

Gln Ala Glu Asp Glu Ala Asp Tyr Tyr Cys Gln Ser Tyr Asp Thr Ser
                 85                  90                  95

Leu Thr Gly Trp Val Phe Gly Gly Gly Thr Lys Val Thr Val Leu Gly
            100                 105                 110

Ala Ala Ala Gly Gln Pro Lys Ala Ala Pro Ser Val Thr Leu Phe Pro
            115                 120                 125

Pro Ser Ser Glu Glu Leu Gln Ala Asn Lys Ala Thr Leu Val Cys Leu
130                 135                 140

Ile Ser Asp Phe Tyr Pro Gly Ala Val Thr Val Ala Trp Lys Ala Asp
145                 150                 155                 160

Ser Ser Pro Val Lys Ala Gly Val Glu Thr Thr Thr Pro Ser Lys Gln
                165                 170                 175

Ser Asn Asn Lys Tyr Ala Ala Ser Ser Tyr Leu Ser Leu Thr Pro Glu
            180                 185                 190

Gln Trp Lys Ser His Arg Ser Tyr Ser Cys Gln Val Thr His Glu Gly
            195                 200                 205

Ser Thr Val Glu Lys Thr Val Ala Pro Thr Glu Cys Ser
    210                 215                 220

<210> SEQ ID NO 222
<211> LENGTH: 663
<212> TYPE: DNA
<213> ORGANISM: Artificial sequence
<220> FEATURE:
<223> OTHER INFORMATION: Light chain of CR5080
<220> FEATURE:
<221> NAME/KEY: CDS
<222> LOCATION: (1)..(663)

<400> SEQUENCE: 222 cag tct gtg ctg act cag cca ccc tca gtg tct ggg gcc cca ggg cag      48
Gln Ser Val Leu Thr Gln Pro Pro Ser Val Ser Gly Ala Pro Gly Gln
1               5                   10                  15 agg gtc acc atc tcc tgc act ggg agc agc tcc aac atc ggg gca ggt      96
Arg Val Thr Ile Ser Cys Thr Gly Ser Ser Ser Asn Ile Gly Ala Gly
            20                  25                  30 tat gat gta cac tgg tac cag cag ctt cca gga aca gcc ccc aaa ctc     144
Tyr Asp Val His Trp Tyr Gln Gln Leu Pro Gly Thr Ala Pro Lys Leu
         35                  40                  45 ctc atc tat ggt aac agc aat cgg ccc tca ggg gtc cct gac cga ttc     192
Leu Ile Tyr Gly Asn Ser Asn Arg Pro Ser Gly Val Pro Asp Arg Phe
 50                  55                  60 tct ggc tcc aag tct ggc acc tca gcc tcc ctg gcc atc act ggg ctc     240
Ser Gly Ser Lys Ser Gly Thr Ser Ala Ser Leu Ala Ile Thr Gly Leu
 65                  70                  75                  80 cag gct gag gat gag gct gat tat tac tgc cag tcc tat gac agc agc     288
Gln Ala Glu Asp Glu Ala Asp Tyr Tyr Cys Gln Ser Tyr Asp Ser Ser
                 85                  90                  95 ctg agt ggt tgg gcg ttc ggc gga ggg acc aag ctg acc gtc cta ggt     336
Leu Ser Gly Trp Ala Phe Gly Gly Gly Thr Lys Leu Thr Val Leu Gly
            100                 105                 110
```

-continued

```
gcg gcc gca ggc cag ccc aag gcc gct ccc agc gtg acc ctg ttc ccc    384
Ala Ala Ala Gly Gln Pro Lys Ala Ala Pro Ser Val Thr Leu Phe Pro
        115                 120                 125 ccc tcc tcc gag gag ctg cag gcc aac aag gcc acc ctg gtg tgc ctc    432
Pro Ser Ser Glu Glu Leu Gln Ala Asn Lys Ala Thr Leu Val Cys Leu
130                 135                 140 atc agc gac ttc tac cct ggc gcc gtg acc gtg gcc tgg aag gcc gac    480
Ile Ser Asp Phe Tyr Pro Gly Ala Val Thr Val Ala Trp Lys Ala Asp
145                 150                 155                 160 agc agc ccc gtg aag gcc ggc gtg gag acc acc ccc agc aag cag        528
Ser Ser Pro Val Lys Ala Gly Val Glu Thr Thr Pro Ser Lys Gln
            165                 170                 175 agc aac aac aag tac gcc gcc agc agc tac ctg agc ctc acc ccc gag    576
Ser Asn Asn Lys Tyr Ala Ala Ser Ser Tyr Leu Ser Leu Thr Pro Glu
            180                 185                 190 cag tgg aag agc cac cgg agc tac agc tgc cag gtg acc cac gag ggc    624
Gln Trp Lys Ser His Arg Ser Tyr Ser Cys Gln Val Thr His Glu Gly
        195                 200                 205 agc acc gtg gag aag acc gtg gcc ccc acc gag tgc agc                663
Ser Thr Val Glu Lys Thr Val Ala Pro Thr Glu Cys Ser
        210                 215                 220
```

<210> SEQ ID NO 223
<211> LENGTH: 221
<212> TYPE: PRT
<213> ORGANISM: Artificial sequence
<220> FEATURE:
<223> OTHER INFORMATION: Light chain of CR5080

<400> SEQUENCE: 223

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Trp Ala Phe Gly Gly Gly Thr Lys Leu Thr Val Leu Gly
            100                 105                 110

Ala Ala Ala Gly Gln Pro Lys Ala Ala Pro Ser Val Thr Leu Phe Pro
        115                 120                 125

Pro Ser Ser Glu Glu Leu Gln Ala Asn Lys Ala Thr Leu Val Cys Leu
130                 135                 140

Ile Ser Asp Phe Tyr Pro Gly Ala Val Thr Val Ala Trp Lys Ala Asp
145                 150                 155                 160

Ser Ser Pro Val Lys Ala Gly Val Glu Thr Thr Pro Ser Lys Gln
            165                 170                 175

Ser Asn Asn Lys Tyr Ala Ala Ser Ser Tyr Leu Ser Leu Thr Pro Glu
            180                 185                 190

Gln Trp Lys Ser His Arg Ser Tyr Ser Cys Gln Val Thr His Glu Gly
        195                 200                 205

Ser Thr Val Glu Lys Thr Val Ala Pro Thr Glu Cys Ser
        210                 215                 220
```

<210> SEQ ID NO 224
<211> LENGTH: 663
<212> TYPE: DNA
<213> ORGANISM: Artificial sequence
<220> FEATURE:
<223> OTHER INFORMATION: Light chain of CR5085
<220> FEATURE:
<221> NAME/KEY: CDS
<222> LOCATION: (1)..(663)

<400> SEQUENCE: 224

```
cag tct gtc gtg acg cag ccg ccc tca gtg tct ggg gcc cca ggg cag        48
Gln Ser Val Val Thr Gln Pro Pro Ser Val Ser Gly Ala Pro Gly Gln
 1               5                  10                  15 agg gtc acc atc tcc tgc act ggg agc agc tcc aac atc ggg gca ggt        96
Arg Val Thr Ile Ser Cys Thr Gly Ser Ser Ser Asn Ile Gly Ala Gly
             20                  25                  30 tat gat gta cac tgg tac cag cag ctt cca gga aca gcc ccc aaa ctc       144
Tyr Asp Val His Trp Tyr Gln Gln Leu Pro Gly Thr Ala Pro Lys Leu
         35                  40                  45 ctc atc tat ggt aac agc aat cgg ccc tca ggg gtc cct gac cga ttc       192
Leu Ile Tyr Gly Asn Ser Asn Arg Pro Ser Gly Val Pro Asp Arg Phe
     50                  55                  60 tct ggc tcc aag tct ggc acc tca gcc tcc ctg gcc atc act ggg ctc       240
Ser Gly Ser Lys Ser Gly Thr Ser Ala Ser Leu Ala Ile Thr Gly Leu
 65                  70                  75                  80 cag gct gag gat gag act gat tat tac tgc cag tcc tat gac agc agc       288
Gln Ala Glu Asp Glu Thr Asp Tyr Tyr Cys Gln Ser Tyr Asp Ser Ser
                 85                  90                  95 ctg aat ggt tgg gtg ttc ggc gga ggg acc aag ctg acc gtc cta ggt       336
Leu Asn Gly Trp Val Phe Gly Gly Gly Thr Lys Leu Thr Val Leu Gly
            100                 105                 110 gcg gcc gca ggc cag ccc aag gcc gct ccc agc gtg acc ctg ttc ccc       384
Ala Ala Ala Gly Gln Pro Lys Ala Ala Pro Ser Val Thr Leu Phe Pro
        115                 120                 125 ccc tcc tcc gag gag ctg cag gcc aac aag gcc acc ctg gtg tgc ctc       432
Pro Ser Ser Glu Glu Leu Gln Ala Asn Lys Ala Thr Leu Val Cys Leu
    130                 135                 140 atc agc gac ttc tac cct ggc gcc gtg acc gtg gcc tgg aag gcc gac       480
Ile Ser Asp Phe Tyr Pro Gly Ala Val Thr Val Ala Trp Lys Ala Asp
145                 150                 155                 160 agc agc ccc gtg aag gcc ggc gtg gag acc acc acc ccc agc aag cag       528
Ser Ser Pro Val Lys Ala Gly Val Glu Thr Thr Thr Pro Ser Lys Gln
                165                 170                 175 agc aac aac aag tac gcc gcc agc agc tac ctg agc ctc acc ccc gag       576
Ser Asn Asn Lys Tyr Ala Ala Ser Ser Tyr Leu Ser Leu Thr Pro Glu
            180                 185                 190 cag tgg aag agc cac cgg agc tac agc tgc cag gtg acc cac gag ggc       624
Gln Trp Lys Ser His Arg Ser Tyr Ser Cys Gln Val Thr His Glu Gly
        195                 200                 205 agc acc gtg gag aag acc gtg gcc ccc acc gag tgc agc                   663
Ser Thr Val Glu Lys Thr Val Ala Pro Thr Glu Cys Ser
    210                 215                 220
```

<210> SEQ ID NO 225
<211> LENGTH: 221
<212> TYPE: PRT
<213> ORGANISM: Artificial sequence
<220> FEATURE:
<223> OTHER INFORMATION: Light chain of CR5085

<400> SEQUENCE: 225

```
Gln Ser Val Val Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Thr Asp Tyr Tyr Cys Gln Ser Tyr Asp Ser Ser
                85                  90                  95

Leu Asn Gly Trp Val Phe Gly Gly Gly Thr Lys Leu Thr Val Leu Gly
            100                 105                 110

Ala Ala Ala Gly Gln Pro Lys Ala Ala Pro Ser Val Thr Leu Phe Pro
            115                 120                 125

Pro Ser Ser Glu Glu Leu Gln Ala Asn Lys Ala Thr Leu Val Cys Leu
130                 135                 140

Ile Ser Asp Phe Tyr Pro Gly Ala Val Thr Val Ala Trp Lys Ala Asp
145                 150                 155                 160

Ser Ser Pro Val Lys Ala Gly Val Glu Thr Thr Thr Pro Ser Lys Gln
                165                 170                 175

Ser Asn Asn Lys Tyr Ala Ala Ser Ser Tyr Leu Ser Leu Thr Pro Glu
            180                 185                 190

Gln Trp Lys Ser His Arg Ser Tyr Ser Cys Gln Val Thr His Glu Gly
            195                 200                 205

Ser Thr Val Glu Lys Thr Val Ala Pro Thr Glu Cys Ser
        210                 215                 220

<210> SEQ ID NO 226
<211> LENGTH: 663
<212> TYPE: DNA
<213> ORGANISM: Artificial sequence
<220> FEATURE:
<223> OTHER INFORMATION: Light chain of CR5088
<220> FEATURE:
<221> NAME/KEY: CDS
<222> LOCATION: (1)..(663)

<400> SEQUENCE: 226 cag tct gtc gtg acg cag ccg ccc tca gtg tct ggg gcc cca ggg cag      48
Gln Ser Val Val Thr Gln Pro Pro Ser Val Ser Gly Ala Pro Gly Gln
1               5                   10                  15 agg atc acc atc tcc tgc act ggg agc agc tcc aac atc ggg gca ggt      96
Arg Ile Thr Ile Ser Cys Thr Gly Ser Ser Ser Asn Ile Gly Ala Gly
            20                  25                  30 tat gat gta cac tgg tac cag cag ctt cca gga aca gcc ccc aaa ttc     144
Tyr Asp Val His Trp Tyr Gln Gln Leu Pro Gly Thr Ala Pro Lys Phe
            35                  40                  45 ctc atc tat ggt aac agc aat cgg ccc tca ggg gtc cct gac cga ttc     192
Leu Ile Tyr Gly Asn Ser Asn Arg Pro Ser Gly Val Pro Asp Arg Phe
50                  55                  60 tct ggc tcc aag tct ggc acc tca gcc tcc ctg gcc atc act ggg ctc     240
Ser Gly Ser Lys Ser Gly Thr Ser Ala Ser Leu Ala Ile Thr Gly Leu
65                  70                  75                  80 cag gct gag gat gag gct gat tat tac tgc cag tcc tat gac agc agc     288
Gln Ala Glu Asp Glu Ala Asp Tyr Tyr Cys Gln Ser Tyr Asp Ser Ser
                85                  90                  95
```

-continued

```
ctg agt ggt tgg gtg ttc ggc gga ggg acc aag ctg acc gtc cta ggt      336
Leu Ser Gly Trp Val Phe Gly Gly Gly Thr Lys Leu Thr Val Leu Gly
        100                 105                 110 gcg gcc gca ggc cag ccc aag gcc gct ccc agc gtg acc ctg ttc ccc      384
Ala Ala Ala Gly Gln Pro Lys Ala Ala Pro Ser Val Thr Leu Phe Pro
            115                 120                 125 ccc tcc tcc gag gag ctg cag gcc aac aag gcc acc ctg gtg tgc ctc      432
Pro Ser Ser Glu Glu Leu Gln Ala Asn Lys Ala Thr Leu Val Cys Leu
    130                 135                 140 atc agc gac ttc tac cct ggc gcc gtg acc gtg gcc tgg aag gcc gac      480
Ile Ser Asp Phe Tyr Pro Gly Ala Val Thr Val Ala Trp Lys Ala Asp
145                 150                 155                 160 agc agc ccc gtg aag gcc ggc gtg gag acc acc acc ccc agc aag cag      528
Ser Ser Pro Val Lys Ala Gly Val Glu Thr Thr Thr Pro Ser Lys Gln
                165                 170                 175 agc aac aac aag tac gcc gcc agc agc tac ctg agc ctc acc ccc gag      576
Ser Asn Asn Lys Tyr Ala Ala Ser Ser Tyr Leu Ser Leu Thr Pro Glu
            180                 185                 190 cag tgg aag agc cac cgg agc tac agc tgc cag gtg acc cac gag ggc      624
Gln Trp Lys Ser His Arg Ser Tyr Ser Cys Gln Val Thr His Glu Gly
        195                 200                 205 agc acc gtg gag aag acc gtg gcc ccc acc gag tgc agc                  663
Ser Thr Val Glu Lys Thr Val Ala Pro Thr Glu Cys Ser
    210                 215                 220

<210> SEQ ID NO 227
<211> LENGTH: 221
<212> TYPE: PRT
<213> ORGANISM: Artificial sequence
<220> FEATURE:
<223> OTHER INFORMATION: Light chain of CR5088

<400> SEQUENCE: 227

Gln Ser Val Val Thr Gln Pro Pro Ser Val Ser Gly Ala Pro Gly Gln
1               5                   10                  15

Arg Ile Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Phe
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Trp Val Phe Gly Gly Gly Thr Lys Leu Thr Val Leu Gly
            100                 105                 110

Ala Ala Ala Gly Gln Pro Lys Ala Ala Pro Ser Val Thr Leu Phe Pro
        115                 120                 125

Pro Ser Ser Glu Glu Leu Gln Ala Asn Lys Ala Thr Leu Val Cys Leu
    130                 135                 140

Ile Ser Asp Phe Tyr Pro Gly Ala Val Thr Val Ala Trp Lys Ala Asp
145                 150                 155                 160

Ser Ser Pro Val Lys Ala Gly Val Glu Thr Thr Thr Pro Ser Lys Gln
                165                 170                 175

Ser Asn Asn Lys Tyr Ala Ala Ser Ser Tyr Leu Ser Leu Thr Pro Glu
            180                 185                 190
```

```
Gln Trp Lys Ser His Arg Ser Tyr Ser Cys Gln Val Thr His Glu Gly
        195                 200                 205

Ser Thr Val Glu Lys Thr Val Ala Pro Thr Glu Cys Ser
    210                 215                 220

<210> SEQ ID NO 228
<211> LENGTH: 771
<212> TYPE: DNA
<213> ORGANISM: Artificial sequence
<220> FEATURE:
<223> OTHER INFORMATION: SC05-074
<220> FEATURE:
<221> NAME/KEY: CDS
<222> LOCATION: (1)..(771)

<400> SEQUENCE: 228 cag gtc acc ttg aag gag tct ggt cct acg ctg gtg aaa ccc aca cag        48
Gln Val Thr Leu Lys Glu Ser Gly Pro Thr Leu Val Lys Pro Thr Gln
1               5                   10                  15 acc ctc acg ttg acc tgc acc ttc tct ggg ttc tca ctc agc act agt        96
Thr Leu Thr Leu Thr Cys Thr Phe Ser Gly Phe Ser Leu Ser Thr Ser
            20                  25                  30 gga gtg ggt gtg ggc tgg atc cgt cag ccc cca gga aag gcc ctg gag       144
Gly Val Gly Val Gly Trp Ile Arg Gln Pro Pro Gly Lys Ala Leu Glu
        35                  40                  45 tgg ctt gca gtc att tat tgg aat gat gat aag ctc tac agg cca tct       192
Trp Leu Ala Val Ile Tyr Trp Asn Asp Asp Lys Leu Tyr Arg Pro Ser
    50                  55                  60 ctg aag agc agg ctc acc atc acc aag gac acc tcc aaa aac cag gtg       240
Leu Lys Ser Arg Leu Thr Ile Thr Lys Asp Thr Ser Lys Asn Gln Val
65                  70                  75                  80 gtc ctt aca atg acc aag atg gac cct gtg gac aca gcc aca tat tac       288
Val Leu Thr Met Thr Lys Met Asp Pro Val Asp Thr Ala Thr Tyr Tyr
                85                  90                  95 tgt gca cac aga cac cgt tac tat gat att agt ggt tat tac cgt ctc       336
Cys Ala His Arg His Arg Tyr Tyr Asp Ile Ser Gly Tyr Tyr Arg Leu
            100                 105                 110 ttc tct gat gct ttt gat atc tgg ggc caa ggg aca atg gtc acc gtc       384
Phe Ser Asp Ala Phe Asp Ile Trp Gly Gln Gly Thr Met Val Thr Val
        115                 120                 125 tcg agc ggt acg ggc ggt tca ggc gga acc ggc agc ggc act ggc ggg       432
Ser Ser Gly Thr Gly Gly Ser Gly Gly Thr Gly Ser Gly Thr Gly Gly
    130                 135                 140 tcg acg cag tct gtg ttg acg cag ccg ccc tca gtg tct ggg gcc cca       480
Ser Thr Gln Ser Val Leu Thr Gln Pro Pro Ser Val Ser Gly Ala Pro
145                 150                 155                 160 ggg cag agg gtc acc atc tcc tgc act ggg agc agc tcc aac atc ggg       528
Gly Gln Arg Val Thr Ile Ser Cys Thr Gly Ser Ser Ser Asn Ile Gly
                165                 170                 175 aca ggt tat gat gta cac tgg tac cag cag ctt cca gga aca gcc ccc       576
Thr Gly Tyr Asp Val His Trp Tyr Gln Gln Leu Pro Gly Thr Ala Pro
            180                 185                 190 aaa ctc ctc atc tat gct gac acc aat cgg ccc tca ggg gtc cct gac       624
Lys Leu Leu Ile Tyr Ala Asp Thr Asn Arg Pro Ser Gly Val Pro Asp
        195                 200                 205 cga ttc tct ggc tcc aag tct ggc acc tca gcc tcc ctg gcc atc act       672
Arg Phe Ser Gly Ser Lys Ser Gly Thr Ser Ala Ser Leu Ala Ile Thr
    210                 215                 220 ggg gtc cag gct gag gat gag gct gat tat tac tgc cag tcc tat gac       720
Gly Val Gln Ala Glu Asp Glu Ala Asp Tyr Tyr Cys Gln Ser Tyr Asp
225                 230                 235                 240
```

```
acc agc ctg act ggt tgg gtg ttc ggc gga ggg acc aag gtc acc gtc    768
Thr Ser Leu Thr Gly Trp Val Phe Gly Gly Gly Thr Lys Val Thr Val
            245                 250                 255 cta                                                                 771
Leu
```

<210> SEQ ID NO 229
<211> LENGTH: 257
<212> TYPE: PRT
<213> ORGANISM: Artificial sequence
<220> FEATURE:
<223> OTHER INFORMATION: SC05-074

<400> SEQUENCE: 229

```
Gln Val Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Val Ile Tyr Trp Asn Asp Asp Lys Leu Tyr Arg Pro Ser
     50                  55                  60

Leu Lys Ser Arg Leu Thr Ile Thr Lys Asp Thr Ser Lys Asn Gln Val
 65                  70                  75                  80

Val Leu Thr Met Thr Lys Met Asp Pro Val Asp Thr Ala Thr Tyr Tyr
                 85                  90                  95

Cys Ala His Arg His Arg Tyr Tyr Asp Ile Ser Gly Tyr Tyr Arg Leu
            100                 105                 110

Phe Ser Asp Ala Phe Asp Ile Trp Gly Gln Gly Thr Met Val Thr Val
        115                 120                 125

Ser Ser Gly Thr Gly Gly Ser Gly Gly Thr Gly Ser Gly Thr Gly Gly
    130                 135                 140

Ser Thr Gln Ser Val Leu Thr Gln Pro Pro Ser Val Ser Gly Ala Pro
145                 150                 155                 160

Gly Gln Arg Val Thr Ile Ser Cys Thr Gly Ser Ser Ser Asn Ile Gly
                165                 170                 175

Thr Gly Tyr Asp Val His Trp Tyr Gln Gln Leu Pro Gly Thr Ala Pro
            180                 185                 190

Lys Leu Leu Ile Tyr Ala Asp Thr Asn Arg Pro Ser Gly Val Pro Asp
        195                 200                 205

Arg Phe Ser Gly Ser Lys Ser Gly Thr Ser Ala Ser Leu Ala Ile Thr
    210                 215                 220

Gly Val Gln Ala Glu Asp Glu Ala Asp Tyr Tyr Cys Gln Ser Tyr Asp
225                 230                 235                 240

Thr Ser Leu Thr Gly Trp Val Phe Gly Gly Gly Thr Lys Val Thr Val
                245                 250                 255

Leu
```

<210> SEQ ID NO 230
<211> LENGTH: 771
<212> TYPE: DNA
<213> ORGANISM: Artificial sequence
<220> FEATURE:
<223> OTHER INFORMATION: SC05-080
<220> FEATURE:
<221> NAME/KEY: CDS
<222> LOCATION: (1)..(771)

<400> SEQUENCE: 230

```
cag gtc acc ttg aag gag tct ggt cct acg ctg gtg aaa ccc aca cag      48
Gln Val Thr Leu Lys Glu Ser Gly Pro Thr Leu Val Lys Pro Thr Gln
 1               5                  10                  15 acc ctc acg ttg acc tgc acc ttc tct ggg ttc tca ctc agc act agt      96
Thr Leu Thr Leu Thr Cys Thr Phe Ser Gly Phe Ser Leu Ser Thr Ser
             20                  25                  30 gga gtg ggt gtg ggc tgg atc cgt cag ccc cca gga aag gcc ctg gag     144
Gly Val Gly Val Gly Trp Ile Arg Gln Pro Pro Gly Lys Ala Leu Glu
         35                  40                  45 tgg ctt gca gtc att tat tgg aat gat gat aag ctc tac agg cca tct     192
Trp Leu Ala Val Ile Tyr Trp Asn Asp Asp Lys Leu Tyr Arg Pro Ser
 50                  55                  60 ctg aag agc agg ctc acc atc acc aag gac acc tcc aaa aac cag gtg     240
Leu Lys Ser Arg Leu Thr Ile Thr Lys Asp Thr Ser Lys Asn Gln Val
 65                  70                  75                  80 gtc ctt aca atg acc aag atg gac cct gtg gac aca gcc aca tat tac     288
Val Leu Thr Met Thr Lys Met Asp Pro Val Asp Thr Ala Thr Tyr Tyr
                 85                  90                  95 tgt gca cac aga cac cgt tac tat gat att agt ggt tat tac cgt ctc     336
Cys Ala His Arg His Arg Tyr Tyr Asp Ile Ser Gly Tyr Tyr Arg Leu
             100                 105                 110 ttc tct gat gct ttt gat atc tgg ggc caa ggg aca atg gtc acc gtc     384
Phe Ser Asp Ala Phe Asp Ile Trp Gly Gln Gly Thr Met Val Thr Val
         115                 120                 125 tcg agc ggt acg ggc ggt tca ggc gga acc ggc agc ggc act ggc ggg     432
Ser Ser Gly Thr Gly Gly Ser Gly Gly Thr Gly Ser Gly Thr Gly Gly
 130                 135                 140 tcg acg cag tct gtg ctg act cag cca ccc tca gtg tct ggg gcc cca     480
Ser Thr Gln Ser Val Leu Thr Gln Pro Pro Ser Val Ser Gly Ala Pro
145                 150                 155                 160 ggg cag agg gtc acc atc tcc tgc act ggg agc agc tcc aac atc ggg     528
Gly Gln Arg Val Thr Ile Ser Cys Thr Gly Ser Ser Ser Asn Ile Gly
                 165                 170                 175 gca ggt tat gat gta cac tgg tac cag cag ctt cca gga aca gcc ccc     576
Ala Gly Tyr Asp Val His Trp Tyr Gln Gln Leu Pro Gly Thr Ala Pro
             180                 185                 190 aaa ctc ctc atc tat ggt aac agc aat cgg ccc tca ggg gtc cct gac     624
Lys Leu Leu Ile Tyr Gly Asn Ser Asn Arg Pro Ser Gly Val Pro Asp
         195                 200                 205 cga ttc tct ggc tcc aag tct ggc acc tca gcc tcc ctg gcc atc act     672
Arg Phe Ser Gly Ser Lys Ser Gly Thr Ser Ala Ser Leu Ala Ile Thr
     210                 215                 220 ggg ctc cag gct gag gat gag gct gat tat tac tgc cag tcc tat gac     720
Gly Leu Gln Ala Glu Asp Glu Ala Asp Tyr Tyr Cys Gln Ser Tyr Asp
225                 230                 235                 240 agc agc ctg agt ggt tgg gcg ttc ggc gga ggg acc aag ctg acc gtc     768
Ser Ser Leu Ser Gly Trp Ala Phe Gly Gly Gly Thr Lys Leu Thr Val
                 245                 250                 255 cta                                                                 771
Leu

<210> SEQ ID NO 231
<211> LENGTH: 257
<212> TYPE: PRT
<213> ORGANISM: Artificial sequence
<220> FEATURE:
<223> OTHER INFORMATION: SC05-080

<400> SEQUENCE: 231

Gln Val Thr Leu Lys Glu Ser Gly Pro Thr Leu Val Lys Pro Thr Gln
```

```
                1               5                  10                 15
            Thr Leu Thr Leu Thr Cys Thr Phe Ser Gly Phe Ser Leu Ser Thr Ser
                            20                 25                 30

Gly Val Gly Val Gly Trp Ile Arg Gln Pro Pro Gly Lys Ala Leu Glu
                        35                 40                 45

Trp Leu Ala Val Ile Tyr Trp Asn Asp Asp Lys Leu Tyr Arg Pro Ser
                50                 55                 60

Leu Lys Ser Arg Leu Thr Ile Thr Lys Asp Thr Ser Lys Asn Gln Val
             65                 70                 75                 80

Val Leu Thr Met Thr Lys Met Asp Pro Val Asp Thr Ala Thr Tyr Tyr
                            85                 90                 95

Cys Ala His Arg His Arg Tyr Tyr Asp Ile Ser Gly Tyr Tyr Arg Leu
                            100                105                110

Phe Ser Asp Ala Phe Asp Ile Trp Gly Gln Gly Thr Met Val Thr Val
                            115                120                125

Ser Ser Gly Thr Gly Gly Ser Gly Gly Thr Gly Ser Gly Thr Gly Gly
                        130                135                140

Ser Thr Gln Ser Val Leu Thr Gln Pro Pro Ser Val Ser Gly Ala Pro
            145                150                155                160

Gly Gln Arg Val Thr Ile Ser Cys Thr Gly Ser Ser Ser Asn Ile Gly
                            165                170                175

Ala Gly Tyr Asp Val His Trp Tyr Gln Gln Leu Pro Gly Thr Ala Pro
                            180                185                190

Lys Leu Leu Ile Tyr Gly Asn Ser Asn Arg Pro Ser Gly Val Pro Asp
                            195                200                205

Arg Phe Ser Gly Ser Lys Ser Gly Thr Ser Ala Ser Leu Ala Ile Thr
                        210                215                220

Gly Leu Gln Ala Glu Asp Glu Ala Asp Tyr Tyr Cys Gln Ser Tyr Asp
            225                230                235                240

Ser Ser Leu Ser Gly Trp Ala Phe Gly Gly Gly Thr Lys Leu Thr Val
                            245                250                255

Leu

<210> SEQ ID NO 232
<211> LENGTH: 771
<212> TYPE: DNA
<213> ORGANISM: Artificial sequence
<220> FEATURE:
<223> OTHER INFORMATION: SC05-085
<220> FEATURE:
<221> NAME/KEY: CDS
<222> LOCATION: (1)..(771)

<400> SEQUENCE: 232 cag gtc acc ttg aag gag tct ggt cct acg ctg gtg aaa ccc aca cag     48
Gln Val Thr Leu Lys Glu Ser Gly Pro Thr Leu Val Lys Pro Thr Gln
 1               5                  10                 15 acc ctc acg ttg acc tgc acc ttc tct ggg ttc tca ctc agc act agt     96
Thr Leu Thr Leu Thr Cys Thr Phe Ser Gly Phe Ser Leu Ser Thr Ser
                20                  25                  30 gga gtg ggt gtg ggc tgg atc cgt cag ccc cca gga aag gcc ctg gag    144
Gly Val Gly Val Gly Trp Ile Arg Gln Pro Pro Gly Lys Ala Leu Glu
            35                  40                  45 tgg ctt gca gtc att tat tgg aat gat gat aag ctc tac agg cca tct    192
Trp Leu Ala Val Ile Tyr Trp Asn Asp Asp Lys Leu Tyr Arg Pro Ser
        50                  55                  60 ctg aag agc agg ctc acc atc acc aag gac acc tcc aaa aac cag gtg    240
```

```
Leu Lys Ser Arg Leu Thr Ile Thr Lys Asp Thr Ser Lys Asn Gln Val
 65                  70                  75                  80 gtc ctt aca atg acc aag atg gac cct gtg gac aca gcc aca tat tac      288
Val Leu Thr Met Thr Lys Met Asp Pro Val Asp Thr Ala Thr Tyr Tyr
                 85                  90                  95 tgt gca cac aga cac cgt tac tat gat att agt ggt tat tac cgt ctc      336
Cys Ala His Arg His Arg Tyr Tyr Asp Ile Ser Gly Tyr Tyr Arg Leu
            100                 105                 110 ttc tct gat gct ttt gat atc tgg ggc caa ggg aca atg gtc acc gtc      384
Phe Ser Asp Ala Phe Asp Ile Trp Gly Gln Gly Thr Met Val Thr Val
        115                 120                 125 tcg agc ggt acg ggt ggt tca ggc gga acc ggc agc ggc act ggc ggg      432
Ser Ser Gly Thr Gly Gly Ser Gly Gly Thr Gly Ser Gly Thr Gly Gly
130                 135                 140 tcg acg cag tct gtc gtg acg cag ccg ccc tca gtg tct ggg gcc cca      480
Ser Thr Gln Ser Val Val Thr Gln Pro Pro Ser Val Ser Gly Ala Pro
145                 150                 155                 160 ggg cag agg gtc acc atc tcc tgc act ggg agc agc tcc aac atc ggg      528
Gly Gln Arg Val Thr Ile Ser Cys Thr Gly Ser Ser Ser Asn Ile Gly
                165                 170                 175 gca ggt tat gat gta cac tgg tac cag cag ctt cca gga aca gcc ccc      576
Ala Gly Tyr Asp Val His Trp Tyr Gln Gln Leu Pro Gly Thr Ala Pro
            180                 185                 190 aaa ctc ctc atc tat ggt aac agc aat cgg ccc tca ggg gtc cct gac      624
Lys Leu Leu Ile Tyr Gly Asn Ser Asn Arg Pro Ser Gly Val Pro Asp
        195                 200                 205 cga ttc tct ggc tcc aag tct ggc acc tca gcc tcc ctg gcc atc act      672
Arg Phe Ser Gly Ser Lys Ser Gly Thr Ser Ala Ser Leu Ala Ile Thr
210                 215                 220 ggg ctc cag gct gag gat gag act gat tat tac tgc cag tcc tat gac      720
Gly Leu Gln Ala Glu Asp Glu Thr Asp Tyr Tyr Cys Gln Ser Tyr Asp
225                 230                 235                 240 agc agc ctg aat ggt tgg gtg ttc ggc gga ggg acc aag ctg acc gtc      768
Ser Ser Leu Asn Gly Trp Val Phe Gly Gly Gly Thr Lys Leu Thr Val
                245                 250                 255 cta                                                                  771
Leu

<210> SEQ ID NO 233
<211> LENGTH: 257
<212> TYPE: PRT
<213> ORGANISM: Artificial sequence
<220> FEATURE:
<223> OTHER INFORMATION: SC05-085

<400> SEQUENCE: 233

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Val Ile Tyr Trp Asn Asp Asp Lys Tyr Tyr Arg Pro Ser
    50                  55                  60

Leu Lys Ser Arg Leu Thr Ile Thr Lys Asp Thr Ser Lys Asn Gln Val
65                  70                  75                  80

Val Leu Thr Met Thr Lys Met Asp Pro Val Asp Thr Ala Thr Tyr Tyr
                85                  90                  95

Cys Ala His Arg His Arg Tyr Tyr Asp Ile Ser Gly Tyr Tyr Arg Leu
```

-continued

```
                        100                 105                 110
            Phe Ser Asp Ala Phe Asp Ile Trp Gly Gln Gly Thr Met Val Thr Val
                    115                 120                 125

Ser Ser Gly Thr Gly Gly Ser Gly Gly Thr Gly Ser Gly Thr Gly Gly
            130                 135                 140

Ser Thr Gln Ser Val Val Thr Gln Pro Pro Ser Val Ser Gly Ala Pro
            145                 150                 155                 160

Gly Gln Arg Val Thr Ile Ser Cys Thr Gly Ser Ser Asn Ile Gly
                            165                 170                 175

Ala Gly Tyr Asp Val His Trp Tyr Gln Gln Leu Pro Gly Thr Ala Pro
                        180                 185                 190

Lys Leu Leu Ile Tyr Gly Asn Ser Asn Arg Pro Ser Gly Val Pro Asp
                        195                 200                 205

Arg Phe Ser Gly Ser Lys Ser Gly Thr Ser Ala Ser Leu Ala Ile Thr
                        210                 215                 220

Gly Leu Gln Ala Glu Asp Glu Thr Asp Tyr Tyr Cys Gln Ser Tyr Asp
            225                 230                 235                 240

Ser Ser Leu Asn Gly Trp Val Phe Gly Gly Gly Thr Lys Leu Thr Val
                        245                 250                 255

Leu

<210> SEQ ID NO 234
            <211> LENGTH: 771
            <212> TYPE: DNA
            <213> ORGANISM: Artificial sequence
            <220> FEATURE:
            <223> OTHER INFORMATION: SC05-088
            <220> FEATURE:
            <221> NAME/KEY: CDS
            <222> LOCATION: (1)..(771)

<400> SEQUENCE: 234 cag gtc acc ttg aag gag tct ggt cct acg ctg gtg aaa ccc aca cag       48
            Gln Val Thr Leu Lys Glu Ser Gly Pro Thr Leu Val Lys Pro Thr Gln
            1               5                   10                  15 acc ctc acg ttg acc tgc acc ttc tct ggg ttc tca ctc agc act agt       96
            Thr Leu Thr Leu Thr Cys Thr Phe Ser Gly Phe Ser Leu Ser Thr Ser
                            20                  25                  30 gga gtg ggt gtg ggc tgg atc cgt cag ccc cca gga aag gcc ctg gag      144
            Gly Val Gly Val Gly Trp Ile Arg Gln Pro Pro Gly Lys Ala Leu Glu
                        35                  40                  45 tgg ctt gca gtc att tat tgg aat gat gat aag ctc tac agg cca tct      192
            Trp Leu Ala Val Ile Tyr Trp Asn Asp Asp Lys Leu Tyr Arg Pro Ser
                    50                  55                  60 ctg aag agc agg ctc acc atc acc aag gac acc tcc aaa aac cag gtg      240
            Leu Lys Ser Arg Leu Thr Ile Thr Lys Asp Thr Ser Lys Asn Gln Val
            65                  70                  75                  80 gtc ctt aca atg acc aag atg gac cct gtg gac aca gcc aca tat tac      288
            Val Leu Thr Met Thr Lys Met Asp Pro Val Asp Thr Ala Thr Tyr Tyr
                            85                  90                  95 tgt gca cac aga cac cgt tac tat gat att agt ggt tat tac cgt ctc      336
            Cys Ala His Arg His Arg Tyr Tyr Asp Ile Ser Gly Tyr Tyr Arg Leu
                        100                 105                 110 ttc tct gat gct ttt gat atc tgg ggc caa ggg aca atg gtc acc gtc      384
            Phe Ser Asp Ala Phe Asp Ile Trp Gly Gln Gly Thr Met Val Thr Val
                    115                 120                 125 tcg agc ggt acg ggc ggt tca ggc gga acc ggc agc ggc act ggc ggg      432
            Ser Ser Gly Thr Gly Gly Ser Gly Gly Thr Gly Ser Gly Thr Gly Gly
            130                 135                 140
```

-continued

```
tcg acg cag tct gtc gtg acg cag ccg ccc tca gtg tct ggg gcc cca      480
Ser Thr Gln Ser Val Val Thr Gln Pro Pro Ser Val Ser Gly Ala Pro
145                 150                 155                 160 ggg cag agg atc acc atc tcc tgc act ggg agc agc tcc aac atc ggg      528
Gly Gln Arg Ile Thr Ile Ser Cys Thr Gly Ser Ser Ser Asn Ile Gly
                165                 170                 175 gca ggt tat gat gta cac tgg tac cag cag ctt cca gga aca gcc ccc      576
Ala Gly Tyr Asp Val His Trp Tyr Gln Gln Leu Pro Gly Thr Ala Pro
            180                 185                 190 aaa ttc ctc atc tat ggt aac agc aat cgg ccc tca ggg gtc cct gac      624
Lys Phe Leu Ile Tyr Gly Asn Ser Asn Arg Pro Ser Gly Val Pro Asp
        195                 200                 205 cga ttc tct ggc tcc aag tct ggc acc tca gcc tcc ctg gcc atc act      672
Arg Phe Ser Gly Ser Lys Ser Gly Thr Ser Ala Ser Leu Ala Ile Thr
    210                 215                 220 ggg ctc cag gct gag gat gag gct gat tat tac tgc cag tcc tat gac      720
Gly Leu Gln Ala Glu Asp Glu Ala Asp Tyr Tyr Cys Gln Ser Tyr Asp
225                 230                 235                 240 agc agc ctg agt ggt tgg gtg ttc ggc gga ggg acc aag ctg acc gtc      768
Ser Ser Leu Ser Gly Trp Val Phe Gly Gly Gly Thr Lys Leu Thr Val
                245                 250                 255 cta                                                                  771
Leu
```

<210> SEQ ID NO 235
<211> LENGTH: 257
<212> TYPE: PRT
<213> ORGANISM: Artificial sequence
<220> FEATURE:
<223> OTHER INFORMATION: SC05-088

<400> SEQUENCE: 235

```
Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Val Ile Tyr Trp Asn Asp Asp Lys Leu Tyr Arg Pro Ser
    50                  55                  60

Leu Lys Ser Arg Leu Thr Ile Thr Lys Asp Thr Ser Lys Asn Gln Val
65                  70                  75                  80

Val Leu Thr Met Thr Lys Met Asp Pro Val Asp Thr Ala Thr Tyr Tyr
                85                  90                  95

Cys Ala His Arg His Arg Tyr Tyr Asp Ile Ser Gly Tyr Tyr Arg Leu
            100                 105                 110

Phe Ser Asp Ala Phe Asp Ile Trp Gly Gln Gly Thr Met Val Thr Val
        115                 120                 125

Ser Ser Gly Thr Gly Gly Ser Gly Gly Thr Gly Ser Gly Thr Gly Gly
    130                 135                 140

Ser Thr Gln Ser Val Val Thr Gln Pro Pro Ser Val Ser Gly Ala Pro
145                 150                 155                 160

Gly Gln Arg Ile Thr Ile Ser Cys Thr Gly Ser Ser Ser Asn Ile Gly
                165                 170                 175

Ala Gly Tyr Asp Val His Trp Tyr Gln Gln Leu Pro Gly Thr Ala Pro
            180                 185                 190

Lys Phe Leu Ile Tyr Gly Asn Ser Asn Arg Pro Ser Gly Val Pro Asp
```

```
                195                 200                 205
Arg Phe Ser Gly Ser Lys Ser Gly Thr Ser Ala Ser Leu Ala Ile Thr
    210                 215                 220

Gly Leu Gln Ala Glu Asp Glu Ala Asp Tyr Tyr Cys Gln Ser Tyr Asp
225                 230                 235                 240

Ser Ser Leu Ser Gly Trp Val Phe Gly Gly Thr Lys Leu Thr Val
                245                 250                 255

Leu

<210> SEQ ID NO 236
<211> LENGTH: 14
<212> TYPE: PRT
<213> ORGANISM: Artificial sequence
<220> FEATURE:
<223> OTHER INFORMATION: LCDR1

<400> SEQUENCE: 236

Thr Gly Ser Ser Ser Asn Ile Gly Thr Gly Tyr Asp Val His
1               5                   10

<210> SEQ ID NO 237
<211> LENGTH: 14
<212> TYPE: PRT
<213> ORGANISM: Artificial sequence
<220> FEATURE:
<223> OTHER INFORMATION: LCDR1

<400> SEQUENCE: 237

Thr Gly Ser Ser Ser Asn Ile Gly Ala Gly Tyr Asp Val His
1               5                   10

<210> SEQ ID NO 238
<211> LENGTH: 14
<212> TYPE: PRT
<213> ORGANISM: Artificial sequence
<220> FEATURE:
<223> OTHER INFORMATION: LCDR1

<400> SEQUENCE: 238

Thr Gly Ser Ser Ser Asn Ile Gly Ala Gly Tyr Asp Val His
1               5                   10

<210> SEQ ID NO 239
<211> LENGTH: 14
<212> TYPE: PRT
<213> ORGANISM: Artificial sequence
<220> FEATURE:
<223> OTHER INFORMATION: LCDR1

<400> SEQUENCE: 239

Thr Gly Ser Ser Ser Asn Ile Gly Ala Gly Tyr Asp Val His
1               5                   10

<210> SEQ ID NO 240
<211> LENGTH: 7
<212> TYPE: PRT
<213> ORGANISM: Artificial sequence
<220> FEATURE:
<223> OTHER INFORMATION: LCDR2

<400> SEQUENCE: 240

Ala Asp Thr Asn Arg Pro Ser
1               5
```

```
<210> SEQ ID NO 241
<211> LENGTH: 7
<212> TYPE: PRT
<213> ORGANISM: Artificial sequence
<220> FEATURE:
<223> OTHER INFORMATION: LCDR2

<400> SEQUENCE: 241

Gly Asn Ser Asn Arg Pro Ser
1               5

<210> SEQ ID NO 242
<211> LENGTH: 7
<212> TYPE: PRT
<213> ORGANISM: Artificial sequence
<220> FEATURE:
<223> OTHER INFORMATION: LCDR2

<400> SEQUENCE: 242

Gly Asn Ser Asn Arg Pro Ser
1               5

<210> SEQ ID NO 243
<211> LENGTH: 7
<212> TYPE: PRT
<213> ORGANISM: Artificial sequence
<220> FEATURE:
<223> OTHER INFORMATION: LCDR2

<400> SEQUENCE: 243

Gly Asn Ser Asn Arg Pro Ser
1               5

<210> SEQ ID NO 244
<211> LENGTH: 11
<212> TYPE: PRT
<213> ORGANISM: Artificial sequence
<220> FEATURE:
<223> OTHER INFORMATION: LCDR3

<400> SEQUENCE: 244

Gln Ser Tyr Asp Thr Ser Leu Thr Gly Trp Val
1               5                   10

<210> SEQ ID NO 245
<211> LENGTH: 11
<212> TYPE: PRT
<213> ORGANISM: Artificial sequence
<220> FEATURE:
<223> OTHER INFORMATION: LCDR3

<400> SEQUENCE: 245

Gln Ser Tyr Asp Ser Ser Leu Ser Gly Trp Ala
1               5                   10

<210> SEQ ID NO 246
<211> LENGTH: 11
<212> TYPE: PRT
<213> ORGANISM: Artificial sequence
<220> FEATURE:
<223> OTHER INFORMATION: LCDR3

<400> SEQUENCE: 246

Gln Ser Tyr Asp Ser Ser Leu Asn Gly Trp Val
1               5                   10

<210> SEQ ID NO 247
```

```
<211> LENGTH: 11
<212> TYPE: PRT
<213> ORGANISM: Artificial sequence
<220> FEATURE:
<223> OTHER INFORMATION: LCDR3

<400> SEQUENCE: 247

Gln Ser Tyr Asp Ser Ser Leu Ser Gly Trp Val
1               5                   10

<210> SEQ ID NO 248
<211> LENGTH: 25
<212> TYPE: DNA
<213> ORGANISM: Artificial sequence
<220> FEATURE:
<223> OTHER INFORMATION: Sense primer WN-313F

<400> SEQUENCE: 248
aacaaacaaa cagcgatgaa acacc                                      25

<210> SEQ ID NO 249
<211> LENGTH: 24
<212> TYPE: DNA
<213> ORGANISM: Artificial sequence
<220> FEATURE:
<223> OTHER INFORMATION: Antisense primer WN-2588R

<400> SEQUENCE: 249
tgtggcgttt cagggtaata cttg                                       24

<210> SEQ ID NO 250
<211> LENGTH: 22
<212> TYPE: DNA
<213> ORGANISM: Artificial sequence
<220> FEATURE:
<223> OTHER INFORMATION: Antisense primer WN1617R

<400> SEQUENCE: 250
ccactcacga tggaccaaga ac                                         22

<210> SEQ ID NO 251
<211> LENGTH: 22
<212> TYPE: DNA
<213> ORGANISM: Artificial sequence
<220> FEATURE:
<223> OTHER INFORMATION: Primer WN-1242F

<400> SEQUENCE: 251
cagacaagga gtggtggaca gg                                         22

<210> SEQ ID NO 252
<211> LENGTH: 20
<212> TYPE: DNA
<213> ORGANISM: Artificial sequence
<220> FEATURE:
<223> OTHER INFORMATION: Primer WN-708F

<400> SEQUENCE: 252
caccaagaca cgccactcaa                                            20

<210> SEQ ID NO 253
<211> LENGTH: 21
<212> TYPE: DNA
<213> ORGANISM: Artificial sequence
<220> FEATURE:
<223> OTHER INFORMATION: Primer WN-1026F
```

```
<400> SEQUENCE: 253
ggtggatttg gttctcgaag g                                              21

<210> SEQ ID NO 254
<211> LENGTH: 21
<212> TYPE: DNA
<213> ORGANISM: Artificial sequence
<220> FEATURE:
<223> OTHER INFORMATION: Primer WN-1449F

<400> SEQUENCE: 254
cactcaggca gggagattca g                                              21

<210> SEQ ID NO 255
<211> LENGTH: 21
<212> TYPE: DNA
<213> ORGANISM: Artificial sequence
<220> FEATURE:
<223> OTHER INFORMATION: Primer WN-1991F

<400> SEQUENCE: 255
cagtggcttc attgaacgac c                                              21

<210> SEQ ID NO 256
<211> LENGTH: 25
<212> TYPE: DNA
<213> ORGANISM: Artificial sequence
<220> FEATURE:
<223> OTHER INFORMATION: Primer WN-315F

<400> SEQUENCE: 256
caaacaaaca gcgatgaaac acctt                                          25

<210> SEQ ID NO 257
<211> LENGTH: 24
<212> TYPE: DNA
<213> ORGANISM: Artificial sequence
<220> FEATURE:
<223> OTHER INFORMATION: Primer WN-2585R

<400> SEQUENCE: 257
ggcgtttcag ggtaatactt gtac                                           24

<210> SEQ ID NO 258
<211> LENGTH: 21
<212> TYPE: DNA
<213> ORGANISM: Artificial sequence
<220> FEATURE:
<223> OTHER INFORMATION: Primer WN-2086R

<400> SEQUENCE: 258
caatcaggac cttagcgttg g                                              21

<210> SEQ ID NO 259
<211> LENGTH: 19
<212> TYPE: DNA
<213> ORGANISM: Artificial sequence
<220> FEATURE:
<223> OTHER INFORMATION: Primer WN-1560R

<400> SEQUENCE: 259
ggtgtcaatc cctgaccgt                                                 19

<210> SEQ ID NO 260
<211> LENGTH: 21
```

-continued

```
<212> TYPE: DNA
<213> ORGANISM: Artificial sequence
<220> FEATURE:
<223> OTHER INFORMATION: Primer WN-1049R

<400> SEQUENCE: 260
tcgccttcga gaaccaaatc c                                              21

<210> SEQ ID NO 261
<211> LENGTH: 21
<212> TYPE: DNA
<213> ORGANISM: Artificial sequence
<220> FEATURE:
<223> OTHER INFORMATION: Primer WN-741R

<400> SEQUENCE: 261
cctccgactg cgtcttgagt g                                              21

<210> SEQ ID NO 262
<211> LENGTH: 29
<212> TYPE: DNA
<213> ORGANISM: Artificial sequence
<220> FEATURE:
<223> OTHER INFORMATION: Primer K307E forward

<400> SEQUENCE: 262
cggcgtgtgc agcgaggcct tcaagttcc                                      29

<210> SEQ ID NO 263
<211> LENGTH: 29
<212> TYPE: DNA
<213> ORGANISM: Artificial sequence
<220> FEATURE:
<223> OTHER INFORMATION: Primer K307E reverse

<400> SEQUENCE: 263
ggaacttgaa ggcctcgctg cacacgccg                                      29

<210> SEQ ID NO 264
<211> LENGTH: 28
<212> TYPE: DNA
<213> ORGANISM: Artificial sequence
<220> FEATURE:
<223> OTHER INFORMATION: Primer T332K forward

<400> SEQUENCE: 264
gcagtacacc ggcaaggacg gcccctgc                                       28

<210> SEQ ID NO 265
<211> LENGTH: 28
<212> TYPE: DNA
<213> ORGANISM: Artificial sequence
<220> FEATURE:
<223> OTHER INFORMATION: Primer T332K reverse

<400> SEQUENCE: 265
gcaggggccg tccttgccgg tgtactgc                                       28

<210> SEQ ID NO 266
<211> LENGTH: 28
<212> TYPE: DNA
<213> ORGANISM: Artificial sequence
<220> FEATURE:
<223> OTHER INFORMATION: Primer A365V forward

<400> SEQUENCE: 266
```

-continued cttcgtgagc gtggtcaccg ccaacgcc          28

<210> SEQ ID NO 267
<211> LENGTH: 28
<212> TYPE: DNA
<213> ORGANISM: Artificial sequence
<220> FEATURE:
<223> OTHER INFORMATION: Primer A365V reverse

<400> SEQUENCE: 267
ggcgttggcg gtgaccacgc tcacgaag          28